United States Patent
Amari et al.

(10) Patent No.: US 9,145,409 B2
(45) Date of Patent: Sep. 29, 2015

(54) BENZHYDRYL DERIVATIVES

(71) Applicant: CHIESI FARMACEUTICI S.p.A., Parma (IT)

(72) Inventors: Gabriele Amari, Parma (IT); Elisabetta Armani, Parma (IT); Carmelida Capaldi, Parma (IT); Renato De Fanti, Parma (IT); Mauro Riccaboni, Parma (IT); Charles Baker-Glenn, Saffron Walden (GB); Hervé Van De Poël, Saffron Walden (GB)

(73) Assignee: CHIESI FARMACEUTICI S.p.A, Parma (IT)

( * ) Notice: Subject to any disclaimer, the term of this patent is extended or adjusted under 35 U.S.C. 154(b) by 0 days.

(21) Appl. No.: 14/560,009

(22) Filed: Dec. 4, 2014

(65) Prior Publication Data
US 2015/0158857 A1  Jun. 11, 2015

(30) Foreign Application Priority Data

Dec. 5, 2013 (EP) .................................... 13195932

(51) Int. Cl.
| C07D 453/02 | (2006.01) |
| A61K 31/444 | (2006.01) |
| A61K 31/4545 | (2006.01) |
| A61K 31/496 | (2006.01) |

(52) U.S. Cl.
CPC ............ *C07D 453/02* (2013.01); *A61K 31/444* (2013.01); *A61K 31/4545* (2013.01); *A61K 31/496* (2013.01)

(58) Field of Classification Search
None
See application file for complete search history.

(56) References Cited

U.S. PATENT DOCUMENTS

| 2014/0155373 A1 | 6/2014 | Armani et al. |
| 2014/0155427 A1 | 6/2014 | Armani et al. |
| 2014/0155428 A1 | 6/2014 | Armani et al. |

FOREIGN PATENT DOCUMENTS

| WO | 2011/141180 | 11/2011 |
| WO | 2013/057013 | 4/2013 |

OTHER PUBLICATIONS

Extended European Search Report in Application No. 13195932.2 issued Feb. 4, 2014.

*Primary Examiner* — Timothy R Rozof
(74) *Attorney, Agent, or Firm* — Oblon, McClelland, Maier & Neustadt, L.L.P.

(57) ABSTRACT

Compounds having a benzhydryl structure represented by formula (I) described herein are both phosphodiesterase 4 (PDE4) enzyme inhibitors and muscarinic M3 receptor antagonists and are useful for treating diseases of the respiratory tract.

17 Claims, No Drawings

BENZHYDRYL DERIVATIVES

CROSS REFERENCES TO RELATED APPLICATIONS

This application claims priority to European Patent Application No. 13195932.2 filed on Dec. 5, 2013, which is incorporated herein by reference in its entirety.

BACKGROUND OF THE INVENTION

1. Field of the Invention

The present invention relates to novel compounds having a benzhydryl structure which are both phosphodiesterase 4 (PDE4) enzyme inhibitors and muscarinic M3 receptor antagonists. More particularly, the present invention relates to compounds of formula (I) as below described, methods of preparing such compounds, compositions containing them and therapeutic use thereof.

2. Discussion of the Background

Chronic obstructive pulmonary disease (COPD) is a respiratory disorder characterized by progressive, not fully reversible, airflow limitation associated with an abnormal pulmonary inflammatory response to noxious particles or gases. For this reason, bronchial relaxation and inflammatory response suppression represent a mechanistic approach to the treatment of COPD that might improve symptoms such as dyspnea, wheezing, chest tightness, cough and mucus secretion, improve health status and reduce exacerbations.

Nowadays, the drug therapy options for COPD fall into two general classes: bronchodilators, (β2-adrenoceptor agonists, antimuscarinic agents and methylxanthines) and antiinflammatory agents (glucocorticosteroids and selective phosphodiesterase-4 (PDE4) inhibitors). Bronchodilator drugs are the current mainstay of treatment for symptoms' relief.

As anticholinergic bronchodilators, the efficacy of muscarinic M3 antagonists is based on the fact that the major reversible component of airflow narrowing in COPD patients is the increase of acetylcholine (ACh) released to airway smooth muscle, by the bronchial postganglionic vagal efferent in some pathological conditions. Therefore, compounds that antagonize the action of ACh at muscarinic receptors are able to counteract the bronchoconstriction and thus improve lung function in these patients.

Muscarinic antagonists block the effects of ACh at muscarinic receptors. Currently, there are five known muscarinic receptor subtypes (M1-M5); human airway smooth muscle contains M1, M2 and M3 receptors. M1 receptors facilitate neurotransmission through parasympathetic ganglia and are weakly expressed on submucosal glands in human airways. The M2 receptors are located on the smooth-muscle fibers. Some studies have suggested a small role of M2 mediating the inhibition of airway smooth-muscle relaxation caused by adenylyl cyclase activation by compounds such as beta agonists. In addition, presynaptic M2 receptors are found on postganglionic parasympathetic nerves that project to airway smooth muscle and mucus-producing cells. These presynaptic M2 autoreceptors provide a negative feedback mechanism, which, when stimulated, inhibit further release of ACh. Postsynaptic M3 receptors are known to mediate both contraction of smooth muscle in the respiratory tract and mucus secretion, making them a major target for symptomatic relief of COPD. Consequently, in the airways, the major effects of muscarinic antagonists are bronchodilation and reduction of mucus secretion via blockage of ACh-induced effects in the parasympathetic nervous system.

Given the distribution of muscarinic receptors, systemically available agents that bind to muscarinic receptors outside of the respiratory tract have the potential to produce unwanted side effects such as tachycardia, dry mouth, urinary retention, and constipation. Whereas dry mouth is the most common systemic anticholinergic side effect associated with the use of antimuscarinic antagonists as a result of the systemic blockade of M1 and M3 receptors the most potentially serious systemic effect is tachycardia, which results from the blockade of cardiac M2 receptors.

Inhaled anticholinergic antimuscarinic drugs approved for the treatment of COPD include ipratropium bromide (Atrovent®), oxitropium bromide (Oxivent®) and tiotropium bromide (Spiriva®). Both ipratropium and oxitropium are short-acting agents. In contrast, tiotropium bromide is the only long-acting antimuscarinic agent (LAMA) currently marketed for COPD, proved to be suitable for once-daily administration as a dry powder. Several others newer LAMAs are newly registered for the treatment of COPD, including aclidinium bromide and glycopyrrolate bromide, or are currently in phase III development, including umeclidinium.

Although bronchodilators are quite effective to improve symptoms, they do not address the underlying chronic inflammation or the changes in airway structure.

Standard treatment with glucocorticosteroids as antiinflammatory agents has demonstrated limited efficacy. However, among the antiinflammatory agents currently being developed, PDE4 inhibitors proved to be effective in attenuating the responses of various inflammatory cells, through their ability to elevate cAMP levels.

PDE4 is the predominant PDE expressed in neutrophils and T cells, suggesting that PDE4 inhibitors would be effective in controlling inflammation in COPD. Inhibition of PDE4 in inflammatory cells influences various specific responses, such as the production and/or release of pro-inflammatory mediators including cytokines and reactive oxygen species, with a well-documented efficacy in animal models mimicking certain aspects of asthma and COPD, as well as inflammatory bowel disease, atopic dermatitis, psoriasis and rheumatoid arthritis.

The selective PDE4 inhibitor, roflumilast (Daxas®) is an approved phosphodiesterase-4 inhibitor for the treatment of COPD associated with chronic bronchitis and a history of exacerbations. Roflumilast inhibits lung inflammation and emphysema in a smoking model of COPD in mice. In COPD patients, oral roflumilast given over 4 weeks significantly reduces the numbers of neutrophils (by 36%) and CXCL8 concentrations in sputum. In clinical trials roflumilast (500 mg once daily) given over 12 months improved lung function in COPD patients to a small extent but had little effect in reducing exacerbations or improving quality of life. More recently roflumilast has been shown to significantly improve FEV 1 (by approximately 50 mL) and reduce exacerbation (by about 15%) in patients with severe disease who have frequent exacerbations and mucus hypersecretion. Roflumilast provides clinical benefit when added to salmeterol or tiotropium and so may be used as an additional treatment in patients with severe disease.

However, the clinical utility of PDE4 inhibitors has so far been compromised by the occurrence of mechanism-associated side effects, including headache, nausea and emesis, which often limited the maximally tolerated dose. This problem could be overcome by inhaled delivery and designing compounds with a potentially more advantageous therapeutic window.

Since bronchial relaxation and inflammatory response suppression represent a mechanistic approach to the treatment of COPD, the combination of muscarinic M3 antagonism with selective PDE4 inhibition may lead to a new class of drugs, combining both bronchodilating and antiinflammatory properties in one molecule, which may open new perspectives in the management of COPD.

SUMMARY OF THE INVENTION

Accordingly, it is one object of the present invention to provide novel compounds which are both phosphodiesterase 4 (PDE4) enzyme inhibitors and muscarinic M3 receptor antagonists.

It is another object of the present invention to provide novel methods of preparing such compounds.

It is another object of the present invention to provide novel compositions which contain such a compound.

It is another object of the present invention to provide novel methods for preventing and/or treating certain diseases and conditions by administering an effective amount of such a compound to a subject in need thereof.

These and other objects, which will become apparent during the following detailed description, have been achieved by the inventors' discovery that of the compounds of formula (I) described below.

Thus, the present invention is directed to compounds acting both as inhibitors of the phosphodiesterase 4 (PDE4) enzyme and as muscarinic M3 receptor antagonists, methods of preparing said compounds, compositions containing them and therapeutic use thereof.

In particular the present invention provides compounds of formula (I),

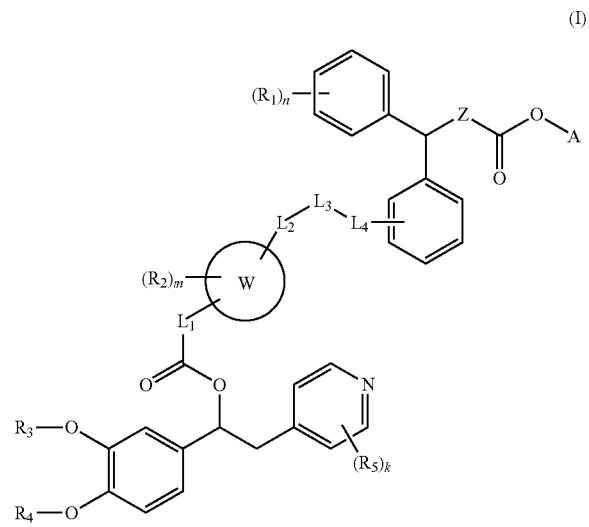

wherein
each $R_1$ is hydrogen or is selected in the group consisting of: halogen, $(C_1\text{-}C_4)$ alkyl, $(C_1\text{-}C_4)$ alkoxy, $(C_1\text{-}C_4)$ haloalkyl, hydroxy, $-SO_2NR_6R_7$, $-CN$, $-NR_8SO_2R_9$, $-NR_6R_7$, $-CONR_6R_7$ and $-NR_8COR_9$ and wherein said $(C_1\text{-}C_4)$ alkyl is optionally substituted by one or more groups selected from $(C_3\text{-}C_7)$ cycloalkyl, hydroxy and $-NR_6R_7$ and wherein said $(C_1\text{-}C_4)$ alkoxy is optionally substituted by one or more halogens or groups $(C_3\text{-}C_7)$ cycloalkyl wherein,
$R_6$ is hydrogen or $(C_1\text{-}C_6)$ alkyl;
$R_7$ is hydrogen or $(C_1\text{-}C_6)$ alkyl;
$R_8$ is hydrogen or $(C_1\text{-}C_6)$ alkyl;
$R_9$ is hydrogen or $(C_1\text{-}C_6)$ alkyl;

n is an integer ranging from 1 to 3;
each $R_2$ is hydrogen or is selected from the group consisting of: halogen, $(C_1\text{-}C_4)$ alkyl, $(C_1\text{-}C_4)$ alkoxy, $(C_1\text{-}C_4)$ haloalkyl, hydroxy, $-SO_2NR_{10}R_{11}$, $-CN$ and $-NR_{12}SO_2R_{13}$ and wherein said $(C_1\text{-}C_4)$ alkyl and said $(C_1\text{-}C_4)$ alkoxy are optionally substituted by one group $(C_3\text{-}C_7)$ cycloalkyl wherein
$R_{10}$ is hydrogen or $(C_1\text{-}C_6)$ alkyl;
$R_{11}$ is hydrogen or $(C_1\text{-}C_6)$ alkyl;
$R_{12}$ is hydrogen or $(C_1\text{-}C_6)$ alkyl;
$R_{13}$ is hydrogen or $(C_1\text{-}C_6)$ alkyl;
m is an integer ranging from 1 to 3;
$R_3$ and $R_4$ are different or the same and are independently selected from the group consisting of:
H;
$-(C_3\text{-}C_7)$ cycloalkylcarbonyl;
$(C_1\text{-}C_6)$ alkyl, optionally substituted by one or more substituents selected from $(C_3\text{-}C_7)$ cycloalkyl or $(C_5\text{-}C_7)$ cycloalkenyl;
$(C_1\text{-}C_6)$ haloalkyl;
$(C_3\text{-}C_7)$ cycloalkyl;
$(C_5\text{-}C_7)$ cycloalkenyl;
$(C_2\text{-}C_6)$ alkenyl; and
$(C_2\text{-}C_6)$ alkynyl;
or $R_3$ and $R_4$, together with the interconnecting atoms, form a 2,2-difluoro-1,3-dioxolane ring of formula (r) fused to the phenyl moiety which bears groups $-OR_3$ and $-OR_4$, wherein asterisks indicate carbon atoms shared with such phenyl ring:

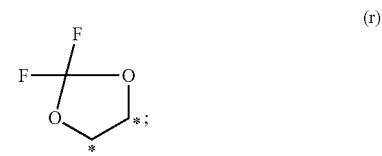

each $R_5$ is selected from the group consisting of: CN, $NO_2$, $CF_3$ and halogen atoms;
k is 0 or an integer ranging from 1 to 3;
$L_1$ is selected from the group consisting of:
a bond,
$-(CH2)_p$-,
[3]-$(CH_2)_p$—O-[4]
[3]-$(CH_2)_p$—$NR_{10}$—$(CH_2)_t$-[4]
[3]-$(CH_2)_p$—OC(O)-[4]
[3]-$(CH_2)_p$—$NR_{10}$C(O)-[4]
[3]-$(CH_2)_p$—$NR_{10}$S($O_2$)-[4] and
[3]-$(CH_2)_p$—S($O_2$)—N($R_{10}$)-[4]
wherein [3] and [4] represent, respectively the point of attachment of group $L_1$ to the carbonyl group and to the ring W and wherein
$R_{10}$ is as described above,
p is an integer ranging from 1 to 4 and
t is an integer ranging from 1 to 4
W is a divalent group selected from arylene, $(C_5\text{-}C_6)$ heteroarylene and saturated monocyclic $(C_3\text{-}C_7)$ heterocloalkylene;
$L_2$ is a bond or is a group selected from $-C(O)-$, $-S-$, $-S(O)-$, $-S(O)_2-$ and $-(CH_2)_q-$ wherein q is 1 or 2;
$L_3$ is absent or is selected from ortho-, meta-, para-phenylene, and a bivalent $(C_5\text{-}C_6)$ heteroarylene
$L_4$ is a group selected from $-(CH2)_r$-, [1]—$(CH_2)_r$—O-[2], [1]-OC(O)-[2] and [1]-C(O)O-[2] wherein r is 1 or 2 and

[1] and [2] represent respectively the point of attachment of group $L_4$ to the group $L_2$ (or $L_3$ when present) and to the phenyl ring;

Z is selected from NH, $CH_2$ and O; and

A is a nitrogen containing group which may be selected from:
- a group (a) which is $-(CH_2)_s-NR_{16}R_{17}$ wherein s is an integer ranging from 1 to 4 and $R_{16}$ and $R_{17}$ are independently hydrogen or ($C_1$-$C_4$) alkyl; and
- a group (b) which is a saturated monocyclic, bicyclic or tricyclic heterocyclic ring system optionally substituted by one or two groups $R_{18}$ which are at each occurrence independently selected from ($C_1$-$C_4$) alkyl and benzyl, their N-oxides on the pyridine ring, deuterated derivative, and pharmaceutically acceptable salts, or solvates thereof.

The present invention further provides the corresponding N-oxides on the pyridine ring of compounds of formula (I) which are represented by the formula (IA):

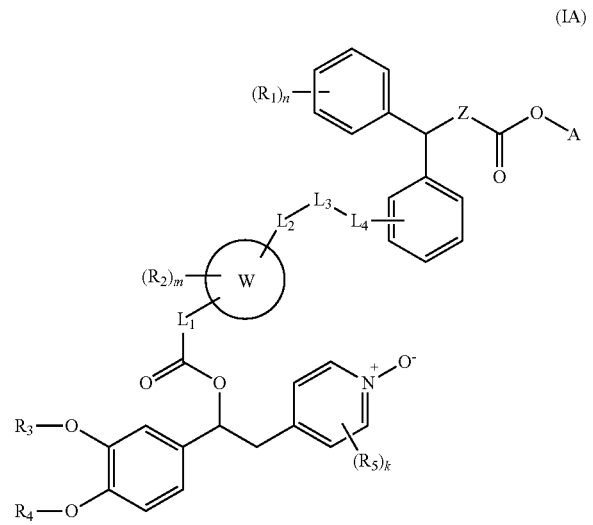

(IA)

wherein $R_1$, $R_2$, $R_3$, $R_4$, $R_5$, A, $L_1$, W, $L_2$, $L_3$, $L_4$, Z, m, n and k are as described above.

The present invention further provides the corresponding deuterated derivatives of compounds of formula (I) wherein at least one hydrogen atom is substituted by corresponding atoms of deuterium.

The present invention also provides the pharmaceutically acceptable salts and/or solvates thereof.

The term "pharmaceutically acceptable salts", as used herein, refers to derivatives of compounds of formula (I) or of their corresponding N-oxides on the pyridine ring wherein the parent compound is suitably modified by converting any of the free acid or basic groups, if present, into the corresponding addition salt with any base or acid conventionally intended as being pharmaceutically acceptable. Suitable examples of said salts may thus include mineral or organic acid addition salts of basic residues such as amino groups, as well as mineral or organic acid residues such as carboxylic groups.

Cations of inorganic bases which can be suitably used to prepare salts within the present invention comprise ions of alkali or alkaline earth metals such as potassium, sodium, calcium or magnesium.

Those obtained by reacting the main compound, functioning as a base, with an inorganic or organic acid to form a salt comprise, for example, salts of hydrochloric acid, hydrobromic acid, sulfuric acid, phosphoric acid, acetic acid, methane sulfonic acid, camphor sulfonic acid, oxalic acid, maleic acid, fumaric acid, succinic acid and citric acid.

Those skilled in the art of organic chemistry will appreciate that many organic compounds can form complexes with solvents in which they are reacted or from which they are precipitated or crystallized. These complexes are known as "solvates". Pharmaceutically acceptable solvates of compound of the present invention are within the scope of the present invention.

Included within the scope of the present invention are also polymorphs and crystalline forms of compounds of formula (I), of their N-oxides on the pyridine ring, or of pharmaceutically acceptable salts, or solvates thereof. Hereinafter, compounds of formula (I), (IA), (IB), (IC), (ID), (Ia), (Ib), (Ic), (Id) and (I)', corresponding N-oxides on the pyridine ring, enantiomers, diastereoisomers thereof, their pharmaceutically acceptable salts and solvates, and polymorphs or crystalline forms thereof defined in any aspect of the present invention (except intermediate compounds described in the chemical processes) are referred to as "compounds of the present invention".

The present invention further provides a process for the preparation of compounds of the present invention.

The present invention also provides pharmaceutical compositions of compounds of the present invention either alone or in combination, in admixture with one or more pharmaceutically acceptable carriers.

In a further aspect, the present invention provides the use of the compounds of the present invention as a medicament.

In one aspect, the present invention provides the use of the compounds of the present invention for the manufacture of a medicament.

In particular, the present invention provides the use of the compounds of the present invention for the prevention and/or treatment of any disease wherein an inhibition of PDE4 activity along with muscarinic M3 receptor antagonism is desirable.

In particular, the compounds of the present invention alone or combined with other active ingredients may be administered for the prevention and/or treatment of a disease of the respiratory tract characterized by airway obstruction such as asthma and COPD. In one embodiment, the compounds of the present invention may be administered for the prevention and/or treatment of COPD.

In a further aspect, the present invention provides the use of compounds of the present invention for the preparation of a medicament for the prevention and/or treatment of any disease wherein an inhibition of PDE4 activity along with muscarinic M3 receptor antagonism is desirable.

Moreover, the present invention provides a method for prevention and/or treatment of any disease wherein an inhibition of PDE4 activity along with muscarinic M3 receptor antagonism is desirable, said method comprises administering to a patient in need of such treatment a therapeutically effective amount of a compound of the present invention.

A further aspect of the present invention provides a suitable inhalation device, comprising a pharmaceutical composition of a compound of the present invention, which may be respectively selected from a single- or multi-dose dry powder inhaler, a pressurized metered dosed inhaler or a nebulizer and in particular a soft mist nebulizer.

A further aspect of the invention provides a kit comprising a pharmaceutical compositions of a compound of the present invention either alone or in combination with one or more active ingredient and a device which may be a single- or multi-dose dry powder inhaler, a metered dose inhaler or a nebulizer.

DETAILED DESCRIPTION OF THE PREFERRED EMBODIMENTS

The term "halogen atoms" as used herein includes fluorine, chlorine, bromine, and iodine, preferably chlorine.

As used herein, the term "$(C_1-C_x)$ alkyl" where x is an integer greater than 1, refers to straight-chained and branched alkyl groups wherein the number of constituent carbon atoms is in the range 1 to x. Particular alkyl groups are methyl, ethyl, n-propyl, i-propyl, n-butyl, sec-butyl, i-butyl, and t-butyl.

By analogy, the term "$(C_1-C_x)$alkylene", refers to a divalent $(C_1-C_x)$alkyl radical, wherein $(C_1-C_x)$alkyl is as above defined.

The term "$(C_1-C_x)$ alkoxy" where x is an integer greater than 1, refers to straight-chained and branched alkoxy groups wherein the number of constituent carbon atoms is in the range 1 to x. Particular alkoxy groups are methoxy, ethoxy, n-propoxy, i-propoxy, n-butoxy, sec-butoxy, i-butoxy, and t-butoxy.

The expressions "$(C_1-C_x)$haloalkyl" refer to the above defined "$(C_1-C_x)$alkyl" groups wherein one or more hydrogen atoms are replaced by one or more halogen atoms, which can be the same or different from each other. Non-limiting examples of said $(C_1-C_6)$haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "$(C_3-C_y)$ cycloalkyl", where y is an integer greater than or equal to 3, refers to saturated cyclic hydrocarbon groups containing from 3 to y ring carbon atoms. Non-limiting examples include cyclopropyl, cyclobutyl, cyclopentyl, cyclohexyl, and cycloheptyl.

The expression "$(C_3-C_y)$cycloalkylcarbonyl" refers to $(C_3-C_y)$cycloalkylCO— groups wherein the group "$(C_3-C_y)$cycloalkyl" has the meaning above defined.

The term "$(C_2-C_6)$alkenyl" refers to straight or branched, conjugated or not conjugated, carbon chains with one or more double bonds, in cis or trans configuration, wherein the number of atoms is in the range 2 to 6.

The term "$(C_5-C_z)$ cycloalkenyl", where z is an integer greater than or equal to 5, refers to cyclic hydrocarbon groups containing from 5 to z ring carbon atoms and one or more double bonds.

The term "$(C_2-C_6)$alkynyl" refers to straight or branched carbon chains with one or more triple bonds wherein the number of atoms is in the range 2 to 6.

The expression "arylene" refers to divalent mono or bi-cyclic ring systems which have 6 to 10 ring atoms, wherein at least one ring is aromatic.

The expression "$(C_5-C_6)$ heteroarylene" refers to divalent monocyclic ring systems with 5 to 6 ring atoms, and in which at least one ring atom is a heteroatom (e.g. N, NH, S, or O).

Non-limiting examples of suitable arylene or $(C_5-C_6)$ heteroarylene monocyclic systems include, for instance, phenylene, thiophenediyl, furanediyl, pyrrolediyl, pyrazolediyl, imidazolediyl, triazolediyl, tetrazolediyl, isoxazolediyl, oxazolediyl, isothiazolediyl, thiazolediyl, pyridinediyl radicals at any suitable position and the like.

Non-limiting examples of suitable arylene bicyclic systems include naphthalenediyl, biphenylenediyl, tetrahydronaphthalenediyl radicals at any suitable position and the like.

The expression "$(C_3-C_y)$ heterocycloalkylene" refers to divalent saturated monocyclic $(C_3-C_y)$cycloalkyl groups, in which at least one ring carbon atom is replaced by a heteroatom (e.g. N, NH, S or O). Non-limiting examples of $(C_3-C_y)$ heterocycloalkylene are represented by: azetidinediyl, pyrrolidinediyl, pyrazolinediyl, piperazinediyl, piperidinediyl, oxazolidinediyl, thiazolidinediyl, morpholinediyl, thiomorpholinediyl at any suitable position and the like.

As used herein, the expression "heterocyclic ring system" refers to optionally substituted mono-, bi- or tri-cyclic ring systems which may be saturated, partially unsaturated or unsaturated, such as $(C_3-C_7)$ heterocycloalkyl or heteroaryl having 5 to 11 ring atoms in which at least one ring atom is a heteroatom (e.g. N, S or O). Non-limiting examples of "heterocyclic ring system" are represented by: pyrrolidinyl, imidazolidinyl, piperazinyl, piperidinyl, quinuclidinyl, 8-azabicyclo[3.2.1]octanyl or dehydroxy scopine radical all optionally substituted by $(C_1-C_x)$ alkyl or benzyl on a nitrogen atom.

The present invention is directed to a class of compounds acting both as inhibitors of the phosphodiesterase 4 (PDE4) enzyme and as muscarinic M3 receptor antagonists.

The present invention relates to derivatives of general formula (I), N-oxides on the pyridine ring, deuterated derivatives and pharmaceutically acceptable salts or solvates thereof:

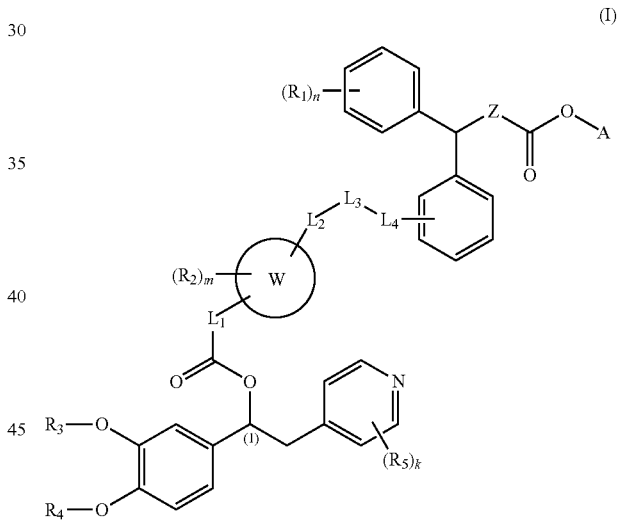

(I)

wherein $R_1$, $R_2$, $R_3$, $R_4$, $R_5$, A, $L_1$, W, $L_2$, $L_3$, $L_4$, Z, m, n and k are as described above.

It will be apparent to those skilled in the art that compounds of general formula (I) at least contain one stereogenic center, namely represented by the carbon atom (1), and therefore exist as optical stereoisomers.

It will be apparent to the skilled person that compounds according to the present invention may have at least two stereogenic centers, thus they may accordingly exist at least as four diastereoisomers. Where the compounds according to the present invention possess more than two stereogenic centers, they will exist as $2^n$ diastereoisomers (wherein n here refers to the number of stereogenic centers). It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown herebelow:

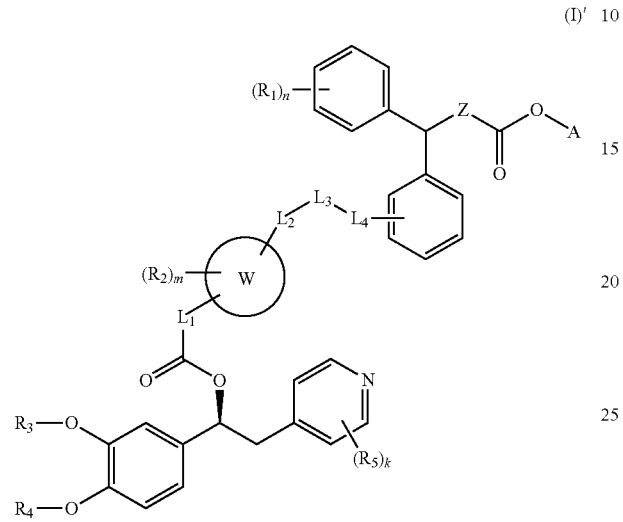

(I)'

The absolute configuration for carbon (1) is assigned on the basis of Cahn-Ingold-Prelog nomenclature based on groups'priorities.

In one preferred embodiment, for compounds of formula (I), absolute configuration at carbon (1) is (S).

In one embodiment, when A is a group of formula (i) as below defined, compounds of formula (I) may exist as at least four diastereoisomers couples (Ia), (Ib), (Ic) and (Id) herebelow reported, which are comprised within the scope of the present invention; each couple of diastereoisomers (Ia), (Ib), (Ic), (Id) is constituted by a mixture of corresponding epimers at stereogenic centre identified as (2).

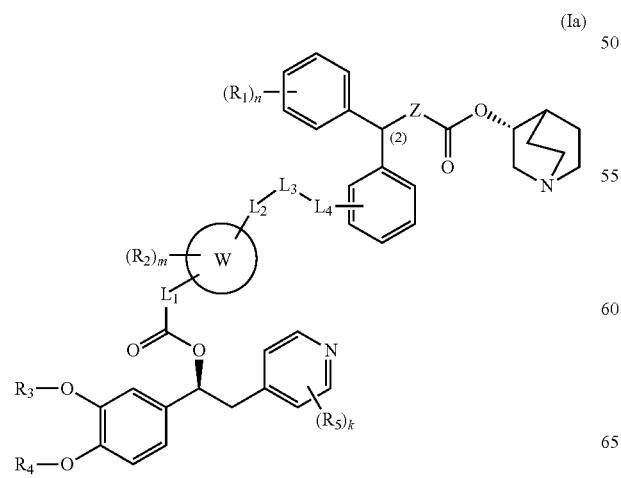

(Ia)

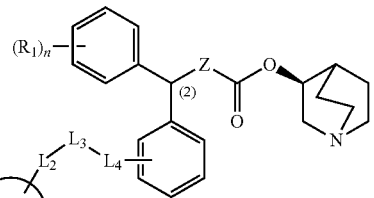

(Ib)

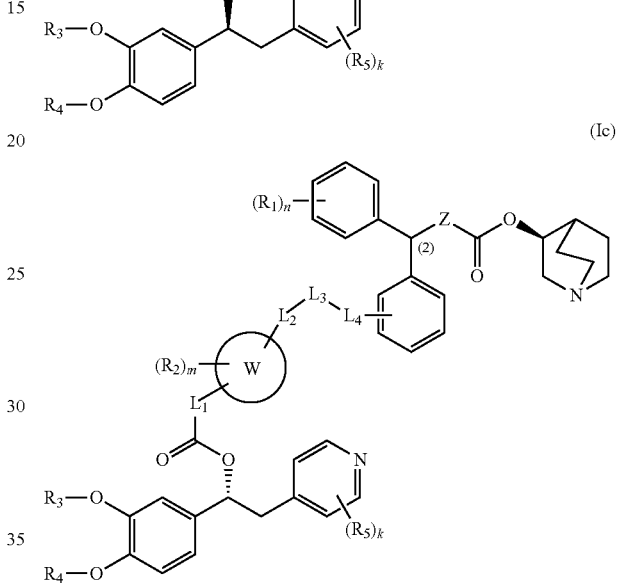

(Ic)

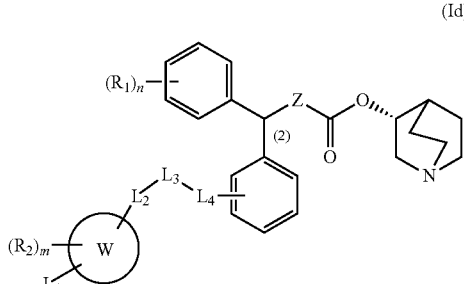

(Id)

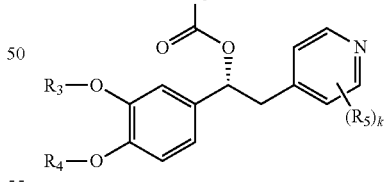

It will be apparent to the skilled person that compounds of formula (Ia), (Ib), (Ic), (Id) may be also obtained as single diastereoisomers wherein stereogenic centre at carbon atom identified as (2) is defined as R or S.

In one embodiment, compounds of formula (Ia) are provided as above reported, or single diastereoisomers thereof.

It is to be understood that all preferred groups or embodiments described herebelow and hereabove for compounds of formula (I) may be combined among each other and apply to compounds of formula (IA), (IB), (IC), (ID), (Ia), (Ib), (Ic), (Id) and (I)' as well mutatis mutandis.

In a preferred embodiment, the present invention provides compounds of formula (IA), which are N-oxides on the pyridine ring of compounds of formula (I), deuterated derivatives and pharmaceutically acceptable salts and solvates thereof:

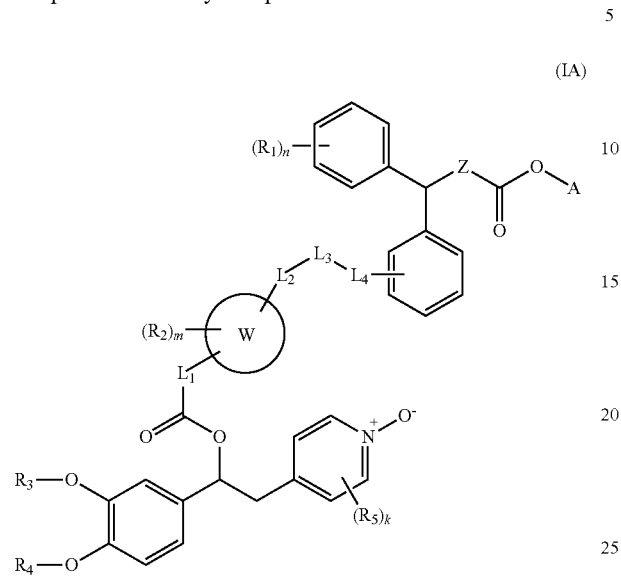

(IA)

wherein $R_1$, $R_2$, $R_3$, $R_4$, $R_5$, A, $L_1$, W, $L_2$, $L_3$, $L_4$, m, n, k and Z are as above defined.

In a preferred embodiment, k is 2 and $R_5$ are halogen atoms. In a further preferred embodiment, $R_5$ are two chlorine atoms at positions 3 and 5 of the pyridine ring.

In one preferred embodiment, $R_4$ is selected from ($C_1$-$C_6$) haloalkyl and ($C_1$-$C_6$) alkyl and $R_3$ is selected from ($C_3$-$C_7$) cycloalkyl and ($C_1$-$C_6$) alkyl which is optionally substituted by ($C_3$-$C_7$) cycloalkyl.

In another preferred embodiment, $R_3$ and $R_4$, together with the interconnecting atoms, form a 2,2-difluoro-1,3-dioxolane ring of formula (r) fused to the phenyl moiety which bears groups —$OR_3$ and —$OR_4$, wherein asterisks indicate carbon atoms shared with such phenyl ring:

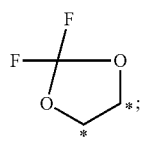

(r)

In a further preferred embodiment, $R_4$ is ($C_1$-$C_6$) haloalkyl and $R_3$ is ($C_1$-$C_6$) alkyl which is substituted by ($C_3$-$C_7$) cycloalkyl.

In another preferred embodiment, $R_3$ is ($C_1$-$C_6$) alkyl and $R_4$ is ($C_1$-$C_6$) alkyl.

A preferred group of compounds is that wherein the 4-pyridinyl ring is substituted in 3 and 5 with two atoms of chlorine, according to the general formula (IB)

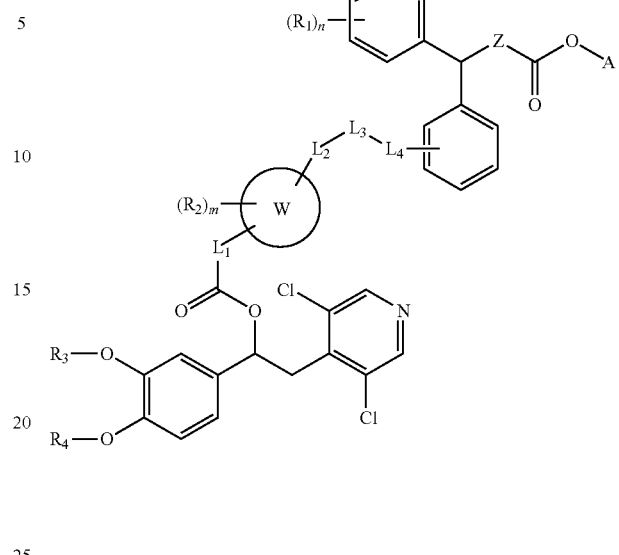

(IB)

wherein $R_1$, $R_2$, $R_3$, $R_4$, A, $L_1$, W, $L_2$, $L_3$, $L_4$, m, n and Z are as defined above for compounds of formula (I); and the corresponding N-oxide on the pyridine ring, deuterated derivatives and pharmaceutically acceptable salts and solvates thereof Another preferred group of compounds is that shown below according to general formula (IC):

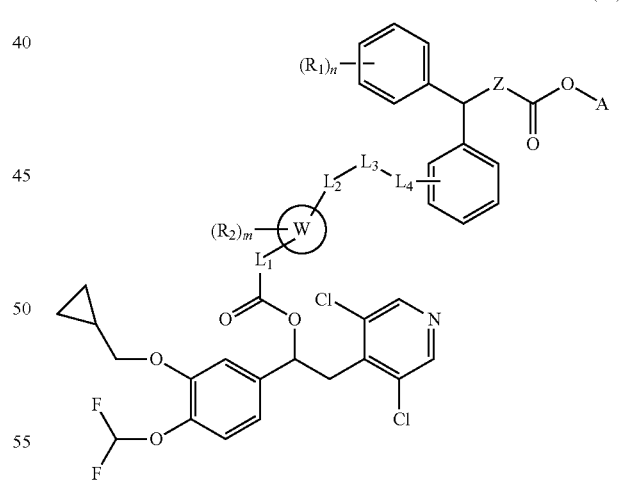

(IC)

wherein $R_1$, $R_2$, A, $L_1$, W, $L_2$, $L_3$, $L_4$, m, n and Z are as defined above for compounds of formula (I); and the corresponding N-oxide on the pyridine ring, or pharmaceutically acceptable salts thereof.

A more preferred group of compounds is that shown below according to general formula (ID):

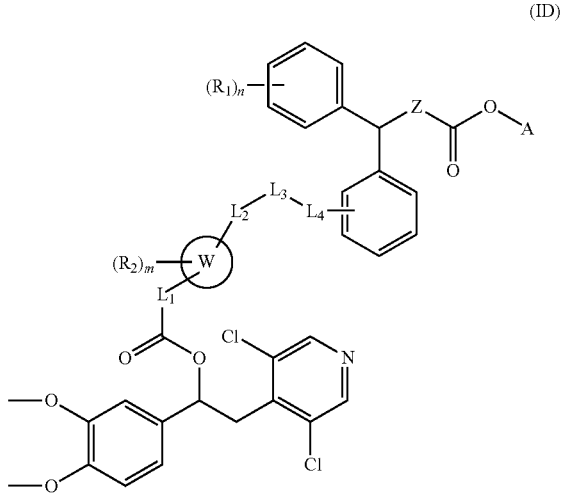

(ID)

wherein R$_1$, R$_2$, A, L$_1$, W, L$_2$, L$_3$, L$_4$, m, n and Z are as defined above for compounds of formula (I), the corresponding N-oxide on the pyridine ring, and pharmaceutically acceptable salts and solvates thereof.

In one embodiment, A is a group (b) represented by a group of formula (i), (ii), (iii) or (iv):

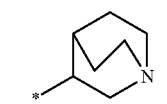
(i)

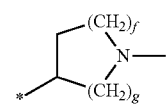
(ii)

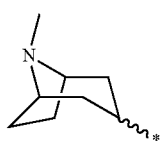
(iii)

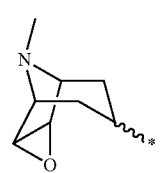
(iv)

wherein
f=1, 2 or 3;
g=1, 2 or 3.

In another embodiment, A is a group (b) represented by a group of formula (i):

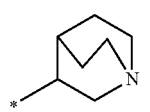
(i)

According to a preferred embodiment, the present invention provides the compounds reported below:

[(1S)-1-[3-(cyclopropylmethoxy)-4-(difluoromethoxy)phenyl]-2-(3,5-dichloro-1-oxido-pyridin-1-ium-4-yl)ethyl] (2S)-1-[3-[3-[(S)-phenyl-[[(3R)-quinuclidin-3-yl]oxycarbonylamino]methyl]phenoxy]carbonylphenyl] sulfonylpyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[3-[3-[(S)-phenyl-[[(3R)-quinuclidin-3-yl]oxycarbonylamino]methyl]phenoxy]carbonylphenyl] sulfonylazetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-3-[3-[3-[phenyl-[[(3R)-quinuclidin-3-yl]oxycarbonylamino]methyl]phenoxy]carbonylphenyl] sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-3-[3-[3-[phenyl-[[(3R)-quinuclidin-3-yl]oxycarbonylamino]methyl]phenoxy]carbonylphenyl] sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-3-[[3-[3-[(S)-phenyl-[[(3R)-quinuclidin-3-yl]oxycarbonylamino]methyl]phenoxy]carbonylphenyl]methyl] thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-3-[[3-[3-[(S)-phenyl-[[(3R)-quinuclidin-3-yl]oxycarbonylamino]methyl]benzoyl]oxyphenyl]methyl] thiazolidine-2-carboxylate;

[(1S)-2-(3,5-dichloro-1-oxido-pyridin-1-ium-4-yl)-1-(3,4-dimethoxyphenyl)ethyl]4-[[3-[(S)-phenyl-[[(3R)-quinuclidin-3-yl]oxycarbonylamino]methyl]phenoxy]methyl] benzoate;

[(1S)-2-(3,5-dichloro-1-oxido-pyridin-1-ium-4-yl)-1-(3,4-dimethoxyphenyl)ethyl]3-[[3-[(S)-phenyl-[[(3R)-quinuclidin-3-yl]oxycarbonylamino]methyl]phenoxy]methyl] benzoate;

[(1S)-2-(3,5-dichloro-1-oxido-pyridin-1-ium-4-yl)-1-(3,4-dimethoxyphenyl)ethyl]3-methoxy-5-[[3-[(S)-phenyl-[[(3R)-quinuclidin-3-yl]oxycarbonylamino]methyl]phenoxy]methyl]benzoate;

[(1S)-2-(3,5-dichloro-1-oxido-pyridin-1-ium-4-yl)-1-(3,4-dimethoxyphenyl)ethyl]6-[[3-[(S)-phenyl-[[(3R)-quinuclidin-3-yl]oxycarbonylamino]methyl]phenoxy]methyl] pyridine-3-carboxylate;

[(1S)-2-(3,5-dichloro-1-oxido-pyridin-1-ium-4-yl)-1-(3,4-dimethoxyphenyl)ethyl]1-methyl-5-[[3-[(S)-phenyl-[[(3R)-quinuclidin-3-yl]oxycarbonylamino]methyl]phenoxy]methyl]pyrazole-3-carboxylate;

[(1S)-2-(3,5-dichloro-1-oxido-pyridin-1-ium-4-yl)-1-[4-(difluoromethoxy)-3-ethoxy-phenyl]ethyl]5-[[3-[(S)-phenyl-[[(3R)-quinuclidin-3-yl]oxycarbonylamino]methyl] phenoxy]methyl]furan-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[3-[(S)-phenyl-[[(3R)-quinuclidin-3-yl]oxycarbonylamino]methyl]phenoxy]methyl]furan-2-carboxylate;

[2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]phenoxy]methyl]-furan-2-carboxylate;

[(1S)-2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]phenoxy]methyl]furan-2-carboxylate;

[(1R)-2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]phenoxy]methyl]furan-2-carboxylate;

[2-(3,5-dichloro-1-oxido-pyridin-1-ium-4-yl)-1-(3,4-dimethoxyphenyl)ethyl]4-[[3-[phenyl-[[(3R)-quinuclidin-3-yl]oxycarbonylamino]methyl]phenoxy]methyl]-benzoate;

[2-(3,5-dichloro-1-oxido-pyridin-1-ium-4-yl)-1-(3,4-dimethoxyphenyl)ethyl]3-[[3-[phenyl-[[(3R)-quinuclidin-3-yl]oxycarbonylamino]methyl]phenoxy]methyl]-benzoate;

[(1S)-2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]phenoxy]methyl]thiophene-2-carboxylate;

[(1S)-2-(3,5-dichloro-1-oxido-pyridin-1-ium-4-yl)-1-(3,4-dimethoxyphenyl)ethyl]2-[3-[[3-[(S)-phenyl-[[(3R)-quinuclidin-3-yl]oxycarbonylamino]methyl]phenoxy]methyl]phenyl]acetate;

[(1S)-2-(3,5-dichloro-1-oxido-pyridin-1-ium-4-yl)-1-(3,4-dimethoxyphenyl)ethyl]1-[4-[[3-[(S)-phenyl-[[(3R)-quinuclidin-3-yl]oxycarbonylamino]methyl]phenoxy]methyl]benzoyl]azetidine-3-carboxylate;

[(1S)-2-(3,5-dichloro-1-oxido-pyridin-1-ium-4-yl)-1-(3,4-dimethoxyphenyl)ethyl]1-[3-[[3-[(S)-phenyl-[[(3R)-quinuclidin-3-yl]oxycarbonylamino]methyl]phenoxy]methyl]benzoyl]azetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]benzoyl]pyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]benzoyl]piperidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]phenoxy]methyl]benzoyl]piperidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]phenoxy]methyl]benzoyl]pyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]benzoyl]azetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[3-[[3-[(S)-phenyl-[[(3R)-quinuclidin-3-yl]oxycarbonylamino]methyl]phenoxy]methyl]benzoyl]azetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[4-[[3-[(S)-phenyl-[[(3R)-quinuclidin-3-yl]oxycarbonylamino]methyl]phenoxy]methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[3-[(S)-phenyl-[[(3R)-quinuclidin-3-yl]oxycarbonylamino]methyl]phenoxy]methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[1-methyl-5-[[3-[(S)-phenyl-[[(3R)-quinuclidin-3-yl]oxycarbonylamino]methyl]phenoxy]methyl]pyrazole-3-carbonyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]phenoxy]methyl]phenyl]sulfonylpyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]phenyl]sulfonylpyrrolidine-2-carboxylate;

[(1S)-2-(3,5-dichloro-1-oxido-pyridin-1-ium-4-yl)-1-(3,4-dimethoxyphenyl)ethyl](2S)-1-[4-[[3-[(S)-phenyl-[[(3R)-quinuclidin-3-yl]oxycarbonylamino]methyl]phenoxy]methyl]phenyl]sulfonylpyrrolidine-2-carboxylate;

[(1S)-2-(3,5-dichloro-1-oxido-pyridin-1-ium-4-yl)-1-(3,4-dimethoxyphenyl)ethyl](2S)-1-[3-[[3-[(S)-phenyl-[[(3R)-quinuclidin-3-yl]oxycarbonylamino]methyl]phenoxy]methyl]phenyl]sulfonylpyrrolidine-2-carboxylate;

[(1S)-2-(3,5-dichloro-1-oxido-pyridin-1-ium-4-yl)-1-(3,4-dimethoxyphenyl)ethyl]1-[4-[[3-[(S)-phenyl-[[(3R)-quinuclidin-3-yl]oxycarbonylamino]methyl]phenoxy]methyl]phenyl]sulfonylazetidine-3-carboxylate;

[(1S)-2-(3,5-dichloro-1-oxido-pyridin-1-ium-4-yl)-1-(3,4-dimethoxyphenyl)ethyl]1-[3-[[3-[(S)-phenyl-[[(3R)-quinuclidin-3-yl]oxycarbonylamino]methyl]phenoxy]methyl]phenyl]sulfonylazetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[3-[[3-[(S)-phenyl-[[(3R)-quinuclidin-3-yl]oxycarbonylamino]methyl]phenoxy]methyl]phenyl]sulfonylazetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]phenyl]sulfonylazetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]phenyl]sulfonylpiperidine-4-carboxylate;

[(1S)-2-(3,5-dichloro-1-oxido-pyridin-1-ium-4-yl)-1-(3,4-dimethoxyphenyl)ethyl]1-[4-[[3-[(S)-phenyl-[[(3R)-quinuclidin-3-yl]oxycarbonylamino]methyl]phenoxy]methyl]phenyl]sulfonylpiperidine-4-carboxylate;

[(1S)-1-[3-(cyclopropylmethoxy)-4-(difluoromethoxy)phenyl]-2-(3,5-dichloro-1-oxido-pyridin-1-ium-4-yl)ethyl]2-[4-[4-[[3-[(S)-phenyl-[[(3R)-quinuclidin-3-yl]oxycarbonylamino]methyl]phenoxy]methyl]phenyl]sulfonylpiperazin-1-yl]acetate;

[(1S)-1-[3-(cyclopropylmethoxy)-4-(difluoromethoxy)phenyl]-2-(3,5-dichloro-1-oxido-pyridin-1-ium-4-yl)ethyl]2-[1-[4-[[3-[(S)-phenyl-[[(3R)-quinuclidin-3-yl]oxycarbonylamino]methyl]phenoxy]methyl]phenyl]sulfonylazetidin-3-yl]acetate;

[(1S)-1-[3-(cyclopropylmethoxy)-4-(difluoromethoxy)phenyl]-2-(3,5-dichloro-1-oxido-pyridin-1-ium-4-yl)ethyl]

(2S)-1-[4-[[3-[(S)-phenyl-[[(3R)-quinuclidin-3-yl]oxy-carbonylamino]methyl]benzoyl]amino]phenyl]sulfonylpyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-1-[2-[4-[3-[(S)-phenyl-[[(3R)-quinuclidin-3-yl]oxy-carbonylamino]methyl]phenyl]carbamoyl]phenyl]sulfonylpiperidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl] (2S)-1-[2-[4-[3-[(S)-phenyl-[[(3R)-quinuclidin-3-yl]oxy-carbonylamino]methyl]benzoyl]oxyphenyl]ethyl]pyrrolidine-2-carboxylate;

[4-[(1S)-2-(3,5-dichloro-1-oxido-pyridin-1-ium-4-yl)-1-(3,4-dimethoxyphenyl)ethoxy]carbonylphenyl]methyl 3-[(S)-phenyl-[[(3R)-quinuclidin-3-yl]oxycarbonylamino]methyl]benzoate;

[(1S)-2-(3,5-dichloro-1-oxido-pyridin-1-ium-4-yl)-1-(3,4-dimethoxyphenyl)ethyl]5-[[4-[phenyl-[[(3R)-quinuclidin-3-yl]oxycarbonylamino]methyl]phenoxy]methyl]furan-2-carboxylate;

[(1S)-2-(3,5-dichloro-1-oxido-pyridin-1-ium-4-yl)-1-(3,4-dimethoxyphenyl)ethyl]5-[[4-[(R)-phenyl-[[(3R)-quinuclidin-3-yl]oxycarbonylamino]methyl]phenoxy]methyl]furan-2-carboxylate;

[(1S)-2-(3,5-dichloro-1-oxido-pyridin-1-ium-4-yl)-1-(3,4-dimethoxyphenyl)ethyl]2-[[3-[(S)-phenyl-[[(3R)-quinuclidin-3-yl]oxycarbonylamino]methyl]phenoxy]methyl]oxazole-4-carboxylate and pharmaceutically acceptable salts and solvates thereof Compounds of the present invention may be prepared according to appropriate adaptation of synthetic approaches herebelow described in the Experimental Section, Examples 1, 5, 6, 7, 19, 21, 23, 29, 32, 45, 46, 47, 48, 50.

The processes which can be used for the preparation of the compounds of the present invention and which are below described should not be viewed as limiting the scope of the synthetic methods available for the preparation of the compounds of the invention.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form. In particular, functional groups present in the compounds of the invention or intermediates thereof which could generate unwanted side reaction and by-products, need to be properly protected before the alkylation, acylation, coupling, oxidation or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art [see, for a general reference, T. W. Green; Protective Groups in Organic Synthesis (Wiley, N.Y. 1999) which is incorporated herein by reference in its entirety].

Likewise, selective protection and deprotection of any of the said groups, for instance including carbonyl, hydroxyl or amino groups, may be accomplished according to very well-known methods commonly employed in organic synthetic chemistry.

In one embodiment, the process for preparation of compounds of formula (I), or embodiments thereof, is performed starting from N-oxide on the pyridine ring of intermediate compounds, thus allowing the preparation of compound of formula (I), or embodiments thereof, in the form of N-oxides on the pyridine ring.

Optional salification of the compounds of formula (I), or N-oxides on the pyridine ring thereof, may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the present invention, may be conveniently modified so that to adapt the reaction conditions to the specific needs, for instance by choosing appropriate condensing agents, solvents and protective groups, as the case may be.

The present invention also provides pharmaceutical compositions of compounds of the present invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention or may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the present invention including such solid forms as tablets, gelcaps, capsules, caplets, granules, lozenges and bulk powders. The compounds of the present invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous for administering the compounds of the present invention.

Various liquid oral dosage forms may also be used for administering compounds of the present invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the present invention are preferably administered by inhalation.

Inhalable preparations include inhalable powders, propellant-containing metered aerosols or propellant-free inhalable formulations and may be administered through a suitable inhalation device which may be respectively selected from dry powder inhaler, pressurized metered dosed inhaler, or a nebulizer.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the present invention either in solution or in dispersed form. The propellant-driven formulations may also contain other ingredients such as co-solvents, stabilizers and optionally other excipients.

The propellant-free inhalable formulations comprising the compounds of the present invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the present invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

The present invention also provides combinations of a compound of the present invention, with a β2-agonist selected from the group consisting of carmoterol, vilanterol (GSK-642444), indacaterol, milveterol, arformoterol, formoterol, salbutamol, levalbuterol, terbutaline, AZD-3199, olodaterol (BI-1744-CL), abediterol (LAS-100977), bambuterol, isoproterenol, procaterol, clenbuterol, reproterol, fenoterol and ASF-1020 and salts thereof.

The present invention also provides combinations of a compound of the present invention, with a corticosteroid selected from the group consisting of fluticasone propionate, fluticasone furoate, mometasone furoate, beclometasone dipropionate, ciclesonide, budesonide, GSK 685698, and GSK 870086.

The present invention also provides combinations of a compound of the present invention, with an antimuscarinic agent selected from the group consisting of aclidinium, tiotropium, ipratropium, trospium, glycopyrronium, and oxitropium salts.

The present invention also provides combinations of a compound of the present invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the present invention, with a P38 MAP kinase inhibitor selected from the group consisting of semapimod, talmapimod, pirfenidone, PH-797804, GSK-725, minokine and losmapimod and salts thereof.

In a preferred embodiment, the present invention provides combinations of a compound of the present invention with an IKK2 inhibitor.

The invention also provides combinations of a compound of the present invention with a HNE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C, and prolastin inhaled.

The invention also provides combinations of a compound of the present invention with a leukotriene modulator selected from the group consisting of montelukast, zafirlukast, and pranlukast.

The invention also provides combinations of a compound of the present invention with a NSAID selected from the group consisting of ibuprofen and ketoprofen.

The invention also provides combinations of a compound of the present invention with a mucus regulator selected from the group consisting of INS-37217, diquafosol, sibenadet, CS-003, talnetant, DNK-333, MSI-1956, and gefitinib.

The dosages of the compounds of the present invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of the present invention may be administered for example, at a dosage of 0.001 to 1000 mg/day, preferably 0.1 to 500 mg/day.

When they are administered by inhalation route, the dosage of the compounds of the present invention is advantageously 0.01 to 20 mg/day, preferably 0.1 to 10 mg/day.

Preferably, the compounds of the present invention alone or combined with other active ingredients may be administered for the prevention and/or treatment of any obstructive respiratory disease such as asthma, chronic bronchitis and chronic obstructive pulmonary disease (COPD).

However the compounds of the present invention may be administered for the prevention and/or treatment of any disease wherein PDE4 inhibition or M3 antagonism is required. Said diseases include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia areata, hypertrophic scars, discoid lupus erythematosus, systemic lupus erythematosus, follicular and wide-area pyodermias, endogenous and exogenous acne, acne rosacea, Behçet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolaterosclerosis (ALS), multiple systems atrophy (MSA), schizophrenia, Parkinson's disease, Huntington's disease, Pick's disease, depression, stroke, and spinal cord injury.

Other features of the invention will become apparent in the course of the following descriptions of exemplary embodiments which are given for illustration of the invention and are not intended to be limiting thereof.

EXAMPLES

Abbreviations
DCC=N,N'-dicyclohexylcarbodiimide;
HOBt=hydroxybenzotriazole;
HATU=(dimethylamino)-N,N-dimethyl(3H-[1,2,3]triazolo [4,5-b]pyridin-3-yloxy) methaniminium hexafluorophosphate;
EDC=1-ethyl-3-(3-dimethylaminopropyl) carbodiimide hydrochloride;
DMAP=4-dimethylaminopyridine;
DMF=dimethylformamide;
DMSO=dimethyl sulfoxide;
EtOAc=ethyl acetate;
RT=room temperature;
THF=tetrahydrofuran;
DCM=dichloromethane;
MeOH=methyl alcohol;
EtOH=ethyl alcohol;
LHMDS=lithium bis(trimethylsilyl)amide;
m-CPBA=meta-chloroperoxybenzoic acid;
TFA=trifluoroacetic acid;
LC-MS=liquid chromatography/mass spectrometry;
HPLC=high pressure liquid chromatography;
MPLC=medium pressure liquid chromatography;
SFC=supercritical fluid chromatography;
NMR=nuclear magnetic resonance

GENERAL EXPERIMENTAL DETAILS

Analytical Methods
Liquid Chromatography-Mass Spectrometry
Method 1

LC-MS was performed on a Waters 2795 Alliance HT HPLC with Waters 2996 Diode Array Detector coupled to a Micromass ZQ, single quadrupole mass spectrometer using a Phenomenex Luna C18 (2) column (5 µm, 100×4.6 mm plus guard cartridge) with a linear gradient of 5-95% acetonitrile/water (with 0.1% formic acid in each mobile phase) within 3.5 minutes and held at 95% for 2.0 minutes.
Method 2

LC-MS was performed on a Waters 2795 Alliance HT HPLC with Waters 2996 Diode Array Detector coupled to a Micromass ZQ, single quadrupole mass spectrometer using a Waters Xterra MS C18 column (5 µm, 100×4.6 mm plus guard cartridge) being initially held at 5% acetonitrile/water (with 10 mM ammonium bicarbonate in the aqueous mobile phase) for 0.5 minutes, followed by a linear gradient of 5-95% within 3.5 minutes and then held at 95% for 1.5 minutes.

NMR

[1]H Nuclear magnetic resonance (NMR) spectroscopy was carried out using a Bruker instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; m, multiplet; br, broad.

Preparative Reverse-Phase HPLC Conditions

Preparative HPLC purification was performed by reverse phase HPLC using a Waters Fractionlynx preparative HPLC system (2525 pump, 2996/2998 UV/VIS detector, 2767 liquid handler) or an equivalent HPLC system such as a Gilson Trilution UV directed system. The Waters 2767 liquid handler acted as both auto-sampler and fraction collector.

The columns used for the preparative purification of the compounds were a Waters Sunfire OBD Phenomenex Luna Phenyl Hexyl or Waters Xbridge Phenyl at 10 µm 19×150 mm or Waters CSH Phenyl Hexyl, 19×150, 5 µm column.

Appropriate focused gradients were selected based on acetonitrile and methanol solvent systems under either acidic or basic conditions.

The modifiers used under acidic/basic conditions were formic acid or trifluoroacetic acid (0.1% V/V) and ammonium bicarbonate (10 mM) respectively.

The purification was controlled by Waters Fractionlynx software through monitoring at 210-400 nm, and triggered a threshold collection value at 260 nm and, when using the Fractionlynx, the presence of target molecular ion as observed under APi conditions. Collected fractions were analyzed by LCMS (Waters Acquity systems with Waters SQD).

Compound Preparation

Where the preparation of starting materials is not described, these are commercially available, known in the literature, or readily obtainable by those skilled in the art using standard procedures. Where it is stated that compounds were prepared "analogously" or "similarly" to earlier examples or intermediates, it will be appreciated by the skilled person that the reaction time, number of equivalents of reagents and temperature can be modified for each specific reaction and that it may be necessary or desirable to employ different work-up or purification techniques.

Flash chromatography refers to silica gel chromatography and is carried out using an Isolera MPLC system (manufactured by Biotage); pre-packed silica gel cartridges (supplied by Biotage); or using conventional glass column chromatography.

In the procedures that follow, after each starting material, reference to a compound number may be provided. This is provided merely for assistance to the skilled chemist. The starting material may not necessarily have been prepared from the batch referred to.

Many of the compounds described in the following Examples have been prepared from stereochemically pure starting materials, for example 95% enantiomeric excess (ee).

The stereochemistry of the compounds in the Examples, where indicated, has been assigned on the assumption that absolute configuration at resolved stereogenic centers of staring materials is maintained throughout any subsequent reaction conditions.

Intermediate 1/A (I-1/A). (S)-3,5-Dichloro-4-(2-(3,4-dimethoxyphenyl)-2-hydroxyethyl)pyridine 1-oxide
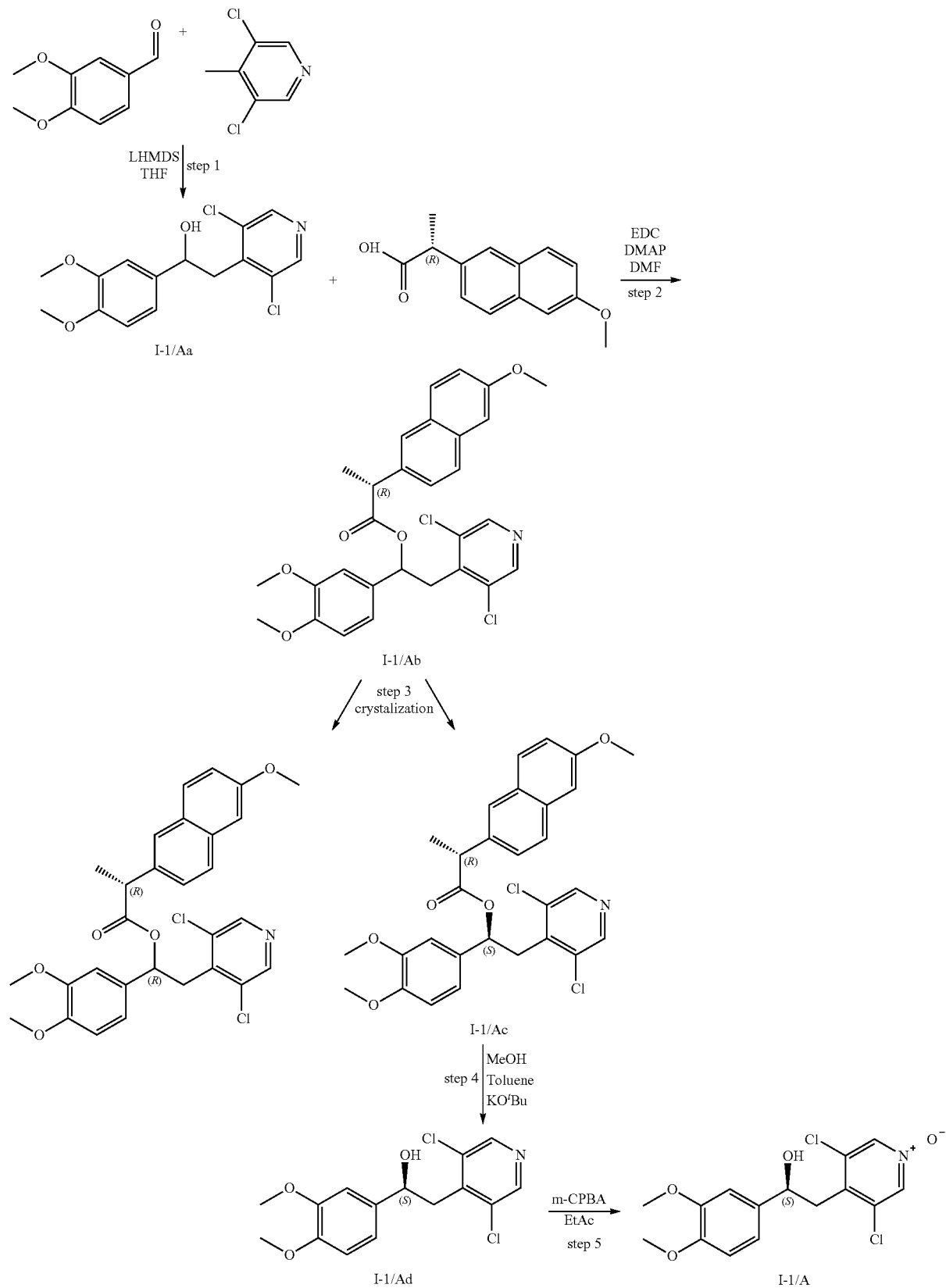

Step 1: Preparation of (R,S)-2-(3,5-dichloropyridin-4-yl)-1-(3,4-dimethoxyphenyl)ethanol (I-1/Aa)

3,5-dichloro-4-methylpyridine (54 g, 331 mmol) was dissolved in dry THF (480 mL) under argon atmosphere and cooled at −78° C. in dry-ice/acetone bath. LHMDS 1N THF solution (331 mL, 331 mmol) was added drop-wise keeping the temperature at −78°. The mixture was stirred at −78° for 1 h. Thereafter, a solution of 3,4-dimethoxybenzaldehyde (50 g, 301 mmol) in dry THF (120 mL) was added drop-wise keeping the temperature at −78° C. When the addition was completed, the mixture was allowed to warm at RT.

The reaction was poured into ice and water (1 L) and the mixture was stirred until a copious precipitate formed. The solid was filtered, and dissolved in ethyl acetate (500 mL), dried over $Na_2SO_4$ and the solvent evaporated under vacuum. The crude was crystallized in $CHCl_3$/hexane. The precipitate was filtered, washed with hexane and dried under vacuum at 40° C. for 8 h to give 55 g of the title compound (45% yield). The mother liquor solution was evaporated under vacuum at 40° C., dissolved in ethyl acetate (200 mL) and extracted with 200 mL of water. The organic solution was dried over $Na_2SO_4$ and the solvent evaporated under vacuum at 40° C. The crude was crystallized in $CHCl_3$/hexane, and additional 15 g of the title product were obtained (70% overall yield).

Step 2: Preparation of (R,S)-2-(3,5-dichloropyridin-4-yl)-1-(3,4-dimethoxyphenyl)ethyl)(R)-2-(6-methoxynaphthalen-2-yl)propanoate (I-1/Ab)

(R,S)-2-(3,5-dichloropyridin-4-yl)-1-(3,4-dimethoxyphenyl)ethanol (50 g, 152 mmol), (R)-2-(6-methoxynaphthalen-2-yl)propanoic acid (38.6 g, 168 mmol), DMAP (20.5 g, 168 mmol) and EDC (43.8 g, 229 mmol) were dissolved in DMF (300 mL) and the reaction mixture was stirred at RT for 2 h. Thereafter, water (500 mL) was added, and the solution stirred till complete precipitation occurs. The solid was filtered and dissolved in DCM (500 mL). The organic solution was washed with aqueous HCl 1N (2×500 mL), saturated aqueous $NaHCO_3$ solution (500 mL) and dried over $Na_2SO_4$. The solvent was evaporated under vacuum and the solid residue sonicated in EtOH (300 mL) and triturated for 1 h. The resulting precipitate was collected by filtration and dried under vacuum at 40° C. for 4 h to give 79 g (99% yield) of the title compound, as diastereoisomeric mixture.

Step 3: Preparation of (S)-2-(3,5-dichloropyridin-4-yl)-1-(3,4-dimethoxyphenyl)ethyl)(R)-(2-(6-methoxynaphthalen-2-yl)propanoate (I-1/Ac)

(R,S)-2-(3,5-dichloropyridin-4-yl)-1-(3,4-dimethoxyphenyl)ethyl) (R)-(6-methoxynaphthalen-2-yl)propanoate (diastereoisomeric mixture, 79 g, 146 mmol) was dissolved in $CHCl_3$ (100 mL) and MeOH (30 mL) was slowly added up to persistent opalescence and the mixture left at RT for 2 h. The solid formed was collected by filtration and re-crystallized by $CHCl_3$/MeOH (70 mL/20 mL) solvent system to obtain 35 g of the desired compound (yield 88%, ee 98%). Chiral HPLC analysis:Chiralcel OD column, 10 μm, 250×4.6 mm; Flow=0.8 ml/min; eluent=hexane:isopropanol 97/3; $R_t$=42.33 min;

$^1$H NMR (600 MHz, CHLOROFORM-d) δ ppm 8.04 (s, 2 H), 7.67 (d, J=8.79 Hz, 1 H), 7.58 (d, J=8.52 Hz, 1 H), 7.53 (m, 1 H), 7.12-7.20 (m, 3 H), 6.95 (dd, J=8.24, 1.92 Hz, 1 H), 6.78-6.88 (m, 2 H), 6.14 (dd, J=10.44, 4.12 Hz, 1 H), 3.95 (s, 3 H), 3.88 (s, 3 H), 3.78-3.81 (m, 4 H), 3.55 (dd, J=13.73, 10.44 Hz, 1 H), 3.14 (dd, J=13.60, 4.26 Hz, 1 H), 1.44 (d, J=7.14 Hz, 3 H).

Step 4: Preparation of (S)-2-(3,5-dichloropyridin-4-yl)-1-(3,4-dimethoxyphenyl)ethanol, (I-1/Ad)

(S)-2-(3,5-dichloropyridin-4-yl)-1-(3,4-dimethoxyphenyl)ethyl) (R)-2-(6-methoxynaphthalen-2-yl)propanoate (30 g, 56 mmol) was dissolved in MeOH, and toluene was slowly added. Potassium tert-butoxide was slowly added to the suspension. The mixture was stirred for 24 h at RT. The reaction was diluted with water (500 mL) and the aqueous mixture was extracted with $CHCl_3$ (500 mL). The organic layer was dried over $Na_2SO_4$ and the solvent was evaporated under vacuum. The residue was crystallized from $CHCl_3$ (100 mL) and hexane (20 mL). The mother liquor was concentrated and recrystallized with an analogous procedure giving a second crop of desired compound. In total, 16 g of the title compound (87% yield) were obtained. Chiral HPLC analysis: Chiralcel OD column, 10 250×4.6 mm; flow=0.8 ml/min; eluent=hexane:isopropanol 95/5; $R_t$=58.03 min; $[\alpha]_D$=+10.21 (c=0.506, Methanol); $^1$H NMR (400 MHz, acetone) δ ppm 8.47 (s, 2 H), 6.96-7.15 (m, 1 H), 6.87 (m, 2 H), 4.93-5.21 (m, 1 H), 4.50 (d, J=3.97 Hz, 1 H), 3.78 (s, 6 H), 3.44 (dd, J=12.79, 8.38 Hz, 1 H), 3.22 (dd, J=13.01, 5.51 Hz, 1 H). MS/ESI$^+$ [MH]$^+$: 328.19.

Step 5: Preparation of (S)-3,5-dichloro-4-(2-(3,4-dimethoxyphenyl)-2-hydroxyethyl)pyridine 1-oxide (I-1/A)

(S)-2-(3,5-dichloropyridin-4-yl)-1-(3,4-dimethoxyphenyl)ethanol (4 g, 12 mmol) was dissolved in ethyl acetate, and m-CPBA was added to the solution. The mixture was stirred at RT for 5 h. The formed solid was collected by filtration, washed with ethyl acetate and dried under vacuum to give 1.72 g of (S)-2-(3,5-dichloropyridin-4-yl)-1-(3,4-dimethoxyphenyl)ethanol (41% yield). Chiral HPLC analysis: Chiralcel OD column, 10 μm, 250×4.6 mm; Flow=0.8 ml/min; eluent=hexane:isopropanol 60/40; $R_t$=22.16 min; $[\alpha]_D$=+ 68.91 (c=0.253, Methanol/$CHCl_3$ 1:1); $^1$H NMR (400 MHz, CHLOROFORM-d) δ ppm 8.15 (s, 2 H), 6.99 (m, 1 H), 6.79-6.88 (m, 2 H), 5.03 (dd, J=8.50, 5.32 Hz, 1 H), 3.75-3.98 (m, 6 H), 3.42 (dd, J=13.57, 8.56 Hz, 1 H), 3.19 (dd, J=13.51, 5.32 Hz, 1 H), 2.06-2.15 (m, 1 H); MS/ESI$^+$ [MH]$^+$: 344

Intermediates I-1/B, I-1/C, I-1/D, I-1/E, I-1/F

The racemic alcohol intermediates reported in table below are described in patent application WO2009/018909, which is incorporated herein by reference in its entirety, or may be obtained following the above procedure (only step 1 followed by step 5) substituting 3,4-dimethoxybenzaldehyde with the suitable 3,4-dialkoxybenzaldehyde.

Table of racemic alcohol intermediates

| Structure | Name | Intermediate | Analytical data |
|---|---|---|---|
| 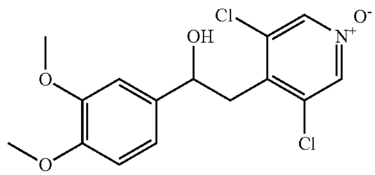 | (R,S)-3,5-dichloro-4-(2-(3,4-dimethoxyphenyl)-2-hydroxyethyl)pyridine 1-oxide | I-1/B | $^1$H NMR (400 MHz, (CDCl3) δ ppm 8.15 (s, 2 H), 6.99 (m, 1 H), 6.79-6.88 (m, 2 H), 5.03 (dd, J = 8.50, 5.32 Hz, 1 H), 3.75-3.98 (m, 6 H), 3.42 (dd, J = 13.57, 8.56 Hz, 1 H), 3.19 (dd, J = 13.51, 5.32 Hz, 1 H), 2.06-2.15 (m, 1 H); MS/ESI$^+$ [MH]$^+$: 344 |
| 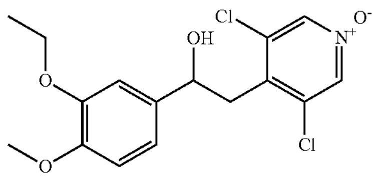 | (R,S)-3,5-dichloro-4-(2-(3-ethoxy-4-methoxyphenyl)-2-hydroxyethyl)pyridine 1-oxide | I-1/C | MS/ESI$^+$ [MH]$^+$: 358 |
| 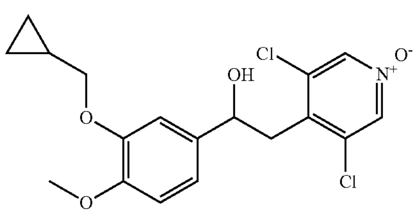 | (R,S)-3,5-dichloro-4-(2-(3-cyclopropylmethoxy-4-methoxyphenyl)-2-hydroxyethyl)pyridine 1-oxide | I-1/D | $^1$H NMR (400 MHz, CDCl3): δ 8.13 (s, 2 H), 6.97 (s, 1 H), 6.83-6.81 (m, 2 H), 5.00-4.97 (m, 1 H), 3.87-3.84 (m, 5 H), 3.41-3.13 (m, 1 H), 3.18-3.13 (m, 1 H), 2.13-2.11 (br s, 1 H), 1.35-1.31 (m, 1 H), 0.68-0.63 (m, 2 H), 0.37-0.35 (m, 2 H).<br>LCMS (Method 1): [MH+] = 384 at 3.21 min. |
| 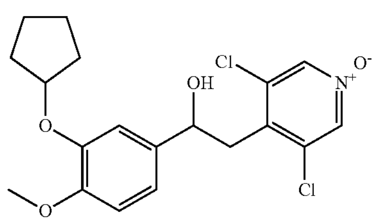 | (R,S)-3,5-dichloro-4-(2-(3-(cyclopentyloxy)-4-methoxyphenyl)-2-hydroxyethyl)pyridine 1-oxide | I-1/E | $^1$H NMR (400 MHz, CDCl$_3$): δ 8.13 (s, 2 H), 6.94 (s, 1 H), 6.82-6.81 (m, 2 H), 5.01-4.80 (m, 1 H), 4.79-4.76 (m, 1 H), 3.42 (s, 3 H), 3.41-3.36 (m, 1 H), 3.19-3.14 (m, 1 H), 1.95-1.79 (m, 6 H), 1.65-1.57 (m, 3 H).<br>LCMS (Method 2): [MH+] = 398 at 3.13 min. |
| 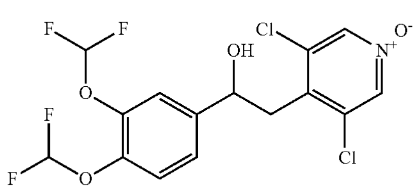 | (R,S)-4-(2-(3,4-bis(difluoromethoxy)phenyl)-2-hydroxyethyl)-3,5-dichloropyridine 1-oxide | I-1/F | $^1$H NMR (400 MHz, CDCl3): δ 8.15 (s, 2 H), 7.33 (s, 1 H), 7.28-7.19 (m, 2 H), 6.55 (t, J = 73.4 Hz, 1 H), 6.53 (t, J = 73.4 Hz, 1 H), 5.08 (app t, J = 6.4 Hz, 1 H), 3.38 (dd, J = 13.6, 8.7 Hz, 1 H), 3.17 (dd, J = 13.6, 5.2 Hz, 1 H), 2.29 (s, 1 H).<br>LCMS (Method 1): [MH+] = 416 at 3.54 min. |

Intermediate 1/G (I-1/G). (S)-3,5-dichloro-4-(2-(3-(cyclopropylmethoxy)-4-(difluoromethoxy)phenyl)-2-hydroxyethyl)pyridine 1-oxide

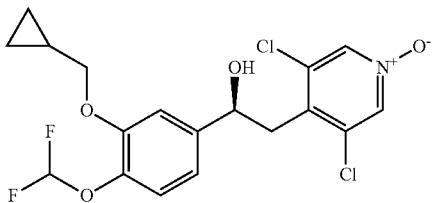 [SMILES: [O-][n+]1cc(Cl)c(C[C@H](O)c2ccc(OC(F)F)c(OCC3CC3)c2)c(Cl)c1]

The intermediate I-1/G may be obtained following the procedure described in patent application WO2010/089107, which is incorporated herein by reference in its entirety.

Intermediate 1/H (I-1/H). (S)-3,5-dichloro-4-(2-(4-(difluoromethoxy)-3-methoxyphenyl)-2-hydroxyethyl)pyridine 1-oxide

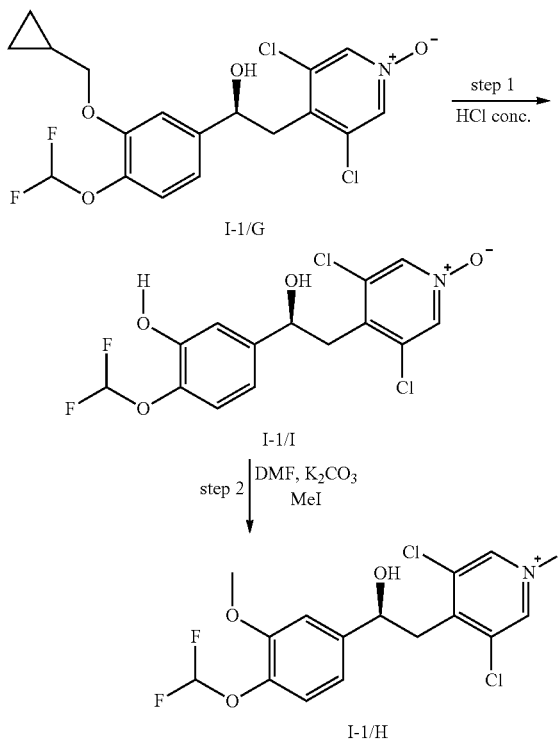

Step 1: (S)-3,5-dichloro-4-(2-(4-(difluoromethoxy)-3-hydroxyphenyl)-2-hydroxyethyl)pyridine 1-oxide (I-1/I)

(S)-3,5-dichloro-4-(2-(3-(cyclopropylmethoxy)-4-(difluoromethoxy)phenyl)-2-hydroxyethyl)pyridine 1-oxide (5 g, 11.90 mmol) was added to 100 mL of 37% HCl and stirred at room temperature for about 3 min., to obtain a yellow solution. After stirring for further 3 min. the solution was poured into a solution of NaOH (48 g) in water (500 mL). The red solution was added with 1 M HCl to pH 1. The brown solid was filtered, washed with water and triturated with hot EtOH (50 mL). After stirring at r.t. for 1 h the solid was filtered, washed with EtOH and dried under vacuum at 40 C yielding 2.4 of the title compound.

$^1$H NMR (400 MHz, DMSO-$d_6$) δ ppm 9.84 (br. s., 1 H), 8.54 (s, 2 H), 7.03 (d, J=8.38 Hz, 1 H), 6.98 (t, J=75.00 Hz, 1 H), 6.95 (d, J=1.76 Hz, 1 H), 6.74 (dd, J=8.16, 1.54 Hz, 1 H), 5.54 (br. s., 1 H), 4.78 (t, J=6.39 Hz, 1 H), 3.14 (dd, J=13.23, 8.38 Hz, 1 H), 2.97 (dd, J=13.23, 5.29 Hz, 1 H)

MS/ESI$^+$ [MH]$^+$: 366

Step 2: S)-3,5-dichloro-4-(2-(4-(difluoromethoxy)-3-methoxyphenyl)-2-hydroxyethyl)pyridine 1-oxide (I-1/H)

(S)-3,5-dichloro-4-(2-(4-(difluoromethoxy)-3-hydroxyphenyl)-2-hydroxyethyl)pyridine 1-oxide (2 g, 5.46 mmol) was dissolved in DMF (16 mL) then $K_2CO_3$ (2 g, 14.47 mmol) and iodomethane (1.72 g, 12.12 mmol) were added and the mixture was stirred at r.t, for 4 h. The mixture was poured into 200 mL of water, filtered, washed with water and dried under vacuum at 40° C. 1.98 g of whitish solid was obtained.

$^1$H NMR (400 MHz, DMSO-d6): δ ppm 8.53 (s, 2 H), 7.08-7.13 (m, 2 H), 7.01 (t, J=75.00 Hz, 1 H), 6.88 (dd, J=7.94, 1.76 Hz, 1 H), 5.64 (d, J=4.41 Hz, 1 H), 4.77-4.94 (m, 1 H), 3.81 (s, 3 H), 3.17 (d, J=8.38 Hz, 1 H), 3.05 (d, J=5.73 Hz, 1 H) MS/ESI$^+$ [MH]$^+$: 380

Intermediates I-1/J, I-1/K, I-1/L, I-1/M, I-1/N

The intermediates reported in table below, I-1/J, I-1/K, I-1/L, I-1/M, I-1/N, may be obtained following the procedure described above for intermediate 1/H, by reacting intermediate 1/I with a suitable alkylating agent.

| Structure | Name | Intermediate | Analytical data |
|---|---|---|---|
| 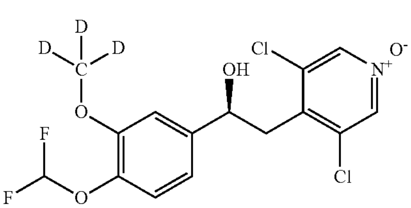 | (S)-3,5-dichloro-4-(2-(4-(difluoromethoxy)-3-trideuteromethoxyphenyl)-2-hydroxyethyl)pyridine 1-oxide | I-1/J | $^1$H NMR (400 MHz, DMSO-$d_6$): δ ppm 8.53 (s, 2 H), 7.06-7.13 (m, 2 H), 7.01 (t, J = 75.00 Hz, 1 H), 6.88 (dd, J = 8.38, 1.76 Hz, 1 H), 5.63 (d, J = 4.41 Hz, 1 H), 4.64-4.91 (m, 1 H), 3.19 (dd, J = 13.23, 8.38 Hz, 1 H), 3.05 (d, J = 5.73 Hz, 1 H) MS/ESI+ [MH]$^+$: 383 |

| Structure | Name | Intermediate | Analytical data |
|---|---|---|---|
| 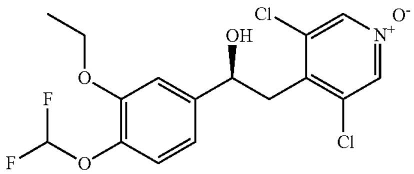 | (S)-3,5-dichloro-4-(2-(4-(difluoromethoxy)-3-ethoxyphenyl)-2-hydroxyethyl)pyridine 1-oxide | I-1/K | $^1$H NMR (400 MHz, DMSO-$d_6$): δ ppm 8.53 (s, 2 H), 7.06-7.13 (m, 2 H), 7.01 (t, J = 75.00 Hz, 1 H), 6.86 (dd, J = 8.16, 1.54 Hz, 1 H), 5.62 (d, J = 3.97 Hz, 1 H), 4.72-4.97 (m, 1 H), 3.91-4.19 (m, 2 H), 3.18 (dd, J = 13.23, 8.38 Hz, 1 H), 3.02 (dd, J = 13.23, 5.29 Hz, 1 H), 1.33 (t, J = 7.06 Hz, 3 H) MS/ESI+ [MH]$^+$: 394 |
| 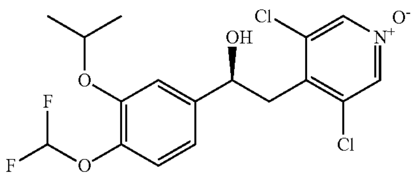 | (S)-3,5-dichloro-4-(2-(4-(difluoromethoxy)-3-isopropoxyphenyl)-2-hydroxyethyl)pyridine 1-oxide | I-1/L | $^1$H NMR (400 MHz, DMSO-$d_6$): δ ppm 8.52 (s, 2 H), 7.04-7.13 (m, 2 H), 6.97 (t, J = 75.00 Hz, 1 H), 6.86 (dd, J = 7.94, 1.76 Hz, 1 H), 5.63 (d, J = 3.53 Hz, 1 H), 4.81-4.90 (m, 1 H), 4.46-4.65 (m, 1 H), 3.16 (d, J = 7.94 Hz, 1 H), 3.04 (d, J = 6.17 Hz, 1 H), 1.26 (dd, J = 13.67, 6.17 Hz, 6 H) MS/ESI+ [MH]$^+$: 408 |
| 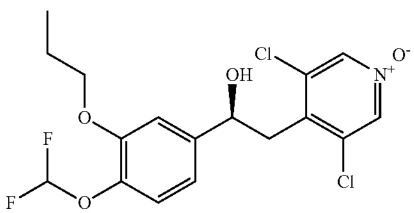 | (S)-3,5-dichloro-4-(2-(4-(difluoromethoxy)-3-propoxyphenyl)-2-hydroxyethyl)pyridine 1-oxide | I-1/M | $^1$H NMR (400 MHz, DMSO-$d_6$) δ ppm 8.53 (s, 2 H), 7.09-7.14 (m, 1 H), 7.04-7.08 (m, 1 H), 6.99 (t, J = 75.00 Hz, 1 H), 6.84-6.91 (m, 1 H), 5.55-5.70 (m, 1 H), 4.79-4.99 (m, 1 H), 3.88-4.06 (m, 2 H), 3.12-3.22 (m, 1 H), 2.91-3.10 (m, 1 H), 1.60-1.86 (m, 2 H), 0.98 (m, 3 H) MS/ESI+ [MH]$^+$: 408 |
| 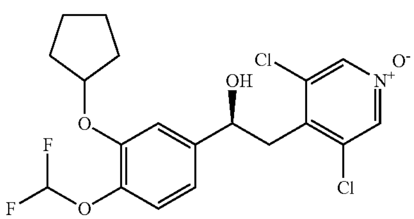 | (S)-3,5-dichloro-4-(2-(3-(cyclopentyloxy)-4-(difluoromethoxy)phenyl)-2-hydroxyethyl)pyridine 1-oxide | I-1/N | MS/ESI+ [MH]$^+$: 434 |

Intermediate 1. 4-((S)-2-(((S)-3-(tert-butoxycarbonyl)thiazolidine-2-carbonyl)oxy)-2-(3-(cyclopropylmethoxy)-4-(difluoromethoxy)phenyl)ethyl)-3,5-dichloropyridine 1-oxide

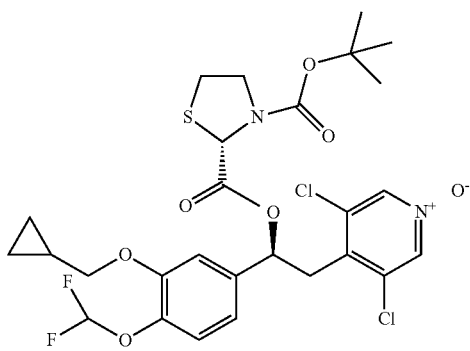

(S)-3,5-dichloro-4-(2-(3-(cyclopropylmethoxy)-4-(difluoromethoxy)phenyl)-2-hydroxyethyl)pyridine 1-oxide (obtained following the procedure described in patent application WO2010/089107, which is incorporated herein by reference in its entirety, 843 mg, 2.01 mmol), (S)-3-(tert-butoxycarbonyl)thiazolidine-2-carboxylic acid (749 mg, 3.21 mmol), DMAP (245 mg, 2.006 mmol) and EDC.HCl (1.154 g, 6.02 mmol) were dissolved in DMF (10 ml). The reaction was stirred at RT for 2 h and the reaction mixture was diluted with water. The precipitate was washed with water, dissolved in EtOAc and extracted with HCl 1N, saturated aqueous Na$_2$CO$_3$ and brine. The organic phase was dried over Na$_2$SO$_4$ and concentrated in vacuo to give 4-((S)-2-((S)-3-(tert-butoxycarbonyl)thiazolidine-2-carbonyloxy)-2-(3-(cyclopropylmethoxy)phenyl)ethyl)-3,5-dichloropyridine 1-oxide (1.2 g, 1.89 mmol, 94%) MS/ESI+ [MH+]=635.2.

The following intermediates were synthesised via a similar method as that of Intermediate 1.

| Structure | Example number | Analytical Data |
|---|---|---|
| 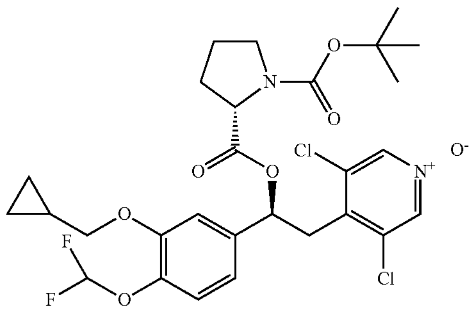 | Intermediate 2 | ¹H NMR (400 MHz, CDCl₃): δ 8.16* (s, 2 H), 8.15† (s, 2 H), 7.14 (dd, J = 8.2, 2.9 Hz, 1 H), 7.03* (d, J = 2.0 Hz, 1 H), 6.94-6.89 (m, 2 H), 6.62* (t, J = 75 Hz, 1 H), 6.61† (t, J = 75 Hz, 1 H), 6.03* (dd, J = 10.1, 4.6 Hz, 1 H), 6.00† (dd, J = 10.0, 5.3 Hz, 1 H), 4.29† (dd, J = 8.8, 3.5 Hz, 1 H), 4.23-4.17* (m, 1 H), 3.97-3.88* (m, 2 H), 3.88† (d, J = 6.9 Hz, 2 H), 3.53* (ddd, J = 13.5, 9.2, 3.2 Hz, 1 H), 3.47† (t, J = 6.6 Hz, 1 H), 3.46-3.39* (m, 1 H), 3.38-3.29† (m, 1 H), 3.26-3.17 (m, 1 H), 2.29-2.16* (m, 1 H), 2.18-2.08† (m, 1 H), 1.87-1.75 (m, 2 H), 1.75-1.63 (m, 1 H), 1.44* (s, 9 H), 1.32-1.24 (m, 1 H), 1.21† (s, 9 H), 0.68-0.63 (m, 2 H), 0.41-0.35 (m, 2 H) * and † refer to different rotamers. LCMS (Method 1): [MH+] = 617 at 4.38 min. |
| 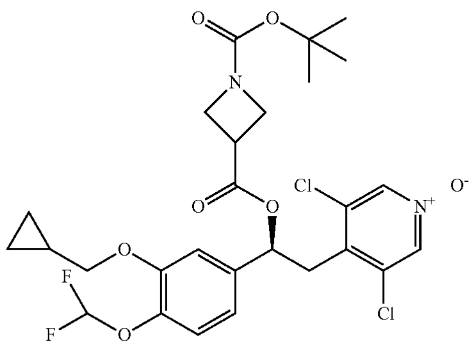 | Intermediate 3 | ¹H NMR (400 MHz, CDCl₃): δ 8.17 (s, 2 H), 7.17 (d, J = 8.1 Hz, 1 H), 6.97-6.91 (m, 2 H), 6.63 (t, J = 75.3 Hz, 1 H), 6.04 (dd, J = 9.6, 4.5 Hz, 1 H), 4.07 (td, J = 8.9, 2.0 Hz, 2 H), 3.96 (ddd, J = 18.1, 8.6, 6.0 Hz, 2 H), 3.88 (d, J = 6.9 Hz, 2 H), 3.54 (dd, J = 14.0, 9.6 Hz, 1 H), 3.34-3.25 (m, 1 H), 3.23 (dd, J = 14.0, 4.5 Hz, 1 H), 1.43 (s, 9 H), 1.32-1.23 (m, 1 H), 0.70-0.64 (m, 2 H), 0.41-0.34 (m, 2 H). LCMS (Method 1): [MH+] = 603 at 4.30 min. |
| 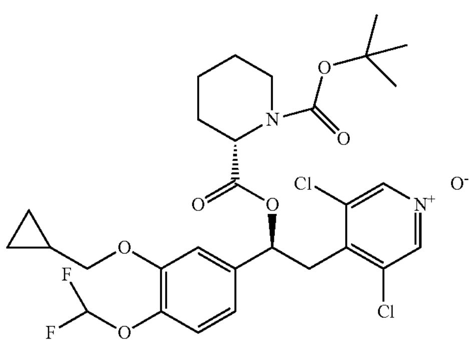 | Intermediate 4 | ¹H NMR (400 MHz, CDCl₃): δ 8.15 (s, 2 H), 7.14 (d, J = 8.2 Hz, 1 H), 6.98-6.90 (m, 1 H), 6.89 (dd, J = 8.0, 1.5 Hz, 1 H), 6.62 (t, J = 7.5.4 Hz, 1 H), 6.03 (dd, J = 9.3, 4.9 Hz, 1 H), 4.87* (d, J = 5.5 Hz, 1 H), 4.70-4.65† (m, 1 H), 4.06-3.98† (m, 1 H), 3.98-3.89 (m, 3 H), 3.57-3.46 (m, 1 H), 3.26-3.20† (m, 1 H), 3.21* (dd, J = 13.9, 5.1 Hz, 1 H), 2.83-2.63 (m, 1 H), 2.27-2.09 (m, 1 H), 1.75-1.49 (m, 3 H), 1.57† (s, 9 H), 1.46* (s, 9 H), 1.48-1.13 (m, 3 H), 1.10-1.94 (m, 1 H), 0.69-0.63 (m, 2 H), 0.39-0.34 (m, 2 H) * and † refer to different rotamers LCMS (Method 1): [MH+] = 631 at 4.47 min. |

Intermediate 5. 3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (I5)

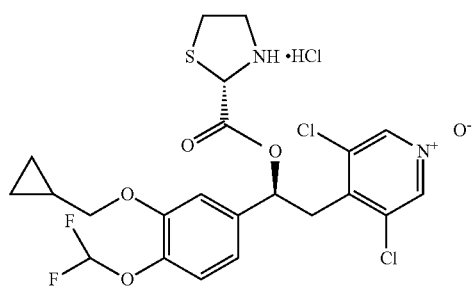

4-((S)-2-((S)-3-(tert-butoxycarbonyl)thiazolidine-2-carbonyloxy)-2-(3-(cyclopropylmethoxy)-4-(difluoromethoxy)phenyl)ethyl)-3,5-dichloropyridine 1-oxide (4.22 g, 6.64 mmol) was dissolved in ethyl acetate (10 mL). HCl in ethyl acetate (50 mL, 4.2 M, 210 mmol) was added, and the reaction was stirred at room temperature for 5 minutes. A white precipitate formed, and it was filtered, washed with Ethyl Acetate (2×) and hexane, and dried in a vacuum oven to yield 3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (3.19 g, 5.6 mmol, 84%)

¹H NMR (400 MHz, DMSO) δ 8.57 (s, 2 H), 7.19 (d, J=7.94 Hz, 1 H), 7.12 (d, J=1.76 Hz, 1 H), 7.08 (t, J=75.00 Hz, 1 H), 6.93-7.00 (m, 1 H), 5.89-5.98 (m, 1 H), 5.12 (s, 1 H), 3.91 (d, J=7.06 Hz, 2 H), 3.37-3.47 (m, 1 H), 3.10-3.31 (m, 3 H), 2.77-2.93 (m, 2 H), 1.05-1.36 (m, 1 H), 0.51-0.63 (m, 2 H), 0.34 (d, J=4.85 Hz, 2 H).

MS/ESI+ [MH+]=535.2

Intermediate 6

Step 1: Preparation of (3-Methoxyphenyl)(phenyl)methanone (I6a)

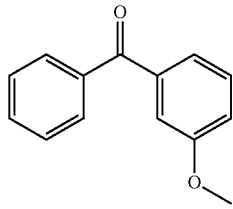 [SMILES: COc1cccc(C(=O)c2ccccc2)c1]

To the mixture of phosphorus pentachloride (3763 g, 18.1 mol) in 7.5 L of benzene, 3-methoxy benzoic acid (2500 g, 16.4 mol) was added in portions. The mixture was stirred for 50 minutes until it became homogenous. The formation of the acid chloride was controlled by TLC. After completion, the mixture was cooled down to 10° C., reactor was covered with aluminum foil and aluminium trichloride (4820 g, 36.1 mol) was added in portions (internal temperature was held up to 30° C. maximum). Stirring was continued for 18 hours at RT. The reaction was monitored by TLC (AcOEt:hex 1:9). After completion, the reaction mixture was poured into ice and was diluted with AcOEt (7 L). Then organic layer was separated and the aqueous layer was extracted with AcOEt (2×10 L, 1×6 L). The combined organic layers were washed with water (5×3 L) to pH-6-7, saturated aqueous sodium hydrogen carbonate solution (15 L), dried (sodium sulfate), filtered and the solvent evaporated at reduced pressure to give a crude oil. The product was purified by vacuum distillation (130-139° C., 2 mbar) to obtain title compound (2637 g, 76%) as a pale yellow oil.

$^1$H NMR (600 MHz, CDCl$_3$), δ 7.80 (m, 2 H), 7.57 (m, 1 H), 7.46 (m, 2 H), 7.32-7.37 (m, 3 H), 7.12 (m, 1 H), 3.83 (s, 3 H).

Step 2: Preparation of (3-Hydroxyphenyl)(phenyl)methanone (I6b)

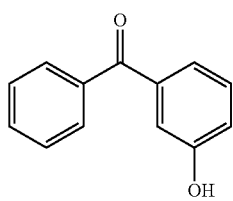 [SMILES: O=C(c1ccccc1)c1cccc(O)c1]

1458 g (6.9 mol) of (3-methoxyphenyl)(phenyl)methanone was dissolved in 2090 mL of AcOH. To the solution, 2320 mL (20.6 mol) of 48% HBr was added and the mixture was stirred at 90° C. for 18 hours. The reaction was monitored by TLC (AcOEt:hex 1:9). After reaction was completed the mixture was cooled down to RT and poured into ice with stirring. The precipitated solid was filtered, washed with water and dried yielding the title compound as a white solid (1234 g, 91%).

$^1$H NMR (600 MHz, CDCl$_3$), δ 7.80 (m, 2 H), 7.58 (m, 1 H), 7.47 (m, 2 H), 7.39 (m, 1 H), 7.28-7.34 (m, 2 H), 7.11 (m, 1 H), 5.59 (br s, 1 H).

Step 3: Preparation of 3-(Amino(phenyl)methyl)phenol (I6c)

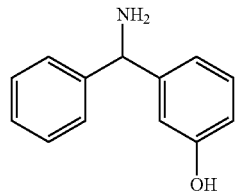 [SMILES: NC(c1ccccc1)c1cccc(O)c1]

3-Hydroxyphenyl)(phenyl)methanone (400 g, 2 mol) was dissolved in methanol (4 L). Hydroxylamine hydrochloride (168 g, 2.4 mol) and sodium acetate (331 g, 4 mol) were added to the resulting solution. The mixture was heated at reflux for 18 hours. After cooling to RT solvent was evaporated at reduced pressure, then water (3 L) was added to the residue. The product was extracted with ethyl acetate (3×3 L). The combined organic extracts were washed with saturated aqueous sodium hydrogen carbonate, brine, dried (sodium sulfate), filtered and the solvent evaporated at reduced pressure. The crude residue (1085 g) was used in the next step without purification. The crude oxime, 362 g, (287 g, 1.3 mol of pure oxime based on analysis) was dissolved in ethanol (860 mL) and 25% aqueous ammonia (3000 mL). To this mixture ammonium acetate (52 g, 0.7 mol) was added followed by portion wise addition of zinc powder (440 g, 6.7 mol) to maintain an internal not exceeding 40° C. The mixture was stirred without heating for 18 hours then filtered through a pad of celite. The filter cake was washed with ethyl acetate. The filtrate was collected and the formed layers were separated. The aqueous layer was extracted with ethyl acetate (5×5 L). The combined organic extracts layers were washed with brine (×2) and the solvent was removed in vacuo. The product was dried in vacuo (35° C., 18 hours) to yield the product.

$^1$H NMR (600 MHz, DMSO), δ 9.25 (brs, 1 H), 7.36 (m, 2 H), 7.25 (m, 2 H), 7.15 (m, 1 H), 7.03 (m, 1 H), 6.79 (m, 2 H), 6.54 (m, 1 H), 4.98 (s, 1 H), 2.17 (brs, 2 H).

Step 4: Crystallization of (S)-3-(amino(phenyl)methyl)phenol (S)-mandelate (I6d)

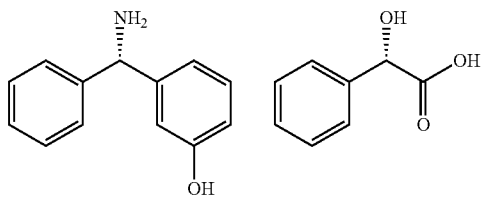

Salt formation: 3-(Amino(phenyl)methyl)phenol (1081 g, 5.4 mol) was dissolved in iso-propanol (21.62 L) and heated to reflux. To the mixture a solution of S-mandelic acid (908 g, 6 mol) in iso-propanol (2160 mL) was added dropwise. The mixture was heated at reflux for 1 hour and then allowed to cool to 10° C. (over 18 hours). The precipitate formed was filtered, washed with cold iso-propanol and dried in vacuo at 35° C. The obtained salt was refluxed in 95% iso-propanol for 1 hour. The mixture was allowed to cool down to 10° C. over 18 hours. The solid was filtered, washed with cold iso-propanol and dried in vacuum oven at 35° C. The crystallization process was repeated two or more times until the ee was >98% by chiral HPLC analysis.

Step 5: Preparation of (S)-3-(Amino(phenyl)methyl)phenol hydrochloride (I6e)

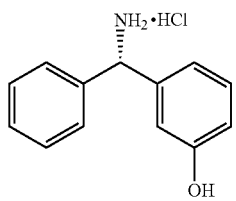 [SMILES: Cl ; N[C@@H](c1ccccc1)c1cccc(O)c1]

(S)-3-(Amino(phenyl)methyl)phenol (S)-mandelate (1027 g, 2.9 mol) of was suspended in ethyl acetate. A solution of sodium hydrogen carbonate (737 g, 8.8 mol) in water (11.05 L) was added drop wise and the mixture was stirred at RT for 18 hours. The mixture was separated and aqueous layer was extracted with ethyl acetate (5×10 L). The combined organic extracts were combined and the solvent evaporated at reduced pressure to give 464 g (85%) of amine as a pale yellow crystals. The amine (464 g, 2.3 mol) was suspended in methanol and 4M HCl in EtOAc (3500 mL, 14 mol) was added dropwise. The mixture was stirred for 18 hours and the solvent evaporated at reduced pressure. The residue was triturated with ether (2740 mL) for 18 hours. The suspension was filtered, the filter cake washed with ether and dried.

$^1$H NMR (600 MHz, DMSO), δ 9.74 (s, 1 H), 9.19 (s, 3 H), 7.54 (m, 2 H), 7.40 (m, 2 H), 7.33 (m, 1 H), 7.19 (m, 1 H), 7.00 (m, 1 H), 6.89 (m, 1 H), 6.78 (m, 1 H), 5.49 (s, 1 H, CH).

Step 6: Preparation of (R)-quinuclidin-3-yl ((S)-(3-hydroxyphenyl)(phenyl)methyl) carbamate (I6)

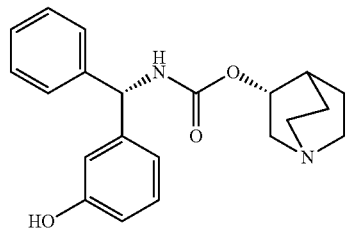 [SMILES: O=C(N[C@@H](c1ccccc1)c1cccc(O)c1)O[C@H]1CN2CCC1CC2]

To a stirred solution of (R)-3-quinuclidinol (2.5 g, 19.66 mmol) in acetonitrile (200 mL) was added trichloromethyl chloroformate (3.06 mL, 25.57 mmol) dropwise at 0° C. and the mixture was allowed to stir at 0° C. for 1 hour. The reaction mixture was then stirred at RT for 16 hrs and then the solvent was removed in vacuo to afford (R)-Quinuclidin-3-yl carbonochloridate hydrochloride as a white solid (4.39 g, 98%).

To a solution of (S)-3-(amino(phenyl)methyl)phenol hydrochloride (1.0 g, 5.04 mmol) in pyridine (12 mL) was added (R)-quinuclidin-3-yl carbonochloridate hydrochloride (1.32 g, 5.84 mmol) in one portion. The reaction mixture was slowly warmed to room temperature for 16 h and concentrated to dryness. The residue was purified via silica gel chromatography, eluting with 0-100% 1.4N methanolic ammonia in isohexane, to afford 1.3 g of the title product as a white foam.

LCMS (Method 1): [MH+]=353 at 2.42 min.

Intermediate 7. tert-Butyl ((3-hydroxyphenyl)(phenyl)methyl)carbamate (I7)

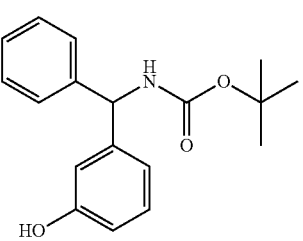 [SMILES: CC(C)(C)OC(=O)NC(c1ccccc1)c1cccc(O)c1]

3-(Amino(phenyl)methyl)phenol hydrochloride (I6e, 29.09 g, 123.4 mmol) in dichloromethane (450 mL) was cooled to 0° C. and diisopropylethylamine (65.9 mL, 370.2 mmol) and di-tert-butyl dicarbonate (59.2 g, 271.5 mmol) was added slowly. The reaction was stirred at 0° C. for 2 hours then warmed to RT over 16 hours. The solvent was removed and the residue purified through a silica plug, eluting with 0-20% ethyl acetate in iso-hexane to give a black oil. To this mixture in methanol (300 mL) was added potassium carbonate (51 g, 370.2 mmol) and stirred at RT for 16 hours. The suspension was filtered, the filtrate was evaporated at reduced pressure and the residue redissolved in ethyl acetate (370 mL). Silica (73 g) was added and the suspension was stirred for 30 minutes, filtered, and the filter cake washed with further ethyl acetate. The filtrate was evaporated to dryness. The dark solid residue was dissolved in ethyl acetate (200 mL), charcoal was added and the suspension was heated under refluxed for 1 hour. The suspension was filtered through celite and the solvent removed at reduced pressure. The dark solid was dissolved in dichloromethane, iso-hexane was added and the solvent evaporated (repeated 3 times) to give the title compound as a yellow solid (34.81 g, 92%). $^1$H NMR (400 MHz, CDCl$_3$): δ 7.36-7.16 (m, 6 H); 6.80 (d, J=7.79 Hz, 1 H); 6.74-6.69 (m, 2 H); 5.83 (s, 1 H); 5.15 (s, 1 H); 1.53-1.30 (s, 9 H).

Intermediate 8. (S)-tert-Butyl ((3-hydroxyphenyl)(phenyl)methyl)carbamate (I8)

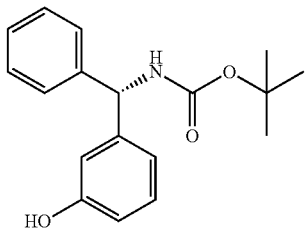 [SMILES: CC(C)(C)OC(=O)N[C@@H](c1ccccc1)c1cccc(O)c1]

Racemic N-((3-Hydroxyphenyl)(phenyl)methyl)formamide was purified by SFC using a CHIRALPAK® AD 20 μM 250×110 mm column using n-heptane/2-propanol/diethylamine (60/40/0.1) as eluant with a flow rate of 570 ml/min at 25° C. From 54.1 g of crude material (S)-tert-butyl ((3-hydroxyphenyl)(phenyl)methyl)carbamate (R$_f$=8.5-8.6 min, 23.9 g, 99.2 e.e.) was obtained.

Intermediate 9. (R)-quinuclidin-3-yl ((3-hydroxyphenyl)(phenyl)methyl)carbamate (I9)

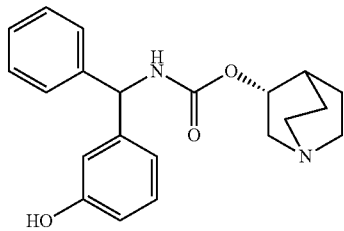 [SMILES: O=C(NC(c1ccccc1)c1cccc(O)c1)O[C@H]1CN2CCC1CC2]

(R)-quinuclidin-3-yl ((3-hydroxyphenyl)(phenyl)methyl) carbamate was prepared from (I6c) according to the same procedure described for Intermediate 6, Step 6.

Examples 1-4 can be obtained using the procedure in Scheme A.

Scheme A

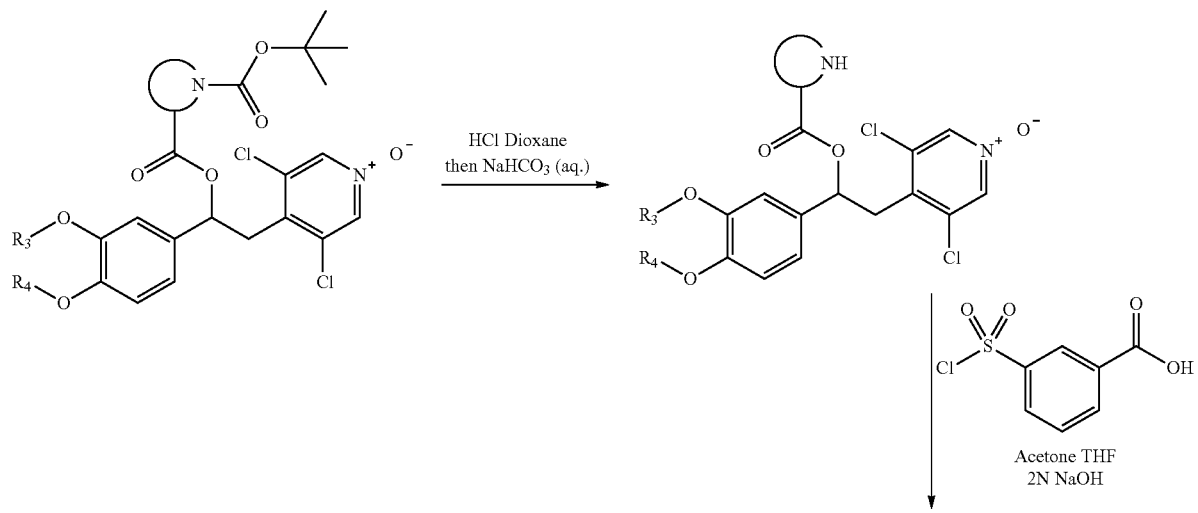

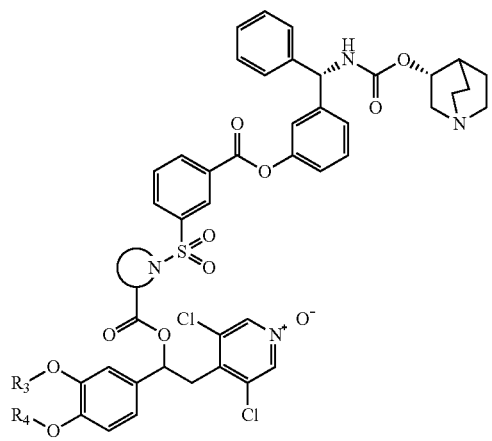 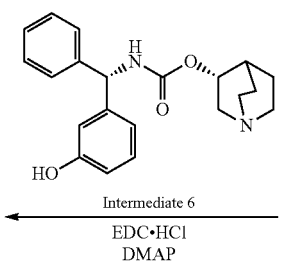 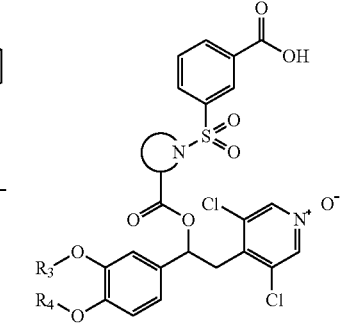

Example 1

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[3-[(S)-phenyl-[[(3R)-quinuclidin-3-yl]oxycarbonylamino]methyl]phenoxy]carbonylphenyl]sulfonylpyrrolidine-2-carboxylate (E1)

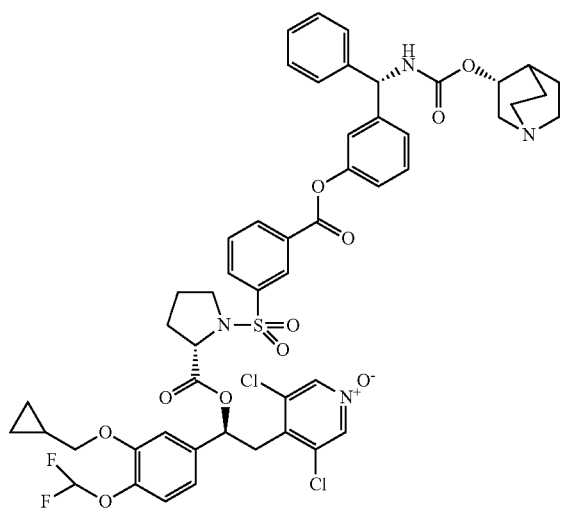

To a solution of 4-((S)-2-(((S)-1-(tert-butoxycarbonyl)pyrrolidine-2-carbonyl)oxy)-2-(3-(cyclopropylmethoxy)-4-(difluoromethoxy)phenyl)ethyl)-3,5-dichloropyridine 1-oxide (I2, 270 mg, 0.44 mmol) dissolved in EtOAc (6 mL) was added a solution of HCl in dioxane (4 N, 7.2 mL, 28.8 mmol) at 0° C. The resulting mixture was stirred at 0° C. for 1 h before addition of HCl in dioxane (4 N, 2 mL, 8.0 mmol). The resulting slurry was stirred for 1 h and then the solvent was removed in vacuo. The residue was redissolved in DCM (50 mL) and washed with saturated aqueous NaHCO$_3$ (20 mL). The organic phase was passed through a hydrophobic fit and the solvent was removed in vacuo to yield an oil that was used immediately without further purification. The residue was then taken up in acetone (4 mL) and THF (4 mL). 3-Chlorosulfonyl benzoic acid (845 mg, 3.86 mmol) and 2 M NaOH (3.86 mL, 7.72 mmol) were added at room temperature and the resulting mixture stirred for 16 h. After concentration in vacuo, the residue was diluted in DCM (50 mL) and the pH adjusted to 2 with an aqueous 1 N HCl saturated with brine. The organic phase was dried over MgSO$_4$ and concentrated in vacuo. The resulting oil (195 mg) was used directly in the next step without further purification. To a solution of the carboxylic acid, (R)-quinuclidin-3-yl ((S)-(3-hydroxyphenyl)(phenyl)methyl)carbamate (197 mg, 0.56 mmol), 4-(dimethylamino)-pyridine (17 mg, 0.14 mmol) in DMF (2.5 mL) was added N-(3-dimethylaminopropyl)-N'-ethylcarbodiimide hydrochloride (107 mg, 0.56 mmol).

The resulting mixture was stirred at room temperature for 16 h and partitioned between EtOAc (50 mL) and water (20 mL). The layers were separated, the organic layer dried over MgSO$_4$ and the solvent removed in vacuo. The residue was dissolved in DMSO (1.5 mL) and purified by preparative HPLC to provide the title compound as a solid (9 mg, 2% over three steps).

$^1$H NMR (400 MHz, DMSO): δ 8.57 (s, 2 H), 8.46-8.35 (m, 2 H), 8.17-8.11 (m, 1 H), 7.92-7.85 (m, 1 H), 7.48-7.41 (m, 2

H), 7.40-7.29 (m, 6 H), 7.28-7.21 (m, 2 H), 7.19 (d, J=8.2 Hz, 1 H), 7.15-7.11 (m, 1 H), 7.08 (t, J=75 Hz, 1 H), 6.98 (d, J=8.3 Hz, 1 H), 6.04 (dd, J=9.5, 4.2 Hz, 1 H), 5.96-5.89 (m, 1 H), 4.62-4.53 (m, 1 H), 4.25-4.21 (m, 1 H), 3.92 (d, J=6.9 Hz, 2 H), 3.54-3.19 (m, 7 H), 2.78-2.54 (m, 3 H), 2.07-1.94 (m, 1 H), 1.94-1.85 (m, 1 H), 1.75-1.64 (m, 2 H), 1.64-1.53 (m, 2 H), 1.52-1.40 (m, 1 H), 1.37-1.26 (m, 1 H), 1.26-1.17 (m, 2 H), 0.59-0.51 (m, 2 H), 0.36-0.31 (m, 2 H). LCMS (Method 1): [MH+]=1035 at 3.19 min.

Compounds herebelow reported were prepared starting from the appropriate starting materials using analogous procedures as those hereabove described in Example 1.

| Structure | Example number | Precursor | Analytical Data |
| --- | --- | --- | --- |
| [(1S)-1-[3-(cyclopropylmethoxy)-4-(difluoromethoxy)phenyl]-2-(3,5-dichloro-1-oxido-pyridin-1-ium-4-yl)ethyl]-1-[3-[(S)-phenyl-[[(3R)-quinuclidin-3-yl]oxycarbonylamino]methyl]phenoxy]carbonylphenyl]sulfonylazetidine-3-carboxylate 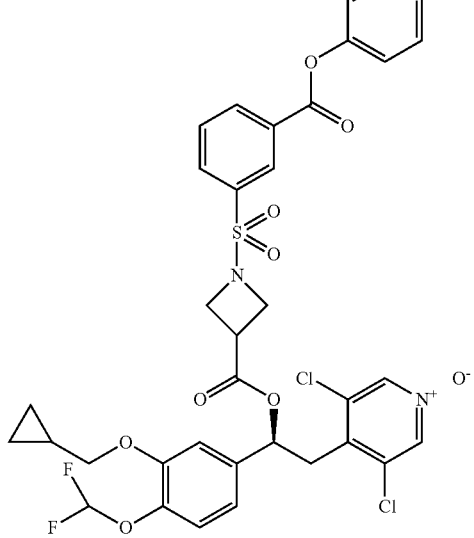 | Example 2 | Intermediate 3 and Intermediate 6 | ¹H NMR (400 MHz, DMSO): δ 8.55 (s, 2 H), 8.46 (dd, J = 7.8, 1.5 Hz, 1 H), 8.39-8.37 (m, 1 H), 8.15 (d, J = 7.8 Hz, 1 H), 7.94 (t, J = 7.8 Hz, 1 H), 7.48-7.42 (m, 1 H), 7.39-7.29 (m, 7 H), 7.27-7.19 (m, 2 H), 7.16 (d, J = 8.1 Hz, 1 H), 7.07 (t, J = 75 Hz, 1 H), 7.03 (s, 1 H), 6.88-6.83 (m, 1 H), 5.99-5.89 (m, 1 H), 5.89-5.82 (m, 1 H), 4.62-4.55 (m, 1 H), 4.01-3.90 (m, 3 H), 3.89-3.88 (d, J = 6.7 Hz, 2 H), 3.80-3.73 (m, 1 H), 3.66 (t, J = 7.4 Hz, 1 H), 3.49-3.36 (m, 3 H), 3.15 (dd, J = 14.2, 4.7 Hz, 1 H), 2.78-2.54 (m, 2 H), 1.93-1.85 (m, 1 H), 1.83-1.71 (m, 1 H), 1.62-1.53 (m, 1 H), 1.51-1.39 (m, 2 H), 1.35-1.26 (m, 1 H), 1.25-1.14 (m, 2 H), 0.59-0.53 (m, 2 H), 0.36-0.31 (m, 2 H). LCMS (Method 1): [MH+] = 1021 at 3.15 min. |
| [(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[3-[phenyl-[[(3R)-quinuclidin-3-yl]oxycarbonylamino]methyl]phenoxy]carbonylphenyl]sulfonylthiazolidine-2-carboxylate | Example 3 | Intermediate 5 and Intermediate 9 | ¹H NMR (400 MHz, DMSO): δ ppm 8.55 (s, 2 H), 8.44-8.47 (m, 2 H), 8.31 (s, 2 H), 8.24-8.26 (m, 1 H), 7.90 (m, 1 H), 7.41-7.50 (m, 1 H), 7.33-7.40 (m, 6 H), 7.24 (d, J = 7.63 Hz, 2 H), 7.17-7.20 (m, 1 H), 7.09 (m, 2 H), 6.90-7.01 (m, 1 H), 5.96-6.09 (m, 1 H), 5.84-5.94 (m, 1 |

-continued

| Structure | Example number | Precursor | Analytical Data |
|---|---|---|---|
| 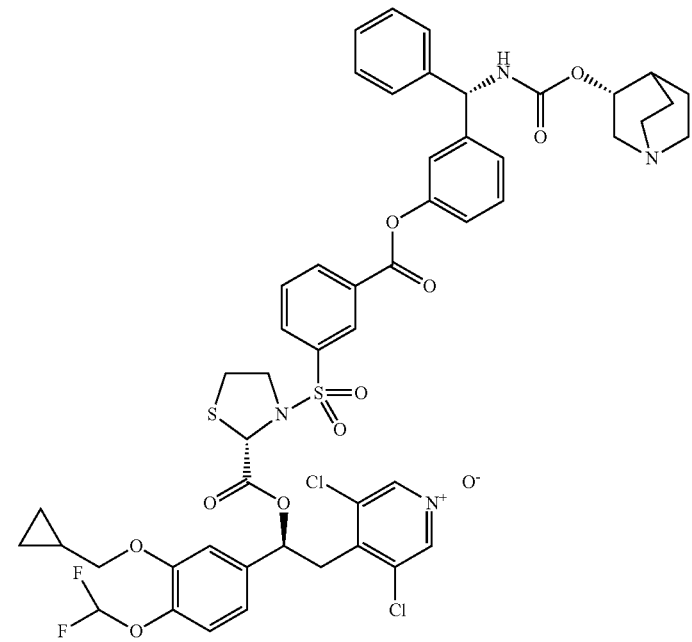 | | | H), 5.54 (s, 1 H), 4.46-4.64 (m, 1 H), 3.90 (d, J = 7.04 Hz, 2 H), 3.76-3.84 (m, 1 H), 3.61-3.73 (m, 1 H), 3.42-3.55 (m, 4 H), 2.56-2.85 (m, 6 H), 1.24-1.55 (m, 5 H), 0.76-0.91 (m, 1 H), 0.57 (m, 2 H), 0.32 (d, J = 5.09 Hz, 2 H). MS/ESI+ [MH+] = 1053.2 |
| [(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[3-[phenyl-[[(3R)-quinuclidin-3-yl]oxycarbonylamino]methyl]phenoxy]carbonylphenyl]sulfonylthiazolidine-2-carboxylate 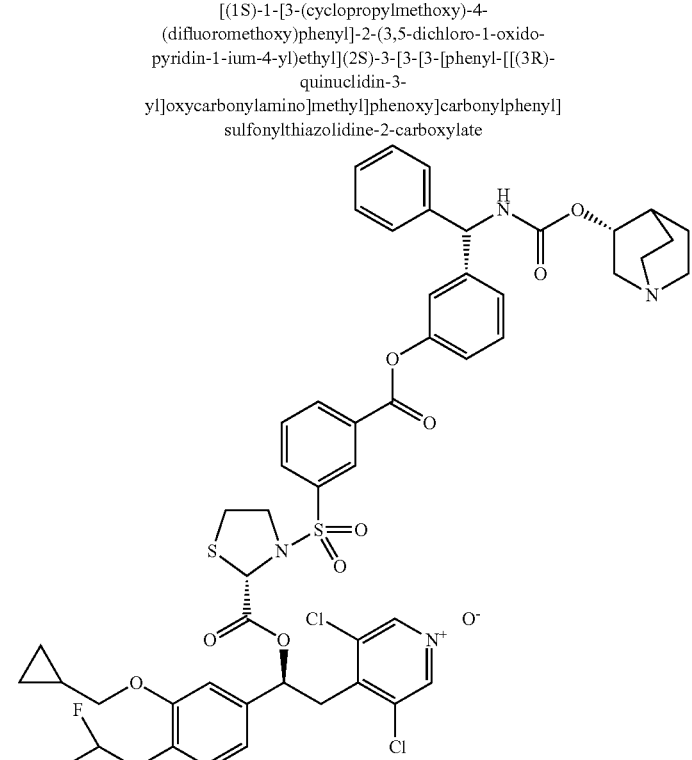 | Example 4 | Intermediate 5 and Intermediate 6 | 1H NMR (400 MHz, DMSO) δ ppm 8.55 (s, 2 H), 8.39-8.49 (m, 2 H), 8.25 (m, 2 H), 8.19 (s, 2 H), 7.90 (t, J = 7.94 Hz, 1 H), 7.41-7.49 (m, 1 H), 7.30-7.39 (m, 6 H), 7.20-7.28 (m, 2 H), 7.18 (d, J = 8.38 Hz, 1 H), 7.11 (d, J = 1.76 Hz, 1 H), 7.08 (t, J = 75.00 Hz, 1 H), 6.96 (dd, J = 8.38, 1.32 Hz, 1 H), 6.02 (dd, J = 8.82, 4.85 Hz, 1 H), 5.54-5.97 (m, 1 H), 5.54 (s, 1 H), 4.51-4.62 (m, 1 H), 3.90 (d, J = 7.06 Hz, 2 H), 3.80 (m, 1 H), 3.71 (d, J = 6.17 Hz, 1 H), 3.39-3.49 (m, 2 H), 2.88-3.14 (m, 4 H), 2.75 (dd, J = 11.25, 5.95 Hz, 4 H), 1.23-1.93 (m, 6 H), 0.47-0.60 (m, 2 H), 0.33 (d, J = 5.29 Hz, 2 H). MS/ESI+ [MH+] = 1053.22 |

Example 5 can be obtained using the procedure of Scheme B.
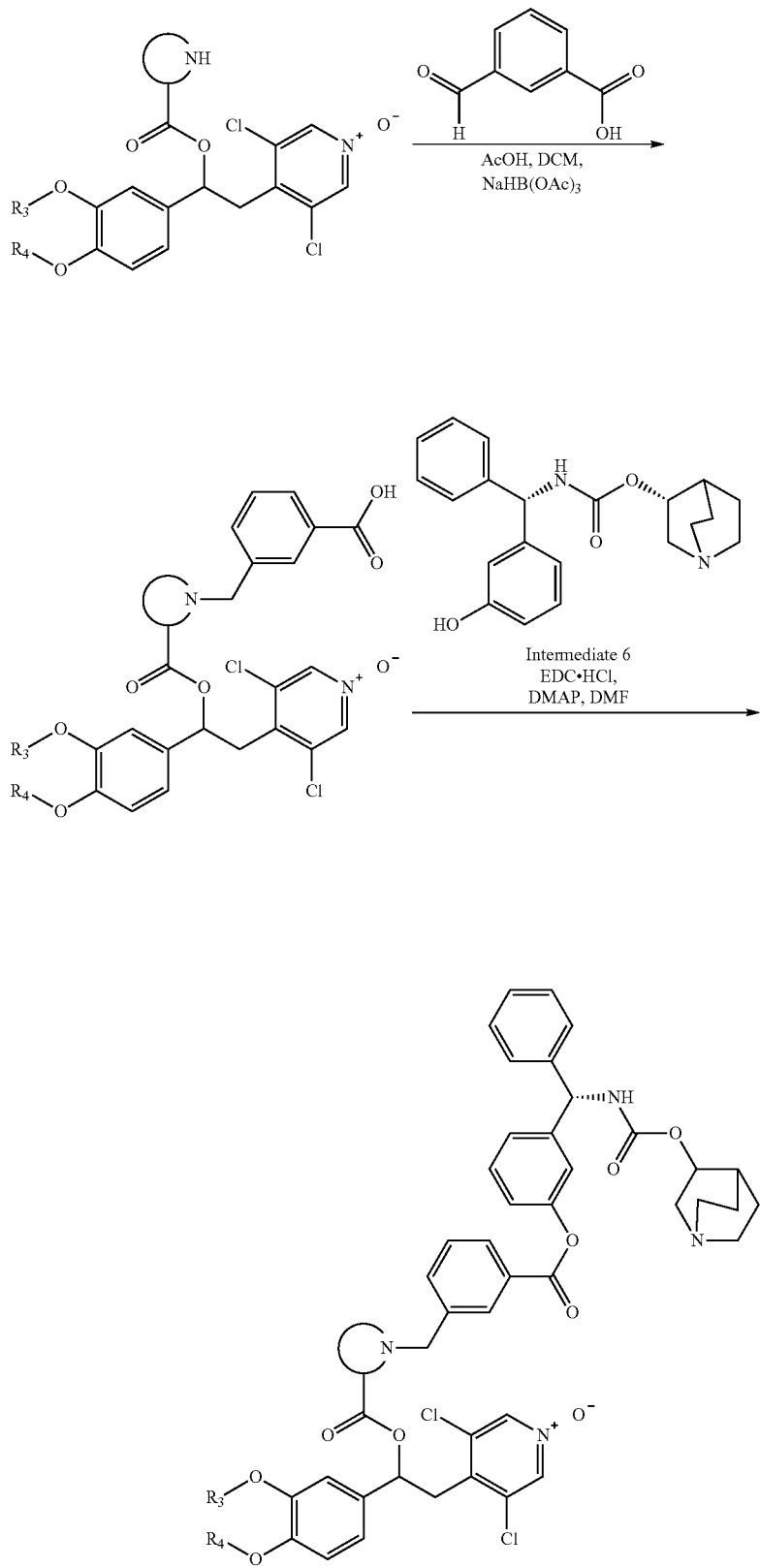

Example 5

[(1S)-1-[3-(cyclopropylmethoxy)-4-(difluoromethoxy)phenyl]-2-(3,5-dichloro-1-oxido-pyridin-1-ium-4-yl)ethyl](2S)-3-[[3-[3-[(S)-phenyl-[[(3R)-quinuclidin-3-yl]oxycarbonylamino]methyl]phenoxy]carbonylphenyl]methyl]thiazolidine-2-carboxylate formate salt (E5)

Step 1: preparation of 4-((S)-2-(((S)-3-(3-carboxybenzyl)thiazolidine-2-carbonyl)oxy)-2-(3-(cyclopropylmethoxy)-4-(difluoromethoxy)phenyl)ethyl)-3,5-dichloropyridine 1-oxide (E5a)

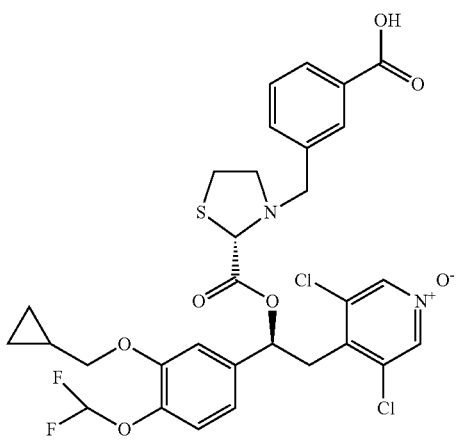

To a stirred solution of 3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (I5, 570 mg, 1.0 mmol) in DCM (5 mL) was added 3-formylbenzoic acid (180 mg, 1.2 mmol) followed by glacial AcOH (0.17 mL, 3.3 mmol). The reaction was stirred at room temperature for 18 h. Sodium triacetoxyborohydride (690 mg, 3.12 mmol) was added and the reaction was stirred at room temperature for 1.5 h. Additional 3-formylbenzoic acid (180 mg, 1.2 mmol) was added and the reaction mixture was stirred at room temperature for 2 days. DCM (25 mL) and 1 N HCl (15 mL) were added to quench the reaction and the mixture was passed through a hydrophobic frit and the solvent was removed in vacuo to give the title compound.

LCMS (Method 2): [MH+]=669 at 3.17 min.

Step 2: preparation of [(1S)-1-[3-(cyclopropylmethoxy)-4-(difluoromethoxy)phenyl]-2-(3,5-dichloro-1-oxido-pyridin-1-ium-4-yl)ethyl](2S)-3-[[3-[3-[(S)-phenyl-[[(3R)-quinuclidin-3-yl]oxycarbonylamino]methyl]phenoxy]carbonylphenyl]methyl]-thiazolidine-2-carboxylate formate salt (E5)

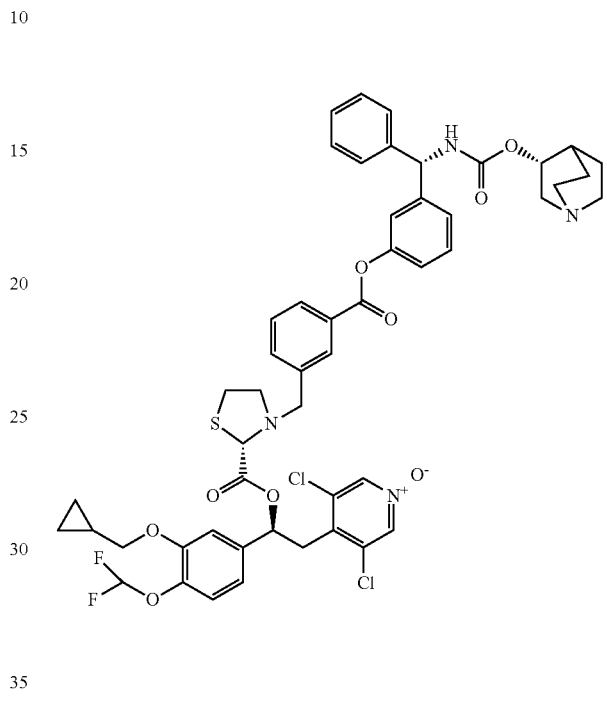

The carboxylic acid previously obtained was dissolved in DMF (2.5 mL) and (R)-quinuclidin-3-yl ((S)-(3-hydroxyphenyl)(phenyl)methyl)carbamate (I6, 291 mg, 0.83 mmol), 4-(dimethylamino)-pyridine (35 mg, 0.29 mmol) and N-(3-dimethylaminopropyl)-N'-ethylcarbodiimide hydrochloride (219 mg, 1.14 mmol) were added. The resulting mixture was stirred at room temperature for 18 h. The solvent was removed in vacuo and the residue was partitioned between EtOAc (50 mL) and water (20 mL). The layers were separated, the organic layer dried over MgSO$_4$, filtered and the solvent was removed in vacuo. The residue was dissolved in DMSO (1.5 mL) and purified by preparative HPLC to provide the title compound (78 mg, 8% over two steps) as a white solid.

$^1$H NMR (400 MHz, DMSO): δ 8.43 (s, 2 H), 8.35-8.27 (m, 1 H), 8.22 (s, 1 H), 8.12-8.06 (m, 2 H), 7.69 (d, J=7.6 Hz, 1 H), 7.61 (t, J=7.6 Hz, 1 H), 7.44 (t, J=8.1 Hz, 1 H), 7.37-7.28 (m, 5 H), 7.28-7.19 (m, 2 H), 7.18 (d, J=8.6 Hz, 1 H), 7.10 (d, J=2.0 Hz, 1 H), 7.08 (t, J=74.8 Hz, 1 H), 6.95 (dd, J=8.3, 1.9 Hz, 1 H), 5.94-5.87 (m, 2 H), 4.82 (s, 1 H), 4.62-4.54 (m, 1 H), 3.90 (d, J=7.0 Hz, 2 H), 3.66 (s, 2 H), 3.40-3.27 (m, 4 H), 3.22 (dd, J=14.3, 4.9 Hz, 1 H), 3.15-3.05 (m, 2 H), 3.03-2.96 (m, 1 H), 2.94-2.88 (m, 1 H), 2.76-2.69 (m, 2 H), 2.65-2.54 (m, 2 H), 1.95-1.85 (m, 1 H), 1.82-1.71 (m, 1 H), 1.63-1.52 (m, 1 H), 1.52-1.40 (m, 1 H), 1.37-1.27 (m, 1 H), 1.24-1.19 (m, 1 H), 0.58-0.53 (m, 2 H), 0.36-0.32 (m, 2H). LCMS (Method 1): [MH+]=1003 at 3.3 min.

Intermediate 10. (S)-3-(((tert-butoxycarbonyl)amino)(phenyl)methyl)benzoic acid (I10)

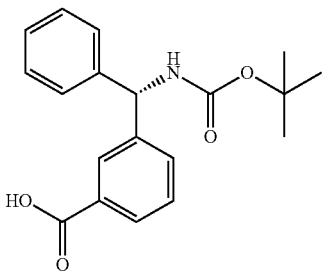 [SMILES: CC(C)(C)OC(=O)N[C@@H](c1ccccc1)c1cccc(C(=O)O)c1]

To a solution of tert-butyl N—[(S)-(3-hydroxyphenyl)-phenyl-methyl]carbamate (I8, 900 mg, 3.01 mmol) in pyridine (5 mL) was slowly added triflic anhydride (1.19 mL, 4.5 mmol) at 0° C. The reaction mixture was stirred at 0° C. for 30 min and water (5 mL) was cautiously added to quench the excess of triflic anhydride. EtOAc (100 mL) and water (40 mL) were added, the layers separated, the organic phase washed with brine (40 mL) and dried over MgSO$_4$. After concentration in vacuo, the oil was transferred to a microwaves vial with toluene (15 mL), Et$_3$N (0.83 mL, 6.0 mmol) and phenyl formate (732 mg, 6.0 mmol) and N$_2$ was bubbled through the mixture for 15 min. Pd(OAc)$_2$ (34 mg, 0.15 mmol) and Xantphos (173 mg, 0.30 mmol) were added and N$_2$ was bubbled through the mixture again for 5 min before heating under microwaves irradiation for 30 min at 120° C. EtOAc (100 mL) and water (50 mL) were added, the layers separated and the organic phase was dried over MgSO$_4$. The mixture was filtered and the solvent was removed in vacuo and the residue was purified via silica gel chromatography, eluting with 0-20% EtOAc in isohexane, to give the corresponding phenyl ester compound (579 mg). The solid was dissolved in THF (5 mL) and MeOH (5 mL) and a solution of 1 N LiOH (2.72 mL, 2.72 mmol) was added at room temperature and the reaction mixture stirred for 16 h. 2N HCl was added at 0° C. to adjust the pH to ~2. After concentration in vacuo, the residue was taken in DCM (50 mL) and water (20 mL), the layers separated through a hydrophobic frit and the organic phase concentrated in vacuo to yield the title compound (384 mg, 39% over three steps) as a white solid. $^1$H NMR (400 MHz, DMSO): δ 9.31 (s, 1 H), 8.08 (d, J=9.6 Hz, 1 H), 7.92 (s, 1 H), 7.81 (d, J=7.7 Hz, 1 H), 7.54 (d, J=7.8 Hz, 1 H), 7.44 (t, J=7.7 Hz, 1 H), 7.35-7.29 (m, 4 H), 7.27-7.21 (m, 1 H), 7.16 (t, J=7.7 Hz, 1 H), 6.79-6.73 (m, 2 H), 5.90 (d, J=9.2 Hz, 1 H), 1.40 (s, 9 H).

Example 6 can be obtained using the procedure of Scheme C.

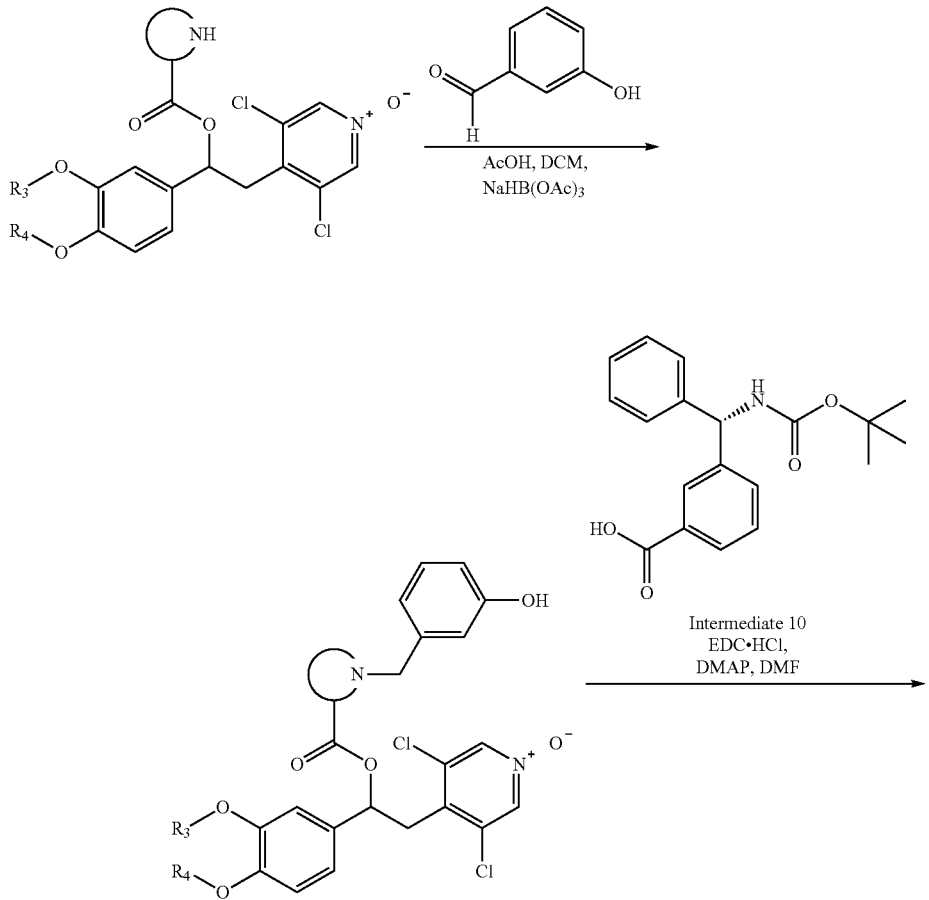

Scheme C

-continued
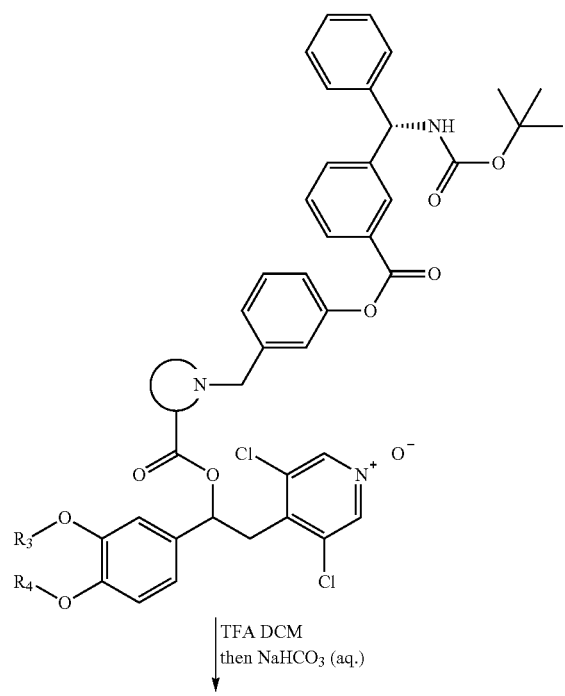
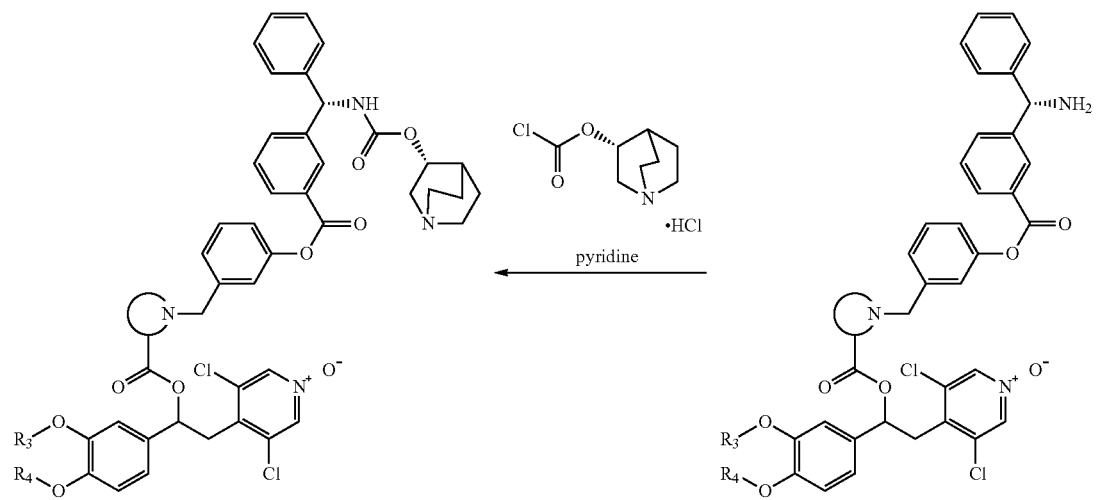

Example 6

[(1S)-1-[3-(cyclopropylmethoxy)-4-(difluoromethoxy)phenyl]-2-(3,5-dichloro-1-oxido-pyridin-1-ium-4-yl)ethyl](2S)-3-[[3-[3-[(S)-phenyl-[[(3R)-quinuclidin-3-yl]oxycarbonylamino]methyl]benzoyl]oxyphenyl]methyl]thiazolidine-2-carboxylate bis formate salt (E6)

Step 1: Preparation of 3,5-dichloro-4-((S)-2-(3-(cyclopropylmethoxy)-4-(difluoromethoxy)phenyl)-2-(((S)-3-(3-hydroxybenzyl)thiazolidine-2-carbonyl)oxy)ethyl)pyridine 1-oxide (E6a)

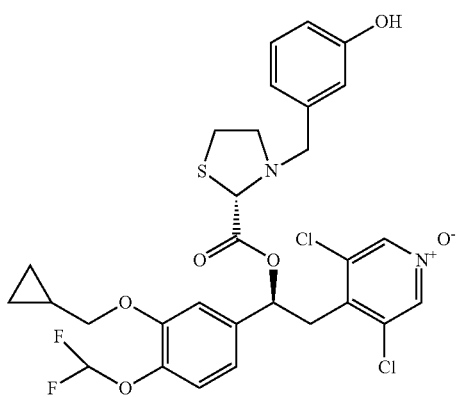

To a stirred solution of 3,5-dichloro-4-((S)-2-(3-(cyclopropylmethoxy)-4-(difluoromethoxy)phenyl)-2-((S)-thiazolidine-2-carbonyloxy)ethyl)pyridine 1-oxide hydrochloride (I5, 300 mg, 0.52 mmol) in DCM (2 mL) was added 3-hydroxybenzaldehyde (172 mg, 1.2 mmol) followed by glacial AcOH (0.11 mL, 2.08 mmol). The reaction was stirred at room temperature for 18 hours. Sodium triacetoxyborohydride (500 mg, 2.26 mmol) was added and the reaction was stirred at room temperature for 4 h. DCM (50 mL) and 1 N HCl (20 mL) were added to quench the reaction. The layers were separated and the organic layer washed with 1 N HCl (2×20 mL), passed through a hydrophobic fit and the solvent was removed in vacuo to give the title compound.

LCMS (Method 2): [MH+]=641 at 3.68 min.

Step 2: Preparation of [(1S)-1-[3-(cyclopropylmethoxy)-4-(difluoromethoxy)phenyl]-2-(3,5-dichloro-1-oxido-pyridin-1-ium-4-yl)ethyl](2S)-3-[[3-[3-[(S)-phenyl-[[(3R)-quinuclidin-3-yl]oxycarbonylamino]methyl]benzoyl]oxyphenyl]methyl]thiazolidine-2-carboxylate bis formate salt (E6)

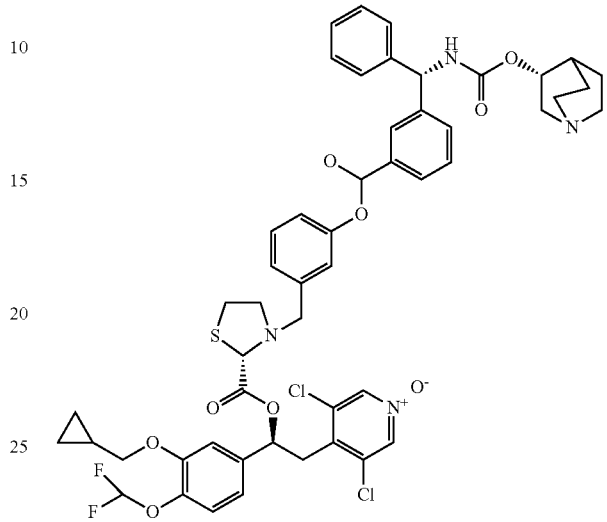

The phenol previously obtained was then dissolved in DMF (5 mL) and (S)-3-(((tert-butoxycarbonyl)amino)(phenyl)methyl)benzoic acid (I10, 196 mg, 0.60 mmol) followed by 4-(dimethylamino)-pyridine (31 mg, 0.25 mmol) and N-(3-dimethylaminopropyl)-N'-ethylcarbodiimide hydrochloride (192 mg, 1.0 mmol). The resulting mixture was stirred at room temperature for 18 h. The solvent was removed in vacuo and the residue was partitioned between EtOAc (50 mL) and saturated aqueous NaHCO$_3$ (30 mL). The organic phase was washed with brine (20 mL), dried over MgSO$_4$ and the solvent was removed in vacuo. The residue was dissolved in DMSO (3.0 mL) and purified by preparative HPLC to give the corresponding ester (79 mg) as white solid. The residue was taken up in DCM (2 mL), and TFA (1 mL) was added at 0° C. The mixture was stirred at 0° C. for 1 h and the solvent was then removed in vacuo. The residue was diluted with DCM (30 mL) and saturated aqueous NaHCO$_3$ (20 mL) and the organic phase was passed through a hydrophobic fit. The solvent was removed in vacuo and the residue was dissolved in pyridine (1 mL) and then (R)-quinuclidin-3-yl carbonochloridate hydrochloride (22 mg, 0.096 mmol, prepared as previously reported for Int 6, Step 6) was added at 0° C. The resulting mixture was stirred at room temperature for 18 h and then diluted with EtOAc (50 mL) and water (20 mL). The layers were separated and the organic phase dried over MgSO$_4$. The mixture was filtered and the solvent was removed in vacuo. The residue was dissolved in DMSO (1.5 mL) and purified by preparative HPLC to provide the title compound (45 mg, 9% over four steps). $^1$H NMR (400 MHz, DMSO at 100° C.): δ 8.28 (s, 2 H), 8.12 (s, 2 H), 8.01 (dt, J=7.8, 1.4 Hz, 1 H), 7.75 (d, J=8.6 Hz, 1 H), 7.66 (d, J=7.8 Hz, 1 H), 7.54 (t, J=7.7 Hz, 1 H), 7.42 (t, J=8.0 Hz, 1 H), 7.37-7.30 (m, 4 H), 7.26-7.21 (m, 3 H), 7.20-7.17 (m, 1 H), 7.14 (d, J=7.9 Hz, 1 H), 7.09 (d, J=2.1 Hz, 1 H), 6.95 (dd, J=8.7, 0.0 Hz, 1 H), 6.94 (t, J=75 Hz, 1 H), 5.98 (d, J=8.8 Hz, 1 H), 5.97 (d, J=8.9 Hz, 1 H), 4.77 (s, 1 H), 4.64-4.59 (m, 1 H), 3.92 (d, J=6.7 Hz, 2 H), 3.66 (s, 2 H), 3.39 (dd, J=14.2, 8.8 Hz, 1 H), 3.36-3.31 (m, 1 H), 3.26 (dd, J=14.1, 5.1 Hz, 1 H), 3.23-3.17 (m, 1 H), 3.07 (dd, J=14.6, 8.1 Hz, 1 H), 2.98 (dt, J=15.7, 4.7

Hz, 1 H), 2.95-2.87 (m, 1 H), 2.70 (t, J=8.1 Hz, 3 H), 2.67-2.55 (m, 1 H), 2.55-2.51 (m, 1 H), 1.94-1.86 (m, 1 H), 1.79-1.68 (m, 1 H), 1.64-1.54 (m, 1 H), 1.52-1.42 (m, 1 H), 1.36-1.24 (m, 1 H), 1.25-1.16 (m, 1 H), 0.58-0.53 (m, 2 H), 0.35-0.32 (m, 2 H), NH not observed. LCMS (Method 1): [MH+]=1003 at 3.35 min.

Intermediate 11. Methyl 1-methyl-5-(((methylsulfonyl)oxy)methyl)-1H-pyrazole-3-carboxylate (I11)

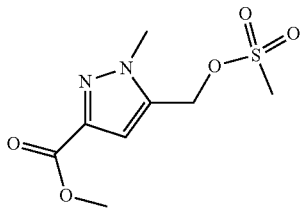 [SMILES: COC(=O)c1cc(COS(C)(=O)=O)n(C)n1]

To an ice-cooled solution of methyl 5-(hydroxymethyl)-1-methyl-1H-pyrazole-3-carboxylate (0.60 g, 3.51 mmol) and triethylamine (1.22 mL, 8.77 mmol) in DCM (10 mL) was added methanesulfonyl chloride (0.41 mL, 5.26 mmol). The reaction mixture was stirred in the ice bath for 15 minutes and then the mixture was allowed to warm to room temperature. The reaction mixture was stirred at RT for 1 hour. The reaction mixture was diluted with DCM and washed with water and brine. The organic phase was dried over magnesium sulfate, filtered and the solvent was evaporated in vacuo. The crude material was used in the next step without further purification.

Intermediate 12. (S)-Methyl 4-((3-(((tert-butoxycarbonyl)amino)(phenyl)methyl)-phenoxy)methyl)benzoate (I12)

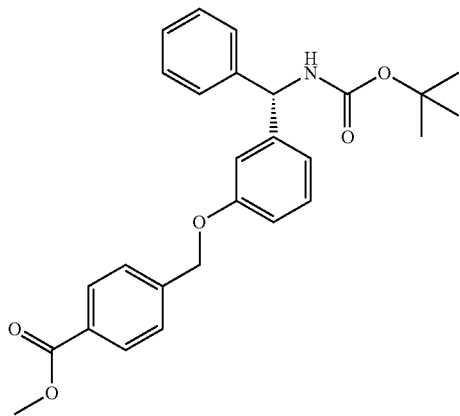 [SMILES: COC(=O)c1ccc(COc2cccc([C@@H](NC(=O)OC(C)(C)C)c3ccccc3)c2)cc1]

A mixture of (S)-tert-butyl ((3-hydroxyphenyl)(phenyl)methyl)carbamate (I8, 3.20 g, 10.7 mmol), methyl 4-(bromomethyl)benzoate (2.70 g, 11.8 mmol) and potassium carbonate (2.20 g, 16.1 mmol) in acetonitrile (54 mL) was stirred at RT for 16 h. The reaction mixture was removed in vacuo and the residue was partitioned between ethyl acetate and water. The aqueous phase was extracted with further ethyl acetate and the combined organic extracts were dried with anhydrous magnesium sulfate, filtered and the solvent was removed in vacuo. The residue was re-crystallised from ethyl acetate and iso-hexane to afford (S)-Methyl 4-((3-(((tert-butoxycarbonyl)amino)(phenyl)methyl)-phenoxy)methyl)benzoate as a white solid (3.25 g, 68%). $^1$H NMR (400 MHz, CDCl$_3$): δ 8.04 (d, J=8.2 Hz, 2 H), 7.46 (d, J=8.2 Hz, 2 H), 7.34-7.20 (m, 6 H), 6.90-6.81 (m, 3 H), 5.87 (s, 1 H), 5.13 (s, 1 H), 5.07 (s, 2 H), 3.92 (s, 3 H), 1.44 (s, 9 H).

Intermediate 13. (S)-methyl 4-((3-(amino(phenyl)methyl)phenoxy)methyl)benzoate (I13)

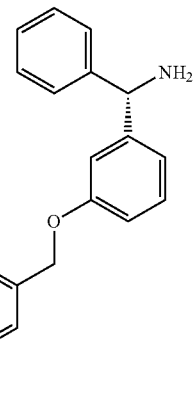

To a solution of (S)-Methyl 4-((3-(((tert-butoxycarbonyl)amino)(phenyl)methyl)-phenoxy)-methyl)benzoate (I12, 3.21 g, 7.20 mmol) in methanol (36 mL) was added hydrogen chloride in dioxane (4 M, 9.0 mL, 36 mmol). The reaction mixture was stirred at RT for 16 h. The solvent was removed in vacuo to afford (S)-Methyl 4-((3-(amino(phenyl)methyl)phenoxy)methyl)benzoate hydrochloride (2.65 g, >95%).
$^1$H NMR (400 MHz, CDCl$_3$): δ 9.21 (s, 2 H), 8.03 (d, J=8.1 Hz, 2 H), 7.64 (d, J=8.1 Hz, 2 H), 7.59 (d, J=7.6 Hz, 2 H), 7.49-7.34 (m, 5 H), 7.17 (d, J=7.7 Hz, 1 H), 7.06 (dd, J=8.3, 2.4 Hz, 1 H), 5.64 (s, 1 H), 5.28 (s, 2 H), 3.91 (s, 3 H).

Intermediate 14. Methyl 4-((3-((S)-phenyl((((R)-quinuclidin-3-yloxy)carbonyl)amino)-methyl)phenoxy)methyl)benzoate (I14)

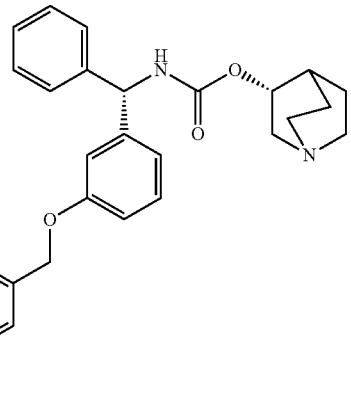

To a stirred solution of (S)-methyl 4-((3-(amino(phenyl)methyl)phenoxy)methyl)-benzoate hydrochloride (I13, 12.0 g, 31.3 mmol) in pyridine (100 mL) at 0° C. was added portion-wise (R)-quinuclidin-3-yl carbonochloridate (8.50 g, 37.5 mmol, prepared as previously reported for Int 6, Step 6). The reaction was stirred at 0° C. for 1 hour and then allowed to warm to RT for 16 h. Water was added to the reaction mixture and the mixture was extracted with ethyl acetate (×3). The combined extracts were washed with brine, dried over sodium sulfate, filtered and the solvent was removed in vacuo. The crude material was purified by chromatography on a KP-NH Biotage cartridge eluting with 0-20% methanol in ethyl acetate to afford the title compound (10.3 g, 66%).

The following intermediates were synthesized via similar method as that used for Intermediate 14.

| Structure | Intermediate number | Analytical Data |
|---|---|---|
| 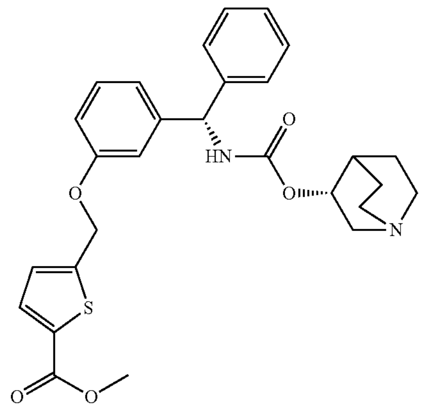 [SMILES: COC(=O)c1ccc(COc2cccc([C@@H](NC(=O)O[C@H]3CN4CCC3CC4)c3ccccc3)c2)s1] | Intermediate 15 | $^1$H NMR (400 MHz, CDCl$_3$): δ 7.66 (d, J = 4.0 Hz, 1 H), 7.35-7.23 (m, 6 H), 7.02 (d, J = 4.0 Hz, 1 H), 6.91-6.85 (m, 3 H), 5.92-5.88 (m, 1 H), 5.43-5.41 (m, 1 H), 5.17 (s, 2 H), 4.73-4.70 (m, 1 H), 3.88 (s, 3 H), 2.87-2.69 (m, 6 H), 2.01-1.24 (m, 5 H). LCMS (Method 2): [MH+] = 507 at 3.72 min. |
| 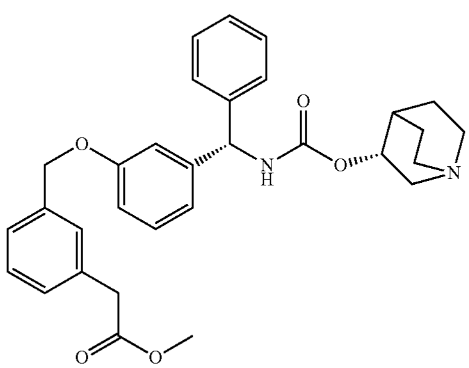 [SMILES: COC(=O)Cc1cccc(COc2cccc([C@@H](NC(=O)O[C@H]3CN4CCC3CC4)c3ccccc3)c2)c1] | Intermediate 16 | $^1$H NMR (400 MHz, CDCl$_3$): δ 7.34-7.22 (m, 10 H), 6.87-6.85 (m, 3 H), 5.91 (br s, 1 H), 5.51 (br s, 1 H), 5.01 (s, 2 H), 4.73-4.71 (m, 1 H), 3.67 (s, 3 H), 3.63 (s, 2 H), 3.28-3.13 (m, 1 H), 2.82-2.54 (m, 5 H), 2.03-2.01 (m, 1 H), 1.84-1.78 (m, 1 H), 1.71-1.68 (m, 1 H), 1.64-1.52 (m, 1 H), 1.37-1.31 (m, 1 H). |

Intermediate 17. 4-((3-((S)-Phenyl((((R)-quinuclidin-3-yloxy)carbonyl)amino)-methyl)phenoxy)methyl)benzoic acid (I17)

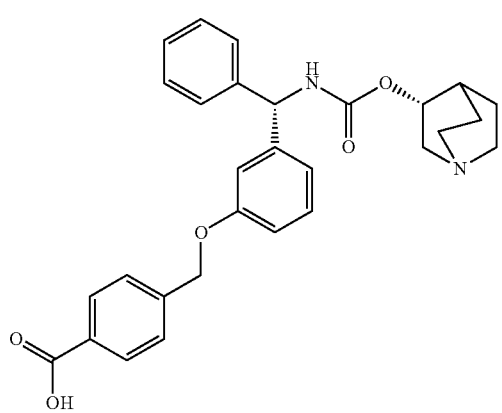 [SMILES: O=C(N[C@@H](c1ccccc1)c1cccc(OCc2ccc(C(=O)O)cc2)c1)O[C@H]1CN2CCC1CC2]

To a stirred solution of methyl 4-((3-((S)-phenyl((((R)-quinuclidin-3-yloxy)carbonyl)amino)methyl) phenoxy)methyl)benzoate (I14, 2.27 g, 4.50 mmol) in THF (23 mL) was added an aqueous solution of lithium hydroxide (2.0 M, 9.0 ml, 18.0 mmol). The mixture was stirred at RT for 16 hours. The pH of the reaction mixture was adjusted to 6 by the addition of 4M aqueous hydrochloric acid. The mixture was then extracted with 10% methanolic ethyl acetate (×2), the organic extracts were combined and the solvent was removed in vacuo. The residue was then dissolved in ethanol and re-evaporated at reduced pressure to afford the title compound as a pale yellow solid (1.85 g, 84%).

$^1$H NMR (400 MHz, DMSO): δ 8.41 (d, J=9.4 Hz, 1 H), 7.99 (d, J=7.9 Hz, 2 H), 7.58 (d, J=8.0 Hz, 2 H), 7.42-7.26 (m, 6 H), 7.09 (s, 1 H), 7.02-6.91 (m, 2 H), 5.87 (d, J=9 Hz, 1 H), 5.21 (s, 2 H), 4.76 (s, 1 H), 3.98-2.72 (m, 6 H), 2.12-1.54 (m, 5 H).

The following intermediates were synthesised via a similar method as that used for Intermediate 17.

| Structure | Intermediate number | Analytical Data |
|---|---|---|
| 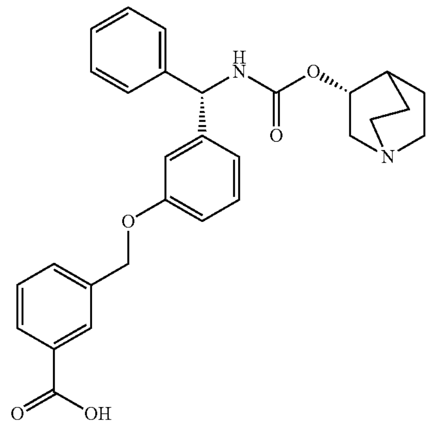 [SMILES: O=C(N[C@@H](c1ccccc1)c1cccc(OCc2cccc(C(=O)O)c2)c1)O[C@H]1CN2CCC1CC2] | Intermediate 18 | ¹H NMR (400 MHz, DMSO): δ 8.34-8.32 (m, 1 H), 8.00 (s, 1 H), 7.89-7.87 (m, 1 H), 7.64-7.62 (m, 1 H), 7.50-7.46 (m, 1 H), 7.35-7.22 (m, 5 H), 7.06-7.04 (m, 1 H), 6.94-6.89 (m, 2 H), 5.83-5.80 (m, 1 H), 5.15 (s, 2 H), 4.70-4.68 (m, 1 H), 4.01-3.92 (m, 1 H), 3.48-2.55 (m, 6 H), 2.11-1.38 (m, 5 H). OH not observed. LCMS (Method 1): [MH+] = 487 at 2.70 min. |
| 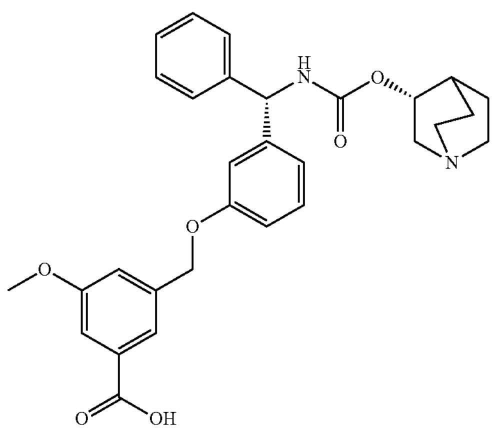 [SMILES: COc1cc(COc2cccc([C@@H](NC(=O)O[C@H]3CN4CCC3CC4)c3ccccc3)c2)cc(C(=O)O)c1] | Intermediate 19 | LCMS (Method 1): [MH+] = 517 and 2.43 min. |
| 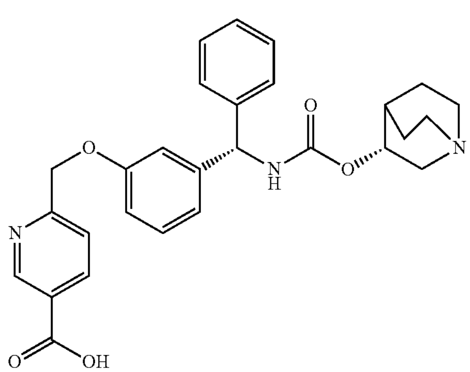 [SMILES: O=C(N[C@@H](c1ccccc1)c1cccc(OCc2ccc(C(=O)O)cn2)c1)O[C@H]1CN2CCC1CC2] | Intermediate 20 | LCMS (Method 1): [MH+] = 488 at 2.57 min. |

| Structure | Intermediate number | Analytical Data |
|---|---|---|
| 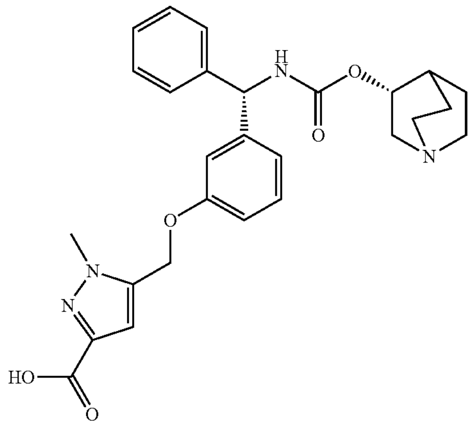 [SMILES: Cn1nc(C(=O)O)cc1COc1cccc([C@@H](NC(=O)O[C@H]2CN3CCC2CC3)c2ccccc2)c1] | Intermediate 21 | $^1$H NMR (400 MHz, DMSO): δ 8.26 (d, J = 9.3 Hz, 1 H), 7.33-7.18 (m, 6 H), 7.07 (s, 1 H), 6.99-6.91 (m, 2 H), 6.74 (s, 1 H), 5.82 (d, J = 9.2 Hz, 1 H), 5.18 (s, 2 H), 4.60 (s, 2 H), 3.88 (s, 3 H), 3.18-3.07 (m, 1 H), 2.74 (m, 4 H), 1.94 (s, 1 H), 1.83 (s, 1 H), 1.62 (s, 1 H), 1.52 (s, 1 H), 1.39 (s, 1 H). |
| 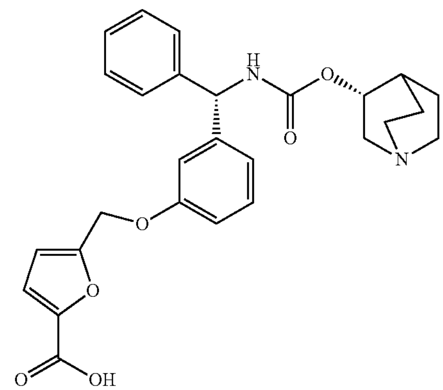 [SMILES: O=C(N[C@@H](c1ccccc1)c1cccc(OCc2ccc(C(=O)O)o2)c1)O[C@H]1CN2CCC1CC2] | Intermediate 22 | $^1$H NMR (400 MHz, DMSO): δ 8.32 (d, J = 9.3 Hz, 1 H), 7.36-7.28 (m, 4 H), 7.28-7.20 (m, 2 H), 7.08 (s, 1 H), 6.91 (t, J = 9.4 Hz, 2 H), 6.83 (d, J = 3.3 Hz, 1 H), 6.58 (d, J = 3.3 Hz, 1 H), 5.82 (d, J = 9.2 Hz, 1 H), 5.06 (s, 2 H), 4.73 (s, 1 H), 2.98 (s, 2 H), 2.88 (s, 2 H), 2.76 (d, J = 14.8 Hz, 1 H), 2.07 (s, 1 H), 1.94 (s, 1 H), 1.73 (s, 1 H), 1.65 (s, 2 H), 1.55 (s, 1 H). |
Examples 7-20 can be obtained using the procedure in Scheme D.
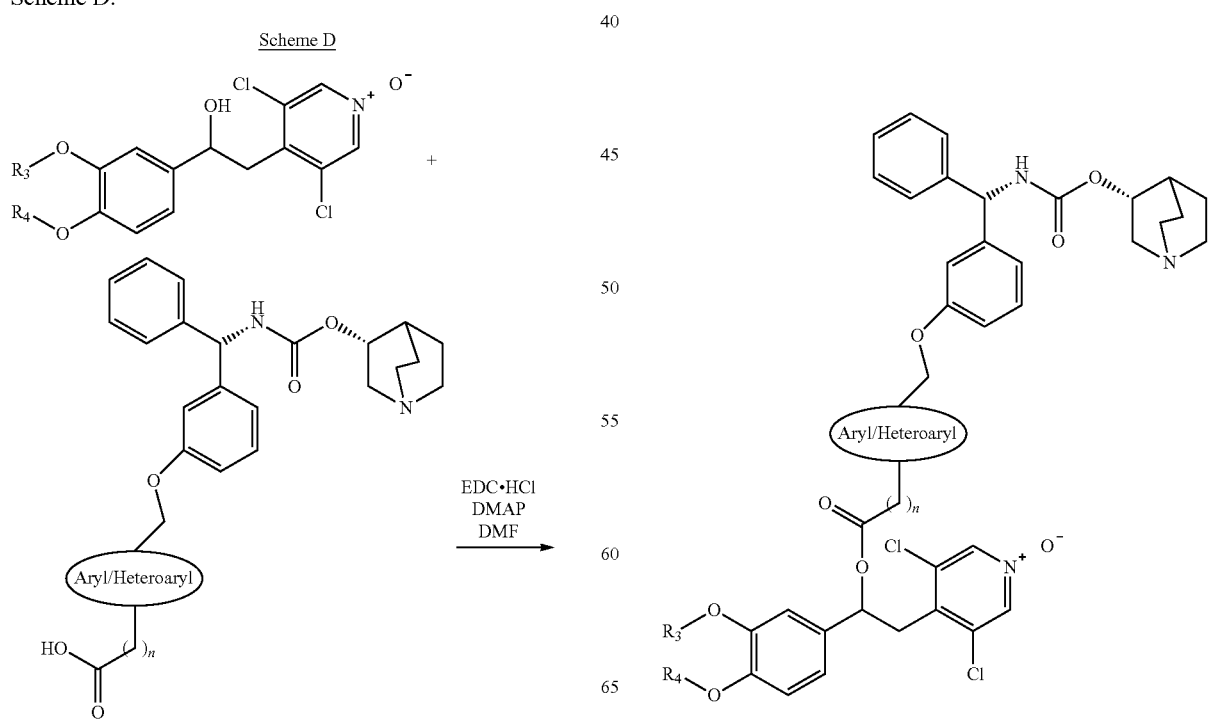
Scheme D

Example 7

[(1S)-2-(3,5-dichloro-1-oxido-pyridin-1-ium-4-yl)-1-(3,4-dimethoxyphenyl)-ethyl]4-[[3-[(S)-phenyl-[[(3R)-quinuclidin-3-yl]oxycarbonylamino]methyl]phenoxy]-methyl]benzoate (E7)

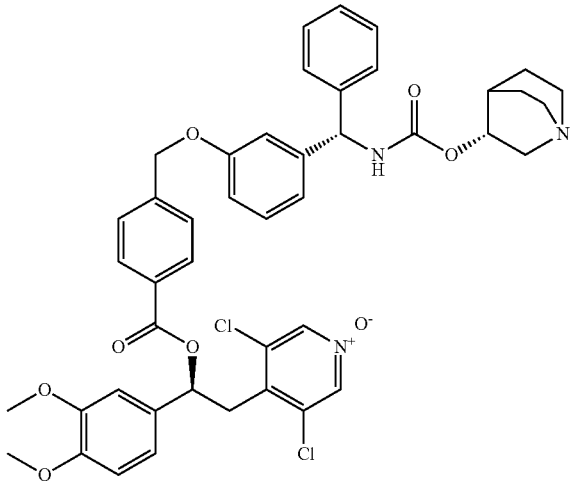

To a stirred solution of 4-((3-((S)-Phenyl((((R)-quinuclidin-3-yloxy)carbonyl)-amino)methyl)phenoxy)methyl)-benzoic acid (I17, 243 mg, 0.5 mmol) in DMF (2 mL) was added a solution of (1S)-2-(3,5-dichloro-1-oxido-pyridin-1-ium-4-yl)-1-(3,4-dimethoxyphenyl)-ethanol (172 mg, 0.5 mmol) in DMF (5 mL), followed by DMAP (31 mg, 0.25 mmol) and EDC.HCl (192 mg, 1 mmol). The mixture was allowed to stir at room temperature for 18 h and then the solvent was removed in vacuo. The residue was partitioned between DCM (15 mL) and saturated sodium bicarbonate solution (15 mL). The organic phase was washed with brine (15 mL), passed through a hydrophobic frit and the solvent was removed in vacuo. Purification was achieved by preparative HPLC to afford the title compound as a white solid (169 mg, 42%). $^1$H NMR (400 MHz, DMSO): δ 8.58 (s, 2 H), 8.27 (s, 1 H), 8.02 (d, J=8.1 Hz, 2 H), 7.59 (d, J=8.0 Hz, 2 H), 7.36-7.19 (m, 6 H), 7.10-6.88 (m, 6 H), 6.25 (dd, J=9.5, 4.4 Hz, 1 H), 5.84 (d, J=9.4 Hz, 1 H), 5.20 (s, 2 H), 4.64-4.57 (m, 1 H), 3.81 (s, 3 H), 3.78 (s, 3 H), 3.67 (dd, J=14.7, 9.7 Hz, 1 H), 3.37 (dd, J=14.1, 4.2 Hz, 1 H), 3.14 (t, J=11.7 Hz, 1 H), 2.83-2.52 (m, 5 H), 1.98-1.90 (m, 1 H), 1.88-1.76 (m, 1 H), 1.69-1.57 (m, 1 H), 1.57-1.44 (m, 1 H), 1.44-1.32 (m, 1 H). LCMS (Method 1): [MH+]=812 at 2.97 min.

The following compounds were synthesized via the same method as Example 7, starting from the appropriate alcohol.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl]3-[[3-[(S)-phenyl-[[(3R)-quinuclidin-3-yl]oxycarbonylamino]methyl]-phenoxy]methyl]benzoate formate salt | Example 8 | Intermediate 18 | $^1$H NMR (400 MHz, DMSO): δ 8.54 (s, 2 H), 8.24-8.22 (m, 1 H), 8.21 (s, 1 H), 8.05 (s, 1 H), 7.94 (d, J = 7.8 Hz, 1 H), 7.70 (d, J = 7.8 Hz, 1 H), 7.53 (t, J = 7.7 Hz, 1 H), 7.31-7.17 (m, 6 H), 7.05-6.88 (m, 6 H), 6.21 (dd, J = 9.5, 4.4 Hz, 1 H), 5.83 (d, J = 9.2 Hz, 1 H), 5.16 (s, 2 H), 4.52-4.59 (m, 1 H), 3.76 (s, 3 H), 3.75 (s, 3 H), 3.64 (dd, J = 14.7, 9.5 Hz, 1 H), 3.32 (dd, J = 14.7, 4.4 Hz, 1 H), 3.13-3.09 (m, 1 H), 2.74-2.51 (m, 5 H), 1.98-1.90 (m, 1 H), 1.88-1.75 (m, 1 H), 1.72-1.58 (m, 1 H), 1.56-1.43 (m, 1 H), 1.42-1.31 (m, 1 H). LCMS (Method 1): [MH+] = 812 at 2.93 min. |
| [(1S)-2-(3,5-dichloro-1-oxido-pyridin-1-ium-4-yl)-1-(3,4-dimethoxyphenyl)ethyl]3-methoxy-5-[[3-[(S)- | Example 9 | Intermediate 19 | $^1$H NMR (400 MHz, DMSO): δ 8.58 (s, 2 H), 8.32-8.21 (m, 2 H), 8.20 (s, 1 H), 7.67 (s, 1 |

| Structure | Example number | Precursor | Analytical Data |
|---|---|---|---|
| phenyl-[[(3R)-quinuclidin-3-yl]oxycarbonylamino]methyl]-phenoxy]methyl]benzoate formate salt 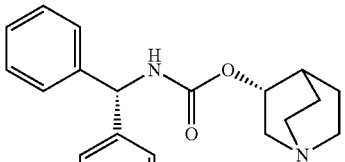 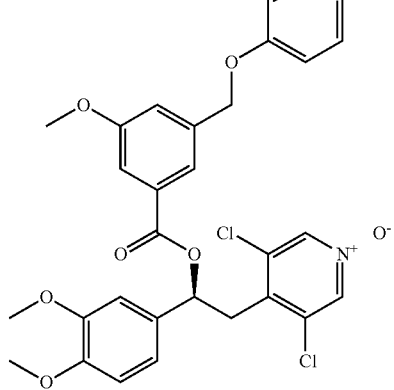 | | | H), 7.44 (s, 1 H), 7.39-7.18 (m, 7 H), 7.12-6.89 (m, 6 H), 6.22 (dd, J = 9.7, 4.3 Hz, 1 H), 5.85 (d, J = 9.1 Hz, 1 H), 5.15 (s, 2 H), 4.67-4.58 (m, 1 H), 3.85 (s, 3 H), 3.80 (s, 3 H), 3.78 (s, 3 H), 3.67 (dd, J = 14.9, 9.8 Hz, 1 H), 3.36 (dd, J = 14.5, 4.9 Hz, 1 H), 3.22-3.12 (m, 1 H), 2.87-2.57 (m, 5 H), 2.00-1.77 (m, 2 H), 1.71-1.34 (m, 3 H). LCMS (Method 1): [MH+] = 842 at 3.02 min. |
| [(1S)-2-(3,5-dichloro-1-oxido-pyridin-1-ium-4-yl)-1-(3,4-dimethoxyphenyl)ethyl]6-[[3-[(S)-phenyl-[[(3R)-quinuclidin-3-yl]oxycarbonylamino]methyl]-phenoxy]methyl]pyridine-3-carboxylate formate salt 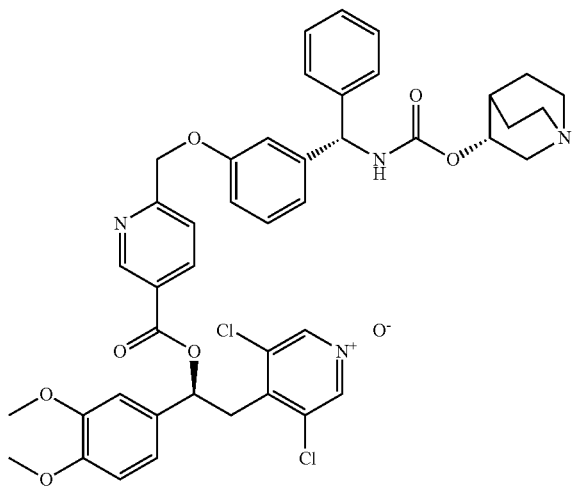 | Example 10 | Intermediate 20 | $^1$H NMR (400 MHz, DMSO): δ 9.13 (d, J = 2.1 Hz, 1 H), 8.58 (s, 2 H), 8.35 (dd, J = 8.2, 2.2 Hz, 1 H), 8.32-8.22 (m, 2 H), 8.21 (s, 1 H), 7.64 (d, J = 8.2 Hz, 1 H), 7.37-6.90 (m, 12 H), 6.27 (dd, J = 9.5, 4.3 Hz, 1 H), 5.84 (d, J = 9.2 Hz, 1 H), 5.28 (s, 2 H), 4.66-4.58 (m, 1 H), 3.82 (s, 3 H), 3.78 (s, 3 H), 3.69 (dd, J = 14.8, 9.7 Hz, 1 H), 3.38 (dd, J = 14.6, 5.0 Hz, 1 H), 3.22-3.12 (m, 1 H), 2.86-2.57 (m, 5 H), 2.00-1.92 (m, 1 H), 1.89-1.77 (m, 1 H), 1.70-1.33 (m, 3 H). LCMS (Method 1): [MH+] = 813 at 2.90 min. |
| [(1S)-2-(3,5-dichloro-1-oxido-pyridin-1-ium-4-yl)-1-(3,4-dimethoxyphenyl)ethyl]1-methyl-5-[[3-[(S)-phenyl-[[(3R)-quinuclidin-3- | Example 11 | Intermediate 21 | $^1$H NMR (400 MHz, DMSO): δ 8.56 (s, 2 H), 8.25 (d, J = 9.2 Hz, 1 H), 7.39-7.26 (m, 5 H), 7.22 (t, J = 7.0 Hz, 1 H), 7.09 (s, 1 H), 7.04- |

| Structure | Example number | Precursor | Analytical Data |
|---|---|---|---|
| yl]oxycarbonylamino]methyl]-phenoxy]methyl]pyrazole-3-carboxylate | | | 6.93 (m, 6 H), 6.20 (dd, J = 9.2, 4.8 Hz, 1 H), 5.86 (d, J = 9.4 Hz, 1 H), 5.22 (s, 2 H), 4.59 (d, J = 7.6 Hz, 1 H), 3.93 (s, 3 H), 3.79 (s, 3 H), 3.78 (s, 3 H), 3.60 (dd, J = 13.5, 8.5 Hz, 2 H), 3.35 (dd, J = 14.1, 4.7 Hz, 1 H), 2.79-2.50 (m, 5 H), 1.95-1.87 (m, 1 H), 1.86-1.75 (m, 1 H), 1.75-1.66 (m, 1 H), 1.53-1.42 (m, 1 H), 1.42-1.27 (m, 1 H). LCMS (Method 1): [MH+] = 816 at 2.73 min. |
| [(1S)-2-(3,5-dichloro-1-oxido-pyridin-1-ium-4-yl)-1-[4-(difluoromethoxy)-3-ethoxy-phenyl]ethyl]5-[[3-[(S)-phenyl-[[(3R)-quinuclidin-3-yl]oxycarbonylamino]-methyl]phenoxy]methyl]furan-2-carboxylate formate salt | Example 12 | Intermediate 22 | $^1$H NMR (400 MHz, DMSO): δ 8.57 (s, 2 H), 8.26 (s, 1 H), 8.23 (s, 1 H), 7.38 (d, J = 3.5 Hz, 1 H), 7.34-7.15 (m, 8 H), 7.07 (t, J = 74.6 Hz, 1 H), 7.09-6.85 (m, 4 H), 6.78 (d, J = 3.5 Hz, 1 H), 6.13 (dd, J = 9.3, 4.6 Hz, 1 H), 5.82 (d, J = 9.3 Hz, 1 H), 5.12 (s, 2 H), 4.61-4.53 (m, 1 H), 4.18-4.04 (m, 2 H), 3.57 (dd, J = 14.1, 9.0 Hz, 1 H), 3.33 (dd, J = 12.6, 5.2 Hz, 1 H), 3.10 (dd, J = 16.2, 8.8 Hz, 1 H), 2.79-2.56 (m, 5 H), 1.94-1.86 (m, 1 H), 1.84-1.72 (m, 1 H), 1.65-1.53 (m, 1 H), 1.53-1.41 (m, 1 H), 1.39-1.30 (m, 1 H), 1.33 (t, J = 6.9 Hz, 3 H). LCMS (Method 2): [MH+] = 852 at 4.17 min. |
| [(1S)-1-[3-(cyclopropylmethoxy)-4-(difluoromethoxy)phenyl]-2-(3,5-dichloro-1-oxido-pyridin-1-ium-4-yl)ethyl]5-[[3-[(S)-phenyl-[[(3R)-quinuclidin-3-yl]oxycarbonylamino]methyl]-phenoxy]methyl]furan-2-carboxylate formate salt | Example 13 | Intermediate 22 | $^1$H NMR (400 MHz, DMSO): δ 8.57 (s, 2 H), 8.26 (s, 1 H), 8.23 (s, 1 H), 7.37 (d, J = 3.5 Hz, 1 H), 7.35-7.16 (m, 8 H), 7.07 (t, J = 74.6 Hz, 1 H), 7.07-6.87 (m, 4 H), 6.78 (d, J = 3.5 Hz, 1 H), 6.12 (dd, J = 9.3, 4.5 Hz, 1 |

-continued

| Structure | Example number | Precursor | Analytical Data |
|---|---|---|---|
| | | | H), 5.82 (d, J = 9.3 Hz, 1 H), 5.11 (s, 2 H), 4.60-4.53 (m, 1 H), 3.92 (d, J = 7.0 Hz, 2 H), 3.57 (dd, J = 14.7, 9.3 Hz, 1 H), 3.32 (dd, J = 14.3, 5.8 Hz, 1 H), 3.10 (dd, J = 16.3, 9.0 Hz, 1 H), 2.78-2.54 (m, 5 H), 1.94-1.85 (m, 1 H), 1.84-1.73 (m, 1 H), 1.65-1.53 (m, 1 H), 1.53-1.41 (m, 1 H), 1.40-1.27 (m, 1 H), 1.26-1.14 (m, 1 H), 0.59-0.53 (m, 2 H), 0.37-0.32 (m, 2 H). LCMS (Method 2): [MH+] = 878 at 3.83 min. |
| [2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]-phenoxy]methyl]furan-2-carboxylate formate salt | Example 14 | Intermediate 22 | 1H NMR (400 MHz, acetone-d6) δ ppm 8.36 (s, 2 H), 7.19-7.58 (m, 8 H), 7.13 (d, J = 2.21 Hz, 1 H), 7.03-7.09 (m, 2 H), 6.87-7.01 (m, 3 H), 6.57-6.73 (m ,1 H), 6.25 (dd, J = 9.70, 4.41 Hz, 1 H), 5.95 (d, J = 8.38 Hz, 1 H), 5.22 (s, 2 H), 4.80 (m, 1 H), 3.77 and 3.85 (2 s, 3 H each, 6 H), 3.71 (dd, J = 13.89, 9.92 Hz, 1 H), 3.39 (dd, J = 14.11, 4.85 Hz, 1 H), 3.18-3.34 (m, 1 H), 2.68-3.02 (m, 5 H), 2.08-2.18 (m, 1 H), 1.48-1.98 (m, 4 H). MS/ESI+ [MH+] = 802.3 |
| [(1S)-2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]-phenoxy]methyl]furan-2-carboxylate formate salt | Example 15 | Intermediate 22 | $^1$H NMR (400 MHz, acetone) δ ppm 8.26 (s, 2 H), 7.19-7.43 (m, 8 H), 7.13 (m, 1 H), 6.81-7.09 (m, 5 H), 6.66 (d, J = 3.53 Hz, 1 H), 6.25 (dd, J = 9.70, 4.41 Hz, 1 H), 5.95 (d, |

| Structure | Example number | Precursor | Analytical Data |
|---|---|---|---|
| Obtained from compound 14 by HPLC separation | | | J = 8.38 Hz, 1 H), 5.19 (s, 2 H), 4.73 (d, J = 3.53 Hz, 1 H), 3.77 and 3.84 (2 s, 3 H each, 6 H), 3.71 (dd, J = 14.11, 9.70 Hz, 1 H), 3.39 (dd, J = 14.11, 4.41 Hz, 1 H), 3.23 (m, 1 H), 2.65-2.90 (m, 5 H), 1.25-1.92 (m, 5 H). MS/ESI+ [MH+] = 802.3 |
| [(1R)-2-(3,5-dichloro-1-oxido-pyridin-1-ium-4-yl)-1-(3,4-dimethoxyphenyl)ethyl]-5-[[3-[(S)-phenyl-[[(3R)-quinuclidin-3-yl]oxycarbonylamino]methyl]-phenoxy]methyl]furan-2-carboxylate formate salt 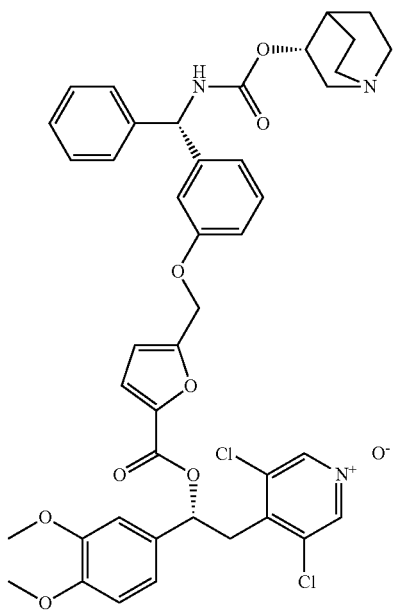 Obtained from compound 14 by HPLC separation | Example 16 | Intermediate 22 | ¹H NMR (400 MHz, acetone) δ ppm 8.25 (2s, 2H), 7.20-7.47 (m, 8 H), 6.81-7.18 (m, 6 H), 6.67 (d, J = 2.65 Hz, 1 H), 6.25 (dd, J = 9.26, 4.41 Hz, 1 H), 5.95 (d, J = 8.38 Hz, 1 H), 5.12 (s, 2 H), 4.63-4.93 (m, 1 H), 3.77 and 3.89 (2 s, 3 H each, 6 H), 3.71 (dd, J = 13.67, 9.70 Hz, 1 H), 3.39 (dd, J = 14.11, 3.97 Hz, 1 H), 3.25 (d, J = 11.03 Hz, 1 H), 2.67-2.98 (m, 5 H), 1.44-1.95 (m, 5 H). MS/ESI+ [MH+] = 802.3 |
| [2-(3,5-dichloro-1-oxido-pyridin-1-ium-4-yl)-1-(3,4-dimethoxyphenyl)ethyl]4-[[3-[phenyl-[[(3R)- | Example 17 | Intermediate 9 | 1H NMR (300 MHz, DMSO) δ ppm 9.46 (br. s., 1 H), 8.54 (s, 2 H), 8.40 (d, 1 H), 7.92- |

| Structure | Example number | Precursor | Analytical Data |
|---|---|---|---|
| quinuclidin-3-yl]oxycarbonylamino]methyl]phenoxy]methyl]benzoate | | | 8.07 (m, 2 H), 7.47-7.63 (m, 2 H), 7.14-7.39 (m, 6 H), 6.76-7.12 (m, 6 H), 6.24 (dd, 1 H), 5.82 (d, 1 H), 5.17 (s, 2 H), 4.72-4.94 (m, 1 H), 3.78 (s, 3 H), 3.76 (s, 3 H), 3.64-3.74 (m, 1 H), 3.64 (dd, 1 H), 3.35 (dd, 1 H), 3.00-3.30 (m, 5 H), 2.15-2.26 (m, 1 H), 1.46-2.15 (m, 4 H).<br>MS/ESI+ [MH+] = 812.6 |
| [2-(3,5-dichloro-1-oxido-pyridin-1-iumn-4-yl)-1-(3,4-dimethoxyphenyl)ethyl]3-[[3-[phenyl-[[(3R)-quinuclidin-3-yl]oxycarbonylamino]methyl]phenoxy]methyl]benzoate | Example 18 | Intermediate 9 | 1H NMR (300 MHz, DMSO) δ ppm 9.44 (br. s., 1 H), 8.52 (s, 2 H), 8.40 (d, 1 H), 8.00-8.06 (m, 1 H), 7.87-7.99 (m, 1 H), 7.65-7.75 (m, 1 H), 7.54 (t, 1 H), 7.14-7.40 (m, 6 H), 6.83-7.10 (m, 6 H), 6.22 (dd, 1 H), 5.83 (d, 1 H), 5.16 (s, 2 H), 4.71-4.93 (m, 1 H), 3.77 (s, 3 H), 3.76 (s, 3 H), 3.61-3.73 (m, 1 H), 3.64 (dd, 1 H), 3.34 (dd, 1 H), 2.91-3.30 (m, 5 H), 2.14-2.25 (m, 1 H), 1.53-2.14 (m, 4 H).<br>MS/ESI+ [MH+] = 812.6 |

Example 19

[(1S)-2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]-methyl]phenoxy]methyl]thiophene-2-carboxylate formate salt

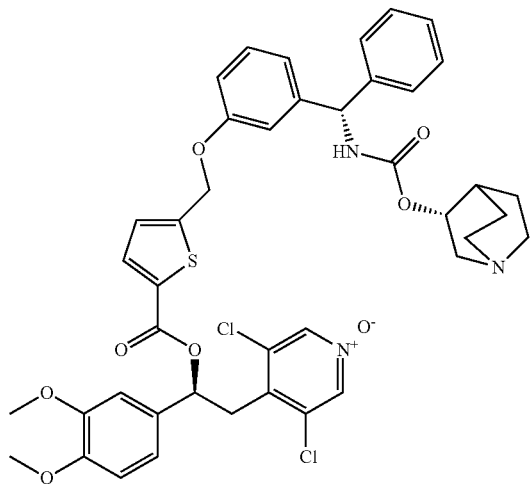

To a stirred solution of methyl 5-((3-((S)-phenyl((((R)-quinuclidin-3-yloxy)carbonyl)amino)methyl)-phenoxy)methyl)thiophene-2-carboxylate (I15, 331 mg, 0.65 mmol) in THF (2 mL) and methanol (2 mL) was added an aqueous solution of lithium hydroxide (1 M, 1.31 mL, 1.31 mmol). The mixture was stirred at room temperature for 16 h. The pH of the reaction mixture was adjusted to 2 by the addition of 1M aqueous solution of hydrochloric acid. The solvents were removed in vacuo to provide a light yellow solid (0.480 mg) which was dried in a vacuum oven for 16 h and taken on to the next step without further purification.

To a stirred solution of the previously obtained residue (214 mg, 0.41 mmol) in DMF (2 mL) was added a solution of (1S)-2-(3,5-dichloro-1-oxido-pyridin-1-ium-4-yl)-1-(3,4-dimethoxyphenyl)-ethanol (100 mg, 0.29 mmol), followed by DMAP (17 mg, 0.14 mmol) and EDC.HCl (111 mg, 0.58 mmol). The mixture was allowed to stir at room temperature for 18 h and then the solvent was removed in vacuo. The residue was partitioned between ethyl acetate (15 mL) and saturated sodium bicarbonate solution (15 mL). The organic phase was washed with brine (15 mL) was passed through a hydrophobic fit and the solvent was removed in vacuo. Purification was achieved by preparative HPLC to afford the title compound as a white solid (37 mg, 11%).

$^1$H NMR (400 MHz, CDCl$_3$): δ 8.46 (s, 1 H), 8.10 (s, 2 H), 7.66 (d, J=3.8 Hz, 1 H), 7.41-7.15 (m, 6 H), 7.03-6.83 (m, 7 H), 6.22 (dd, J=9.8, 4.5 Hz, 1 H), 5.91 (s, 1 H), 5.63 (s, 1 H), 5.18 (s, 2 H), 4.80 (s, 1 H), 3.89 (d, J=9.1 Hz, 6 H), 3.68 (dd, J=14.0, 9.9 Hz, 1 H), 3.31 (dd, J=14.1, 4.7 Hz, 1 H), 3.12-2.65 (m, 6 H), 2.17 (s, 1 H), 2.00 (s, 1 H), 1.77 (s, 1 H), 1.65 (s, 1 H), 1.51 (s, 1 H). LCMS (Method 1): [MH+]=818 at 2.90 min.

The following compound was prepared from Intermediate 16 via a similar method as that of Example 19.

| Structure | Example number | Precursor | Analytical Data |
|---|---|---|---|
| [(1S)-2-(3,5-dichloro-1-oxido-pyridin-1-ium-4-yl)-1-(3,4-dimethoxyphenyl)ethyl]2-[3-[[3-[(S)-phenyl-[[(3R)-quinuclidin-3-yl]oxycarbonylamino]methyl]-phenoxy]methyl]phenyl]acetate formate salt | Example 20 | Intermediate 16 | $^1$H NMR (400 MHz, DMSO): δ 8.52 (s, 2 H), 8.32-8.30 (m, 1 H), 8.27 (s, 1 H), 7.47-7.23 (m, 9 H), 7.16-7.12 (m, 1 H), 7.07-7.04 (m, 1 H), 6.98-6.87 (m, 5 H), 5.99 (dd, J = 9.6, 4.5 Hz, 1 H), 5.87-5.83 (m, 1 H), 5.02 (s, 2 H), 4.66-4.64 (m, 1 H), 3.75 (s, 3 H), 3.71 (s, 3 H), 3.73-3.66 (m, 2 H), 3.44 (dd, J = 14.0, 9.6 Hz, 1 H), 3.20 (dd, J = 14.0, 4.5 Hz, 2 H), 2.84-2.57 (m, 5 H), 2.02-1.93 (m, 1 H), 1.92-1.83 (m, 1 H), 1.73-1.64 (m, 1 H), 1.63-1.51 (m, 1 H), 1.51-1.48 (m, 1 H). LCMS (Method 1): [MH+] = 826 at 2.94 min. |

Intermediate 23. Methyl 1-(4-((3-((S)-phenyl((((R)-quinuclidin-3-yloxy)carbonyl)-amino)methyl)phenoxy)-methyl)benzoyl)azetidine-3-carboxylate (I23)

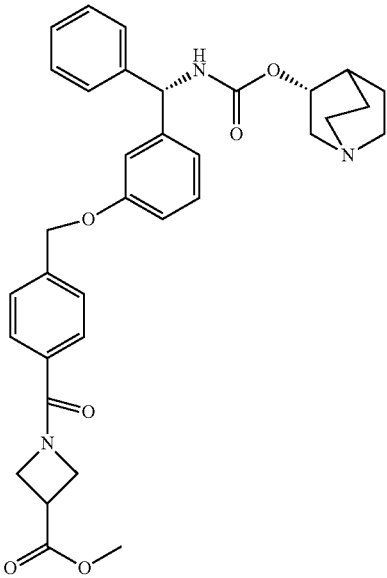 [SMILES: COC(=O)C1CN(C(=O)c2ccc(COc3cccc([C@@H](NC(=O)O[C@H]4CN5CCC4CC5)c4ccccc4)c3)cc2)C1]

To a solution of 4-((3-((S)-Phenyl((((R)-quinuclidin-3-yloxy)carbonyl)amino)-methyl)phenoxy)methyl)benzoic acid (I17, 321 mg, 0.66 mmol)) in DMF (10 mL) was added methyl azetidine-3-carboxylate hydrochloride salt (200 mg, 1.32 mmol) followed by 4-(dimethylamino)-pyridine (81 mg, 0.66 mmol) and N-(3-dimethylaminopropyl)-N'-ethylcarbodiimide hydrochloride (506 mg, 2.64 mmol). The resulting mixture was stirred at room temperature for 16 h. Additional 4-(dimethylamino)-pyridine (40 mg, 0.33 mmol) and N-(3-dimethylaminopropyl)-N'-ethylcarbodiimide hydrochloride (250 mg, 1.32 mmol) was added and the reaction mixture was stirred for 4 h before being partitioned between EtOAc (100 mL) and water (40 mL). The organic layer was dried over $MgSO_4$, filtered and the solvent was removed in vacuo. A thick oily residue was obtained (370 mg) and was used in the next step without further purification.

$^1$H NMR (400 MHz, $CDCl_3$): δ 8.02 (s, 1 H), 7.64 (d, J=8.0 Hz, 2 H), 7.45 (d, J=7.9 Hz, 2 H), 7.38-7.30 (m, 2 H), 7.30-7.20 (m, 3 H), 6.91-6.83 (m, 3 H), 5.98-5.86 (m, 1 H), 5.37-5.24 (m, 1 H), 5.05 (s, 2 H), 4.76-4.69 (m, 1 H), 4.56-4.46 (m, 1 H), 4.41 (t, J=9.2 Hz, 2 H), 4.48-4.28 (m, 1 H), 3.77 (s, 3 H), 3.58-3.42 (m, 1 H), 3.32-3.15 (m, 1 H), 2.90-2.80 (m, 2 H), 2.80-2.62 (m, 3 H), 2.08-1.92 (m, 1 H), 1.90-1.70 (m, 1 H), 1.70-1.46 (m, 2H), 1.45-1.28 (m, 1 H). LCMS (Method 2): [MH+]=584 at 3.47 min.

The following compound was synthesized via a similar method as that of Intermediate 23.

| Structure | Intermediate | Precursor | Analytical Data |
|---|---|---|---|
| 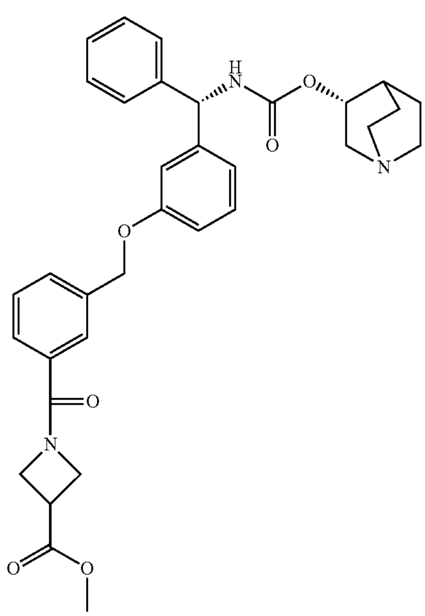 [SMILES: COC(=O)C1CN(C(=O)c2cccc(COc3cccc([C@@H](NC(=O)O[C@H]4CN5CCC4CC5)c4ccccc4)c3)c2)C1] | Intermediate 24 | Intermediate 18 | $^1$H NMR (400 MHz, $CDCl_3$): δ 7.67 (s, 1 H), 7.57 (d, J = 7.6 Hz, 1 H), 7.53-7.49 (m, 1 H), 7.42 (t, J = 7.6 Hz, 1 H), 7.37-7.20 (m, 6 H), 6.87 (t, J = 8.6 Hz, 3 H), 5.97-5.85 (m, 1 H), 5.42-5.28 (m, 1 H), 5.05 (s, 2 H), 4.74-4.70 (m, 1 H), 4.48-4.28 (m, 4 H), 3.77 (s, 3 H), 3.47 (t, J = 8.0 Hz, 1 H), 3.29-3.15 (m, 1 H), 2.92-2.80 (m, 2 H), 2.80-2.63 (m, 3 H), 2.05-1.94 (m, 1 H), 1.88-1.71 (m, 1 H), 1.71-1.46 (m, 2 H), 1.43-1.29 (m, 1 H). LCMS (Method 2): [MH+] = 584 at 3.52 min. |

Examples 21-32 can be obtained using the procedure in Scheme E.
Scheme E
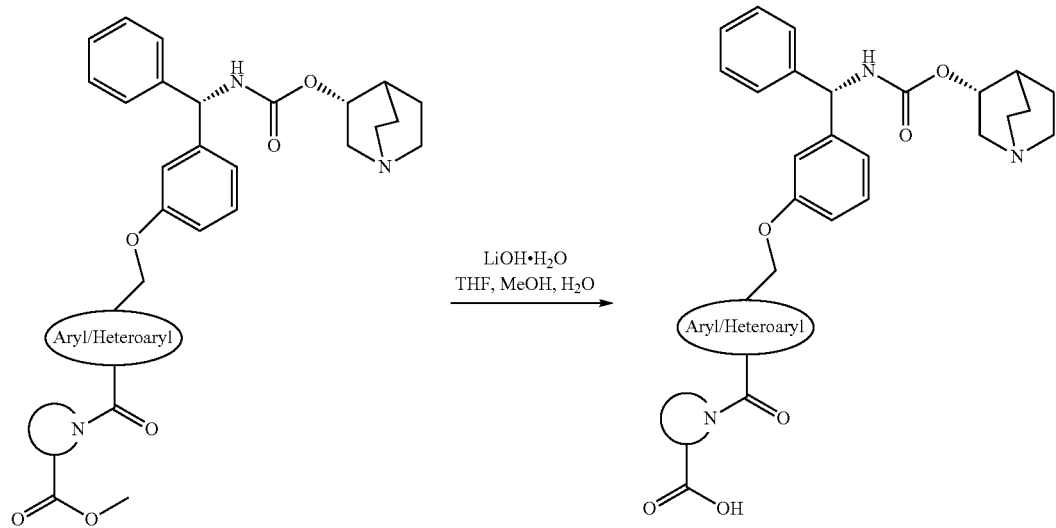
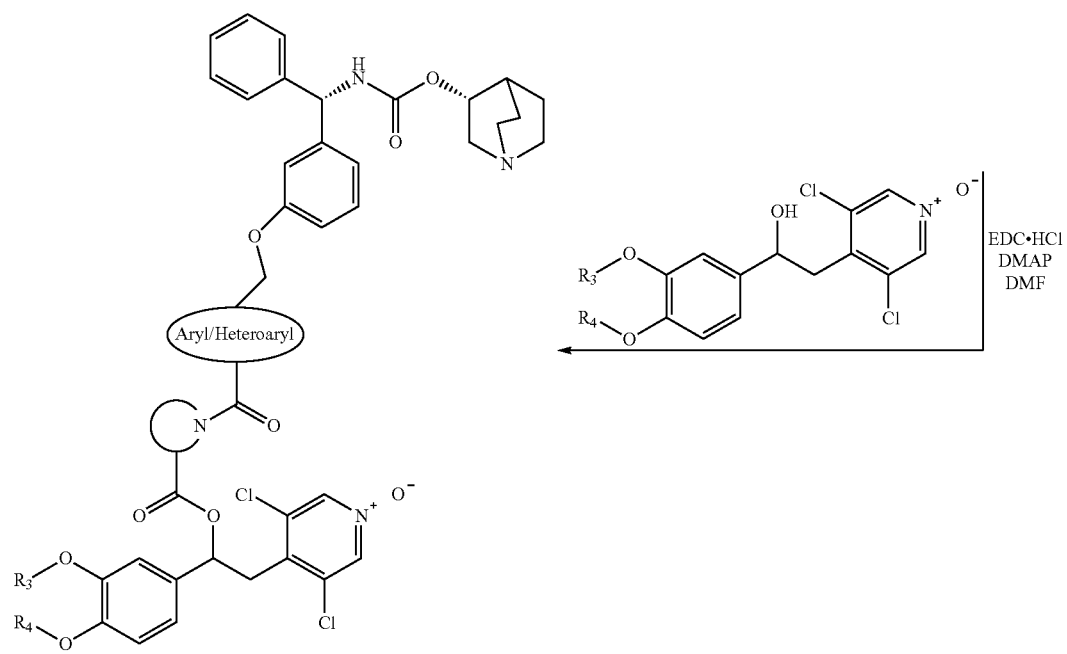

Example 21

[(1S)-2-(3,5-dichloro-1-oxido-pyridin-1-ium-4-yl)-1-(3,4-dimethoxyphenyl)ethyl]1-[4-[[3-[(S)-phenyl-[[(3R)-quinuclidin-3-yl]-oxycarbonylamino]methyl]phenoxy]methyl]benzoyl]azetidine-3-carboxylate (E21)

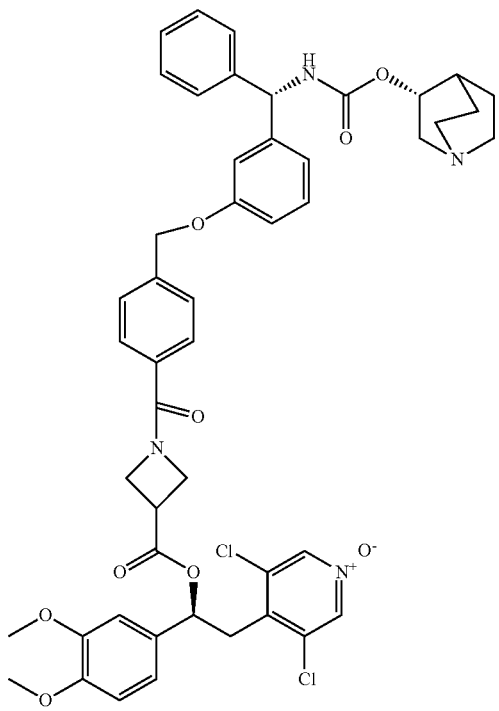

To a solution of methyl 1-(4-((3-((S)-phenyl((((R)-quinuclidin-3-yloxy)carbonyl)amino)methyl)phenoxy)methyl) benzoyl)azetidine-3-carboxylate (I23, 350 mg, 0.60 mmol) in THF (3 mL) and MeOH (3 mL) was added an aqueous solution of LiOH (1 N, 1.2 mL, 1.2 mmol) at room temperature. The resulting mixture was stirred for 16 h before being cooled to 0° C. and acidified with 2 N HCl to pH 2. The resulting mixture was then concentrated in vacuo and azeotroped to dryness with toluene. To a solution of the carboxylic acid in DMF (5 mL) was then added (S)-3,5-dichloro-4-(2-(3,4-dimethoxyphenyl)-2-hydroxyethyl)pyridine 1-oxide (248 mg, 0.72 mmol) followed by 4-(dimethylamino)-pyridine (37 mg, 0.30 mmol) and N-(3-dimethylaminopropyl)-N'-ethyl-carbodiimide hydrochloride (230 mg, 1.20 mmol). The resulting mixture was stirred at room temperature for 16 h and partitioned between EtOAc (50 mL) and water (20 mL). The organic layer was dried over MgSO$_4$, filtered and the solvent was removed in vacuo. The residue was dissolved in DMSO (3.0 mL) and purified by preparative HPLC to provide the title compound (14 mg, 3% over two steps) as white solid.

$^1$H NMR (400 MHz, DMSO at 110° C.): δ 8.33 (s, 2 H), 7.60-7.55 (m, 2 H), 7.53-7.48 (m, 1 H), 7.48 (d, J=8.0 Hz, 2 H), 7.32-7.26 (m, 4 H), 7.24-7.18 (m, 2 H), 7.01 (t, J=2.0 Hz, 1 H), 6.96-6.91 (m, 3 H), 6.91-6.86 (m, 2 H), 6.06 (dd, J=9.0, 4.9 Hz, 1 H), 5.81 (d, J=8.8 Hz, 1 H), 5.13 (s, 2 H), 4.59 (dtd, J=8.3, 3.5, 1.3 Hz, 1 H), 4.34 (t, J=9.2 Hz, 2 H), 4.12 (dd, J=9.2, 5.9 Hz, 2 H), 3.77 (s, 3 H), 3.76 (s, 3 H), 3.59-3.48 (m, 1 H), 3.51 (dd, J=14.5, 9.0 Hz, 1 H), 3.28 (dd, J=14.2, 5.0 Hz, 1 H), 3.05 (dd, J=14.8, 8.2 Hz, 1 H), 2.69 (t, J=8.1 Hz, 3 H), 2.67-2.56 (m, 2 H), 1.90-1.85 (m, 1 H), 1.76-1.69 (m, 1 H), 1.63-1.54 (m, 1 H), 1.49-1.43 (m, 1 H), 1.33-1.25 (m, 1 H). LCMS (Method 1): [MH+]=895 at 2.89 min.

Compounds herebelow reported were prepared starting from the appropriate starting materials according to analogous procedures as those hereabove described in Example 21.

| Structure | Intermediate | Precursor | Analytical Data |
|---|---|---|---|
| [(1S)-2-(3,5-dichloro-1-oxido-pyridin-1-ium-4-yl)-1-(3,4-dimethoxyphenyl)ethyl]1-[3-[[3-[(S)-phenyl-[[(3R)-quinuclidin-3-yl]oxycarbonylamino]-methyl]phenoxy]methyl]benzoyl]-azetidine-3-carboxylate formate salt | Example 22 | Intermediate 24 | $^1$H NMR (400 MHz, DMSO at 100° C.): δ 8.33 (s, 2 H), 8.12 (s, 1 H), 7.62 (s, 1 H), 7.56-7.47 (m, 3 H), 7.44 (t, J = 7.6 Hz, 1 H), 7.31-7.24 (m, 4 H), 7.24-7.18 (m, 2 H), 7.01 (d, J = 2.1 Hz, 1 H), 6.95-6.86 (m, 5 H), 6.06 (dd, J = 9.1, 4.9 Hz, 1 H), 5.81 |

-continued
| Structure | Intermediate | Precursor | Analytical Data |
|---|---|---|---|
| 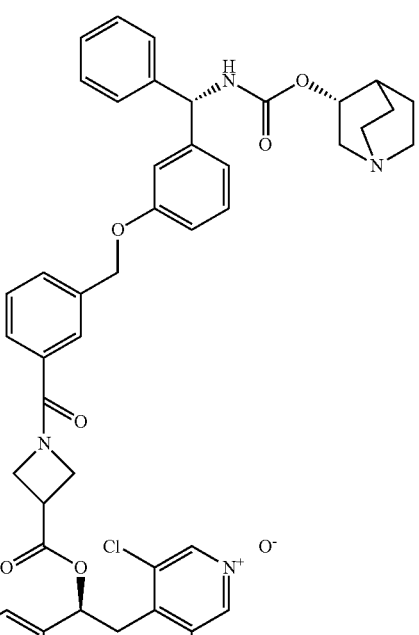 | | | (d, J = 8.8 Hz, 1 H), 5.13 (s, 2 H), 4.61-4.57 (m, 1 H), 4.32 (td, J = 9.1, 2.5 Hz, 2 H), 4.10 (td, J = 7.3, 2.1 Hz, 2 H), 3.77 (s, 3 H), 3.76 (s, 3 H), 3.56-3.47 (m, 2 H), 3.28 (dd, J = 14.2, 5.0 Hz, 1 H), 3.07 (dd, J = 14.6, 8.3 Hz, 1 H), 2.70 (t, J = 8.0 Hz, 3 H), 2.70-2.55 (m, 2 H), 1.90-1.87 (m, 1 H), 1.80-1.68 (m, 1 H), 1.60-1.57 (m, 1 H), 1.48-1.45 (m, 1 H), 1.35-1.23 (m, 1 H). LCMS (Method 1): [MH+] = 895 at 2.87 min. |
Compounds of Examples 23-32 can be obtained using the procedure in Scheme F.
Scheme F
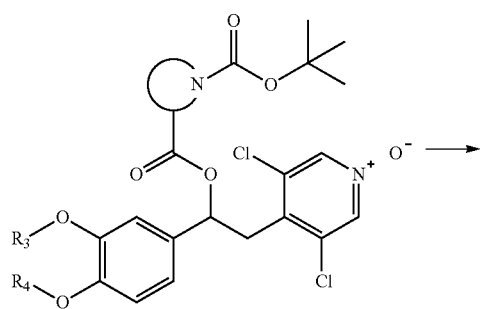

-continued
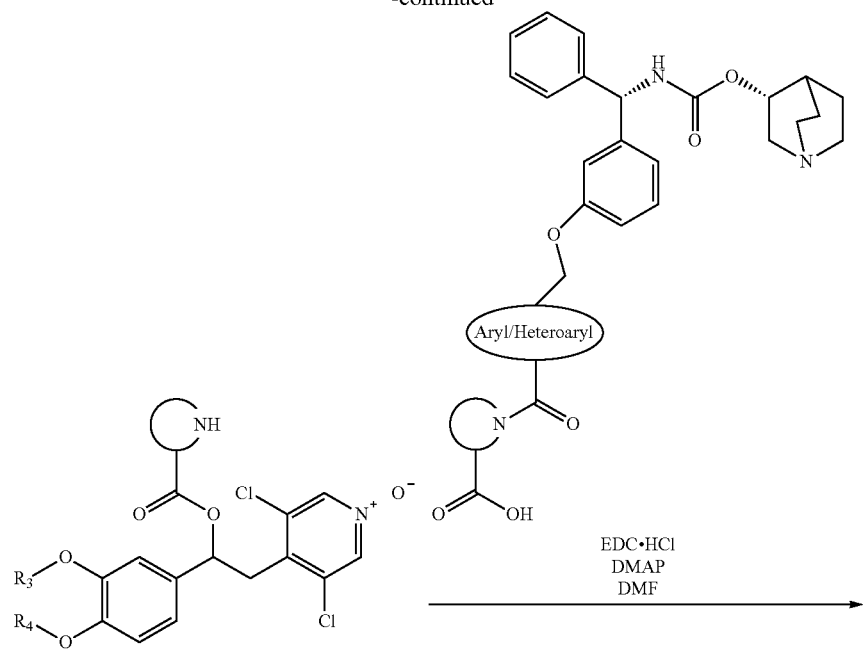
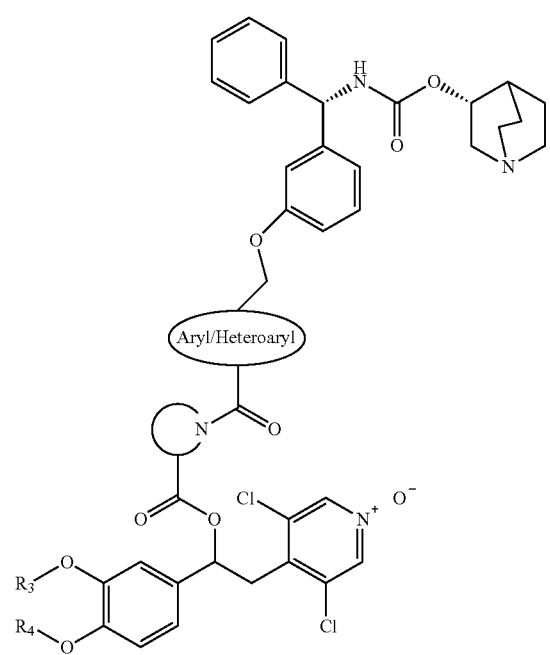

Example 23

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]benzoyl]pyrrolidine-2-carboxylate (E23)

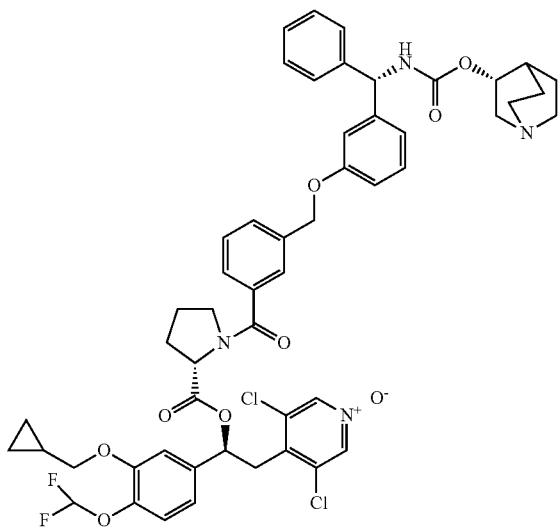

To a solution of 4-((S)-2-(((S)-1-(tert-butoxycarbonyl)pyrrolidine-2-carbonyl)oxy)-2-(3-(cyclopropylmethoxy)-4-(difluoromethoxy)phenyl)ethyl)-3,5-dichloropyridine 1-oxide (I2, 365 mg, 0.60 mmol) dissolved in EtOAc (10 mL) was added a solution of HCl in dioxane (4 N, 6 mL, 20 mmol) at 0° C. The resulting mixture was stirred for 1 h at 0° C. before being concentrated in vacuo. The residue was redissolved in DCM (50 mL) and washed with sat. NaHCO₃ (20 mL). The organic phase was passed through a hydrophobic fit and the solvent was removed in vacuo to give an oil that was used immediately without further purification. To a solution of the carboxylic acid, 3-((3-((S)-phenyl((((R)-quinuclidin-3-yloxy)carbonyl)amino)methyl)-phenoxy)methyl)benzoic acid (I18, 350 mg, 0.72 mmol) and 4-(dimethylamino)-pyridine (37 mg, 0.30 mmol) in DMF (3.0 mL) was added N-(3-dimethylaminopropyl)-N'-ethylcarbodiimide hydrochloride (230 mg, 1.2 mmol) in one portion at room temperature. The resulting mixture was stirred at room temperature for 16 h. EtOAc (50 mL) and water (20 mL) were then added, the layers separated, the organic layer dried over MgSO₄, filtered and the solvent removed in vacuo. The residue was dissolved in DMSO (3.0 mL) and purified by preparative HPLC to provide [(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenyl]carbamoyl]-phenyl]sulfonylpiperidine-2-carboxylate as a white solid (29 mg, 5% over two steps)

$^1$H NMR (400 MHz, DMSO at 110° C.): δ 8.34 (s, 2 H), 7.52-7.45 (m, 3 H), 7.40 (t, J=7.6 Hz, 1 H), 7.34 (d, J=8.2 Hz, 1 H), 7.32-7.26 (m, 4 H), 7.24-7.17 (m, 3 H), 7.12 (d, J=8.2 Hz, 1 H), 7.04 (d, J=2.1 Hz, 1 H), 7.00 (t, J=2.0 Hz, 1 H), 6.92 (dt, J=8.8, 2.1 Hz, 1 H), 6.92 (t, J=75 Hz, 1 H), 6.89 (dd, J=8.3, 2.6 Hz, 1 H), 6.08-5.93 (m, 1 H), 5.80 (s, 1 H), 5.10 (s, 2 H), 4.59-4.56 (m, 1 H), 4.51-4.47 (m, 1 H), 3.85 (d, J=6.7 Hz, 2 H), 3.49-3.41 (m, 2 H), 3.25 (dd, J=14.1, 5.1 Hz, 1 H), 3.04 (dd, J=14.8, 8.4 Hz, 1 H), 2.99-2.87 (m, 1 H), 2.71-2.60 (m, 2 H), 2.66-2.49 (m, 3 H), 2.32-2.28 (m, 1 H), 1.90-1.79 (m, 2H), 1.78 (m, 3 H), 1.64-1.52 (m, 1 H), 1.50-1.39 (m, 1 H), 1.32-1.22 (m, 1 H), 1.19-1.08 (m, 1 H), 0.52-0.47 (m, 2 H), 0.27-0.22 (m, 2 H). LCMS (Method 1): [MH+]=985 at 3.09 min.

Compounds herebelow reported were prepared starting from the appropriate starting materials according to analogous procedures as those hereabove described in Example 23.

| Structure | Example | Precursor | Analytical Data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]benzoyl]piperidine-2-carboxylate | Example 24 | Intermediate 4 and Intermediate 18 | $^1$H NMR (400 MHz, DMSO at 110° C.): δ 8.33 (s, 2 H), 7.52 (d, J = 9.2 Hz, 1 H), 7.47 (d, J = 7.9 Hz, 2 H), 7.33-7.25 (m, 5 H), 7.26-7.17 (m, 2 H), 7.16 (d, J = 8.2 Hz, 1 H), 7.10 (d, J = 2.1 Hz, 1 H), 7.02 (t, J = 2.0 Hz, 1 H), 6.97 (dd, J = 8.7, 2.3 |

| Structure | Example | Precursor | Analytical Data |
|---|---|---|---|
| 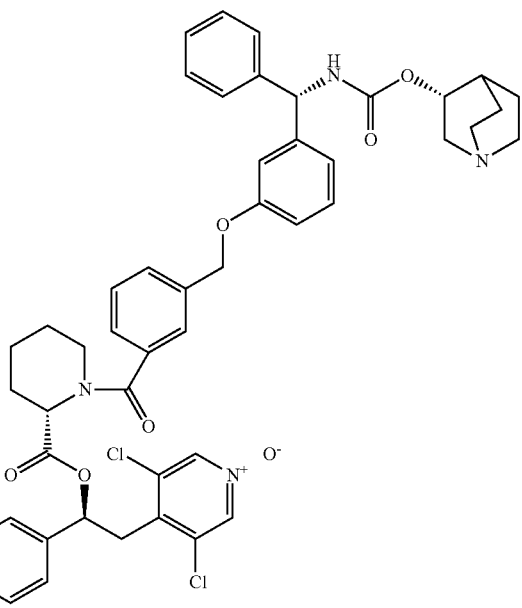 | | | Hz, 2 H), 6.96 (t, J = 76 Hz, 1 H), 6.94-6.88 (m, 2 H), 6.12 (dd, J = 8.8, 5.3 Hz, 1 H), 5.82 (d, J = 8.8 Hz, 1 H), 5.13 (s, 2 H), 4.97-4.86 (m, 1 H), 4.59 (ddt, J = 8.3, 3.5, 1.4 Hz, 1 H), 3.96-3.88 (m, 2 H), 3.86-3.71 (m, 1 H), 3.50 (dd, J = 14.2, 8.8 Hz, 1 H), 3.30 (dd, J = 14.2, 5.3 Hz, 1 H), 3.06 (dd, J = 15.4, 8.7 Hz, 1 H), 2.98-2.86 (m, 1 H), 2.70 (t, J = 8.1 Hz, 2 H), 2.66-2.55 (m, 2 H), 2.55-2.49 (m, 2 H), 2.20-2.12 (m, 1 H), 1.91-1.87 (m, 1 H), 1.81-1.69 (m, 2 H), 1.66-1.62 (m, 1 H), 1.62-1.53 (m, 1 H), 1.52-1.40 (m, 2 H), 1.34-1.25 (m, 1 H), 1.24-1.14 (m, 2 H), 0.58-0.52 (m, 2 H), 0.35-0.29 (m, 2 H). LCMS (Method 1): [MH+] = 999 at 3.22 min. |
| [(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]phenoxy]methyl]benzoyl]piperidine-2-carboxylate<br>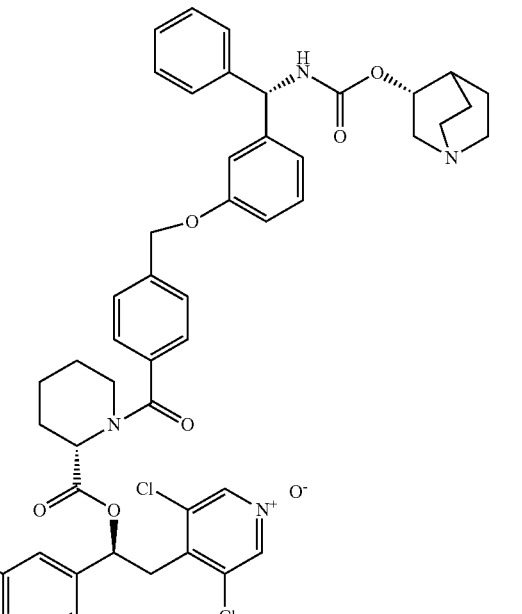 | Example 25 | Intermediate 4 and Intermediate 17 | $^1$H NMR (400 MHz, DMSO): δ 8.31 (s, 2 H), 7.50 (d, J = 8.0 Hz, 2 H), 7.42 (t, J = 7.6 Hz, 1 H), 7.38 (s, 1 H), 7.32-7.25 (m, 4 H), 7.25-7.16 (m, 3 H), 7.15 (d, J = 8.1 Hz, 1 H), 7.09 (d, J = 2.0 Hz, 1 H), 7.01 (t, J = 2.0 Hz, 1 H), 6.96 (dd, J = 8.3, 2.1 Hz, 1 H), 6.95 (t, J = 75 Hz, 1 H), 6.92 (d, J = 7.8 Hz, 1 H), 6.88 (dd, J = 8.2, 2.6 Hz, 1 H), 6.10 (dd, J = 8.8, 5.3 Hz, 1 H), 5.81 (d, J = 8.8 Hz, 1 H), 5.11 (s, 2 H), 5.00-4.86 (m, 1 H), 4.59 (ddt, J = 8.3, 3.6, 1.4 Hz, 1 H), 3.93-3.88 (m, 2 H), 3.79-3.65 (m, 1 H), 3.49 (dd, J = 14.2, 8.8 Hz, 1 H), 3.29 (dd, J = 14.3, 5.5 Hz, 1 H), 3.05 (dd, J = 15.1, 8.2 Hz, 1 H), 2.94-2.85 (m, 1 H), 2.72 (t, J = 8.1 Hz, 2 H), 2.66-2.55 (m, 2 H), 2.55-2.49 (m, 2 H), 2.20-2.11 (m, 1 H), 1.90-1.86 (m, 1 H), 1.79-1.69 (m, 2 H), 1.68-1.54 (m, 2 H), 1.51-1.36 (m, 2 H), 1.32-1.25 (m, 1 H), 1.22-1.13 (m, 2 H), 0.58-0.52 (m, 2 H), 0.34-0.29 (m, 2 H). LCMS (Method 1): [MH+] = 999 at 3.20 min. |
| [(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3- | Example 26 | Intermediate 2 and Inter- | $^1$H NMR (400 MHz, DMSO at 100° C.): δ 8.36 (s, 2 H), 8.14 (s, 1 H), 7.53-7.41 (m, 6 H), 7.32-7.25 (m, 4 H), 7.26-7.18 (m, 2 H), 7.13 (d, J = 8.1 Hz, 1 H), 7.06 |

| Structure | Example | Precursor | Analytical Data |
|---|---|---|---|
| yl]oxycarbonylamino]methyl]phenoxy]methyl]benzoyl]pyrrolidine-2-carboxylate formate salt 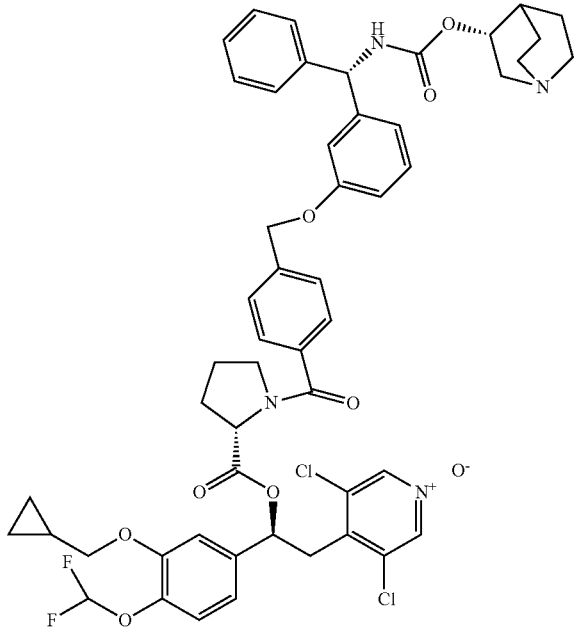 | | mediate 17 | (d, J = 2.1 Hz, 1 H), 7.02 (t, J = 2.1 Hz, 1 H), 6.96-6.91 (m, 1 H), 6.93 (t, J = 75 Hz, 1 H), 6.89 (dd, J = 8.0, 2.4 Hz, 1 H), 6.02 (dd, J = 9.0, 5.4 Hz, 1 H), 5.82 (d, J = 8.8 Hz, 1 H), 5.12 (s, 2 H), 4.62-4.57 (m, 1 H), 4.52 (dd, J = 8.5, 4.8 Hz, 1 H), 3.87 (d, J = 6.7 Hz, 2 H), 3.51 (t, J = 6.3 Hz, 2 H), 3.46 (dd, J = 14.5, 8.5 Hz, 1 H), 3.27 (dd, J = 14.2, 5.5 Hz, 1 H), 3.06 (dd, J = 14.5, 8.3 Hz, 1 H), 2.73-2.67 (m, 2 H), 2.68-2.57 (m, 2 H), 2.53-2.49 (m, 1 H), 2.34-2.24 (m, 1 H), 1.96-1.66 (m, 5 H), 1.64-1.55 (m, 1 H), 1.51-1.42 (m, 1 H), 1.34-1.24 (m, 1 H), 1.17-1.10 (m, 1 H), 0.55-0.49 (m, 2 H), 0.30-0.24 (m, 2 H). ). LCMS (Method 1): [MH+] = 985 at 3.13 min. |
| [(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]benzoyl]azetidine-3-carboxylate 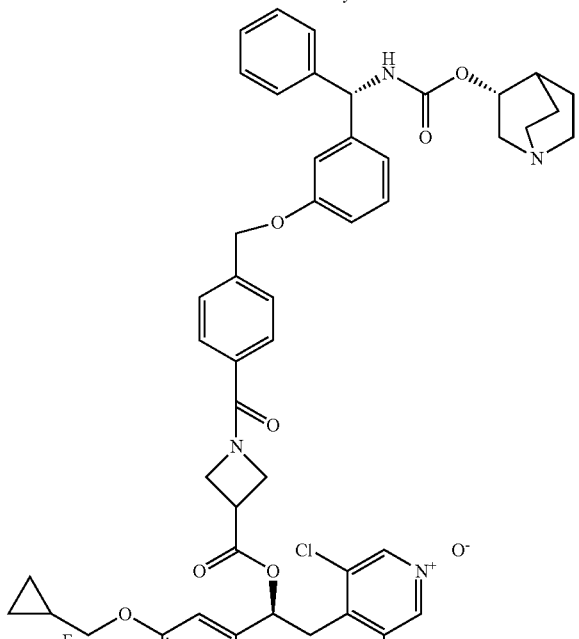 | Example 27 | Intermediate 3 and Intermediate 17 | $^1$H NMR (400 MHz, DMSO at 100° C.): δ 8.34 (s, 2 H), 7.83-7.77 (m, 1 H), 7.59-7.56 (m, 2 H), 7.50-7.46 (m, 2 H), 7.31 (s, 2 H), 7.30 (s, 2 H), 7.26-7.21 (m, 2 H), 7.16 (d, J = 8.2 Hz, 1 H), 7.09 (d, J = 2.1 Hz, 1 H), 7.01-6.98 (m, 2 H), 6.96-6.89 (m, 2 H), 6.95 (t, J = 75 Hz, 1 H), 6.07 (dd, J = 8.9, 4.9 Hz, 1 H), 5.82 (d, J = 8.9 Hz, 1 H), 5.13 (s, 2 H), 4.94-4.88 (m, 1 H), 4.35 (t, J = 9.2 Hz, 2 H), 4.12 (dd, J = 9.1, 5.9 Hz, 2 H), 3.93 (d, J = 6.7 Hz, 2 H), 3.68-3.54 (m, 2 H), 3.50 (dd, J = 14.2, 9.0 Hz, 1 H), 3.29 (dd, J = 14.2, 4.9 Hz, 1 H), 3.26-3.09 (m, 3 H), 3.09-3.06 (m, 2 H), 2.26-2.20 (m, 1 H), 2.05-2.04 (m, 1 H), 1.98-1.79 (m, 2H), 1.78-1.69 (m, 1 H), 1.24-1.15 (m, 1 H), 0.58-0.54 (m, 2 H), 0.35-0.32 (m, 2 H). [MH+] = 971 at 3.08 min. |

| Structure | Example | Precursor | Analytical Data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl]1-[3-[[3-[(S)-phenyl-[[(3R)-quinuclidin-3-yl]oxycarbonylamino]methyl]phenoxy]methyl]benzoyl]azetidine-3-carboxylate 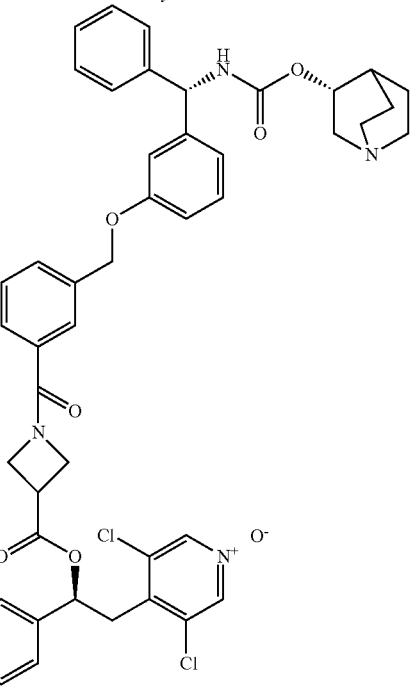 | Example 28 | Intermediate 3 and Intermediate 18 | ¹H NMR (400 MHz, DMSO at 100° C.): δ 8.33 (s, 2 H), 7.64-7.61 (m, 1 H), 7.57-7.48 (m, 3 H), 7.44 (t, J = 7.6 Hz, 1 H), 7.30-7.25 (m, 4 H), 7.26-7.16 (m, 2 H), 7.15 (d, J = 8.3 Hz, 1 H), 7.09 (d, J = 1.8 Hz, 1 H), 7.01-6.95 (m, 2 H), 6.96-6.85 (m, 2 H), 6.94 (t, J = 75 Hz, 1 H), 6.06 (dd, J = 8.9, 5.0 Hz, 1 H), 5.81 (d, J = 8.8 Hz, 1 H), 5.13 (s, 2 H), 4.62-4.57 (m, 1 H), 4.32 (dt, J = 10.5, 4.2 Hz, 2 H), 4.11 (s, 2 H), 3.93 (d, J = 6.6 Hz, 2 H), 3.59-3.51 (m, 1 H), 3.50 (dd, J = 14.2, 9.6 Hz, 1 H), 3.29 (dd, J = 14.2, 5.1 Hz, 1 H), 3.07 (dd, J = 16.8, 9.1 Hz, 1 H), 2.75-2.69 (m, 3 H), 2.66-2.51 (m, 2 H), 1.96-1.85 (m, 1 H), 1.82-1.66 (m, 1 H), 1.66-1.53 (m, 1 H), 1.53-1.41 (m, 1 H), 1.35-1.24 (m, 1 H), 1.23-1.14 (m, 1 H), 0.59-0.53 (m, 2 H), 0.39-0.28 (m, 2 H). LCMS (Method 1): [MH+] = 971 at 3.07 min. |

Example 29

[(1S)-1-[3-(cyclopropylmethoxy)-4-(difluoromethoxy)phenyl]-2-(3,5-dichloro-1-oxido-pyridin-1-ium-4-yl)ethyl](2S)-3-[4-[[3-[(S)-phenyl-[[(3R)-quinuclidin-3-yl]oxycarbonylamino]methyl]phenoxy]methyl]benzoyl]thiazolidine-2-carboxylate (E29)

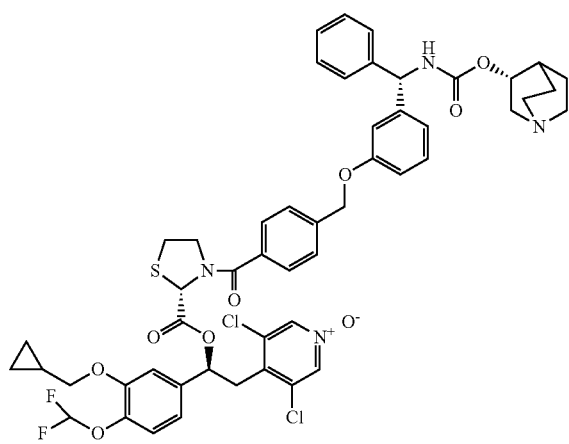

To a stirred solution of 4-((3-((S)-Phenyl((((R)-quinuclidin-3-yloxy)carbonyl)-amino)methyl)phenoxy)methyl)benzoic acid (I17, 61 mg, 0.125 mmol) in DMF (2 mL) was added [(1S)-1-[3-(cyclopropylmethoxy)-4-(difluoromethoxy)phenyl]-2-(3,5-dichloro-1-oxido-pyridin-1-ium-4-yl)ethyl] (2S)-thiazolidine-2-carboxylate hydrochloride (I5, 71 mg, 0.125 mmol) followed by DMAP (8 mg, 0.06 mmol) and EDC.HCl (48 mg, 0.25 mmol). The mixture was allowed to stir at room temperature for 18 h and then the solvent was removed in vacuo. The residue was partitioned between ethyl acetate (10 mL) and saturated sodium bicarbonate solution (10 mL). The organic phase was passed through a hydrophobic frit and the solvent was removed in vacuo. Purification was achieved by preparative HPLC to afford the title compound as a white solid (43 mg, 34%). ¹H NMR (400 MHz, DMSO): δ 8.57 (s, 2 H), 8.23 (d, J=9.4 Hz, 1 H), 7.58-7.42 (m, 4 H), 7.37-6.87 (m, 12 H), 7.10 (t, J=74.4 Hz, 1 H), 6.08-5.97 (m, 1 H), 5.84 (d, J=9.1 Hz, 1 H), 5.58-5.48 (m, 1 H), 5.16 (s, 2 H), 4.60-4.53 (m, 1 H), 4.00-3.88 (m, 1 H), 3.88 (d, J=7.0 Hz, 2 H), 3.83-3.73 (m, 1 H), 3.55-2.92 (m, 5 H), 2.79-2.31 (m, 5 H), 1.93-1.13 (m, 6 H), 0.58-0.52 (m, 2 H), 0.32-0.26 (m, 2 H). LCMS (Method 1): [MH+]=1003 at 3.16 min.

The following compounds were synthesized via a similar method.

| Structure | Example | Precursor | Analytical Data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[3-[(S)-phenyl-[[(3R)-quinuclidin-3-yl]oxycarbonylamino]methyl]phenoxy]methyl]benzoyl]thiazolidine-2-carboxylate 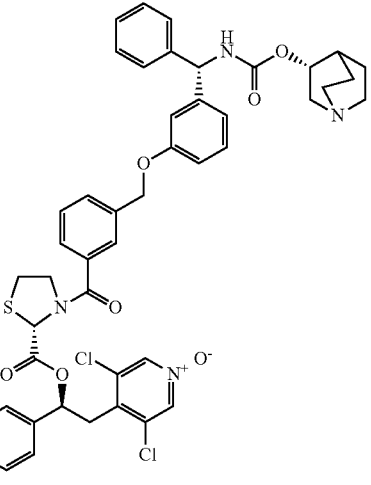 | Example 30 | Intermediate 5 and Intermediate 18 | $^1$H NMR (400 MHz, DMSO): δ 8.56 (s, 2 H), 8.21 (d, J = 9.2 Hz, 1 H), 7.62-6.87 (m, 16 H), 7.08 (t, J = 74.6 Hz, 1 H), 6.06-5.96 (m, 1 H), 5.82 (d, J = 9.1 Hz, 1 H), 5.58-5.48 (m, 1 H), 5.13 (s, 2 H), 4.59-4.51 (m, 1 H), 3.85 (d, J = 6.9 Hz, 2 H), 3.76-3.66 (m, 1 H), 3.51-2.86 (m, 6 H), 2.76-2.38 (m, 5 H), 1.92-1.12 (m, 6 H), 0.57-0.48 (m, 2 H), 0.31-0.22 (m, 2 H). LCMS (Method 1): [MH+] = 1003 at 3.15 min. |
| [(1S)-1-[3-(cyclopropylmethoxy)-4-(difluoromethoxy)phenyl]-2-(3,5-dichloro-1-oxido-pyridin-1-ium-4-yl)ethyl](2S)-3-[1-methyl-5-[[3-[(S)-phenyl-[[(3R)-quinuclidin-3-yl]oxycarbonylamino]methyl]phenoxy]methyl]pyrazole-3-carbonyl]thiazolidine-3-carboxylate trifluoroacetate salt 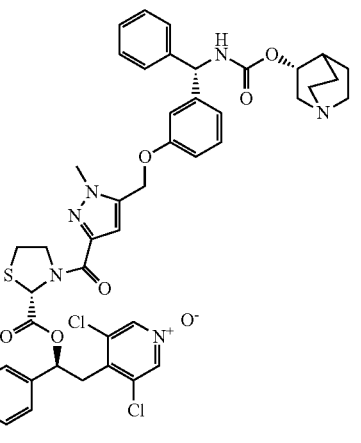 | Example 31 | Intermediate 5 and Intermediate 21 | $^1$H NMR (400 MHz, DMSO, 125° C.) δ 8.39-8.28 (m, 2 H), 7.61-7.55 (m, 1 H), 7.38-6.83 (m, 12 H), 6.78-6.60 (m, 1 H), 6.08-5.74 (m, 3 H), 5.20-5.07 (m, 2 H), 4.92-4.79 (m, 1 H), 4.46-4.30 (m, 1 H), 4.05-3.75 (m, 6 H), 3.61-3.23 (m, 3 H), 3.22-2.36 (m, 8 H), 2.23-2.10 (m, 1 H), 2.03-1.60 (m, 4 H), 1.25-1.12 (m, 1 H), 0.60-0.48 (m, 2 H), 0.39-0.26 (m, 2 H). LCMS (Method 1): [MH+] = 1007 at 3.11 min. |

Intermediate 25. (S)-methyl 1-((4-nitrophenyl)sulfonyl)pyrrolidine-2-carboxylate (I25)

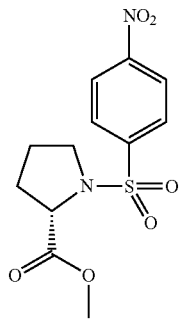 [SMILES: COC(=O)[C@@H]1CCCN1S(=O)(=O)c1ccc([N+](=O)[O-])cc1]

To a solution of (S)-proline methyl ester hydrochloride salt (2.5 g, 15.2 mmol) in DCM (20 mL) was added pyridine (2.6 mL, 33 mmol) and 4-nitrobenzenesulfonyl chloride (3.06 g, 13.8 mmol) at 0° C. The resulting mixture was stirred at room temperature for 18 h and then diluted with EtOAc (100 mL). The organic phase was washed with 1 N HCl (20 mL), brine (20 mL) and dried over MgSO$_4$. The mixture was filtered and the solvent was removed in vacuo to give a crude yellow solid that was used in the next step without further purification.

$^1$H NMR (400 MHz, CDCl$_3$): δ 8.39-8.35 (m, 2 H), 8.10-8.06 (m, 2 H), 4.47 (dd, J=8.6, 3.7 Hz, 1 H), 3.71 (s, 3 H), 3.51-3.42 (m, 2 H), 2.23-2.08 (m, 1 H), 2.09-1.96 (m, 2 H), 1.98-1.84 (m, 1 H). LCMS (Method 2): [MH+]=315 at 3.22 min.

Intermediate 26. (S)-methyl 1-((4-aminophenyl)sulfonyl)pyrrolidine-2-carboxylate (I26)

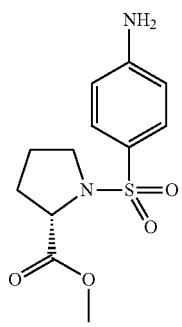

To a solution of (S)-methyl 1-((4-nitrophenyl)sulfonyl)pyrrolidine-2-carboxylate (642 mg, 2.0 mmol) in EtOAc (10 mL) was added SnCl$_2$.2H$_2$O (2.02 g, 9.0 mmol). The resulting mixture was stirred at room temperature for 2 d and diluted with EtOAc (50 mL) and 1 N NaOH (10 mL). The layers were separated and the aqueous phase re-extracted with EtOAc (2×50 mL). The combined organic phases were washed with brine (30 mL) and dried over MgSO$_4$. The mixture was filtered and the solvent was removed in vacuo to yield the title compound as a white solid (531 mg, 93%).

$^1$H NMR (400 MHz, CDCl$_3$): δ 7.68-7.62 (m, 2 H), 6.72-6.66 (m, 2 H), 4.26 (dd, J=8.0, 4.3 Hz, 1 H), 4.15-4.08 (m, 2 H), 3.73 (s, 3 H), 3.49-3.42 (m, 1 H), 3.32-3.24 (m, 1 H), 2.08-1.88 (m, 3 H), 1.80-1.69 (m, 1 H). LCMS (Method 1): [MH+]=285 at 3.07 min.

Intermediate 27. (S)-methyl 1-((4-(3-((S)-((tert-butoxycarbonyl)amino)(phenyl)methyl)-benzamido)phenyl)-sulfonyl)pyrrolidine-2-carboxylate (I27)

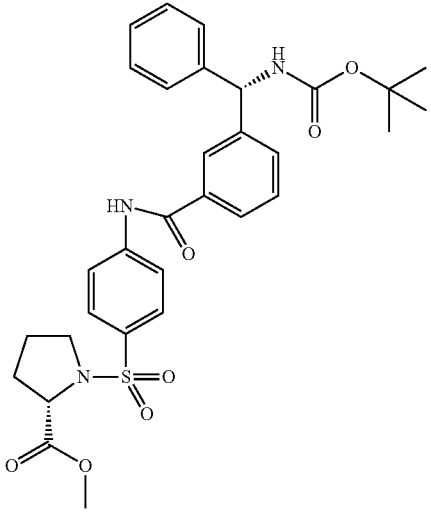 [SMILES: COC(=O)[C@@H]1CCCN1S(=O)(=O)c1ccc(NC(=O)c2cccc([C@@H](NC(=O)OC(C)(C)C)c3ccccc3)c2)cc1]

(S)-methyl 1-((4-(3-((S)-((tert-butoxycarbonyl)amino) (phenyl)methyl)benzamido)phenyl)-sulfonyl)pyrrolidine-2-carboxylate was prepared from Intermediate 26 and Intermediate 10 according to the same procedure described in Example 29.

$^1$H NMR (400 MHz, CDCl$_3$): δ 8.41 (s, 1 H), 7.85-7.74 (m, 6 H), 7.47-7.41 (m, 2 H), 7.36-7.24 (m, 3 H), 7.20 (d, J=7.4 Hz, 2 H), 5.93 (s, 1 H), 5.28 (s, 1 H), 4.30 (dd, J=7.9, 4.1 Hz, 1 H), 3.72 (s, 3 H), 3.53-3.45 (m, 1 H), 3.35-3.28 (m, 1 H), 2.07-1.92 (m, 3 H), 1.84-1.72 (m, 1 H), 1.44 (s, 9 H). LCMS (Method 2): [MH+]=594 at 4.15 min.

Intermediate 28. (S)-methyl 1-((4-((3-((S)-((tert-butoxycarbonyl)amino)(phenyl)-methyl)phenoxy)methyl)phenyl)-sulfonyl)pyrrolidine-2-carboxylate (I28)

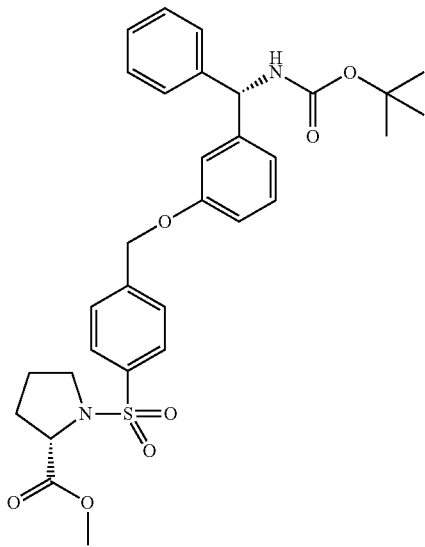 [SMILES: COC(=O)[C@@H]1CCCN1S(=O)(=O)c1ccc(COc2cccc([C@@H](NC(=O)OC(C)(C)C)c3ccccc3)c2)cc1]

To a mixture of (S)-proline methyl ester hydrochloride salt (1.6 g, 9.65 mmol) in THF (20 mL) was added Et₃N (1.34 mL, 9.65 mmol) at 0° C. The reaction mixture was stirred at room temperature for 30 min and cooled back down to 0° C. 3-Bromomethyl-benzenesulfonyl chloride (2.6 g, 9.65 mmol) and Et₃N (1.34 mL, 9.65 mmol) were then added to the slurry. The resulting mixture was stirred at room temperature for 3 h and then diluted with EtOAc (100 mL). The organic phase was washed with water (2×50 mL), brine (20 mL) and dried over MgSO₄. The solvent was removed in vacuo and the crude product was purified by chromatography via silica gel chromatography, eluting with 0-20% EtOAc in isohexane, to give 550 mg of (S)-methyl 1-((3-(bromomethyl)-phenyl)sulfonyl)pyrrolidine-2-carboxylate that was used in the next step without further purification. This residue was taken up in acetone (20 mL) and transferred to a microwave vial. (S)-tert-butyl ((3-hydroxyphenyl)(phenyl)methyl)carbamate (I8, 251 mg, 1.82 mmol) and K₂CO₃ (546 mg, 1.82 mmol) were added, and the mixture was heated to 130° C. under microwaves irradiation for 1 h. The mixture was stirred at room temperature for 18 h and partitioned between EtOAc (50 mL) and water (20 mL). The layers were separated and the aqueous phase extracted with EtOAc (3×30 mL). The combined organic phases were washed with brine (30 mL) and dried over MgSO₄. The mixture was filtered and the solvent was removed in vacuo. The residue was purified via silica gel chromatography, eluting with 0-20% EtOAc in isohexane, to give the title compound (636 mg, 60%).

$^1$H NMR (400 MHz, CDCl₃): δ 7.88 (d, J=8.2 Hz, 2 H), 7.55 (d, J=8.1 Hz, 2 H), 7.35-7.21 (m, 6 H), 6.92-6.82 (m, 3 H), 5.87 (s, 1 H), 5.14 (s, 1 H), 5.08 (s, 2 H), 4.37-4.31 (m, 1 H), 3.70 (s, 3 H), 3.52-3.46 (m, 1 H), 3.37-3.30 (m, 1 H), 2.07-1.94 (m, 3 H), 1.85-1.73 (m, 1 H), 1.44 (s, 9 H). LCMS (Method 1): [MH+]=581 at 4.53 min.

The following intermediates were synthesized via the same method as that of Intermediate 28.

| Structure | Intermediate | Analytical Data |
|---|---|---|
| 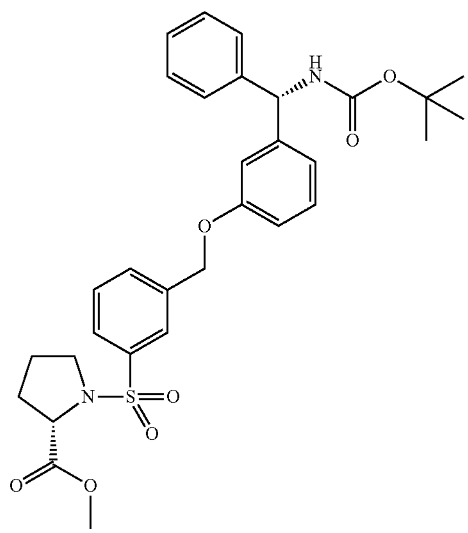 [SMILES: COC(=O)[C@@H]1CCCN1S(=O)(=O)c1cccc(COc2cccc([C@@H](NC(=O)OC(C)(C)C)c3ccccc3)c2)c1] | Intermediate 29 | $^1$H NMR (400 MHz, CDCl₃): δ 7.91-7.88 (m, 1 H), 7.86-7.79 (m, 1 H), 7.63 (d, J = 7.7 Hz, 1 H), 7.57-7.48 (m, 1 H), 7.36-7.28 (m, 2 H), 7.28-7.20 (m, 4 H), 6.92-6.82 (m, 3 H), 5.94-5.80 (m, 1 H), 5.25-5.14 (m, 1 H), 5.09 (s, 2 H), 4.36 (dd, J = 8.2, 3.9 Hz, 1 H), 3.71 (s, 3 H), 3.54-3.42 (m, 1 H), 3.37 (dt, J = 9.5, 7.1 Hz, 1 H), 2.20-1.80 (m, 3 H), 1.86-1.76 (m, 1 H), 1.44 (s, 9 H). LCMS (Method 2): [MH+] = 581 at 3.85 min. |
| 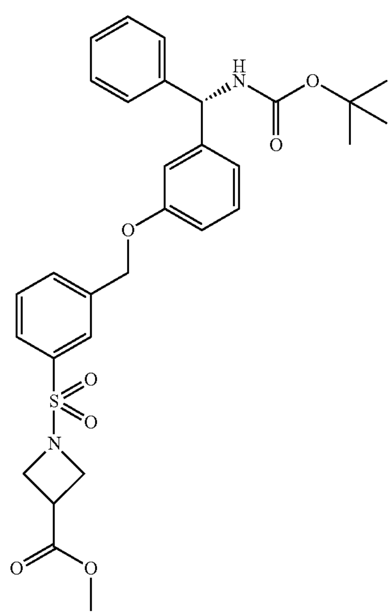 [SMILES: COC(=O)C1CN(S(=O)(=O)c2cccc(COc3cccc([C@@H](NC(=O)OC(C)(C)C)c4ccccc4)c3)c2)C1] | Intermediate 30 | $^1$H NMR (400 MHz, CDCl₃): δ 7.89 (s, 1 H), 7.79 (d, J = 7.7 Hz, 1 H), 7.70 (d, J = 7.7 Hz, 1 H), 7.59 (t, J = 7.7 Hz, 1 H), 7.35-7.29 (m, 2 H), 7.28-7.21 (m, 4 H), 6.91-6.83 (m, 3 H), 5.87 (s, 1 H), 5.21 (s, 1 H), 5.11 (s, 2 H), 3.97 (t, J = 8.6 Hz, 2 H), 3.92 (dd, J = 8.2, 7.1 Hz, 2 H), 3.62 (s, 3 H), 3.21 (tt, J = 8.9, 6.7 Hz, 1 H), 1.43 (s, 9 H). LCMS (Method 2): [MH+] = 567 at 4.28 min. |

| Structure | Intermediate | Analytical Data |
|---|---|---|
| 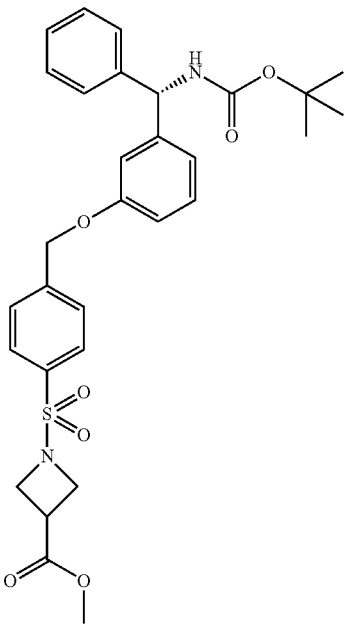 [SMILES: COC(=O)C1CN(S(=O)(=O)c2ccc(COc3cccc([C@@H](NC(=O)OC(C)(C)C)c4ccccc4)c3)cc2)C1] | Intermediate 31 | $^1$H NMR (400 MHz, CDCl$_3$): δ 7.85 (d, J = 8.1 Hz, 2 H), 7.62 (d, J = 8.1 Hz, 2 H), 7.36-7.28 (m, 2 H), 7.30-7.20 (m, 4 H), 6.93-6.81 (m, 3 H), 5.88 (s, 1 H), 5.18 (s, 1 H), 5.12 (s, 2 H), 4.01 (t, J = 8.6 Hz, 2 H), 3.94 (t, J = 7.3 Hz, 2 H), 3.61 (s, 3 H), 3.26 (tt, J = 8.9, 6.6 Hz, 1 H), 1.44 (s, 9 H). LCMS (Method 2): [MH+] = 567 at 4.28 min. |
| 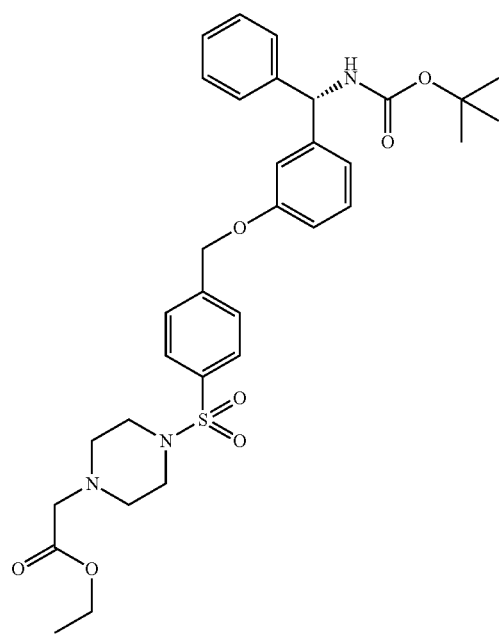 [SMILES: CCOC(=O)CN1CCN(S(=O)(=O)c2ccc(COc3cccc([C@@H](NC(=O)OC(C)(C)C)c4ccccc4)c3)cc2)CC1] | Intermediate 32 | $^1$H NMR (400 MHz, CDCl$_3$): δ 7.75 (d, J = 8.1 Hz, 2 H), 7.55 (d, J = 8.0 Hz, 2 H), 7.36-7.28 (m, 2 H), 7.29-7.21 (m, 4 H), 6.92-6.81 (m, 3 H), 5.88 (s, 1 H), 5.16 (s, 1 H), 5.08 (s, 2 H), 4.16 (q, J = 6.8 Hz, 2 H), 3.18 (s, 2 H), 3.11-3.05 (m, 4 H), 2.68-2.61 (m, 4 H), 1.44 (s, 9 H), 1.25 (t, J = 7.2 Hz, 3 H). LCMS (Method 1): [MH+] = 624 at 4.26 min |

| Structure | Intermediate | Analytical Data |
|---|---|---|
| 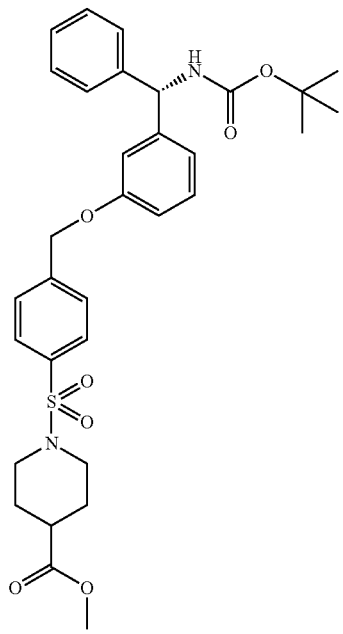 [SMILES: COC(=O)C1CCN(S(=O)(=O)c2ccc(COc3cccc([C@@H](NC(=O)OC(C)(C)C)c4ccccc4)c3)cc2)CC1] | Intermediate 33 | $^1$H NMR (400 MHz, CDCl$_3$): δ 7.68 (d, J = 8.0 Hz, 2 H), 7.49 (d, J = 7.9 Hz, 2 H), 7.27-7.14 (m, 6 H), 6.87-6.75 (m, 3 H), 5.81 (s, 1 H), 5.11 (s, 1 H), 5.01 (s, 2 H), 3.66-3.47 (m, 5 H), 2.48-2.36 (m, 2 H), 2.26-2.14 (m, 1 H), 1.95-1.87 m, 2 H), 1.81-1.69 (m, 2 H), 1.37 (s, 9 H). LCMS (Method 1): [MH+] = 595 at 4.57 min. |
| 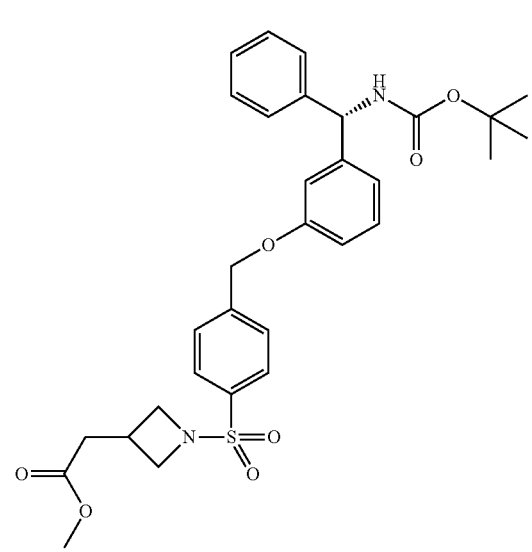 [SMILES: COC(=O)CC1CN(S(=O)(=O)c2ccc(COc3cccc([C@@H](NC(=O)OC(C)(C)C)c4ccccc4)c3)cc2)C1] | Intermediate 34 | $^1$H NMR (400 MHz, CDCl$_3$): δ 7.83 (d, J = 8.1 Hz, 2 H), 7.61 (d, J = 8.1 Hz, 2 H), 7.34-7.21 (m, 6 H), 6.92-6.81 (m, 3 H), 5.88 (s, 1 H), 5.21 (s, 1 H), 5.12 (s, 2 H), 3.93 (t, J = 8.2 Hz, 2 H), 3.62 (s, 3 H), 3.53-3.43 (m, 2 H), 2.82-2.69 (m, 1 H), 2.46 (d, J = 7.8 Hz, 2 H), 1.44 (s, 9 H). LCMS (Method 1): [MH+] = 581 at 3.84 min. |

Intermediate 35. (S)-methyl 1-((4-((3-((S)-phenyl ((((R)-quinuclidin-3-yloxy)carbonyl)amino)methyl)phenoxy)-methyl)phenyl)sulfonyl)pyrrolidine-2-carboxylate (I35)

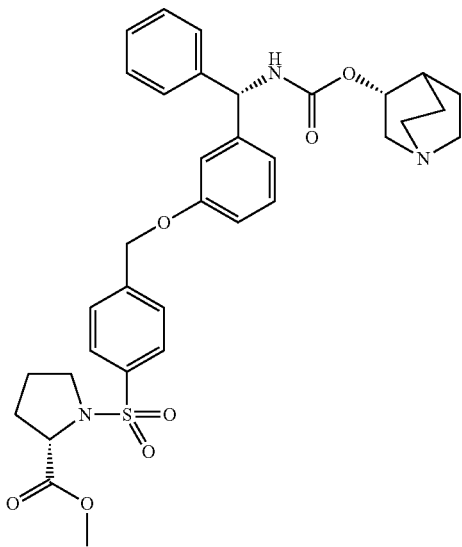 [SMILES: COC(=O)[C@@H]1CCCN1S(=O)(=O)c1ccc(COc2cccc([C@@H](NC(=O)O[C@H]3CN4CCC3CC4)c3ccccc3)c2)cc1]

To a mixture of (S)-methyl 1-((4-((3-((S)-((tert-butoxycarbonyl)amino)(phenyl)-methyl)-phenoxy)methyl)phenyl)-sulfonyl)pyrrolidine-2-carboxylate (I28, 636 mg, 1.1 mmol) in DCM (10 mL) was added TFA (3 mL) at 0° C. The reaction mixture was warmed to room temperature and stirred for 30 min before being concentrated in vacuo. The residue was diluted in DCM (50 mL) and washed with saturated aqueous NaHCO$_3$ (50 mL). The organic phase was passed through a hydrophobic frit and solvent was removed in vacuo. The residue (436 mg) was dissolved in pyridine (4 mL) and the reaction mixture was cooled to 0° C. (R)-quinuclidin-3-yl carbonochloridate hydrochloride (207 mg, 0.92 mmol, prepared as previously reported in 16, step 6) was added and the resulting mixture was stirred at room temperature for 16 h. Additional (R)-quinuclidin-3-yl carbonochloridate hydrochloride (104 mg, 0.46 mmol) was added at 0° C., the mixture was stirred for 2 h and then diluted with EtOAc (50 mL) and water (20 mL). The layers were separated and organic phase dried over MgSO$_4$. The mixture was filtered and the solvent was removed in vacuo to yield 576 mg of the crude title product as a thick oil which was used in the next step without further purification.

$^1$H NMR (400 MHz, CDCl$_3$): δ 7.88 (d, J=8.0 Hz, 2 H), 7.55 (d, J=8.0 Hz, 2 H), 7.36-7.21 (m, 6 H), 6.88 (m, 3 H), 5.95-5.86 (m, 1 H), 5.52-5.36 (m, 1 H), 5.10 (s, 2 H), 4.90 (s, 1 H), 4.36-4.31 (m, 1 H), 3.70 (s, 3 H), 3.52-3.45 (m, 1 H), 3.40-3.30 (m, 1 H), 3.21-3.06 (m, 2 H), 3.05-2.91 (m, 3 H), 2.34-2.19 (m, 1 H), 2.09-1.90 (m, 2 H), 1.88-1.68 (m, 2H). LCMS (Method 1): [MH+]=634 at 2.86 min.

The following intermediates were synthesized using a procedure analogous to that of Intermediate 35.

| Structure | Intermediate | Precursor | Analytical Data |
|---|---|---|---|
| 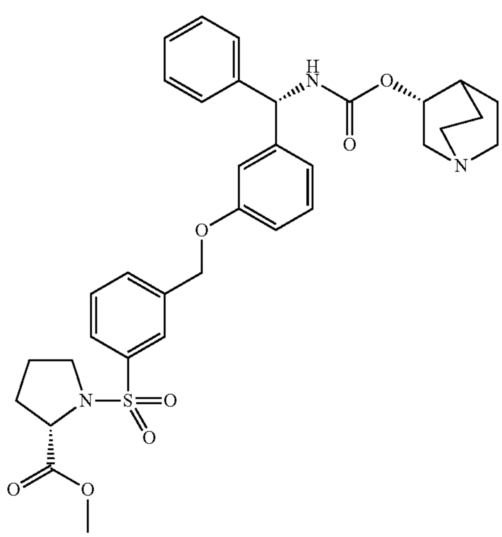 [SMILES: COC(=O)[C@@H]1CCCN1S(=O)(=O)c1cccc(COc2cccc([C@@H](NC(=O)O[C@H]3CN4CCC3CC4)c3ccccc3)c2)c1] | Intermediate 36 | Intermediate 29 | $^1$H NMR (400 MHz, CDCl$_3$): δ 7.92 (s, 1 H), 7.84 (d, J = 7.9 Hz, 1 H), 7.69 (tt, J = 7.6, 1.9 Hz, 1 H), 7.65 (d, J = 8.0 Hz, 1 H), 7.37-7.32 (m, 1 H), 7.34-7.27 (m, 4 H), 7.28-7.26 (m, 1 H), 6.95-6.85 (m, 3 H), 5.93 (s, 1 H), 5.45 (s, 1 H), 5.11 (s, 2 H), 4.82-4.73 (m, 1 H), 4.32 (dd, J = 7.8, 4.7 Hz, 1 H), 3.73-3.67 (m, 1 H), 3.71 (s, 3 H), 3.52-3.44 (m, 1 H), 3.36-3.27 (m, 1 H), 2.99-2.86 (m, 2 H), 2.87-2.72 (m, 3 H), 2.12-1.83 (m, 4 H), 1.80-1.65 (m, 3 H), 1.65-1.52 (m, 1 H), 1.51-1.39 (m, 1 H). LCMS (Method 2): [MH+] = 634 at 3.85 min. |

| Structure | Intermediate | Precursor | Analytical Data |
|---|---|---|---|
| 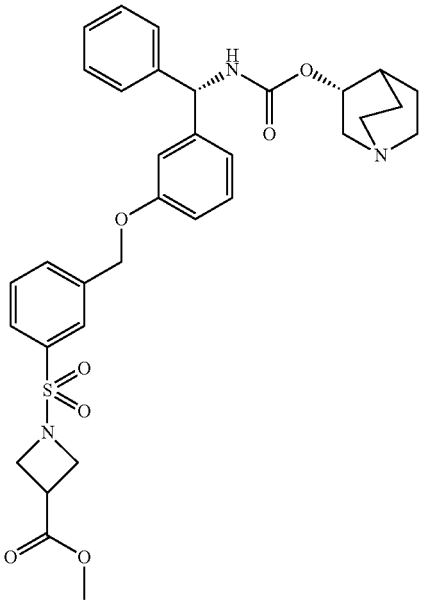 [SMILES: COC(=O)C1CN(S(=O)(=O)c2cccc(COc3cccc([C@@H](NC(=O)O[C@H]4CN5CCC4CC5)c4ccccc4)c3)c2)C1] | Intermediate 37 | Intermediate 30 | $^1$H NMR (400 MHz, CDCl$_3$): δ 7.89 (s, 1 H), 7.80 (d, J = 7.8 Hz, 1 H), 7.73-7.63 (m, 1 H), 7.68 (tt, J = 7.6, 1.9 Hz, 1 H), 7.64-7.55 (m, 1 H), 7.36-7.23 (m, 5 H), 6.93-6.85 (m, 3 H), 5.92 (s, 1 H), 5.47 (s, 1 H), 5.12 (s, 2 H), 4.75-4.70 (m, 1 H), 3.97 (dd, J = 8.6 Hz, 2 H), 3.92 (dd, J = 7.2 Hz, 2 H), 3.62 (s, 3 H), 3.22 (tt, J = 12.0, 4.2 Hz, 1 H), 3.28-3.10 (m, 1 H), 2.96-2.81 (m, 2 H), 2.80-2.61 (m, 3 H), 2.05-1.97 (m, 1 H), 1.89-1.74 (m, 1 H), 1.74-1.58 (m, 1 H), 1.58-1.46 (m, 1 H), 1.43-1.29 (m, 1 H). LCMS (Method 2): [MH+] = 620 at 3.27 min. |
| 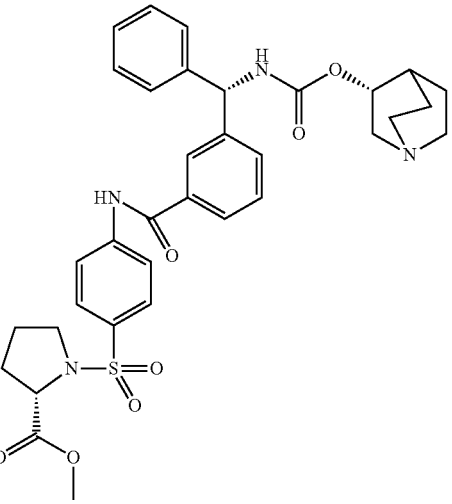 | Intermediate 38 | Intermediate 27 | $^1$H NMR (400 MHz, CDCl$_3$): δ 8.84 (s, 1 H), 7.90 (s, 1 H), 7.86-7.76 (m, 4 H), 7.68 (tt, J = 7.6, 1.8 Hz, 1 H), 7.51-7.41 (m, 2 H), 7.36-7.21 (m, 5 H), 5.98 (s, 2 H), 4.77-4.70 (m, 1 H), 4.28 (dd, J = 7.9, 4.3 Hz, 1 H), 3.71 (s, 3 H), 3.52-3.43 (m, 1 H), 3.30 (td, J = 8.3, 6.7 Hz, 1 H), 3.14 (dd, J = 14.6, 8.4 Hz, 1 H), 2.98-2.63 (m, 5 H), 2.15-2.06 (m, 1 H), 2.05-1.95 (m, 3 H), 1.91-1.81 (m, 1 H), 1.81-1.65 (m, 2 H), 1.63-1.48 (m, 1 H), 1.47-1.36 (m, 1 H). LCMS (Method 2): [MH+] = 647 at 3.09 min. |

-continued

| Structure | Intermediate | Precursor | Analytical Data |
|---|---|---|---|
| 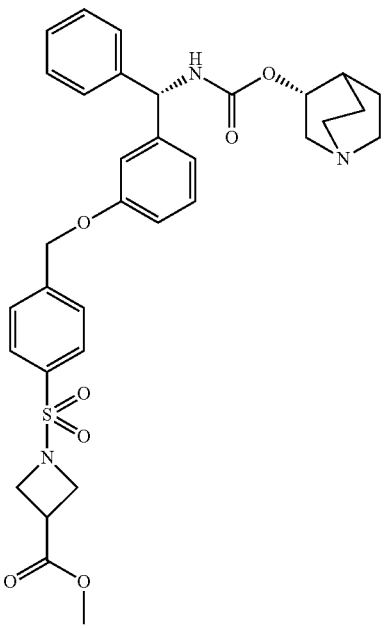 [SMILES: COC(=O)C1CN(S(=O)(=O)c2ccc(COc3cccc([C@@H](NC(=O)O[C@H]4CN5CCC4CC5)c4ccccc4)c3)cc2)C1] | Intermediate 39 | Intermediate 31 | $^1$H NMR (400 MHz, CDCl$_3$): δ 7.84 (d, J = 8.1 Hz, 2 H), 7.67 (tt, J = 7.7, 1.8 Hz, 1 H), 7.61 (d, J = 8.1 Hz, 2 H), 7.36-7.22 (m, 5 H), 6.94-6.84 (m, 3 H), 5.92 (s, 1 H), 5.59 (s, 1 H), 5.11 (s, 2 H), 4.75-4.70 (m, 1 H), 3.99 (dd, J = 8.6 Hz, 2 H), 3.93 (dd, J = 7.4 Hz, 2 H), 3.61 (s, 3 H), 3.26 (tt, J = 8.9, 6.6 Hz, 1 H), 3.31-3.19 (m, 1 H), 2.96-2.79 (m, 2 H), 2.79-2.63 (m, 3 H), 2.09-1.95 (m, 1 H), 1.88-1.75 (m, 1 H), 1.73-1.59 (m, 1 H), 1.59-1.46 (m, 1 H), 1.44-1.29 (m, 1 H). LCMS (Method 1): [MH+] = 620 at 2.85 min. |
| 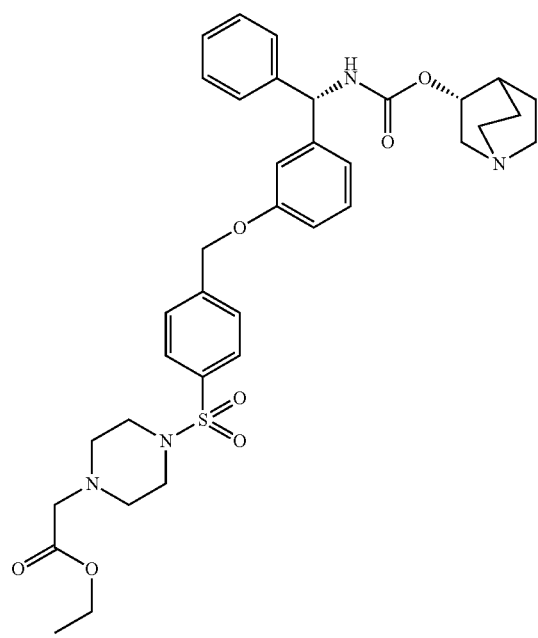 [SMILES: CCOC(=O)CN1CCN(S(=O)(=O)c2ccc(COc3cccc([C@@H](NC(=O)O[C@H]4CN5CCC4CC5)c4ccccc4)c3)cc2)CC1] | Intermediate 40 | Intermediate 32 | $^1$H NMR (400 MHz, CDCl$_3$): δ 7.75 (d, J = 8.0 Hz, 2 H), 7.68 (tt, J = 7.7, 1.9 Hz, 1 H), 7.56 (d, J = 8.0 Hz, 2 H), 7.37-7.22 (m, 5 H), 6.94-6.83 (m, 3 H), 5.92 (s, 1 H), 5.48 (s, 1 H), 5.09 (s, 2 H), 4.84-4.72 (m, 1 H), 4.14 (dq, J = 13.7, 7.1 Hz, 2 H), 3.35-3.22 (m, 1 H), 3.18 (s, 2 H), 3.12-3.04 (m, 4 H), 3.04-2.89 (m, 2 H), 2.89-2.71 (m, 3 H), 2.69-2.60 (m, 4 H), 2.17-2.07 (m, 1 H), 1.95-1.82 (m, 1 H), 1.79-1.67 (m, 1 H), 1.65-1.54 (m, 1 H), 1.53-1.38 (m, 1 H), 1.25 (td, J = 7.1, 3.6 Hz, 3 H). LCMS (Method 1): [MH+] = 677 at 2.70 min. |

-continued
| Structure | Intermediate | Precursor | Analytical Data |
|---|---|---|---|
| 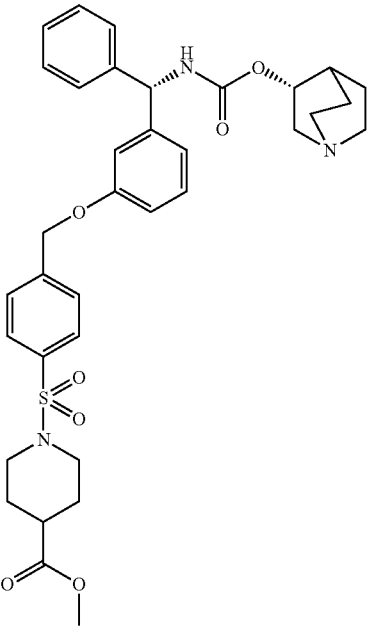 [SMILES: COC(=O)C1CCN(S(=O)(=O)c2ccc(COc3cccc([C@@H](NC(=O)O[C@H]4CN5CCC4CC5)c4ccccc4)c3)cc2)CC1] | Intermediate 41 | Intermediate 33 | 1H NMR (400 MHz, CDCl3): δ 7.76 (d, J = 8.1 Hz, 2 H), 7.57 (d, J = 8.1 Hz, 2 H), 7.38-7.32 (m, 2 H), 7.31-7.25 (m, 4 H), 6.94-6.84 (m, 3 H), 5.91 (s, 1 H), 5.53 (s, 1 H), 5.10 (s, 2 H), 4.93-4.85 (m, 1 H), 3.68-3.60 (m, 2 H), 3.65 (s, 3 H), 3.47-3.33 (m, 1 H), 3.15-3.04 (m, 2 H), 3.02-2.89 (m, 3 H), 2.50 (t, J = 12.0 Hz, 2 H), 2.33-2.20 (m, 1 H), 2.02-1.94 (m, 3 H), 1.89-1.76 (m, 4 H), 1.75-1.66 (m, 1 H), 1.67-1.54 (m, 1 H). LCMS (Method 1): [MH+] = 648 at 2.91 min. |
| 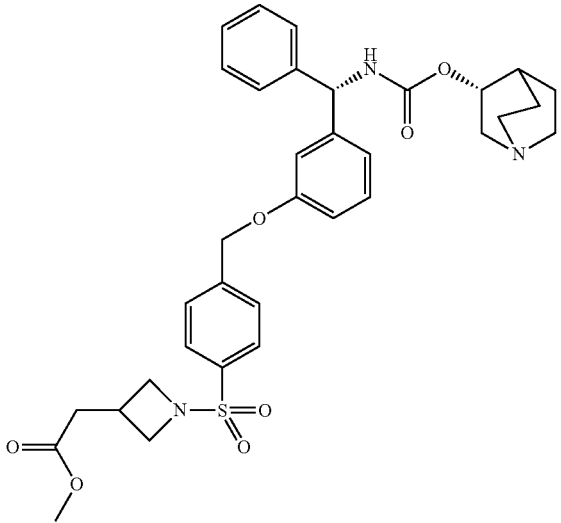 [SMILES: COC(=O)CC1CN(S(=O)(=O)c2ccc(COc3cccc([C@@H](NC(=O)O[C@H]4CN5CCC4CC5)c4ccccc4)c3)cc2)C1] | Intermediate 42 | Intermediate 34 | 1H NMR (400 MHz, CDCl3): δ 7.84 (d, J = 8.1 Hz, 2 H), 7.61 (d, J = 8.0 Hz, 2 H), 7.37-7.12 (m, 6 H), 6.95-6.85 (m, 3 H), 5.91 (s, 1 H), 5.44 (s, 1 H), 5.13 (s, 2 H), 4.88-4.80 (m, 1 H), 3.93 (t, J = 8.2 Hz, 2 H), 3.62 (s, 3 H), 3.50 (dd, J = 8.2, 5.9 Hz, 2 H), 3.41-3.28 (m, 1 H), 3.16-2.94 (m, 2 H), 2.96-2.84 (m, 3 H), 2.83-2.69 (m, 1 H), 2.46 (d, J = 7.8 Hz, 2 H), 2.24-2.13 (m, 1 H), 2.05-1.89 (m, 1 H), 1.87-1.72 (m, 1 H), 1.72-1.59 (m, 1 H), 1.58-1.46 (m, 1 H). LCMS (Method 1): [MH+] = 634 at 2.86 min. |

Examples 32-44 can be obtained using the procedure in Scheme G.
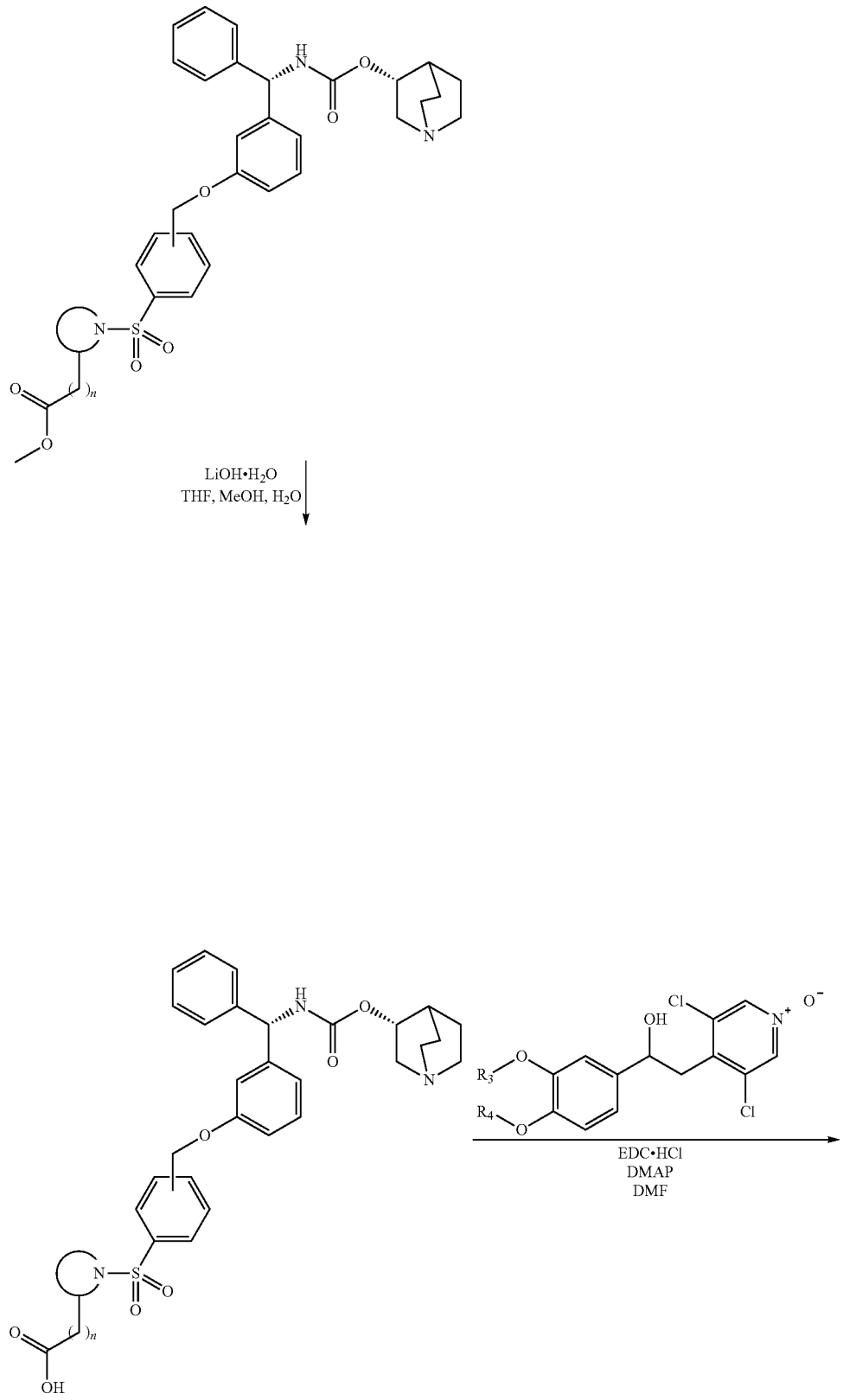

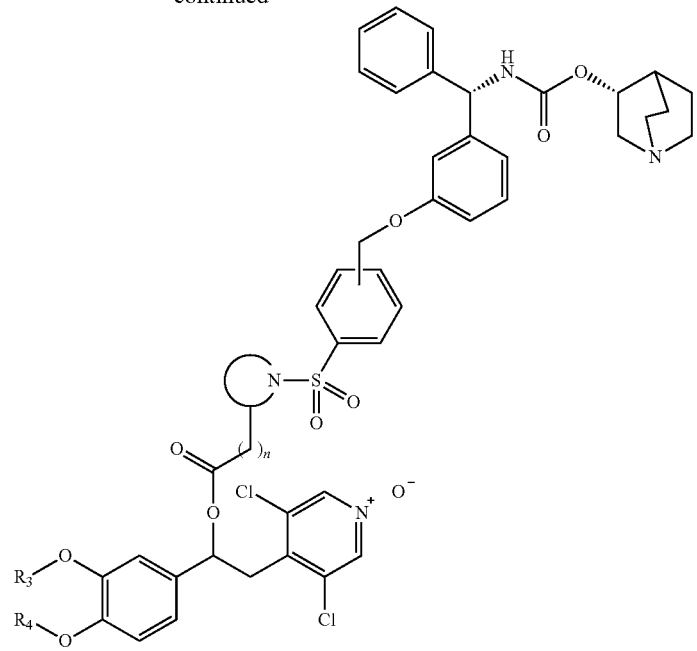

Example 32

[(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]phenoxy]methyl]phenyl]sulfonylpyrrolidine-2-carboxylate formate salt (E32)

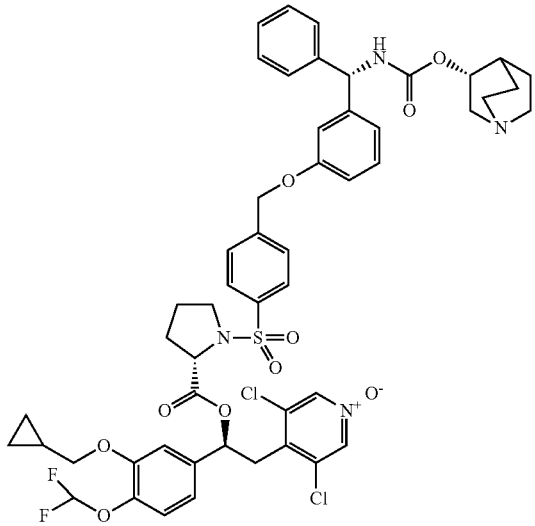

To a solution of (S)-methyl 1-((4-((3-((S)-phenyl((((R)-quinuclidin-3-yloxy)carbonyl)amino)methyl)phenoxy)methyl)phenyl)sulfonyl)pyrrolidine-2-carboxylate (I35, 576 mg, 0.91 mmol) in THF (4 mL) and MeOH (4 mL) was added an aqueous solution of LiOH (1 N, 1.8 mL, 1.8 mmol) at room temperature. The resulting mixture was stirred for 16 h before being cooled to 0° C. and acidified with 2 N HCl to pH 2. The resulting mixture was then concentrated in vacuo and azeotroped to dryness with toluene. The resulting carboxylic acid was redissolved in DMF (9.0 mL). To a solution of the acid in DMF (3 mL, 0.30 mmol) was then added (S)-3,5-dichloro-4-(2-(3-(cyclopropylmethoxy)-4-(difluoromethoxy)phenyl)-2-hydroxyethyl)pyridine 1-oxide (151 mg, 0.36 mmol) followed by 4-(dimethylamino)-pyridine (18 mg, 0.15 mmol) and N-(3-dimethylaminopropyl)-N'-ethylcarbodiimide hydrochloride (151 mg, 0.60 mmol). The resulting mixture was stirred at room temperature for 16 h and partitioned between EtOAc (50 mL) and water (20 mL). The organic layer was dried over $MgSO_4$, filtered and the solvent was removed in vacuo. The residue was dissolved in DMSO (1.5 mL) and purified by preparative HPLC to provide the title compound (90 mg, 29% over two steps) as white solid.

$^1$H NMR (400 MHz, DMSO at 110° C.): δ 8.62 (s, 2 H), 8.27 (d, J=9.7 Hz, 1 H), 8.22 (s, 1 H), 7.79 (d, J=8.1 Hz, 2 H), 7.69 (d, J=8.1 Hz, 2 H), 7.34-7.29 (m, 4 H), 7.31-7.20 (m, 2 H), 7.19 (d, J=8.4 Hz, 1 H), 7.15 (s, 1 H), 7.05 (t, J=75 Hz, 1 H), 7.04 (bs, 1 H), 6.98 (t, J=7.6 Hz, 2 H), 6.91 (d, J=8.2 Hz, 1 H), 6.03 (dd, J=9.7, 4.5 Hz, 1 H), 5.83 (d, J=9.2 Hz, 1 H), 5.20 (s, 2 H), 4.66-4.58 (m, 1 H), 4.14 (dd, J=8.7, 4.0 Hz, 1 H), 3.93 (d, J=7.0 Hz, 2 H), 3.47 (dd, J=14.2, 9.8 Hz, 1 H), 3.39 (dt, J=9.9, 6.1 Hz, 1 H), 3.27 (dd, J=14.2, 4.5 Hz, 1 H), 3.21-3.12 (m, 2 H), 2.86-2.76 (m, 1 H), 2.76-2.64 (m, 2 H), 2.60 (d, J=16.2 Hz, 1 H), 2.56-2.46 (m, 1 H), 2.00-1.88 (m, 2 H), 1.89-1.76 (m, 1 H), 1.71-1.60 (m, 3 H), 1.55-1.47 (m, 2 H), 1.45-1.34 (m, 1 H), 1.25-1.17 (m, 1 H), 0.61-0.53 (m, 2 H), 0.36-0.31 (m, 2 H). LCMS (Method 1): [MH+]=1021 at 3.22 min.

Compounds herebelow reported were prepared starting from the appropriate starting materials according to analogous procedures as that hereabove described in Example 32.

| Structure | Example | Precursor | Analytical data |
|---|---|---|---|
| [(1S)-1-[3-(cyclopropylmethoxy)-4-(difluoromethoxy)-phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]phenyl]sulfonylpyrrolidine-2-carboxylate formate salt 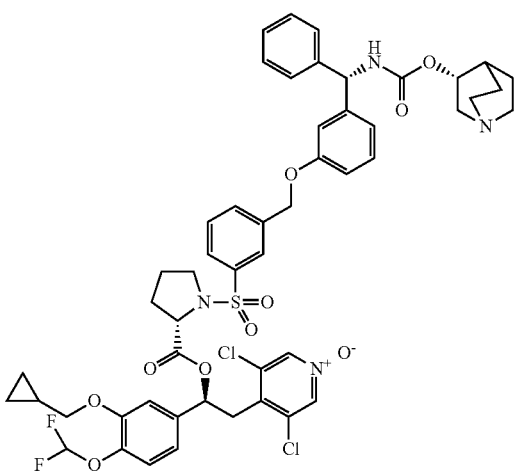 | Example 33 | Intermediate 36 | $^1$H NMR (400 MHz, DMSO at 110° C.): δ 8.36 (s, 2 H), 8.21 (s, 1 H), 7.81 (t, J = 1.7 Hz, 1 H), 7.70 (t, J = 7.1 Hz, 2 H), 7.61 (d, J = 7.6 Hz, 1 H), 7.52-7.48 (m, 1 H), 7.29-7.26 (m, 4 H), 7.24-7.19 (m, 2 H), 7.15 (d, J = 8.5 Hz, 1 H), 7.12 (d, J = 2.1 Hz, 1 H), 7.02 (t, J = 2.0 Hz, 1 H), 6.97 (dd, J = 8.2, 2.1 Hz, 1 H), 6.95 (t, J = 75 Hz, 1 H), 6.93 (d, J = 7.7 Hz, 1 H), 6.90 (dd, J = 8.3, 2.5 Hz, 1 H), 6.07 (dd, J = 9.1, 5.0 Hz, 1 H), 5.81 (d, J = 8.8 Hz, 1 H), 5.20 (s, 2 H), 4.60-4.56 (m, 1 H), 4.20 (dd, J = 12.5, 4.0 Hz, 1 H), 3.94 (d, J = 6.6 Hz, 2 H), 3.49 (dd, J = 14.2, 9.1 Hz, 1 H), 3.37-3.29 (m, 1 H), 3.30 (dd, J = 14.1, 5.0 Hz, 1 H), 3.22-3.14 (m, 1 H), 3.05 (dd, J = 14.5, 8.4 Hz, 1 H), 2.70-2.60 (m, 5 H), 1.93-1.87 (m, 2 H), 1.76-1.66 (m, 3 H), 1.60-1.54 (m, 2 H), 1.49-1.42 (m, 1 H), 1.32-1.20 (m, 2 H), 0.62-0.49 (m, 2 H), 0.34-0.31 (m, 2 H). LCMS (Method 1): [MH+] = 1020 at 3.25 min. |
| [(1S)-2-(3,5-dichloro-1-oxido-pyridin-1-ium-4-yl)-1-(3,4-dimethoxyphenyl)ethyl](2S)-1-[4-[[3-[(S)-phenyl-[[(3R)-quinuclidin-3-yl]oxycarbonylamino]methyl]phenoxy]methyl]phenyl]sulfonylpyrrolidine-2-carboxylate trifluoroacetate salt 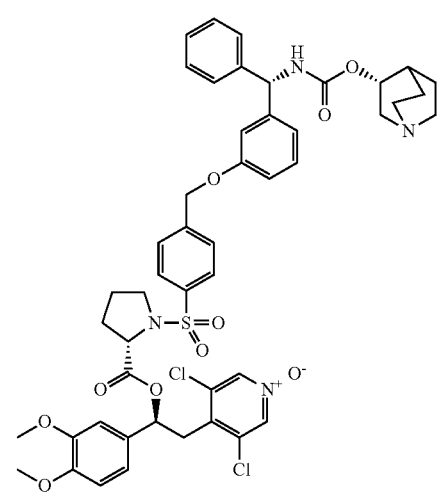 | Example 34 | Intermediate 35 | $^1$H NMR (400 MHz, DMSO at 110° C.): δ 8.37 (s, 2 H), 7.81 (d, J = 8.6 Hz, 1 H), 7.77-7.72 (m, 2 H), 7.61 (d, J = 8.1 Hz, 2 H), 7.32-7.28 (m, 4 H), 7.28-7.21 (m, 2 H), 7.01 (t, J = 2.0 Hz, 1 H), 6.98-6.87 (m, 5 H), 6.05 (dd, J = 9.2, 5.0 Hz, 1 H), 5.83 (d, J = 8.7 Hz, 1 H), 5.18 (s, 2 H), 4.94-4.90 (m, 1 H), 4.24 (dd, J = 8.7, 3.8 Hz, 1 H), 3.78 (s, 3 H), 3.77 (s, 3 H), 3.65 (ddd, J = 13.9, 8.4, 2.6 Hz, 1 H), 3.51 (dd, J = 14.2, 9.3 Hz, 1 H), 3.39-3.13 (m, 2 H), 3.07 (dt, J = 14.3, 2.8 Hz, 1 H), 2.56-2.51 (m, 3 H), 2.45-2.41 (m, 1 H), 2.25-2.20 (m, 1 H), 2.05-1.96 (m, 3 H), 1.94-1.87 (m, 1 H), 1.86-1.79 (m, 1 H), 1.78-1.72 (m, 3 H), 1.66-1.60 (m, 1 H). ). LCMS (Method 1): [MH+] = 945 at 3.00 min. |

| Structure | Example | Precursor | Analytical data |
|---|---|---|---|
| [(1S)-2-(3,5-dichloro-1-oxido-pyridin-1-ium-4-yl)-1-(3,4-dimethoxyphenyl)ethyl](2S)-1-[3-[[3-[(S)-phenyl-[[(3R)-quinuclidin-3-yl]oxycarbonylamino]methyl]phenoxy]methyl]phenyl]sulfonylpyrrolidine-2-carboxylate 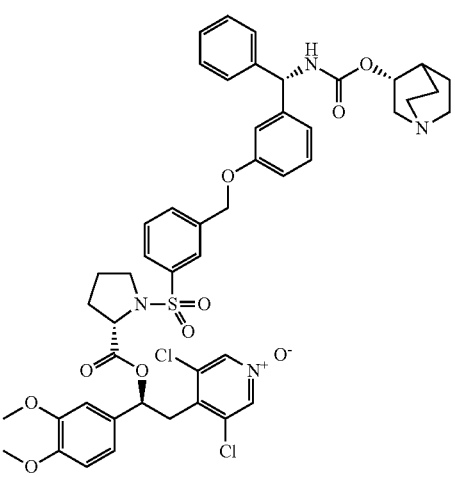 | Example 35 | Intermediate 36 | $^1$H NMR (400 MHz, DMSO at 110° C.): δ 8.35 (s, 2 H), 7.81 (t, J = 1.7 Hz, 1 H), 7.71-7.66 (m, 2 H), 7.59 (t, J = 7.7 Hz, 1 H), 7.49 (d, J = 8.9 Hz, 1 H), 7.29-7.26 (m, 4 H), 7.24-7.19 (m, 2 H), 7.02 (t, J = 2.0 Hz, 1 H), 6.97 (d, J = 2.0 Hz, 1 H), 6.96-6.92 (m, 2 H), 6.90 (dd, J = 8.3, 2.1 Hz, 2 H), 6.05 (dd, J = 9.2, 5.1 Hz, 1 H), 5.81 (d, J = 8.8 Hz, 1 H), 5.20 (s, 2 H), 4.59 (ddt, J = 8.3, 3.7, 1.1 Hz, 1 H), 4.19 (dd, J = 8.7, 3.8 Hz, 1 H), 3.78 (s, 3 H), 3.77 (s, 3 H), 3.51 (dd, J = 14.1, 9.2 Hz, 1 H), 3.35-3.28 (m, 1 H), 3.28 (dd, J = 14, 5.0 Hz, 1 H), 3.22-3.14 (m, 1 H), 3.05 (dd, J = 14.5, 8.3 Hz, 1 H), 2.72-2.63 (m, 3 H), 2.63-2.58 (m, 1 H), 2.45-2.43 (m, 1 H), 1.92-1.87 (m, 2 H), 1.75-1.67 (m, 3 H), 1.61-1.54 (m, 2 H), 1.50-1.43 (m, 1 H), 1.32-1.26 (m, 1 H). LCMS (Method 1): [MH+] = 945 at 2.91 min. |
| [(1S)-2-(3,5-dichloro-1-oxido-pyridin-1-ium-4-yl)-1-(3,4-dimethoxyphenyl)ethyl]1-[4-[[3-[(S)-phenyl-[[(3R)-quinuclidin-3-yl]oxycarbonylamino]methyl]phenoxy]methyl]phenyl]sulfonylazetidine-3-carboxylate 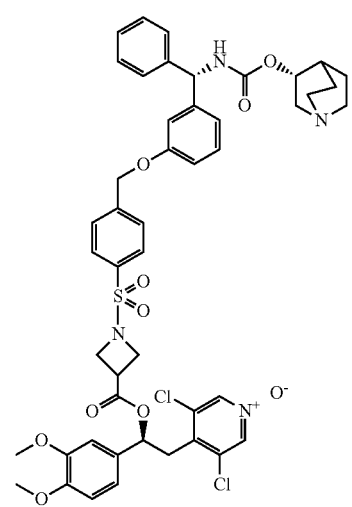 | Example 36 | Intermediate 39 | $^1$H NMR (400 MHz, DMSO at 110° C.): δ 8.34 (s, 2 H), 7.79-7.75 (m, 2 H), 7.66 (d, J = 8.2 Hz, 2 H), 7.51 (d, J = 8.8 Hz, 1 H), 7.30-7.27 (m, 4 H), 7.27-7.20 (m, 2 H), 7.03 (t, J = 2.0 Hz, 1 H), 6.95 (d, J = 7.7 Hz, 1 H), 6.92 (d, J = 8.4 Hz, 1 H), 6.90 (ddd, J = 8.1, 2.5, 0.9 Hz, 1 H), 6.88 (d, J = 2.1 Hz, 1 H), 6.83 (dd, J = 8.3, 2.1 Hz, 1 H), 5.94 (dd, J = 9.0, 4.9 Hz, 1 H), 5.82 (d, J = 8.8 Hz, 1 H), 5.22-5.18 (m, 2 H), 4.61-4.58 (m, 1 H), 3.97 (d, J = 8.1 Hz, 1 H), 3.93 (d, J = 8.2 Hz, 1 H), 3.81-3.76 (dd, J = 7.9, 6.3 Hz, 1 H), 3.76 (s, 6 H), 3.70 (dd, J = 8.0, 6.5 Hz, 1 H), 3.42 (dd, J = 14.1, 9.1 Hz, 1 H), 3.42-3.34 (m, 1 H), 3.21 (dd, J = 14.2, 5.0 Hz, 1 H), 3.07 (dd, J = 14.4, 8.3 Hz, 1 H), 2.70 (t, J = 8.1 Hz, 3 H), 2.68-2.57 (m, 2 H), 1.90-1.87 (m, 1 H), 1.77-1.72 (m, 1 H), 1.63-1.55 (m, 1 H), 1.50-1.46 (m, 1 H), 1.32-1.28 (m, 1 H). LCMS (Method 1): [MH+] = 931 at 2.91 min. |

| Structure | Example | Precursor | Analytical data |
|---|---|---|---|
| [(1S)-2-(3,5-dichloro-1-oxido-pyridin-1-ium-4-yl)-1-(3,4-dimethoxyphenyl) ethyl]1-[3-[[3-[(S)-phenyl-[[(3R)-quinuclidin-3-yl]oxycarbonylamino]methyl]phenoxy]methyl]phenyl]sulfonylazetidine-3-carboxylate formate salt 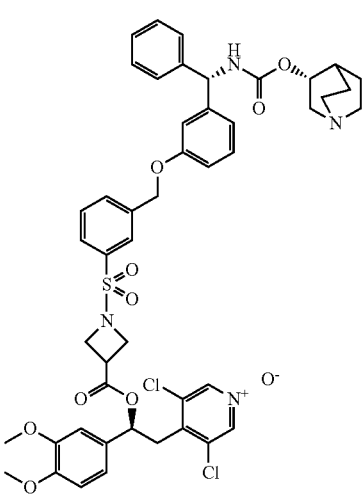 | Example 37 | Intermediate 37 | $^1$H NMR (400 MHz, DMSO at 110° C.): δ 8.33 (s, 2 H), 8.12 (s, 1 H), 7.82 (s, 1 H), 7.73 (dd, J = 13.9, 7.6 Hz, 2 H), 7.63 (t, J = 7.7 Hz, 1 H), 7.51 (d, J = 8.8 Hz, 1 H), 7.31-7.26 (m, 4 H), 7.24-7.17 (m, 2 H), 7.03 (t, J = 1.9 Hz, 1 H), 6.93 (d, J = 7.5 Hz, 1 H), 6.92 (d, J = 8.3 Hz, 1 H), 6.90 (ddd, J = 8.1, 2.7, 0.8 Hz, 1 H), 6.88 (d, J = 2.1 Hz, 1 H), 6.83 (dd, J = 8.2, 2.1 Hz, 1 H), 5.96 (dd, J = 8.9, 5.1 Hz, 1 H), 5.82 (d, J = 8.8 Hz, 1 H), 5.20 (s, 2 H), 4.62-4.57 (m, 1 H), 3.91 (td, J = 8.5, 5.8 Hz, 2 H), 3.78 (dd, J = 8.2, 6.4 Hz, 1 H), 3.76 (s, 3 H), 3.76 (s, 3 H), 3.72 (dd, J = 8.0, 6.4 Hz, 1 H), 3.42 (dd, J = 14.2, 8.9 Hz, 1 H), 3.38-3.31 (m, 1 H), 3.22 (dd, J = 14.2, 5.1 Hz, 1 H), 3.08 (dd, J = 15.4, 8.6 Hz, 1 H), 2.71 (t, J = 8.1 Hz, 3 H), 2.71-2.57 (m, 2 H), 1.90-1.87 (m, 1 H), 1.78-1.72 (m, 1 H), 1.64-1.56 (m, 1 H), 1.52-1.43 (m, 1 H), 1.32-1.27 (m, 1 H). LCMS (Method 1): [MH+] = 931 at 2.92 min. |
| [(1S)-1-[3-(cyclopropylmethoxy)-4-(difluoromethoxy)phenyl]-2-(3,5-dichloro-1-oxido-pyridin-1-ium-4-yl)ethyl]1-[3-[[3-[(S)-phenyl-[[(3R)-quinuclidin-3-yl]oxycarbonylamino]methyl]phenoxy]methyl]phenyl]sulfonylazetidine-3-carboxylate formate salt 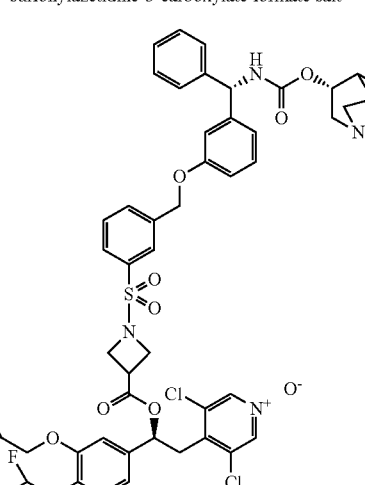 | Example 38 | Intermediate 37 | $^1$H NMR (400 MHz, DMSO at 110° C.): δ 8.34 (s, 2 H), 8.15 (s, 1 H), 7.83 (s, 1 H), 7.75 (d, J = 7.7 Hz, 1 H), 7.72 (d, J = 7.9 Hz, 1 H), 7.64 (t, J = 7.7 Hz, 1 H), 7.51 (d, J = 9.1 Hz, 1 H), 7.32-7.26 (m, 4 H), 7.24-7.17 (m, 2 H), 7.14 (d, J = 8.1 Hz, 1 H), 7.03 (d, J = 2.1 Hz, 2 H), 6.94 (t, J = 75 Hz, 1 H), 6.93 (d, J = 7.8 Hz, 1 H), 6.90 (dd, J = 8.2, 2.2 Hz, 2 H), 5.97 (dd, J = 8.7, 5.1 Hz, 1 H), 5.81 (d, J = 8.8 Hz, 1 H), 5.20 (s, 2 H), 4.61-4.56 (m, 1 H), 3.93 (d, J = 8.0 Hz, 1 H), 3.92 (d, J = 6.8 Hz, 2 H), 3.89 (d, J = 8.0 Hz, 1 H), 3.80 (dd, J = 8.1, 6.4 Hz, 1 H), 3.73 (dd, J = 8.1, 6.4 Hz, 1 H), 3.42 (dd, J = 13.6, 8.6 Hz, 1 H), 3.40-3.32 (m, 1 H), 3.23 (dd, J = 14.1, 5.1 Hz, 1 H), 3.06 (dd, J = 14.7, 8.4 Hz, 1 H), 2.70 (t, J = 8.0 Hz, 3 H), 2.67-2.56 (m, 2 H), 1.90-1.86 (m, 1 H), 1.79-1.68 (m, 1 H), 1.61-1.55 (m, 1 H), 1.51-1.43 (m, 1 H), 1.31-1.27 (m, 1 H), 1.24-1.16 (m, 1 H), 0.59-0.54 (m, 2 H), 0.36-0.31 (m, 2 H). LCMS (Method 1): [MH+] = 1007 at 3.17 min. |

-continued

| Structure | Example | Precursor | Analytical data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]phenyl]sulfonylazetidine-3-carboxylate formate salt 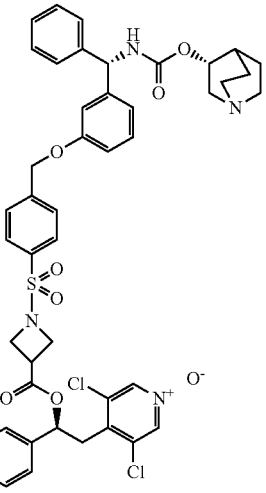 | Example 39 | Intermediate 39 | $^1$H NMR (400 MHz, DMSO at 110° C.): δ 8.34 (s, 2 H), 7.79-7.74 (m, 2 H), 7.67 (d, J = 8.1 Hz, 2 H), 7.52 (d, J = 8.8 Hz, 1 H), 7.30-7.27 (m, 4 H), 7.27-7.19 (m, 2 H), 7.14 (d, J = 8.6 Hz, 1 H), 7.03 (dd, J = 5.0, 2.2 Hz, 2 H), 6.94 (d, J = 7.7 Hz, 1 H), 6.94 (t, J = 75 Hz, 1 H), 6.90 (dd, J = 8.3, 2.0 Hz, 2 H), 5.96 (dd, J = 8.8, 5.0 Hz, 1 H), 5.82 (d, J = 8.8 Hz, 1 H), 5.19 (s, 2 H), 4.62-4.57 (m, 1 H), 3.98-3.90 (m, 2 H), 3.92 (d, J = 6.6 Hz, 2 H), 3.80 (dd, J = 8.1, 6.4 Hz, 1 H), 3.71 (dd, J = 8.1, 6.4 Hz, 1 H), 3.45-3.36 (m, 1 H), 3.41 (dd, J = 14.7, 8.7, 1 H), 3.22 (dd, J = 14.2, 5.1 Hz, 1 H), 3.06 (dd, J = 14.6, 8.3 Hz, 1 H), 2.70 (t, J = 8.1 Hz, 3 H), 2.69-2.56 (m, 2 H), 1.91-1.87 (m, 1 H), 1.77-1.72 (m, 1 H), 1.61-1.57 (m, 1 H), 1.48-1.45 (m, 1 H), 1.30-1.27 (m, 1 H), 1.21-1.17 (m, 1 H), 0.59-0.54 (m, 2 H), 0.36-0.31 (m, 2 H). LCMS (Method 1): [MH+] = 1007 at 3.17 min. |
| [(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]phenyl]sulfonylpiperidine-4-carboxylate formate salt 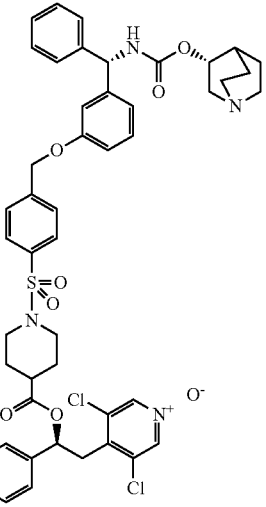 | Example 40 | Intermediate 41 | $^1$H NMR (400 MHz, DMSO at 110° C.): δ 8.35 (s, 2 H), 8.21 (s, 1 H), 7.72 (d, J = 8.2 Hz, 2 H), 7.64 (d, J = 8.1 Hz, 2 H), 7.51 (d, J = 8.8 Hz, 1 H), 7.32-7.28 (m, 4 H), 7.28-7.18 (m, 2 H), 7.14 (d, J = 8.3 Hz, 1 H), 7.04 (d, J = 2.1 Hz, 1 H), 7.02 (t, J = 2.0 Hz, 1 H), 6.95-6.91 (m, 2 H), 6.94 (t, J = 75 Hz, 1 H), 6.90 (dd, J = 8.2, 2.6 Hz, 1 H), 6.00 (dd, J = 9.0, 5.0 Hz, 1 H), 5.82 (d, J = 8.8 Hz, 1 H), 5.18 (s, 2 H), 4.62-4.57 (m, 1 H), 3.92 (d, J = 6.7 Hz, 2 H), 3.51-3.39 (m, 2 H), 3.43 (dd, J = 14.1, 9.1 Hz, 1 H), 3.24 (dd, J = 14.2, 5.0 Hz, 1 H), 3.07 (dd, J = 14.5, 8.3 Hz, 1 H), 2.70 (t, J = 8.0 Hz, 2 H), 2.68-2.57 (m, 4 H), 2.55-2.50 (m, 1 H), 2.46-2.39 (m, 1 H), 1.91-1.82 (m, 3 H), 1.79-1.69 (m, 1 H), 1.64-1.51 (m, 3 H), 1.53-1.41 (m, 1 H), 1.33-1.22 (m, 1 H), 1.24-1.14 (m, 1 H), 0.60-0.53 (m, 2 H), 0.38-0.32 (m, 2 H). LCMS (Method 1): [MH+] = 1034 at 3.26 min. |

-continued

| Structure | Example | Precursor | Analytical data |
|---|---|---|---|
| [(1S)-2-(3,5-dichloro-1-oxido-pyridin-1-ium-4-yl)-1-(3,4-dimethoxyphenyl)ethyl]1-[4-[[3-[(S)-phenyl-[[(3R)-quinuclidin-3-yl]oxycarbonylamino]methyl]phenoxy]methyl]phenyl]sulfonyl-piperidine-4-carboxylate formate salt | Example 41 | Intermediate 41 | $^1$H NMR (400 MHz, DMSO at 110° C.): δ 8.35 (s, 2 H), 8.20 (s, 1 H), 7.74-7.68 (m, 2 H), 7.63 (d, J = 8.1 Hz, 2 H), 7.52 (d, J = 8.7 Hz, 1 H), 7.32-7.24 (m, 4 H), 7.24-7.18 (m, 2 H), 7.02 (d, J = 2.3 Hz, 1 H), 6.94-6.87 (m, 4 H), 6.86 (dd, J = 8.2, 2.3 Hz, 1 H), 5.98 (dd, J = 9.1, 4.9 Hz, 1 H), 5.82 (d, J = 8.8 Hz, 1 H), 5.18 (s, 2 H), 4.62-4.57 (m, 1 H), 3.76 (s, 6 H), 3.49-3.39 (m, 3 H), 3.22 (dd, J = 14.1, 4.9 Hz, 1 H), 3.07 (dd, J = 14.5, 8.3 Hz, 1 H), 2.70 (t, J = 7.9 Hz, 2 H), 2.69-2.57 (m, 4 H), 2.57-2.51 (m, 1 H), 2.44-2.36 (m, 1 H), 1.92-1.81 (m, 3 H), 1.78-1.69 (m, 1 H), 1.63-1.42 (m, 4 H), 1.34-1.24 (m, 1 H). LCMS (Method 1): [MH+] = 959 at 2.98 min. |
| [(1S)-1-[3-(cyclopropylmethoxy)-4-(difluoromethoxy)phenyl]-2-(3,5-dichloro-1-oxido-pyridin-1-ium-4-yl)ethyl]2-[4-[4-[[3-[(S)-phenyl-[[(3R)-quinuclidin-3-yl]oxycarbonylamino]methyl]phenoxy]methyl]phenyl]sulfonylpiperazin-1-yl]acetate | Example 42 | Intermediate 40 | $^1$H NMR (400 MHz, DMSO at 110° C.): δ 8.34 (s, 2 H), 7.72 (d, J = 8.2 Hz, 2 H), 7.64 (d, J = 8.2 Hz, 2 H), 7.54-7.45 (m, 1 H), 7.30-7.27 (m, 4 H), 7.23-7.20 (m, 2 H), 7.14 (d, J = 8.6 Hz, 1 H), 7.06 (d, J = 2.0 Hz, 1 H), 7.02 (s, 1 H), 6.97-6.91 (m, 1 H), 6.94 (t, J = 75 Hz, 1 H), 6.90 (dd, J = 8.2, 2.8 Hz, 1 H), 6.04 (dd, J = 8.8, 5.1 Hz, 1 H), 5.81 (d, J = 8.8 Hz, 1 H), 5.22-5.18 (m, 2 H), 4.62-4.56 (m, 1 H), 3.92 (dd, J = 6.7, 1.3 Hz, 2 H), 3.44 (dd, J = 14.1, 8.8 Hz, 1 H), 3.27 (d, J = 16.5 Hz, 1 H), 3.26 (dd, J = 13.9, 5.2 Hz, 1 H), 3.19 (d, J = 16.5 Hz, 1 H), 3.05 (dd, J = 14.7, 8.2 Hz, 2 H), 2.96 (t, J = 5.0 Hz, 3 H), 2.94-2.86 (m, 2H), 2.69 (t, J = 8.2 Hz, 3 H), 2.64-2.56 (m, 4 H), 2.44-2.42 (m, 1 H), 1.91-1.85 (m, 1 H), 1.80-1.68 (m, 1 H), 1.61-1.53 (m, 1 H), 1.51-1.40 (m, 1 H), 1.34-1.23 (m, 1 H), 1.23-1.13 (m, 1 H), 0.58-0.54 (m, 2 H), 0.35-0.32 (m, 2 H). LCMS (Method 1): [MH+] = 1050 at 3.15 min. LCMS (Method 1): [MH+] = 1050 at 3.15 min. |

-continued

| Structure | Example | Precursor | Analytical data |
|---|---|---|---|
| [(1S)-1-[3-(cyclopropylmethoxy)-4-(difluoromethoxy)phenyl]-2-(3,5-dichloro-1-oxido-pyridin-1-ium-4-yl)ethyl]2-[1-[4-[[3-[(S)-phenyl-[[(3R)-quinuclidin-3-yl]oxycarbonylamino]methyl]phenoxy]methyl]phenyl]sulfonylazetidin-3-yl]acetate formate salt 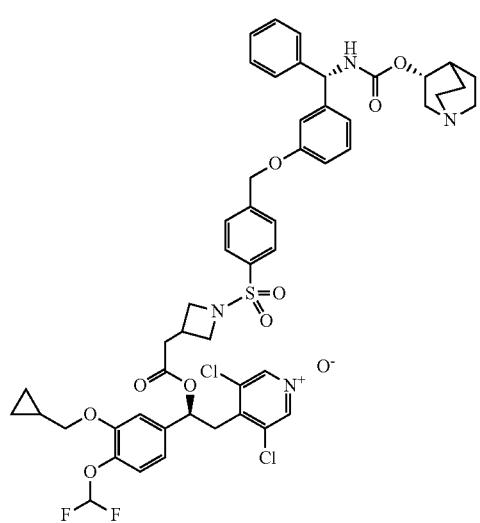 | Example 43 | Intermediate 42 | $^1$H NMR (400 MHz, DMSO at 110° C.): δ 8.55 (s, 2 H), 8.23 (d, J = 9.2 Hz, 1 H), 8.21 (s, 1 H), 7.82 (d, J = 8.1 Hz, 2 H), 7.74 (d, J = 8.1 Hz, 2 H), 7.34-7.17 (m, 6 H), 7.17 (d, J = 8.3 Hz, 1 H), 7.07 (t, J = 75 Hz, 1 H), 7.05 (d, J = 12.3 Hz, 2 H), 6.96 (d, J = 7.7 Hz, 1 H), 6.91 (d, J = 8.4 Hz, 2 H), 5.89 (dd, J = 9.1, 4.6 Hz, 1 H), 5.83 (d, J = 9.3 Hz, 1 H), 5.24 (s, 2 H), 4.60-4.53 (m, 1 H), 3.92-3.86 (m, 2 H), 3.80 (d, J = 8.2 Hz, 1 H), 3.76 (d, J = 7.9 Hz, 1 H), 3.38 (dd, J = 14.3, 8.2 Hz, 2 H), 3.36-3.27 (m, 2 H), 3.16 (dd, J = 14.3, 4.8 Hz, 1 H), 3.08 (dd, J = 12.9, 8.2 Hz, 1 H), 2.79-2.69 (m, 2 H), 2.69-2.55 (m, 3 H), 2.43 (dd, J = 16.8, 7.3 Hz, 1 H), 2.38 (dd, J = 16.5, 8.0 Hz, 1 H), 1.95-1.85 (m, 1 H), 1.85-1.72 (m, 1 H), 1.65-1.52 (m, 1 H), 1.52-1.40 (m, 1 H), 1.39-1.26 (m, 1 H), 1.26-1.14 (m, 1 H), 0.60-0.53 (m, 2 H), 0.38-0.31 (m, 2 H). LCMS (Method 1): [MH+] = 1021 at 3.17 min. |
| [(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]benzoyl]amino]phenyl]sulfonylpyrrolidine-2-carboxylate formate salt 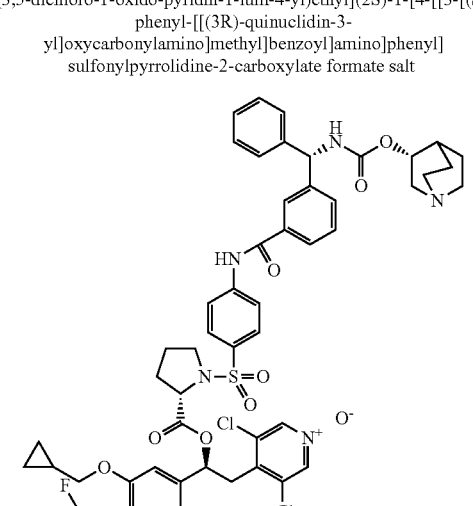 | Example 44 | Intermediate 38 | $^1$H NMR (400 MHz, DMSO): δ 10.64 (s, 1 H), 8.61 (s, 2 H), 8.37 (d, J = 9.2 Hz, 1 H), 8.20 (s, 1 H), 8.03 (d, J = 8.5 Hz, 2 H), 7.95 (s, 1 H), 7.86 (d, J = 7.7 Hz, 1 H), 7.78 (d, J = 8.5 Hz, 2 H), 7.59 (d, J = 7.7 Hz, 1 H), 7.52 (t, J = 7.6 Hz, 1 H), 7.42-7.31 (m, 3 H), 7.30-7.22 (m, 1 H), 7.19 (d, J = 8.2 Hz, 1 H), 7.16 (s, 1 H), 7.09 (t, J = 75 Hz, 1 H), 7.00 (d, J = 8.3 Hz, 1 H), 6.04 (dd, J = 9.6, 4.6 Hz, 1 H), 5.97 (d, J = 9.1 Hz, 1 H), 4.66-4.52 (m, 1 H), 4.14 (dd, J = 8.5, 4.0 Hz, 1 H), 3.93 (d, J = 6.9 Hz, 2 H), 3.47 (dd, J = 14.1, 9.7 Hz, 1 H), 3.42-3.23 (m, 2 H), 3.23-3.12 (m, 2 H), 2.77-2.53 (m, 5 H), 1.98-1.88 (m, 2 H), 1.85-1.77 (m, 1 H), 1.70-1.44 (m, 5 H), 1.41-1.28 (m, 1 H), 1.27-1.17 (m, 1 H), 0.61-0.52 (m, 2 H), 0.36-0.31 (m, 2 H). LCMS (Method 1): [MH+] = 1034 at 3.2 min. |

Intermediate 43. (S)-tert-butyl ((3-aminophenyl)(phenyl)methyl)carbamate (I43)

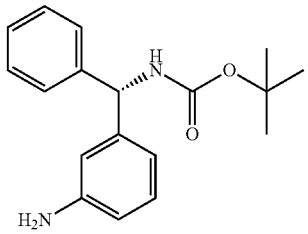 [SMILES: CC(C)(C)OC(=O)N[C@@H](c1ccccc1)c1cccc(N)c1]

To a solution of (S)-3-((((tert-butoxycarbonyl)amino)(phenyl)methyl)benzoic acid (100 mg, 0.31 mmol), Et₃N (0.17 mL, 1.24 mmol) and benzyl alcohol (0.26 mL, 2.48 mmol) in dioxane (1.5 mL) was added diphenyl phosphoryl azide (93 mg, 0.34 mmol) at room temperature. The resulting mixture was heated to reflux for 24 h, cooled to room temperature and partitioned between EtOAc (30 mL) and water (20 mL). The layers were separated and the organic phase dried over MgSO₄. The mixture was filtered and solvent was removed in vacuo. The residue was purified via silica gel chromatography, eluting with 0-20% EtOAc in isohexane, to give the corresponding compound tert-butyl N—[(S)-[3-(benzyloxycarbonylamino)phenyl]-phenyl-methyl]carbamate as a white solid (125 mg). To a solution of the solid (125 mg, 0.29 mg) in EtOAc (4 mL) was added 10% Pd/C (140 mg) and ammonium formate (200 mg, 3.07 mmol). The resulting slurry was refluxed for 2 h. The reaction mixture was then filtered over celite at room temperature, the cake washed with EtOAc (50 mL) and the filtrate concentrated in vacuo. The resulting oil solidified on standing to give the title compound (42 mg, 45% over two steps) as a white solid.

¹H NMR (400 MHz, CDCl₃): δ 7.35-7.21 (m, 5 H), 7.09 (t, J=7.7 Hz, 1 H), 6.63 (d, J=7.7 Hz, 1 H), 6.56 (dd, J=8.1, 2.2 Hz, 1 H), 6.53 (s, 1 H), 5.80 (s, 1 H), 5.16 (s, 1 H), 3.49-2.70 (m, 2 H), 1.43 (s, 9 H). LCMS (Method 1): [MH+]=299 at 3.45 min.

The compound of Example 45 can be obtained using the procedure of Scheme H.

Scheme H

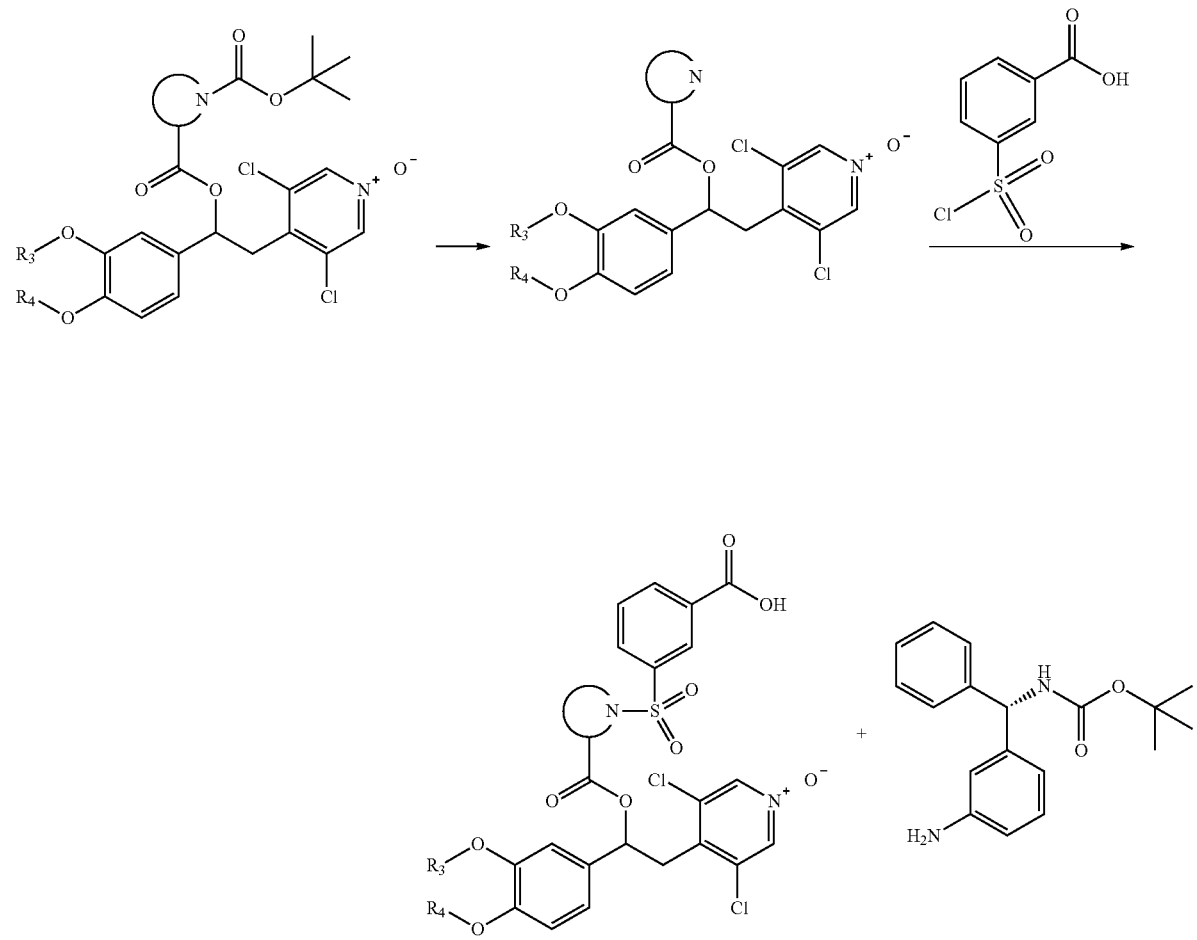

-continued
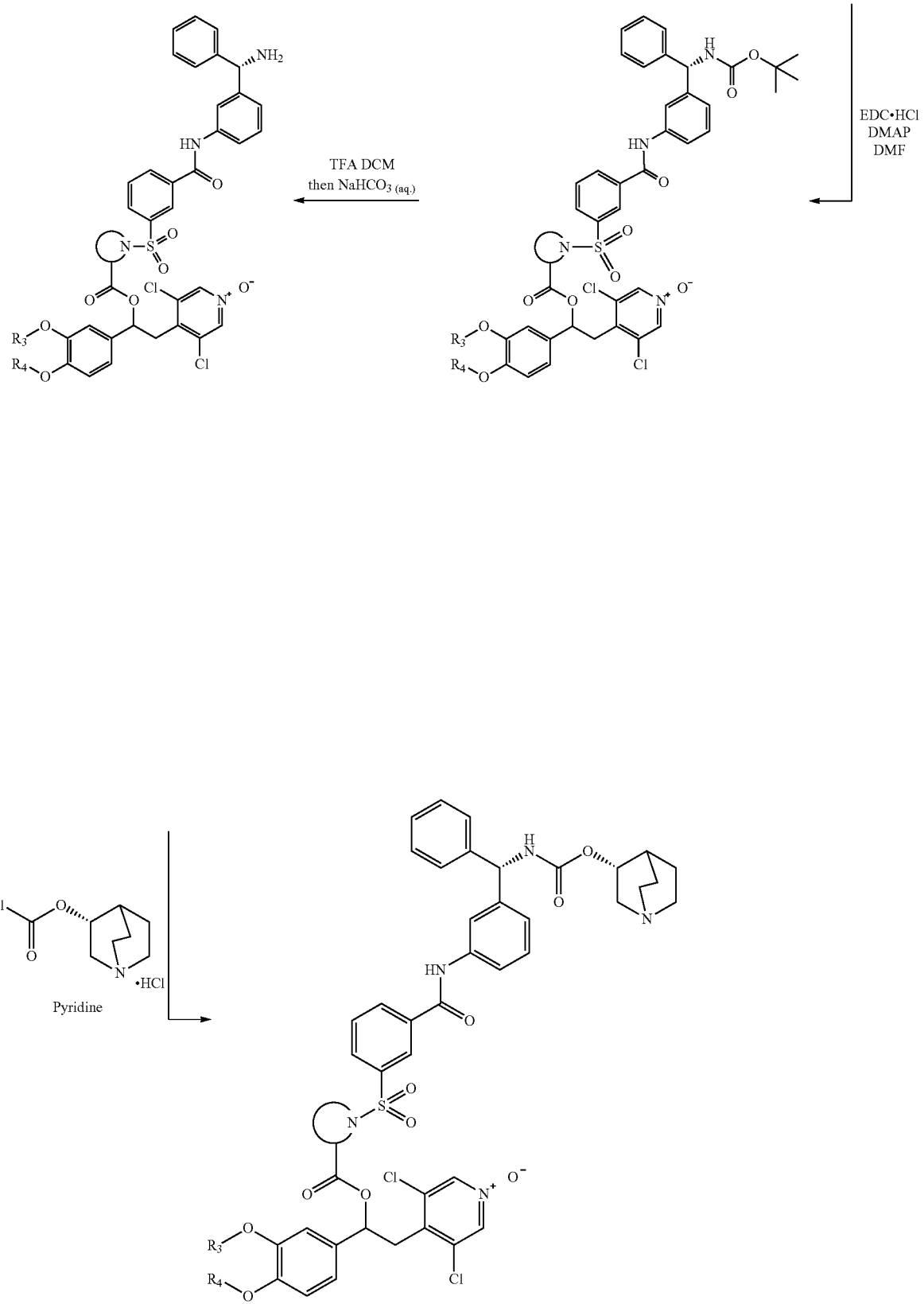

Example 45

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenyl]carbamoyl]phenyl]sulfonylpiperidine-2-carboxylate (E45)

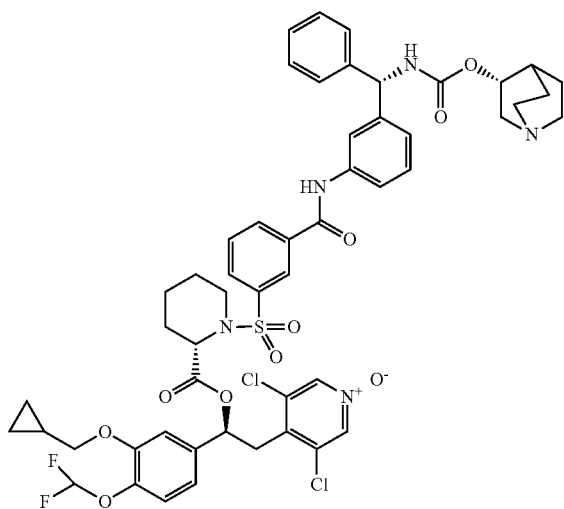

To a solution of 4-((S)-2-(((S)-1-(tert-butoxycarbonyl)piperidine-2-carbonyl)oxy)-2-(3-(cyclopropylmethoxy)-4-(difluoromethoxy)phenyl)ethyl)-3,5-dichloropyridine 1-oxide (I4, 88 mg, 0.14 mmol) dissolved in EtOAc (3 mL) was added a solution of HCl in dioxane (4 N, 1.8 mL, 7.2 mmol) at 0° C. The resulting mixture was warmed to room temperature and stirred for 1 h before being concentrated in vacuo. The residue was redissolved in DCM (50 mL) and washed with sat. NaHCO$_3$ (20 mL). The layers were separated over a hydrophobic frit and the organic phase was concentrated to an oil that was used immediately without further purification. The residue was taken up in acetone (1 mL) and THF (1 mL). 3-chlorosulfonyl benzoic acid (268 mg, 1.22 mmol) and 2 M NaOH (2.44 mL) were added at room temperature and the resulting mixture was stirred for 16 h. The solvent was removed in vacuo and then the residue was diluted in DCM (50 mL) and the pH adjusted to 2 with an aqueous 1 N HCl saturated with brine. The organic phase was dried over MgSO$_4$, filtered and the solvent was removed in vacuo. The resulting oil solidified on standing and was used directly in the next step without further purification.

To a solution of the carboxylic acid, (S)-tert-butyl ((3-aminophenyl)(phenyl)-methyl)carbamate (I43, 42 mg, 0.14 mmol), 4-(dimethylamino)-pyridine (8 mg, 0.07 mmol) in DMF (1.4 mL) was added N-(3-dimethylaminopropyl)-N'-ethylcarbodiimide hydrochloride (54 mg, 0.28 mmol) in one portion at room temperature. The resulting mixture was stirred at room temperature for 16 h. EtOAc (50 mL) and water (20 mL) were then added, the layers separated, the organic layer dried over MgSO$_4$, filtered and the solvent was removed in vacuo. The residue was dissolved in DCM (2 mL). TFA (1 mL) was added at 0° C., and the mixture was stirred at 0° C. for 1 h. The solvent was removed in vacuo and the residue was taken up in DCM (30 mL) and saturated aqueous NaHCO$_3$ (20 mL). The organic phase was passed through a hydrophobic frit and the solvent was removed in vacuo. The residue was dissolved in pyridine (1 mL) and (R)-quinuclidin-3-yl carbonochloridate hydrochloride (32 mg, 0.14 mmol) was added at 0° C. The resulting mixture was stirred at room temperature for 18 h and then diluted with EtOAc (50 mL) and water (20 mL). The layers were separated and the organic phase dried over MgSO$_4$. The mixture was filtered and the solvent was removed in vacuo. The residue was dissolved in DMSO (1 mL) and purified by preparative HPLC twice to provide [(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenyl]carbamoyl]phenyl]sulfonylpiperidine-2-carboxylate as a white solid (8 mg, 5% over three steps)

$^1$H NMR (400 MHz, CD$_3$CN): δ 9.24 (s, 1 H), 8.29 (s, 1 H), 8.19 (d, J=7.4 Hz, 1 H), 8.16 (s, 2 H), 7.91 (d, J=7.8 Hz, 1 H), 7.78 (s, 1 H), 7.71-7.63 (m, 2 H), 7.41-7.34 (m, 4 H), 7.34-7.28 (m, 1 H), 7.15-7.09 (m, 2 H), 7.02 (d, J=2.0 Hz, 1 H), 6.89 (dd, J=8.2, 2.0 Hz, 2 H), 6.68 (t, J=75.4 Hz, 1 H), 5.96-5.89 (m, 2 H), 5.00-4.94 (m, 1 H), 4.67 (d, J=5.4 Hz, 1 H), 3.90 (dd, J=10.1, 7.2 Hz, 1 H), 3.85 (dd, J=10.2, 7.2 Hz, 1H), 3.78 (d, J=13.0 Hz, 1 H), 3.65-3.51 (m, 1 H), 3.46 (dd, J=14.0, 8.8 Hz, 1 H), 3.37-3.09 (m, 6 H), 2.74-2.11 (m, 8 H), 1.89-1.65 (m, 1 H), 1.60 (d, J=12.9 Hz, 2 H), 1.45-1.28 (m, 1 H), 1.28-1.18 (m, 1 H), 1.10-0.97 (m, 1 H), 0.66-0.58 (m, 2 H), 0.37-0.32 (m, 2 H). LCMS (Method 1): [MH+]=1048 at 3.23 min.

The compound of Example 46 can be obtained using the procedure of Scheme I.

Scheme I

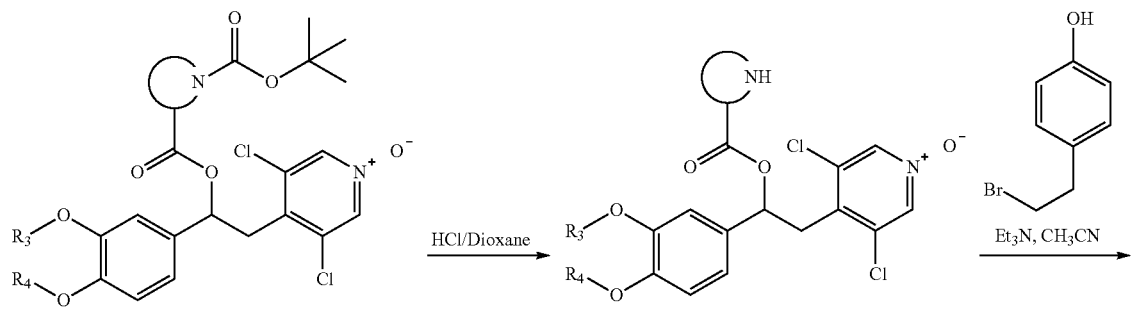

-continued
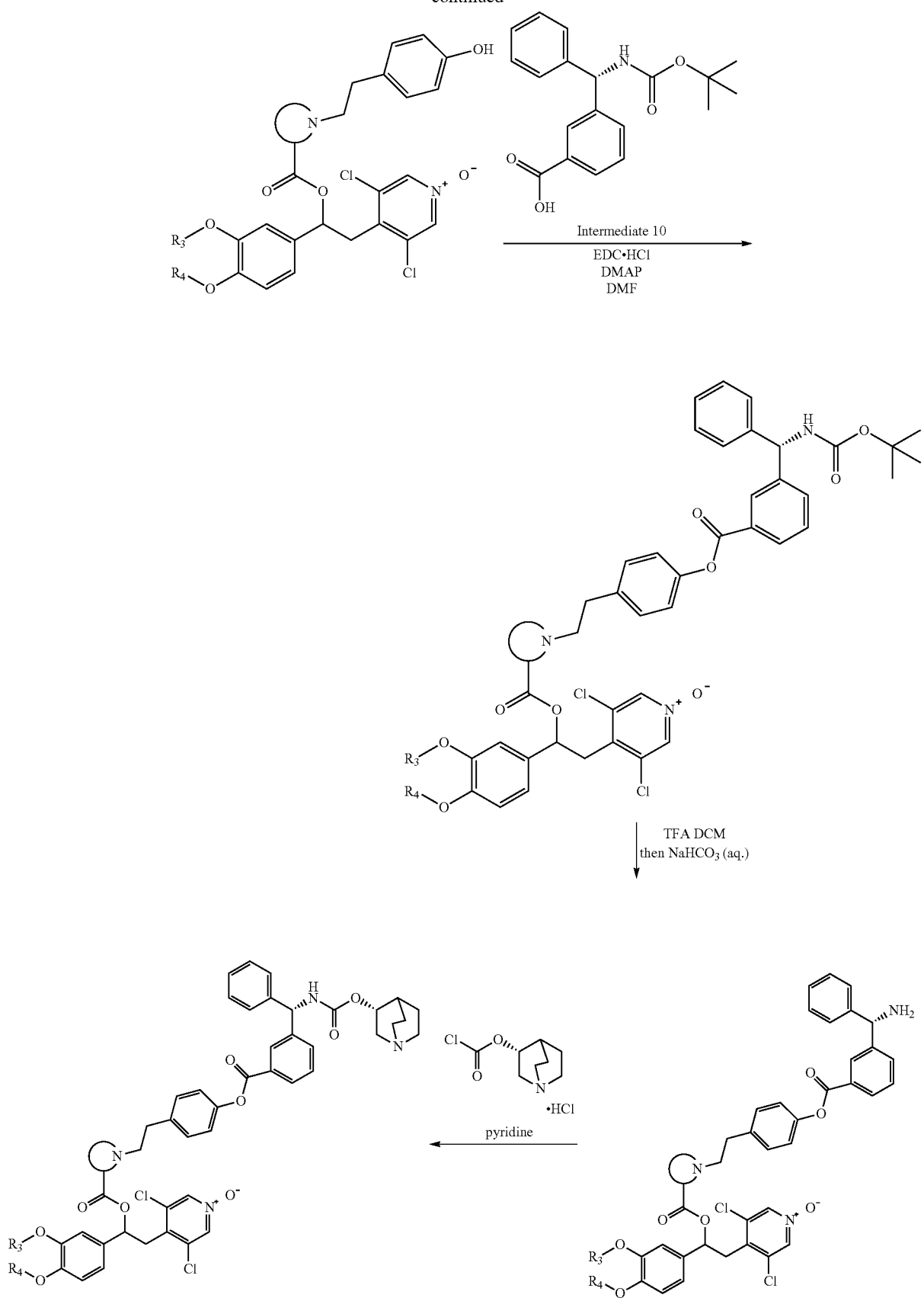

Example 46

[(1S)-1-[3-(cyclopropylmethoxy)-4-(difluoromethoxy)phenyl]-2-(3,5-dichloro-1-oxido-pyridin-1-ium-4-yl)ethyl](2S)-1-[2-[4-[3-[(S)-phenyl-[[(3R)-quinuclidin-3-yl]oxycarbonylamino]methyl]benzoyl]oxyphenyl]ethyl]pyrrolidine-2-carboxylate trifluoroacetate salt (E46)

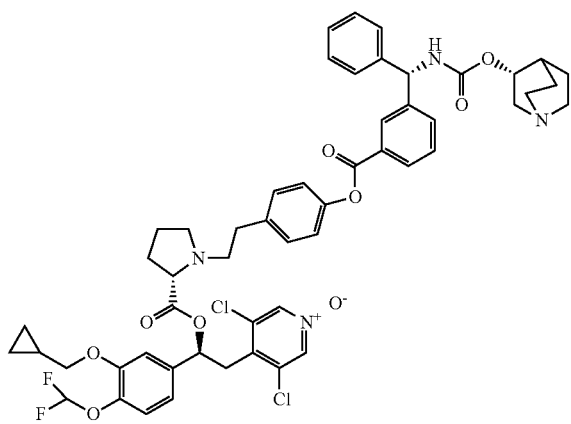

To a solution of 4-((S)-2-(((S)-1-(tert-butoxycarbonyl)pyrrolidine-2-carbonyl)oxy)-2-(3-(cyclopropylmethoxy)-4-(difluoromethoxy)phenyl)ethyl)-3,5-dichloropyridine 1-oxide (I2, 222 mg, 0.36 mmol) dissolved in EtOAc (10 mL) was added a solution of HCl in dioxane (4 N, 12 mL, 28 mmol) at 0° C. The resulting mixture was warmed to room temperature and stirred for 16 h and the solvent was removed in vacuo. The residue was redissolved in DCM (50 mL) and washed with saturated aqueous NaHCO₃ (20 mL). The organic phase was passed through a hydrophobic frit and the solvent was removed in vacuo to yield an oil that was used immediately without further purification.

To a solution of the oil from the previous step in acetonitrile (2 mL) was added 4-(2-bromoethyl)-phenol (101 mg, 0.50 mmol) followed by Et₃N (0.1 mL, 0.72 mmol). The mixture was heated under microwave irradiation at 130° C. for 1 h. EtOAc (100 mL) and water (40 mL) were added, the layers separated, the organic phase washed with brine (40 mL) and dried over MgSO₄. The mixture was filtered and the solvent was removed in vacuo. The residue was purified via silica gel chromatography, eluting with 0-20% EtOAc in isohexane, to give the corresponding phenol as an oil (60 mg).

The phenol previously obtained was then dissolved in DCM (5 mL) and (S)-3-(((tert-butoxycarbonyl)amino)(phenyl)methyl)benzoic acid (I10, 34 mg, 0.10 mmol) followed by 4-(dimethylamino)-pyridine (5 mg, 0.05 mmol) and N-(3-dimethylaminopropyl)-N'-ethylcarbodiimide hydrochloride (35 mg, 1.0 mmol) was added. The resulting mixture was stirred at room temperature for 18 h. The solvent was removed in vacuo then the residue was partitioned between EtOAc (50 mL) and saturated aqueous sodium bicarbonate solution (20 mL). The organic layer was dried over MgSO₄, filtered and the solvent was removed in vacuo. The residue was purified via silica gel chromatography, eluting with 0-10% MeOH in DCM, to give the corresponding bis ester compound (70 mg). The oil was then redissolved in DCM (3 mL) and TFA (1 mL) was added at 0° C. The mixture was stirred at room temperature for 1 h and then the solvent was removed in vacuo. The residue was diluted in DCM (30 mL) and saturated aqueous NaHCO₃ (20 mL) and the separated organic phase was passed through a hydrophobic frit. The solvent was removed in vacuo and the residue was dissolved in pyridine (1 mL) and (R)-quinuclidin-3-yl carbonochloridate hydrochloride (20 mg, 0.089 mmol) was added at 0° C. The resulting mixture was stirred at room temperature for 18 h and then diluted with EtOAc (50 mL) and water (20 mL). The layers were separated and the organic phase dried over MgSO₄. The mixture was filtered and the solvent was removed in vacuo. The residue was dissolved in DMSO (1.5 mL) and purified by preparative HPLC to provide [(1S)-1-[3-(cyclopropylmethoxy)-4-(difluoromethoxy)phenyl]-2-(3,5-dichloro-1-oxido-pyridin-1-ium-4-yl)ethyl](2S)-1-[2-[4-[3-[(S)-phenyl-[[(3R)-quinuclidin-3-yl]oxycarbonylamino]methyl]benzoyl]oxyphenyl]ethyl]pyrrolidine-2-carboxylate as a white solid (6 mg, 2% over five steps).

¹H NMR (400 MHz, CD₃CN): δ 8.08 (s, 2 H), 8.00 (s, 1 H), 7.98 (d, J=8.0 Hz, 1 H), 7.57 (d, J=7.8 Hz, 1 H), 7.47 (t, J=7.7 Hz, 1 H), 7.33-7.25 (m, 2 H), 7.27-7.19 (m, 2 H), 7.19 (d, J=8.3 Hz, 2 H), 7.10 (t, J=8.2 Hz, 2 H), 7.05 (d, J=8.3 Hz, 1 H), 7.01 (d, J=2.0 Hz, 1 H), 6.88 (dd, J=8.3, 2.0 Hz, 1 H), 6.73-6.67 (m, 1 H), 6.67 (t, J=75 Hz, 1 H), 5.93-5.86 (m, 2 H), 4.90-4.81 (m, 1 H), 4.03 (t, J=8.0 Hz, 1 H), 3.83-3.77 (m, 2 H), 3.74-3.62 (m, 1 H), 3.50-3.41 (m, 1 H), 3.47 (dd, J=14.6, 8.7 Hz, 1 H), 3.40-3.28 (m, 1 H), 3.21 (dd, J=14.4, 5.5 Hz, 1 H), 3.17-3.09 (m, 3 H), 3.09-2.97 (m, 4 H), 2.92 (t, J=8.8 Hz, 3 H), 2.13-1.95 (m, 4 H), 1.95-1.87 (m, 2 H), 1.81-1.67 (m, 2 H), 1.21-1.09 (m, 2 H), 0.55-0.49 (m, 2 H), 0.27-0.22 (m, 2 H). LCMS (Method 1): [MH+]=999 at 2.73 min.

Intermediate 44. (S)-3,5-dichloro-4-(2-(3,4-dimethoxyphenyl)-2-((4-(hydroxymethyl)benzoyl)oxy)ethyl)pyridine 1-oxide (I44)

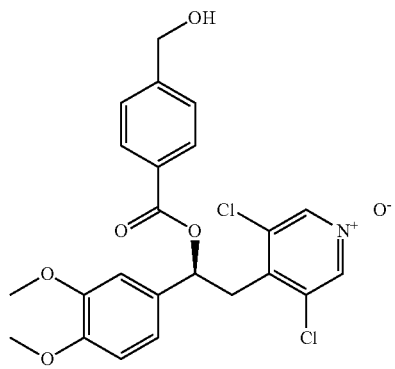

A solution of (S)-3,5-dichloro-4-(2-(3,4-dimethoxyphenyl)-2-hydroxyethyl)pyridine 1-oxide (0.688 g, 2 mmol), 4-formylbenzoic acid (0.300 g, 2 mmol), N-(3-dimethylaminopropyl)-N'-ethylcarbodiimide hydrochloride (0.767 g, 4 mmol) and 4-(dimethylamino)pyridine (0.122 g, 1 mmol) in anhydrous DCM (30 mL) was stirred at RT for 21 h. The reaction mixture was partitioned between saturated aqueous NaHCO₃ (20 mL) and DCM (10 mL) and filtered through a phase separator. The solvent was removed in vacuo and the crude material was purified by silica gel column chromatography eluting with 1:1 DCM:EtOAc to afford (S)-3,5-dichloro-4-(2-(3,4-dimethoxyphenyl)-2-((4-formylbenzoyl)oxy)ethyl)pyridine 1-oxide as an off-white solid (0.863 g, 91%).

To a stirred solution of (S)-3,5-dichloro-4-(2-(3,4-dimethoxyphenyl)-2-((4-formylbenzoyl)oxy)ethyl)pyridine 1-oxide (412 mg, 0.87 mmol) in DCM (10 mL) was added 3-aminopyridazine (165 mg, 1.73 mmol) followed by glacial acetic acid (150 µL, 2.61 mmol). The reaction was stirred at room temperature for 30 minutes then NaB(OAc)₃H (551 mg, 2.61 mmol) was added. The reaction mixture was stirred at room temperature for 18 hours. The reaction was diluted with DCM (10 mL) and quenched with water. The organic phase was washed with saturated aqueous NaHCO₃ solution, filtered through hydrophobic frit and evaporated to dryness. The residue was triturated with DCM (2 mL) and CH₃CN (5 mL). The solid was collected by filtration, washed with DCM and dried to provide the title compound (300 mg, 72%) as white solid.

LCMS (Method 1): [MH+]=478 at 3.21 min.

Intermediate 45. 4-((S)-2-((4-((3-((S)-((tert-butoxycarbonyl)amino)(phenyl)methyl)-benzoyl)oxy)methyl)benzoyl)oxy)-2-(3,4-dimethoxyphenyl)ethyl)-3,5-dichloropyridine 1-oxide (I45)

Intermediate 45 was prepared from Intermediate 44 and Intermediate 10 according to the same procedure described for the preparation of Example 29.

¹H NMR (400 MHz, CDCl₃): δ 8.12 (s, 2 H), 8.04-7.96 (m, 4 H), 7.48-7.28 (m, 8 H), 7.22-7.19 (m, 2 H), 7.02-6.98 (m, 2 H), 6.85 (d, J=8.4 Hz, 1 H), 6.29 (dd, J=4.4, 9.6 Hz, 1 H), 5.98-5.89 (brs, 1 H), 5.39 (s, 2 H), 3.90 (s, 3 H), 3.87 (s, 3 H), 3.72 (dd, J=9.6, 14.0 Hz, 1 H), 3.33 (dd, J=4.4, 14.0 Hz, 1 H), 1.58 (s, 9 H). LCMS (Method 1): [MH+]=787 at 4.58 min.

Example 47 can be obtained using the procedure in Scheme L.

Scheme L

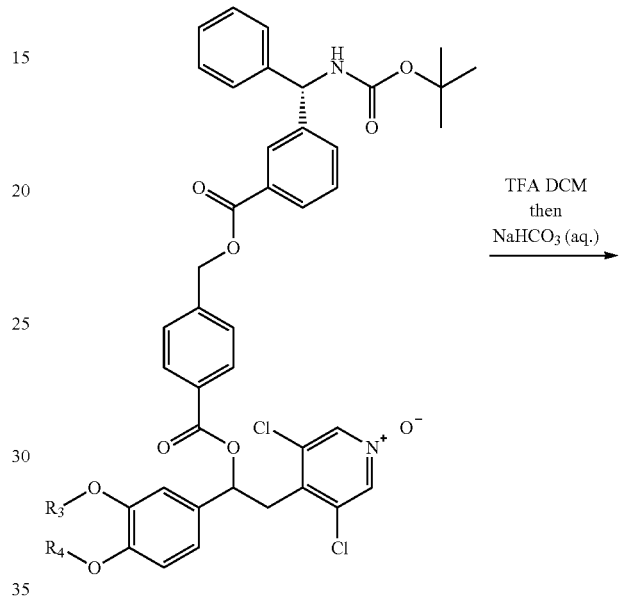

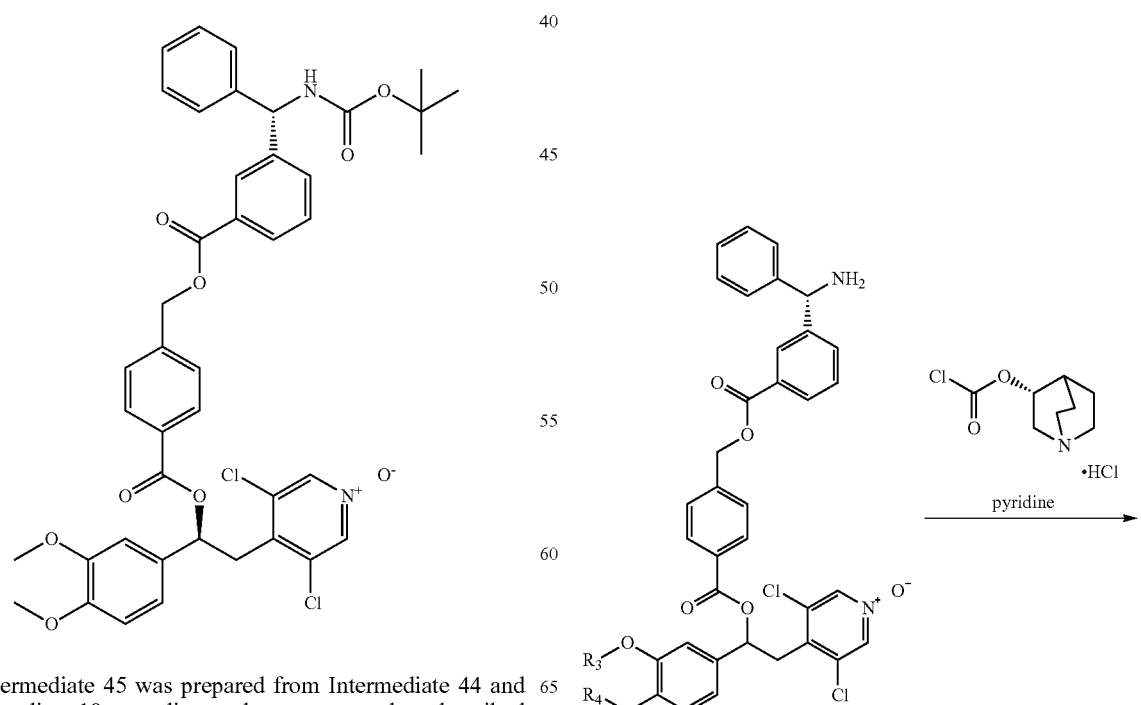

143
-continued

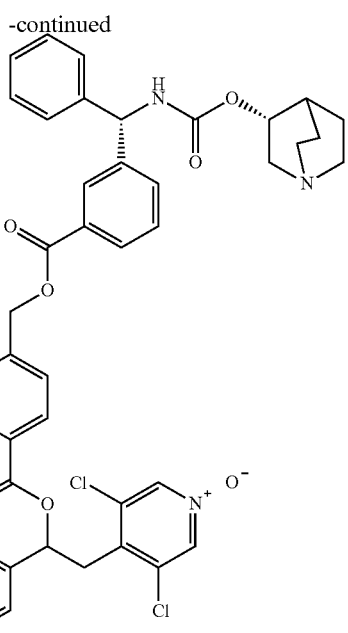

Example 47

[4-[(1S)-2-(3,5-dichloro-1-oxido-pyridin-1-ium-4-yl)-1-(3,4-dimethoxyphenyl)ethoxy]carbonylphenyl]methyl3-[(S)-phenyl-[[(3R)-quinuclidin-3-yl]oxycarbonylamino]methyl]benzoate (E47)

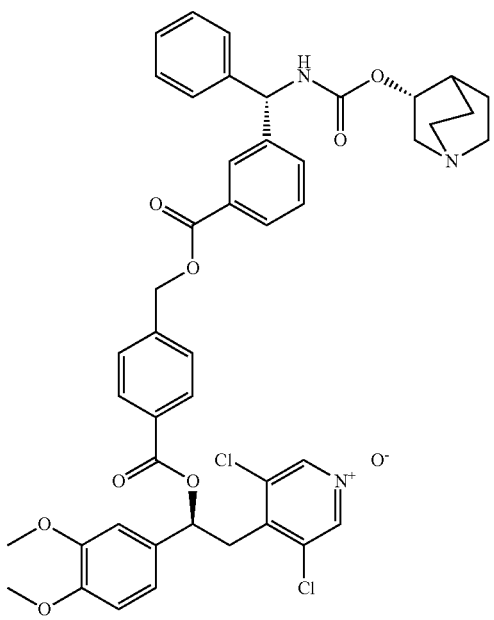

Example 47 was prepared from Intermediate 45 according to the same procedure described for the preparation of Intermediate 35.

$^1$H NMR (400 MHz, CD$_3$CN): δ 8.18 (s, 2 H), 8.08 (d, J=8.4 Hz, 2 H), 7.99-7.97 (m, 2H), 7.60-7.49 (m, 4 H), 7.40-7.31 (m, 5 H), 7.10-7.05 (m, 2 H), 6.95 (d, J=8.0 Hz, 1 H), 6.68-6.57 (brs, 1 H), 6.25 (dd, J=4.4, 9.6 Hz, 1 H), 5.98 (d, J=8.0 Hz, 1 H), 5.41 (s, 2H), 4.76-4.74 (m, 1 H), 3.84 (s, 3 H), 3.82 (s, 3 H), 3.71 (dd, J=9.6, 14.0 Hz, 1 H), 3.38 (dd, J=4.4, 14.0 Hz, 1 H), 3.27-3.23 (m, 1 H), 2.91-2.73 (m, 5 H), 2.15-2.12 (m, 1 H), 1.80-1.32 (m, 4 H). LCMS (Method 1): [MH+]=840 at 3.00 min.

Intermediate 46. Methyl 5-((4-benzoylphenoxy)methyl)furan-2-carboxylate (I46)

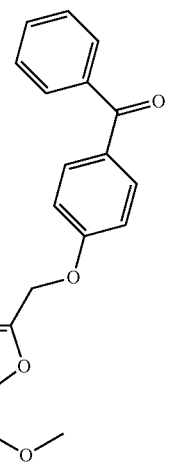

To a stirred solution of 4-hydroxybenzophenone (198.2 mg, 1.0 mmol) in DMF (3 mL) at 0° C. under nitrogen was added potassium carbonate (207 mg, 1.5 mmol) followed by methyl-5-chloromethyl-2-furoate (175 mg, 1.0 mmol). The reaction was allowed to warm to room temperature and the mixture was stirred at room temperature for 24 h. The reaction mixture was partitioned between water and ethyl acetate. The aqueous phase was extracted twice with ethyl acetate and the combined organic phases were washed with 10% aqueous K$_2$CO$_3$ solution, water, brine, dried over MgSO$_4$, filtered and the solvent removed in vacuo to yield the title compound (330 mg, 98.2%) as a yellow oil.

$^1$H NMR (400 MHz, CDCl$_3$): δ 7.84-7.74 (m, 3 H), 7.59-7.55 (m, 3 H), 7.49-7.45 (m, 1 H), 7.18-7.17 (m, 1 H), 7.03-7.01 (m, 2 H), 6.57-6.56 (m, 1 H), 5.14 (s, 2 H), 3.91 (s, 3 H). LCMS (Method 2): [M-OH+]=337 at 4.05 min.

Intermediate 47. Methyl 5-((4-(hydroxy(phenyl)methyl)phenoxy)methyl)furan-2-carboxylate (I47)

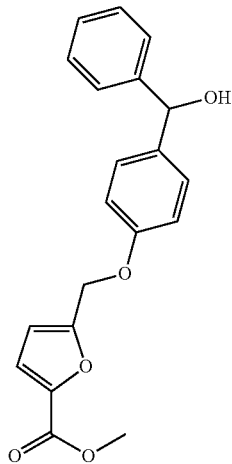 [SMILES: COC(=O)c1ccc(COc2ccc(C(O)c3ccccc3)cc2)o1]

A solution of methyl 5-((4-benzoylphenoxy)methyl)furan-2-carboxylate (330 mg, 1.0 mmol) in methanol (5 mL) and THF (5 mL) was cooled to 0° C. NaBH$_4$ (58 mg, 1.53 mmol) was added in one portion and the reaction was stirred at 0° C. for 2 hours. The reaction was quenched by addition of water (0.75 mL). The mixture was stirred for 10 minutes and the majority of the solvent was removed in vacuo. The residue was partitioned between EtOAc and water and the aqueous phase was extracted twice with EtOAc. The combined organic phases were washed with brine, dried over MgSO$_4$, filtered and the solvent was removed in vacuo to give the title compound (325 mg, 96.1%) as a yellow oil.

$^1$H NMR (400 MHz, CDCl$_3$): δ 7.38-7.24 (m, 7 H), 7.14 (d, J=3.6 Hz, 1 H), 6.93-6.89 (m, 2 H), 6.50 (d, J=3.6 Hz, 1 H), 5.81 (d, J=3.6 Hz, 1 H), 5.04 (s, 2 H), 3.90 (s, 3 H), 2.13 (d, J=3.6 Hz, 1 H). LCMS (Method 2): [M-OH+]=321 at 4.38 min.

Intermediate 48. Methyl 5-((4-(azido(phenyl)methyl)phenoxy)methyl)furan-2-carboxylate (I48)

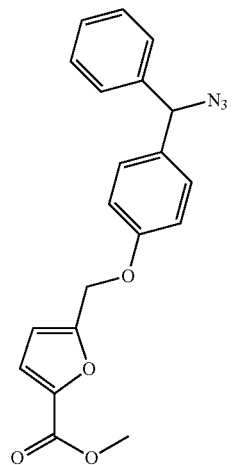 [SMILES: COC(=O)c1ccc(COc2ccc(C(N=[N+]=[N-])c3ccccc3)cc2)o1]

To a stirred solution of methyl 5-((4-(hydroxy(phenyl)methyl)phenoxy)methyl)-furan-2-carboxylate (325 mg, 0.96 mmol) in toluene (4.5 mL) under nitrogen was added diphenylphosphoryl azide (0.25 mL, 1.15 mmol) followed by DBU (0.17 mL, 1.15 mmol). The reaction was heated at 100° C. for 3 h. The reaction was quenched by the addition of saturated ammonium chloride solution. The aqueous phase was extracted with ethyl acetate (×2). The combined organic phases were washed with brine, dried over MgSO$_4$, filtered and the solvent removed in vacuo. The residue was purified via silica gel chromatography, eluting with 0-25% EtOAc in isohexane, to give the title compound as a colourless oil (293 mg, 84%).

$^1$H NMR (400 MHz, CDCl$_3$): δ 7.38-7.19 (m, 8 H), 7.16-7.15 (m, 1 H), 6.95-6.91 (m, 2 H), 6.52-6.51 (m, 1 H), 5.05 (s, 2 H), 3.89 (s, 3 H). LCMS (Method 2): [M-N$_2$+]=338 and [M-N$_3$+]=321 at 4.38 min.

Intermediate 49. Methyl 5-((4-(amino(phenyl)methyl)phenoxy)methyl)furan-2-carboxylate (I49)

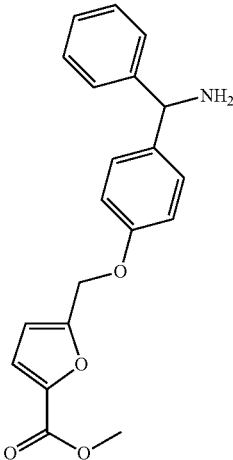 [SMILES: COC(=O)c1ccc(COc2ccc(C(N)c3ccccc3)cc2)o1]

To a suspension of triphenylphosphine polymer supported (633 mg, 0.89 mmol) in THF (3 mL) was added a solution of methyl 5-((4-(azido(phenyl)methyl)phenoxy)-methyl)furan-2-carboxylate (293 mg, 0.81 mmol) in THF (6.1 mL) and H$_2$O (0.12 mL). The reaction was stirred very slowly and heated at 60° C. for 18 h. Triphenylphosphine polymer supported (300 mg) and water (62 µL) were added and the heating was maintained at 60° C. for 5 h. The reaction was then allowed to cool to room temperature. The resin was removed by filtration, washed twice with THF and DCM. The combined organic phases were dried over MgSO$_4$, filtered and the solvent removed in vacuo to give the title compound (301 mg) which was taken on to the next step without further purification.

$^1$H NMR (400 MHz, CDCl$_3$): δ 7.37-7.19 (m, 8 H), 7.15-7.14 (m, 1 H), 3.60-6.87 (m, 2 H), 6.50-6.49 (m, 1 H), 5.03 (s, 2 H), 3.91 (s, 3 H), 1.59 (brs, 2 H). LCMS (Method 1): [MH+]=338 at 2.56 min.

Intermediate 50. Methyl 5-((4-(phenyl((((R)-quinuclidin-3-yloxy)carbonyl)amino)methyl)phenoxy)methyl)furan-2-carboxylate (I50)

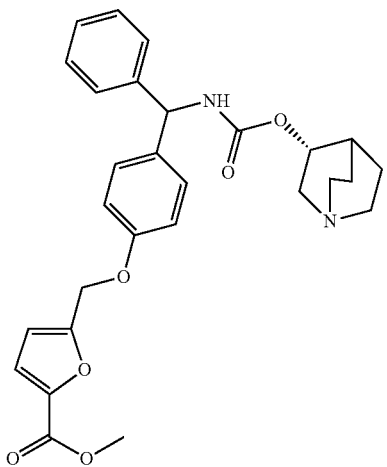 [SMILES: COC(=O)c1ccc(COc2ccc(C(NC(=O)O[C@H]3CN4CCC3CC4)c3ccccc3)cc2)o1]

To a stirred solution of methyl 5-((4-(amino(phenyl)methyl)phenoxy)methyl)-furan-2-carboxylate (301 mg, 0.894 mmol) in anhydrous pyridine (5 mL) at 0° C. under nitrogen was added (R)-quinuclidin-3-yl carbonochloridate hydrochloride (243 mg, 1.07 mmol, prepared as previously reported in 16, Step 6) in one portion. The reaction was stirred at room temperature for 3 days. The reaction was quenched by addition of 10% $K_2CO_3$ solution, extracted with ethyl acetate (3×20 mL). The combined organic phases were washed with brine, dried over $MgSO_4$, filtered and the solvent removed in vacuo. The residue was purified by silica gel chromatography, eluting with 0-10% 7N methanolic ammonia in ethyl acetate, to give the title compound as a yellow oil (280 mg, 64%).

LCMS (Method 1): [MH+]=491 at 2.75 min.

Examples 48-49 can be obtained using the procedure in Scheme M.

Scheme M

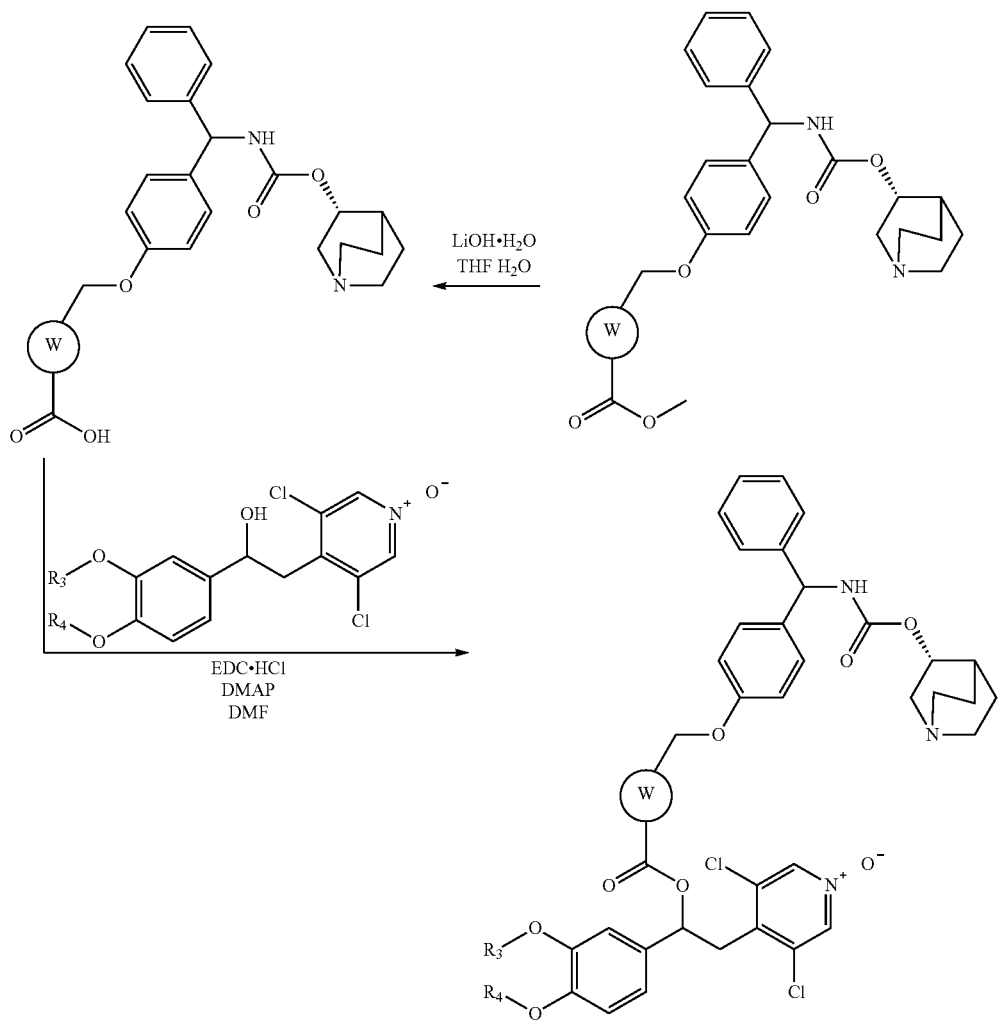

Example 48

[(1S)-2-(3,5-dichloro-1-oxido-pyridin-1-ium-4-yl)-1-(3,4-dimethoxyphenyl)ethyl]5-[[4-[phenyl-[[(3R)-quinuclidin-3-yl]oxycarbonylamino]methyl]phenoxy]methyl]furan-2-carboxylate formate salt (E48)

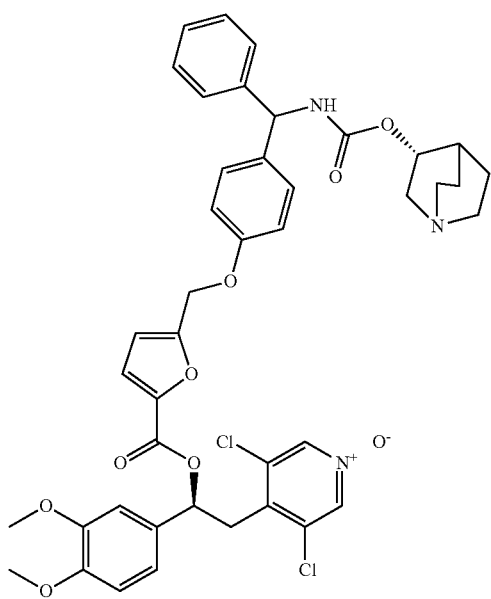

Example 48 was prepared from Intermediate 50 according to the same procedure described for the preparation of Example 32.

$^1$H NMR (400 MHz, DMSO): δ 8.55 (s, 2 H), 8.24-8.17 (m, 2 H), 7.37-7.19 (m, 8 H), 7.03-6.94 (m, 5 H), 6.78 (d, J=3.5 Hz, 1 H), 6.13 (dd, J=9.4, 4.5 Hz, 1 H), 5.80 (d, J=9.2 Hz, 1 H), 5.11 (s, 2 H), 4.63-4.56 (m, 1 H), 3.77 (s, 3 H), 3.75 (s, 3 H), 3.58 (dd, J=14.2, 9.5 Hz, 1 H), 3.31 (dd, J=14.1, 4.6 Hz, 1 H), 3.20-3.10 (m, 1 H), 2.85-2.53 (m, 5 H), 1.97-1.75 (m, 2 H), 1.68-1.31 (m, 3 H). LCMS (Method 1): [MH+]=802 at 2.84 min.

The following compound was prepared via the same method.

| Structure | Example | Analytical data |
| --- | --- | --- |
| [(1S)-2-(3,5-dichloro-1-oxido-pyridin-1-ium-4-yl)-1-(3,4-dimethoxyphenyl)ethyl]5-[[4-[(R)-phenyl-[[(3R)-quinuclidin-3-yl]oxycarbonylamino]methyl]phenoxy]methyl]furan-2-carboxylate formate salt | Example 49 | $^1$H NMR (400 MHz, DMSO): δ 8.54 (s, 2 H), 8.26-8.18 (m, 2 H), 7.37-7.18 (m, 7 H), 7.05-6.87 (m, 6 H), 6.75 (d, J = 3.5 Hz, 1 H), 6.13 (dd, J = 9.4, 4.6 Hz, 1 H), 5.81 (d, J = 9.3 Hz, 1 H), 5.11 (s, 2 H), 4.62-4.54 (m, 1 H), 3.77 (s, 3 H), 3.75 (s, 3 H), 3.59 (dd, J = 14.2, 9.5 Hz, 1 H), 3.31 (dd, J = 14.2, 4.7 Hz, 1 H), 3.18-3.07 (m, 1 H), 2.84-2.54 (m, 5 H), 1.96-1.86 (m, 1 H), 1.85-1.73 (m, 1 H), 1.66-1.54 (m, 1 H), 1.54-1.42 (m, 1 H), 1.39-1.28 (m, 1 H). LCMS (Method 2): [MH+] = 802 at 3.78 min. |

Intermediate 51. Methyl 2-[[3-[(S)-(tert-butoxycarbonylamino)-phenyl-methyl]phenoxy]methyl]oxazole-4-carboxylate (I51)

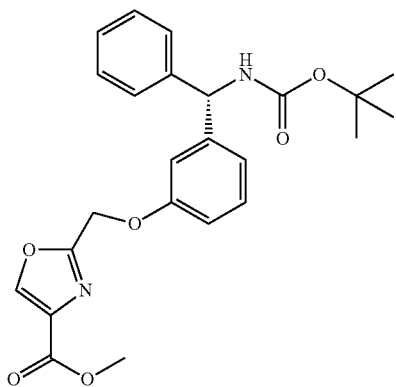 [SMILES: COC(=O)c1coc(COc2cccc([C@@H](NC(=O)OC(C)(C)C)c3ccccc3)c2)n1]

To a stirred solution of (S)-tert-butyl ((3-hydroxyphenyl)(phenyl)methyl)-carbamate (I8, 1 g, 3.34 mmol) in DMF (9.4 mL) at 0° C. under nitrogen was added K$_2$CO$_3$ (0.693 g, 5.01 mmol) followed by methyl 2-(chloromethyl)oxazole-4-carboxylate (0.586 g, 3.34 mmol). After 10 minutes at 0° C., the reaction was allowed to warm to room temperature and the stirring was maintained for 21 h. The reaction mixture was then partitioned between water (10 mL) and ethyl acetate (10 mL). The aqueous phase was extracted with ethyl acetate (2×20 mL) and the combined organic phases were dried over MgSO$_4$, filtered then concentrated in vacuo to give the title compound (1.66 g) as an off-white solid. The residue was taken on to the next step without further purification. LCMS (Method 1): [MH+]=439 at 4.22 min.

Intermediate 52. 2-[[3-[(S)-(tert-butoxycarbonylamino)-phenyl-methyl]phenoxy]methyl]oxazole-4-carboxylic acid (I52)

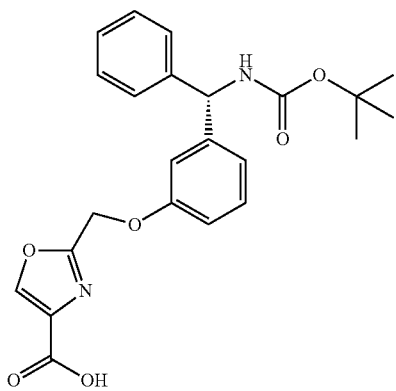 [SMILES: CC(C)(C)OC(=O)N[C@@H](c1ccccc1)c1cccc(OCc2nc(C(=O)O)co2)c1]

To a stirred solution of methyl 2-[[3-[(S)-(tert-butoxycarbonylamino)-phenyl-methyl]phenoxy]methyl]oxazole-4-carboxylate (0.8 g, 1.825 mmol) in THF (9.2 mL) and methanol (9.2 mL) was added a solution of lithium hydroxide monohydrate (153.1 mg, 3.65 mmol) in water (3.6 mL). The reaction was stirred at room temperature for 18 h. The majority of the solvent was removed in vacuo. The residue was diluted with water (50 mL) and cooled to 0° C. 2N aqueous HCl (1.82 mL) was added dropwise. The reaction mixture was extracted with ethyl acetate (3×20 mL) and the combined organic phases were washed with brine, dried over MgSO$_4$, filtered and concentrated in vacuo to give the title compound as a colourless solid (736 mg, 95%).
LCMS (Method 2): [MH+]=425 at 2.54 min.

Intermediate 53. [(1S)-2-(3,5-dichloro-1-oxido-pyridin-1-ium-4-yl)-1-(3,4-dimethoxyphenyl)ethyl]2-[[3-[(S)-(tert-butoxycarbonylamino)-phenyl-methyl]phenoxy]methyl]oxazole-4-carboxylate (I57)

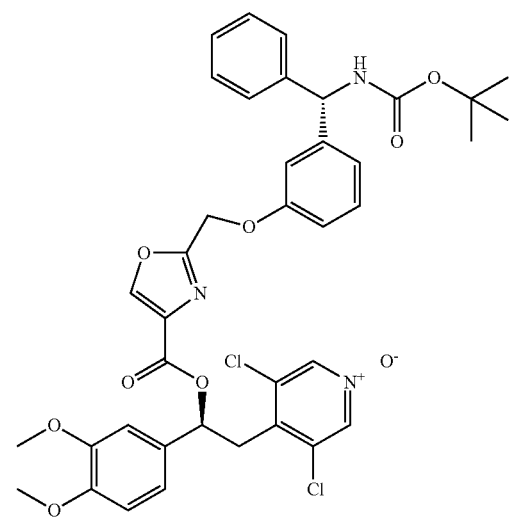

To a stirred suspension of 2-[[3-[(S)-(tert-butoxycarbonylamino)-phenyl-methyl]phenoxy]methyl]oxazole-4-carboxylic acid (350 mg, 0.825 mmol) in DMF (12.3 mL) was added (1S)-2-(3,5-dichloro-1-oxido-pyridin-1-ium-4-yl)-1-(3,4-dimethoxyphenyl)ethanol (284 mg, 0.825 mmol), DMAP (50.4 mg, 0.412 mmol) and EDC hydrochloride (316.2 mg, 1.65 mmol). The reaction was stirred at room temperature for 23 h. The majority of the DMF was removed in vacuo and the residue was partitioned between ethyl acetate (30 mL) and saturated aqueous NaHCO$_3$ solution (30 mL). The aqueous phase was extracted twice with ethyl acetate (20 mL) and the combined organic phases were washed with brine, dried on MgSO$_4$, filtered then concentrated in vacuo. The residue was purified via silica gel chromatography, eluting with 0-50% EtOAc in dichloromethane, to give the title compound (225.6 mg, 36%) as a colourless solid.
LCMS (Method 2): [MH+]=750 at 3.61 min.

Example 50 can be obtained using the procedure of Scheme N.

Scheme N

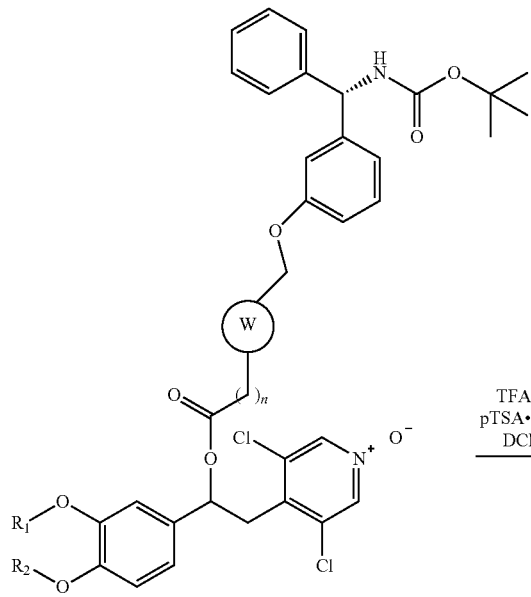

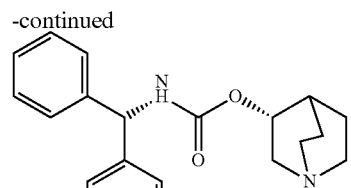

TFA or pTSA•H2O
DCM

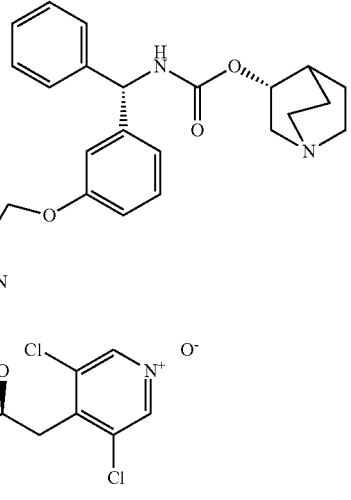

Example 50

[(1S)-2-(3,5-dichloro-1-oxido-pyridin-1-ium-4-yl)-1-(3,4-dimethoxyphenyl)ethyl]2-[[3-[(S)-phenyl-[[(3R)-quinuclidin-3-yl]oxycarbonylamino]methyl]phenoxy]methyl]oxazole-4-carboxylate formate salt (E50)

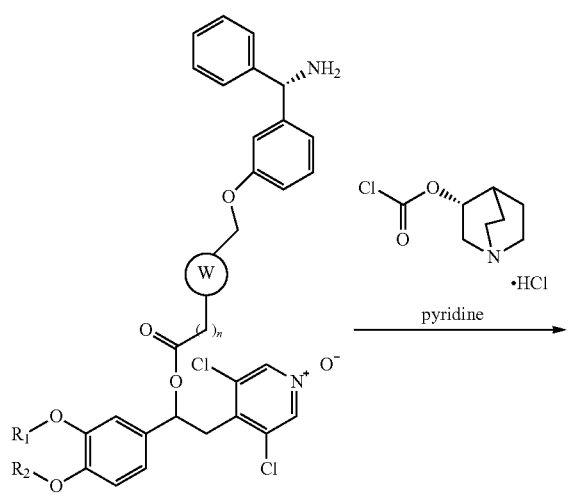

pyridine

To a stirred solution of [(1S)-2-(3,5-dichloro-1-oxido-pyridin-1-ium-4-yl)-1-(3,4-dimethoxyphenyl)ethyl]2-[[3-[(S)-(tert-butoxycarbonylamino)-phenyl-methyl]phenoxy]methyl]-oxazole-4-carboxylate (I53, 214 mg, 0.285 mmol) in DCM (1.5 mL) was added para-toluenesulfonic acid monohydrate (81.2 mg, 0.42 mmol). The reaction was stirred at room temperature for 18 h. The reaction mixture was diluted with methanol (2 mL) and loaded onto a SCX cartridge. The SCX cartridge was then washed with methanol and the product was eluted with 2.3N methanolic ammonia solution. The fractions containing ammonia were concentrated in vacuo. The residue was dissolved in anhydrous pyridine (0.92 mL) at 0° C. under nitrogen and (R)-quinuclidin-3-yl carbonochloridate hydrochloride (48.3 mg, 0.213 mmol, prepared as previously described in Int6, Step 6) was added in one portion. The reaction was stirred at room temperature for 2 days. The reaction was quenched by addition of 10% $K_2CO_3$ solution, extracted with ethyl acetate (3×20 mL). The combined organic phases were washed with brine, dried over $MgSO_4$, filtered and the solvent was removed in vacuo. The residue was dissolved in DMSO (1.5 mL) and purified by preparative HPLC to provide the title compound (21.4 mg, 9.3% over 2 steps) as a yellow solid.

$^1$H NMR (400 MHz, DMSO): δ 8.96 (s, 1 H), 8.57 (s, 2 H), 8.30-8.23 (m, 2 H), 7.37-7.16 (m, 6 H), 7.09-6.91 (m, 6 H), 6.21 (dd, J=9.2, 4.6 Hz, 1 H), 5.84 (d, J=9.1 Hz, 1 H), 5.29 (s, 2 H), 4.65-4.58 (m, 1 H), 3.80 (s, 3 H), 3.78 (s, 3 H), 3.60 (dd, J=15.0, 9.3 Hz, 1 H), 3.35 (dd, J=14.3, 5.6 Hz, 1 H), 3.20-3.11 (m, 1 H), 2.85-2.58 (m, 5 H), 1.98-1.77 (m, 2 H), 1.69-1.32 (m, 3 H).

LCMS (Method 2): [MH+]=803 at 3.11 min.

Pharmacological Activity of the Compounds of the Present Invention.

In Vitro Determination of PDE4 Inhibitory Activity

In vitro determination of PDE4 inhibitory activity for compounds of the present invention may be determined according to one of the protocols herebelow reported:

PDE4B2HTRF Assay.

PDE4B2 activity is detected using the LANCE Ultra cAMP homogeneous time resolved fluorescence resonance energy transfer (TR-FRET) assay from Perkin Elmer. The assay is based on the competition between the europium (Eu) chelate-labeled cAMP tracer and sample cAMP for binding sites on cAMP-specific monoclonal antibodies (mAb) labelled with the ULight™ dye. The assay is carried out in 384-well low volume plates in a volume of 10 μl. Human recombinant PDE4B2 (80 pM) is incubated for 2 h with 3 nM cAMP in buffer containing 1×HBSS, 5 mM HEPES, 3 mM $MgCl_2$, 0.1% BSA, pH 7.4 with or without test compounds. The enzymatic reactions are efficiently stopped by the addition of 500 μM IBMX present in the combined Stop/Detection buffer containing europium (Eu) chelate-labeled cAMP tracer and cAMP-specific monoclonal antibodies (mAb) labelled with the ULight™ dye. Samples are then further incubated for 1 h before plates are read at ex 340 nm and em at 665 nm and 615 nm on an EnVision reader. $IC_{50}$ values are determined from competition curves using a non-linear curve fitting program.

PDE4 Cell Free Assay Protocol.

PDE4 activity is determined in U937 human monocytic supernatants cells lysate. Cells are cultured, harvested and supernatant fraction prepared essentially as described in Torphy T J et al J. Pharmacol. Exp. Ther. 1992; 263:1195-1205, which is incorporated herein by reference in its entirety. U937 cells are grown at 37° C., 5% $CO_2$ in RPMI 1640 with GlutaMAX™-I medium supplemented with 10% fetal bovine serum and 100 μg/mL Pen-strep (Gibco). Cells are harvested and washed twice by centrifugation (150×g, 8 min) in cold PBS. Washed cells are re-suspended in cold Krebs-Ringer-Henseleit buffer at a final concentration 20×10$^6$ cells/mL and sonicated. After centrifugation at 15000×g for 20 min, the supernatants are pooled, divided in aliquots and stored at −80° C. PDE4 activity is determined in cells supernatants by assaying cAMP disappearance from the incubation mixtures. The concentration of the test compounds ranges between $10^{-12}$ M and $10^{-6}$ M. Reactions are stopped by enzyme heat inactivation (2.5 minutes at 100° C.) and residual cAMP content is determined using the 'LANCE cAMP Assay' from PerkinElmer following the provider instructions.

The results, expressed as mean±standard deviation of the molar concentration of the test compound producing 50% inhibition of cAMP disappearance ($IC_{50}$). Percentage of inhibition of PDE4 activity is calculated, assuming cAMP disappearance in the absence of inhibitors as 100% and cAMP disappearance in heat inactivated samples as 0%.

Representative compounds of the present invention, when tested in one of the above reported protocols, displayed an $IC_{50}$ lower than 100 nM.

In Vitro Determination of M3 Antagonism.

In vitro determination of M3 antagonism for compounds of the invention may be determined according to one of the protocols herebelow reported:

M3 Receptor Radioligand Binding Assay.

Human $M_3$ receptor membranes (15 μg/well) from Perkin Elmer are incubated with 0.52 nM Scopolamine Methyl Chloride, [N-methyl-3H] with or without test compounds, or a saturating concentration of Atropine (5 μM) for the determination of non-specific binding. The assay is carried out in 96-well polypropylene plates in a volume of 250 μl. The assay buffer used is 50 mM Tris-HCl, 154 mM NaCl (pH 7.4). The final assay concentration of DMSO is 0.5% (v/v). The plates are sealed and incubated for 2 h at room temperature on an orbital shaker (slow speed). Membranes are harvested onto 96-well unifilter GF/C filter plates pre-treated with 0.5% polyethyleneimine (v/v), using a filter manifold, washed four times with 200 μl of assay buffer. The plates are dried before addition of 50 μl of microscint-0, sealed then read in a Trilux Microbeta scintillation counter. $IC_{50}$ values are determined from competition curves using a non-linear curve fitting program. $K_i$ values are calculated from $IC_{50}$ values by the Cheng and Prusoff equation.

M3 Binding Assay.

CHO-K1 clone cells expressing the human M3-receptor (Swissprot P20309) were harvested in $Ca^{++}/Mg^{++}$ free phosphate-buffered saline and collected by centrifugation at 1500 rpm for 3 min. The pellets were resuspended in ice cold buffer A (15 mM Tris-HCl pH 7.4, 2 mM $MgCl_2$, 0.3 mM EDTA, 1 mM EGTA) and homogenized by a PBI politron (setting 5 for 15 s). The crude membrane fraction was collected by two consecutive centrifugation steps at 40000 g for 20 min at 4° C., separated by a washing step in buffer A. The pellets obtained were finally resuspended in buffer B (75 mM Tris HCl pH 7.4, 12.5 mM $MgCl_2$, 0.3 mM EDTA, 1 mM EGTA, 250 mM sucrose), and aliquots were stored at −80° C.

The day of experiment, frozen membranes were resuspended in buffer C (50 mM Tris-HCl pH 7.4, 2.5 mM $MgCl_2$, 1 mM EDTA). The non-selective muscarinic radioligand [$^3$H]-N-methyl scopolamine (Mol. Pharmacol. 45:899-907, which is incorporated herein by reference in its entirety) was used to label the M3 binding sites. Binding experiments were performed in duplicate (ten point concentrations curves) in 96 well plates at radioligand concentration of 0.1-0.3 nM. The non-specific binding was determined in the presence of cold N-methyl scopolamine 10 μM. Samples (final volume 0.75 mL) were incubated at room temperature for 90 min. The reaction was terminated by rapid filtration through GF/B Unifilter plates and two washes (0.75 mL) with cold buffer C using a Packard Filtermate Harvester. Radioactivity on the filters was measured by a microplate scintillation counter TriCarb 2500 (PerkinElmer).

Representative compounds of the present invention, when tested in one of the above reported protocols, displayed an $IC_{50}$ lower than 100 nM.

Representative compounds of the present invention displayed an $IC_{50}$ lower than 100 nM in both PDE4 cell free and M3 binding assays Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

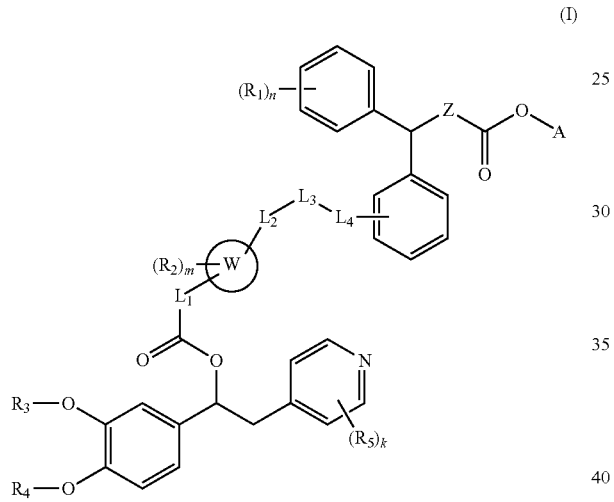

wherein
each $R_1$ is independently hydrogen, halogen, ($C_1$-$C_4$) alkyl, ($C_1$-$C_4$) alkoxy, ($C_1$-$C_4$) haloalkyl, hydroxy, —$SO_2NR_6R_7$, —CN, —$NR_8SO_2R_9$, —$NR_6R_7$, —$CONR_6R_7$, or —$NR_8COR_9$, wherein said ($C_1$-$C_4$) alkyl is optionally substituted by one or more groups selected from the group consisting of ($C_3$-$C_7$) cycloalkyl, hydroxyl, and —$NR_6R_7$ and wherein said ($C_1$-$C_4$) alkoxy is optionally substituted by one or more halogen atoms or ($C_3$-$C_7$) cycloalkyl groups, wherein,
$R_6$ is hydrogen or ($C_1$-$C_6$) alkyl;
$R_7$ is hydrogen or ($C_1$-$C_6$) alkyl;
$R_8$ is hydrogen or ($C_1$-$C_6$) alkyl;
$R_9$ is hydrogen or ($C_1$-$C_6$) alkyl;
n is an integer ranging from 1 to 3;
each $R_2$ is independently hydrogen, halogen, ($C_1$-$C_4$) alkyl, ($C_1$-$C_4$) alkoxy, ($C_1$-$C_4$)haloalkyl, hydroxy, —$SO_2NR_{10}R_{11}$, —CN, or —$NR_{12}SO_2R_{13}$, wherein said ($C_1$-$C_4$) alkyl and said ($C_1$-$C_4$) alkoxy are optionally substituted by one ($C_3$-$C_7$) cycloalkyl groups, wherein
$R_{10}$ is hydrogen or ($C_1$-$C_6$) alkyl;
$R_{11}$ is hydrogen or ($C_1$-$C_6$) alkyl;
$R_{12}$ is hydrogen or ($C_1$-$C_6$) alkyl;
$R_{13}$ is hydrogen or ($C_1$-$C_6$) alkyl;

m is an integer ranging from 1 to 3;
$R_3$ and $R_4$ are different or the same and are independently:
H;
—($C_3$-$C_7$) cycloalkylcarbonyl;
($C_1$-$C_6$) alkyl, optionally substituted by one or more substituents selected from the group consisting of ($C_3$-$C_7$) cycloalkyl and ($C_5$-$C_7$) cycloalkenyl;
($C_1$-$C_6$) haloalkyl;
($C_3$-$C_7$) cycloalkyl;
($C_5$-$C_7$) cycloalkenyl;
($C_2$-$C_6$) alkenyl; and
($C_2$-$C_6$) alkynyl;
or $R_3$ and $R_4$, together with the interconnecting atoms, form a 2,2-difluoro-1,3-dioxolane ring of formula (r) fused to the phenyl moiety which bears groups —$OR_3$ and —$OR_4$, wherein asterisks indicate carbon atoms shared with such phenyl ring:

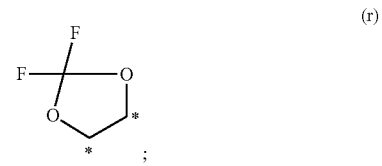

each $R_5$ is independently CN, $NO_2$, $CF_3$, or halogen;
k is 0 or an integer ranging from 1 to 3;
$L_1$ is selected from the group consisting of:
a bond,
—$(CH2)_p$-,
[3]-$(CH_2)_p$—O-[4]
[3]-$(CH_2)_p$—$NR_{10}$—$(CH_2)_r$-[4]
[3]-$(CH_2)_p$—OC(O)-[4]
[3]-$(CH_2)_p$—$NR_{10}$C(O)-[4]
[3]-$(CH_2)_p$—$NR_{10}$S($O_2$)-[4], and
[3]-$(CH_2)_p$—S($O_2$)—N($R_{10}$)-[4]
wherein [3] and [4] represent, respectively, the point of attachment of group $L_1$ to the carbonyl group and to the ring W and wherein
$R_{10}$ is as described above,
p is an integer ranging from 1 to 4 and
t is an integer ranging from 1 to 4
W is a divalent group selected from the group consisting of arylene, ($C_5$-$C_6$)-heteroarylene, and saturated monocyclic ($C_3$-$C_7$)-heterocycloalkylene;
$L_2$ is a bond, —C(O)—, —S—, —S(O)—, —$S(O)_2$—, or —$(CH_2)_q$— wherein q is 1 or 2;
$L_3$ is absent or is ortho-, meta-, or para-phenylene, or bivalent ($C_5$-$C_6$)-heteroarylene
$L_4$ is —(CH2)$_r$-, [1]—(CH$_2$)$_r$—O-[2], [1]-OC(O)-[2], or [1]-C(O)O-[2] wherein r is 1 or 2 and [1] and [2] represent respectively the point of attachment of group $L_4$ to the group $L_2$ (or $L_3$ when present) and to the phenyl ring;
Z is NH, $CH_2$ or O; and
A is a nitrogen containing group which is:
a group (a) which is —(CH$_2$)$_s$—$NR_{16}R_{17}$ wherein s is an integer ranging from 1 to 4 and $R_{16}$ and $R_{17}$ are independently hydrogen or ($C_1$-$C_4$) alkyl; and
a group (b) which is a saturated monocyclic, bicyclic or tricyclic heterocyclic ring system optionally substituted by one or two groups $R_{18}$ which are at each occurrence independently ($C_1$-$C_4$) alkyl or benzyl,
an N-oxide on the pyridine ring, or a pharmaceutically acceptable salt thereof.

2. A compound, N-oxide, or pharmaceutically acceptable salt according to claim 1, which is represented by formula (IB):

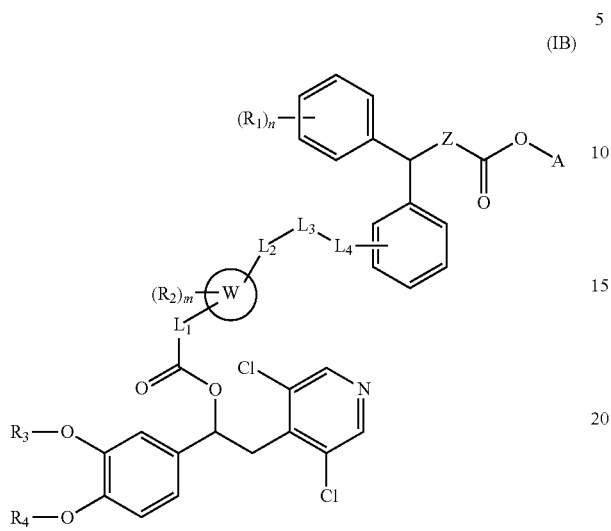

(IB)

an N-oxide on the pyridine ring, or a pharmaceutically acceptable salt.

3. A N-oxide or pharmaceutically acceptable salt according to claim 1, which is represented by formula (IA):

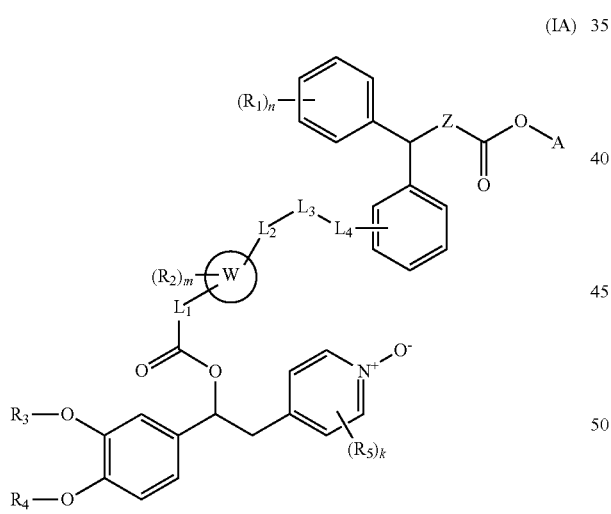

(IA)

or a pharmaceutically acceptable salt thereof.

4. A compound, N-oxide, or pharmaceutically acceptable salt according to claim 1, wherein:

$R_4$ is ($C_1$-$C_6$) haloalkyl or ($C_1$-$C_6$) alkyl; and $R_3$ is ($C_3$-$C_7$) cycloalkyl or ($C_1$-$C_6$) alkyl which is optionally substituted by ($C_3$-$C_7$) cycloalkyl.

5. A compound, N-oxide, or pharmaceutically acceptable salt according to claim 1, which is represented by formula (ID):

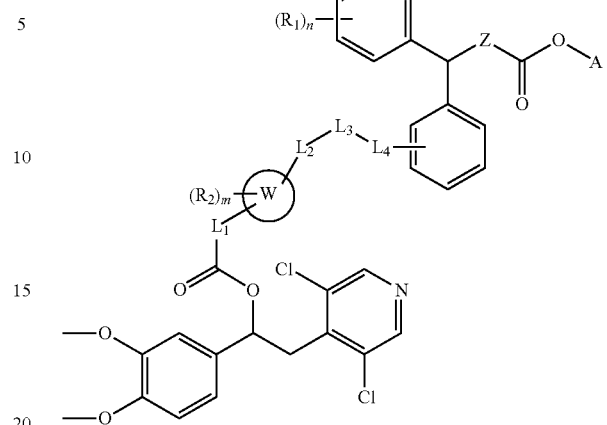

(ID)

an N-oxide on the pyridine ring, or a pharmaceutically acceptable salt thereof.

6. A compound, N-oxide, or pharmaceutically acceptable salt according to claim 1, which is represented by formula (I)' wherein the absolute configuration of carbon (1) is that shown herebelow

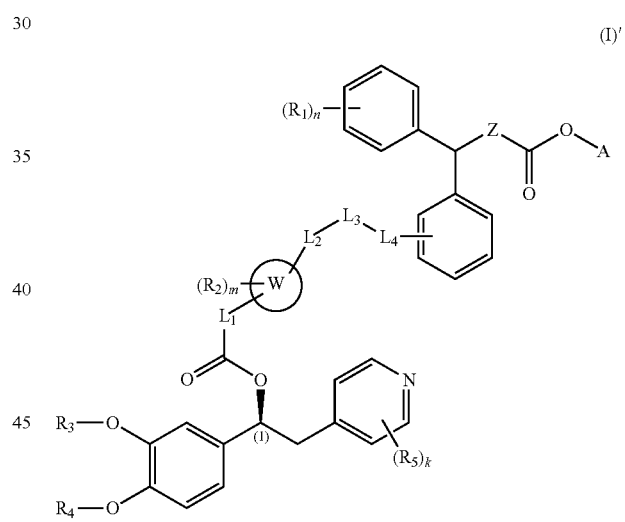

(I)' an N-oxide on the pyridine ring, or a pharmaceutically acceptable salt thereof.

7. A compound, N-oxide, or pharmaceutically acceptable salt according to claim 1, which is a compound selected from the group consisting of

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[3-[(S)-phenyl-[[(3R)-quinuclidin-3-yl]oxycarbonylamino]methyl]phenoxy]carbonylphenyl]sulfonylpyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[3-[3-[(S)-phenyl-[[(3R)-quinuclidin-3-yl]oxycarbonylamino]methyl]phenoxy]carbonylphenyl]sulfonylazetidine-3-carboxylate;

[(1S)-1-[3-(cyclopropylmethoxy)-4-(difluoromethoxy)phenyl]-2-(3,5-dichloro-1-oxido-pyridin-1-ium-4-yl)

ethyl](2S)-3-[3-[3-[phenyl-[[(3R)-quinuclidin-3-yl]oxycarbonylamino]methyl]phenoxy]carbonylphenyl]sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[3-[phenyl-[[(3R)-quinuclidin-3-yl]oxycarbonylamino]methyl]phenoxy]carbonylphenyl]sulfonylthiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[[3-[3-[(S)-phenyl-[[(3R)-quinuclidin-3-yl]oxycarbonylamino]methyl]phenoxy]carbonylphenyl]methyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[[3-[3-[(S)-phenyl-[[(3R)-quinuclidin-3-yl]oxycarbonylamino]methyl]benzoyl]oxyphenyl]methyl]thiazolidine-2-carboxylate;

[(1S)-2-(3,5-dichloro-1-oxido-pyridin-1-ium-4-yl)-1-(3,4-dimethoxyphenyl)ethyl]4-[[3-[(S)-phenyl-[[(3R)-quinuclidin-3-yl]oxycarbonylamino]methyl]phenoxy]methyl]benzoate;

[(1S)-2-(3,5-dichloro-1-oxido-pyridin-1-ium-4-yl)-1-(3,4-dimethoxyphenyl)ethyl]3-[[3-[(S)-phenyl-[[(3R)-quinuclidin-3-yl]oxycarbonylamino]methyl]phenoxy]methyl]benzoate;

[(1S)-2-(3,5-dichloro-1-oxido-pyridin-1-ium-4-yl)-1-(3,4-dimethoxyphenyl)ethyl]3-methoxy-5-[[3-[(S)-phenyl-[[(3R)-quinuclidin-3-yl]oxycarbonylamino]methyl]phenoxy]methyl]benzoate;

[(1S)-2-(3,5-dichloro-1-oxido-pyridin-1-ium-4-yl)-1-(3,4-dimethoxyphenyl)ethyl]6-[[3-[(S)-phenyl-[[(3R)-quinuclidin-3-yl]oxycarbonylamino]methyl]phenoxy]methyl]pyridine-3-carboxylate;

[(1S)-2-(3,5-dichloro-1-oxido-pyridin-1-ium-4-yl)-1-(3,4-dimethoxyphenyl)ethyl]1-methyl-5-[[3-[(S)-phenyl-[[(3R)-quinuclidin-3-yl]oxycarbonylamino]methyl]phenoxy]methyl]pyrazole-3-carboxylate;

[(1S)-2-(3,5-dichloro-1-oxido-pyridin-1-ium-4-yl)-1-[4-(difluoromethoxy)-3-ethoxy-phenyl]ethyl]5-[[3-[(S)-phenyl-[[(3R)-quinuclidin-3-yl]oxycarbonylamino]methyl]phenoxy]methyl]furan-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]5-[[3-[(S)-phenyl-[[(3R)-quinuclidin-3-yl]oxycarbonylamino]methyl]phenoxy]methyl]furan-2-carboxylate;

[2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]phenoxy]methyl]furan-2-carboxylate;

[(1S)-2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]phenoxy]methyl]furan-2-carboxylate;

[(1R)-2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonylamino]methyl]phenoxy]methyl]furan-2-carboxylate;

[2-(3,5-dichloro-1-oxido-pyridin-1-ium-4-yl)-1-(3,4-dimethoxyphenyl)ethyl]4-[[3-[phenyl-[[(3R)-quinuclidin-3-yl]oxycarbonylamino]methyl]phenoxy]methyl]benzoate;

[2-(3,5-dichloro-1-oxido-pyridin-1-ium-4-yl)-1-(3,4-dimethoxyphenyl)ethyl]3-[[3-[phenyl-[[(3R)-quinuclidin-3-yl]oxycarbonylamino]methyl]phenoxy]methyl]benzoate;

[(1S)-2-(3,5-dichloro-1-oxido-pyridin-1-ium-4-yl)-1-(3,4-dimethoxyphenyl)ethyl]5-[[3-[(S)-phenyl-[[(3R)-quinuclidin-3-yl]oxycarbonyl amino]methyl]phenoxy]methyl]thiophene-2-carboxylate;

[(1S)-2-(3,5-dichloro-1-oxido-pyridin-1-ium-4-yl)-1-(3,4-dimethoxyphenyl)ethyl]2-[3-[[3-[(S)-phenyl-[[(3R)-quinuclidin-3-yl]oxycarbonylamino]methyl]phenoxy]methyl]phenyl]acetate;

[(1S)-2-(3,5-dichloro-1-oxido-pyridin-1-ium-4-yl)-1-(3,4-dimethoxyphenyl)ethyl]1-4-[[3-[(S)-phenyl-[[(3R)-quinuclidin-3-yl]oxycarbonylamino]methyl]phenoxy]methyl]benzoyl]azetidine-3-carboxylate;

[(1S)-2-(3,5-dichloro-1-oxido-pyridin-1-ium-4-yl)-1-(3,4-dimethoxyphenyl)ethyl]1-[3-[[3-[(S)-phenyl-[[(3R)-quinuclidin-3-yl]oxycarbonylamino]methyl]phenoxy]methyl]benzoyl]azetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]benzoyl]pyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]benzoyl]piperidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]phenoxy]methyl]benzoyl]piperidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]phenoxy]methyl]benzoyl]pyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]benzoyl]azetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[3-[[3-[(S)-phenyl-[[(3R)-quinuclidin-3-yl]oxycarbonylamino]methyl]phenoxy]methyl]benzoyl]azetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[4-[[3-[(S)-phenyl-[[(3R)-quinuclidin-3-yl]oxycarbonylamino]methyl]phenoxy]methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[3-[[3-[(S)-phenyl-[[(3R)-quinuclidin-3-yl]oxycarbonylamino]methyl]phenoxy]methyl]benzoyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-3-[1-methyl-5-[[3-[(S)-phenyl-[[(3R)-quinuclidin-3-yl]oxycarbonylamino]methyl]phenoxy]methyl]pyrazole-3-carbonyl]thiazolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]phenoxy]methyl]phenyl]sulfonylpyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[[3-[(S)-phenyl-[[(3R)-quinuclidin-3-yl]oxycarbonylamino]methyl]phenoxy]methyl]phenyl]sulfonylpyrrolidine-2-carboxylate;

[(1S)-2-(3,5-dichloro-1-oxido-pyridin-1-ium-4-yl)-1-(3,4-dimethoxyphenyl)ethyl](2S)-1-[4-[[3-[(S)-phenyl-[[(3R)-quinuclidin-3-yl]oxycarbonylamino]methyl]phenoxy]methyl]phenyl]sulfonylpyrrolidine-2-carboxylate;

[(1S)-2-(3,5-dichloro-1-oxido-pyridin-1-ium-4-yl)-1-(3,4-dimethoxyphenyl)ethyl](2S)-1-[3-[[3-[(S)-phenyl-[[(3R)-quinuclidin-3-yl]oxycarbonylamino]methyl]phenoxy]methyl]phenyl]sulfonylpyrrolidine-2-carboxylate;

[(1S)-2-(3,5-dichloro-1-oxido-pyridin-1-ium-4-yl)-1-(3,4-dimethoxyphenyl)ethyl]1-[4-[[3-[(S)-phenyl-[[(3R)-quinuclidin-3-yl]oxycarbonylamino]methyl]phenoxy]methyl]phenyl]sulfonylazetidine-3-carboxylate;

[(1S)-2-(3,5-dichloro-1-oxido-pyridin-1-ium-4-yl)-1-(3,4-dimethoxyphenyl)ethyl]1-[3-[[3-[(S)-phenyl-[[(3R)-quinuclidin-3-yl]oxycarbonylamino]methyl]phenoxy]methyl]phenyl]sulfonylazetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[3-[[3-[(S)-phenyl-[[(3R)-quinuclidin-3-yl]oxycarbonylamino]methyl]phenoxy]methyl]phenyl]sulfonylazetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]phenyl]sulfonylazetidine-3-carboxylate;

[(1S)-1-[3-(cyclopropylmethoxy)-4-(difluoromethoxy)phenyl]-2-(3,5-dichloro-1-oxido-pyridin-1-ium-4-yl)ethyl]1-[4-[[3-[(S)-phenyl-[[(3R)-quinuclidin-3-yl]oxycarbonylamino]methyl]phenoxy]methyl]phenyl]sulfonylpiperidine-4-carboxylate;

[(1S)-2-(3,5-dichloro-1-oxido-pyridin-1-ium-4-yl)-1-(3,4-dimethoxyphenyl)ethyl]1-[4-[[3-[(S)-phenyl-[[(3R)-quinuclidin-3-yl]oxycarbonylamino]methyl]phenoxy]methyl]phenyl]sulfonylpiperidine-4-carboxylate;

[(1S)-1-[3-(cyclopropylmethoxy)-4-(difluoromethoxy)phenyl]-2-(3,5-dichloro-1-oxido-pyridin-1-ium-4-yl)ethyl]2-[4-[[3-[(S)-phenyl-[[(3R)-quinuclidin-3-yl]oxycarbonylamino]methyl]phenoxy]methyl]phenyl]sulfonylpiperazin-1-yl]acetate;

[(1S)-1-[3-(cyclopropylmethoxy)-4-(difluoromethoxy)phenyl]-2-(3,5-dichloro-1-oxido-pyridin-1-ium-4-yl)ethyl]2-[1-[4-[[3-[(S)-phenyl-[[(3R)-quinuclidin-3-yl]oxycarbonylamino]methyl]phenoxy]methyl]phenyl]sulfonylazetidin-3-yl]acetate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[4-[[3-[(S)-phenyl-[[(3R)-quinuclidin-3-yl]oxycarbonylamino]methyl]benzoyl]amino]phenyl]sulfonylpyrrolidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[3-[3-[(S)-phenyl-[[(3R)-quinuclidin-3-yl]oxycarbonylamino]methyl]phenyl]carbamoyl]phenyl]sulfonylpiperidine-2-carboxylate;

[(1S)-1-[3-(cyclopropylmethoxy)-4-(difluoromethoxy)phenyl]-2-(3,5-dichloro-1-oxido-pyridin-1-ium-4-yl)ethyl](2S)-1-[2-[4-[3-[(S)-phenyl-[[(3R)-quinuclidin-3-yl]oxycarbonylamino]methyl]benzoyl]oxyphenyl]ethyl]pyrrolidine-2-carboxylate;

[4-[(1S)-2-(3,5-dichloro-1-oxido-pyridin-1-ium-4-yl)-1-(3,4-dimethoxyphenyl)ethoxy]carbonylphenyl]methyl3-[(S)-phenyl-[[(3R)-quinuclidin-3-yl]oxycarbonylamino]methyl]benzoate;

[(1S)-2-(3,5-dichloro-1-oxido-pyridin-1-ium-4-yl)-1-(3,4-dimethoxyphenyl)ethyl]5-[[4-[phenyl-[[(3R)-quinuclidin-3-yl]oxycarbonylamino]methyl]phenoxy]methyl]furan-2-carboxylate;

[(1S)-2-(3,5-dichloro-1-oxido-pyridin-1-ium-4-yl)-1-(3,4-dimethoxyphenyl)ethyl]5-[[4-[(R)-phenyl-[[(3R)-quinuclidin-3-yl]oxycarbonylamino]methyl]phenoxy]methyl]furan-2-carboxylate;

[(1S)-2-(3,5-dichloro-1-oxido-pyridin-1-ium-4-yl)-1-(3,4-dimethoxyphenyl)ethyl]2-[[3-[(S)-phenyl-[[(3R)-quinuclidin-3-yl]oxycarbonylamino]methyl]phenoxy]methyl]oxazole-4-carboxylate or a pharmaceutically acceptable salt of said compound.

8. A pharmaceutical composition, comprising a compound, N-oxide, or pharmaceutically acceptable salt according to claim 1 in admixture with one or more pharmaceutically acceptable carriers.

9. A pharmaceutical composition according to claim 8, further comprising another active ingredient.

10. A method for the treatment of a disease of the respiratory tract characterized by airway obstruction, comprising administering an effective amount of a compound, N-oxide, or pharmaceutically acceptable salt according to claim 1 to a subject in need thereof.

11. A method according to claim 10, wherein said disease of the respiratory tract is asthma or COPD.

12. A method for the treatment of a disease of the respiratory tract characterized by airway obstruction, comprising administering an effective amount of a pharmaceutical composition according to claim 8 to a subject in need thereof.

13. A method according to claim 12, wherein said disease of the respiratory tract is asthma or COPD.

14. An inhalation device, which contains a pharmaceutical composition according to claim 8.

15. An inhalation device, which contains a pharmaceutical composition according to claim 9.

16. A kit, comprising a pharmaceutical composition according to claim 8 and a device which is a single- or multi-dose dry powder inhaler, a metered dose inhaler, or a nebulizer.

17. A kit, comprising a pharmaceutical composition according to claim 9 and a device which is a single- or multi-dose dry powder inhaler, a metered dose inhaler, or a nebulizer.

* * * * *